(12) United States Patent
Nagata et al.

(10) Patent No.: US 8,563,715 B2
(45) Date of Patent: Oct. 22, 2013

(54) PYRIMIDINE DERIVATIVE HAVING CELL PROTECTING EFFECT AND USES THEREOF

(75) Inventors: Takeshi Nagata, Tokyo (JP); Toshiaki Suzuki, Tokyo (JP); Akira Yoshimura, Tokyo (JP); Naoto Tadano, Tokyo (JP); Toshiyuki Matsuno, Tokyo (JP); Hideki Satoh, Tokyo (JP); Kenichi Saitoh, Tokyo (JP); Soichi Ohta, Tokyo (JP)

(73) Assignee: Zenyaku Kogyo Kabushikikaisha, Tokyo (JP)

( * ) Notice: Subject to any disclaimer, the term of this patent is extended or adjusted under 35 U.S.C. 154(b) by 173 days.

(21) Appl. No.: 12/935,391

(22) PCT Filed: Mar. 31, 2009

(86) PCT No.: PCT/JP2009/056723
§ 371 (c)(1),
(2), (4) Date: Dec. 9, 2010

(87) PCT Pub. No.: WO2009/123221
PCT Pub. Date: Oct. 8, 2009

(65) Prior Publication Data
US 2011/0152519 A1 Jun. 23, 2011

(30) Foreign Application Priority Data

Mar. 31, 2008 (JP) .................................. 2008-094365

(51) Int. Cl.
*C07D 239/26* (2006.01)
*C07D 401/04* (2006.01)
*C07D 401/14* (2006.01)
*C07D 403/04* (2006.01)
*C07D 403/14* (2006.01)
*A61K 31/4545* (2006.01)
*A61K 31/496* (2006.01)
*A61K 31/506* (2006.01)
*A61P 25/00* (2006.01)

(52) U.S. Cl.
USPC ........... 544/242; 544/322; 544/323; 544/326; 544/330; 514/256; 514/269; 514/175

(58) Field of Classification Search
USPC .......... 544/242, 322, 323, 326, 330; 514/256, 514/275, 269
See application file for complete search history.

(56) References Cited

U.S. PATENT DOCUMENTS 3,975,384 A 8/1976 Narr et al.
6,440,965 B1 8/2002 Kelley et al.

FOREIGN PATENT DOCUMENTS

| EP | 0 372 934 A2 | 6/1990 |
| JP | 50-49288 | 5/1975 |
| JP | 2001-519416 | 10/2001 |
| WO | WO 02/098864 A1 | 12/2002 |

OTHER PUBLICATIONS

Wolff Manfred E. "Burger's Medicinal Chemistry, 5ed, Part 1" John Wiley & Sons, 1995, pp. 975-977.*
Banker, G.S. et al, "Modern Pharmaceutices, 3ed.", Marcel Dekker, New York. 1996, pp. 451 and 596.*
West, Anthony R., Solid State Chemistry and its Applications, Wiley, New York, 1988, pp. 358 & 365.*
Vippagunta et al., Advanced Drug Delivery Reviews 48: 3-26, 2001.*
Freshney et al.,Culture of Animal Cells, A Manual of Basic Technique, Alan R. Liss, Inc., 1983, New York, p. 4.*
Dermer et al., Bio/Technology, 1994, 12:320.*
Extended Search Report issued Mar. 30, 2011 in European Patent Application No. 09726592.0-2101 / 2284160.
International Search Report issued May 12, 2009, in Patent Application No. PCT/JP2009/056723.
Tamara Hirsch, et al., "The apoptosis-necrosis paradox. Apoptogenic proteases activated after mitochondrial permeability transition determine the mode of cell death", Oncogene, vol. 15, 1997, pp. 1573-1581.
Guido Kroemer, et al., "The Mitochondrial Death/Life Regulator in Apoptosis and Necrosis", Annu. Rev. Physiol., vol. 60, 1998, pp. 619-642.
Lee J. Martin, "Neuronal cell death in nervous system development, disease, and injury (Review)", International Journal of Molecular Medicine, vol. 7, 2001, pp. 455-478.
Anne-Claire Lukaszevicz, et al., "High Sensitivity of Protoplasmic Cortical Astroglia to Focal Ischemia", Journal of Cerebral Blood Flow & Metabolism, vol. 22, No. 3, 2002, pp. 289-298.

(Continued)

*Primary Examiner* — Venkataraman Balasubramanian
(74) *Attorney, Agent, or Firm* — Oblon, Spivak, McClelland, Maier & Neustadt, L.L.P.

(57) ABSTRACT

[Problem] To provide a prophylactic/therapeutic agent against, for example, nerve diseases and the like such as ischemic brain disease and neurodegenerative disease, or a prophylactic/therapeutic agent against diseases against which antioxidant action is effective, as a cell protecting agent, in particular as an inhibitor of brain cell damage or brain cell death.
[Means of Solving the Problem]
A compound represented by Formula (1), or a pharmaceutically acceptable salt, solvate, hydrate, or prodrug thereof:

[Chemical 253]

(1)

6 Claims, 6 Drawing Sheets

(56) References Cited

OTHER PUBLICATIONS

Julio H. Garcia, et al., "Progression from Ischemic Injury to Infarct Following Middle Cerebral Artery Occlusion in the Rat", American Journal of Pathology, vol. 142, No. 2, Feb. 1993, pp. 623-635.

Lee. J. Martin, PhD, et al., Hypoxia-Ischemia Causes Abnormalities in Glutamate Transporters and Death of Astroglia and Neurons in Newborn Striatum, Annals of Neurology, vol. 42, No. 3, Sep. 1997, pp. 335-348.

Dong Liu, et al., "Astrocytic demise precedes delayed neuronal death in focal ischemic rat brain", Molecular Brain Research, vol. 68, 1999, pp. 29-41.

Nicholas J. Maragakis, et al., "Mechanisms of Disease: astrocytes in neurodegenerative disease", Nature Clinical Practice Neurology, vol. 2, No. 12, Dec. 2006, pp. 679-689.

David R. Cotter, et al., "Glial cell abnormalities in major psychiatric disorders: The evidence and implications", Brain Research Bulletin, vol. 55, No. 5, 2001, pp. 585-595.

J. M. Wardlaw, et al., "Systematic review of evidence on thrombolytic therapy for acute ischaemic stroke", The Lancet, vol. 350, Aug. 30, 1997, pp. 607-614.

Eugene S. Flamm, et al., "Free Radicals in Cerebral Ischemia", Stroke: Journal of the American Heart Association, vol. 9, No. 5, Sep.-Oct. 1978, pp. 445-447.

Dennis W. Choi, "Glutamate Neurotoxicity and Diseases of the Nervous System", Neuron, vol. 1, Oct. 1988, pp. 623-634.

Tibor Kristián, et al., "Calcium in Ischemic Cell Death", Stroke: Journal of the American Heart Association, vol. 29, 1998, pp. 705-718.

Fabio Blandini, et al., "Glutamate and Parkinson's Disease", Molecular Neurobiology, vol. 12, 1996, pp. 73-94.

Nuri B. Farber, et al., "The glutamate synapse in neuropsychiatric disorders. Focus on schizophrenia and Alzheimer's disease", Progress in Brain Research, vol. 116, 1998, pp. 421-437.

K. Kieburtz, "Antiglutamate therapies in Huntington's disease", J. Neural. Transm. [Suppl], vol. 55, 1999, pp. 97-102.

John A. Kemp, et al., "NMDA receptor pathways as drug targets", Nature Neuroscience Supplement, vol. 5, Nov. 2002, pp. 1039-1042.

L. Van Den Bosch, et al., "The role of excitotoxicity in the pathogenesis of amyotrophic lateral sclerosis", Biochimica Et Biophysica Acta, vol. 1762, 2006, pp. 1068-1082.

Stephen M. Berge, et al., "Pharmaceutical Salts", Journal of Pharmaceutical Sciences, vol. 66, No. 1, Jan. 1977, pp. 1-19.

S. G. Sydserff, et al., "Effect of NXY-059 on infarct vol. after transient or permanent middle cerebral artery occlusion in the rat; studies on dose, plasma concentration and therapeutic time window", British Journal of Pharmacology, vol. 135, No. 1, 2002, pp. 103-112.

John E. Cabaj, et al., "Bromine-Mediated Addition of Nucleophiles to the Electron-Rich Pyrimidine Subunit of Tirilazad", The Journal of Organic Chemistry, vol. 59, No. 17, 1994, pp. 5090-5092.

W. C. J. Ross, "Some Derivatives of 4-Styrylpyrimidine", Journal of the Chemical Society, 1948, pp. 1128-1135.

* cited by examiner

[Figure 3]
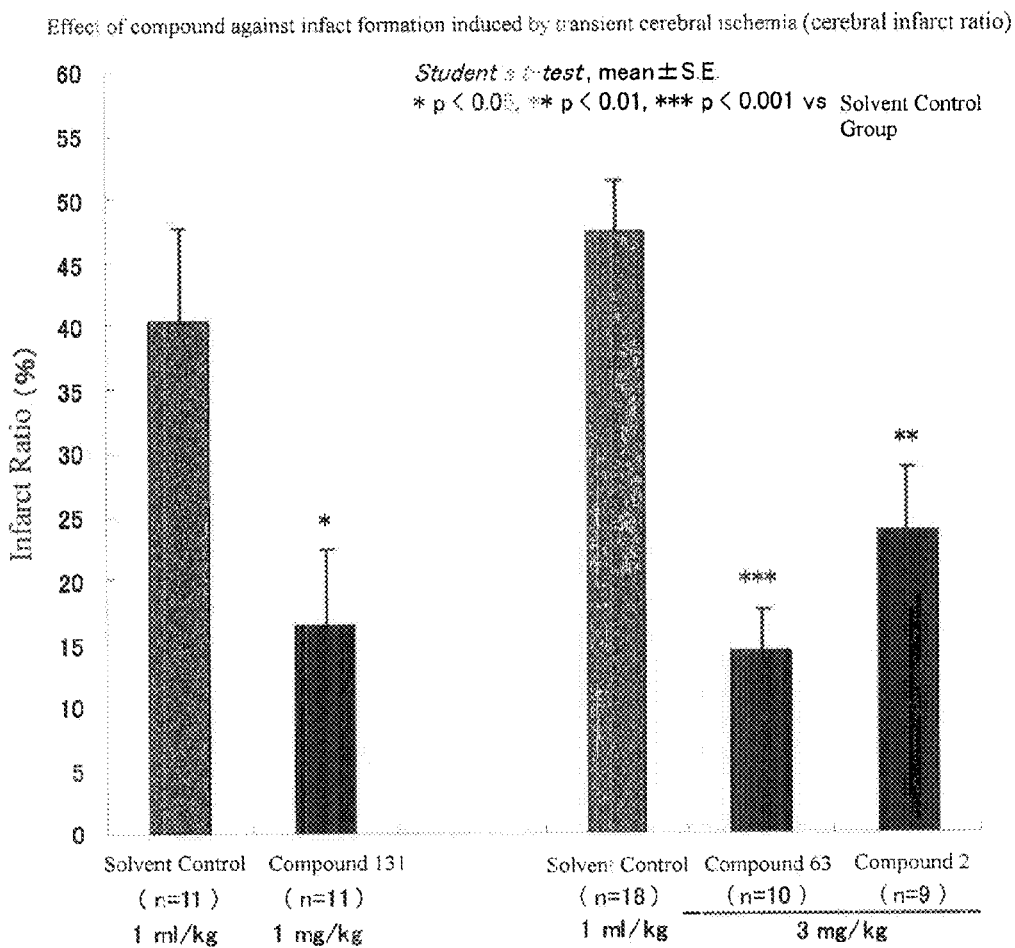

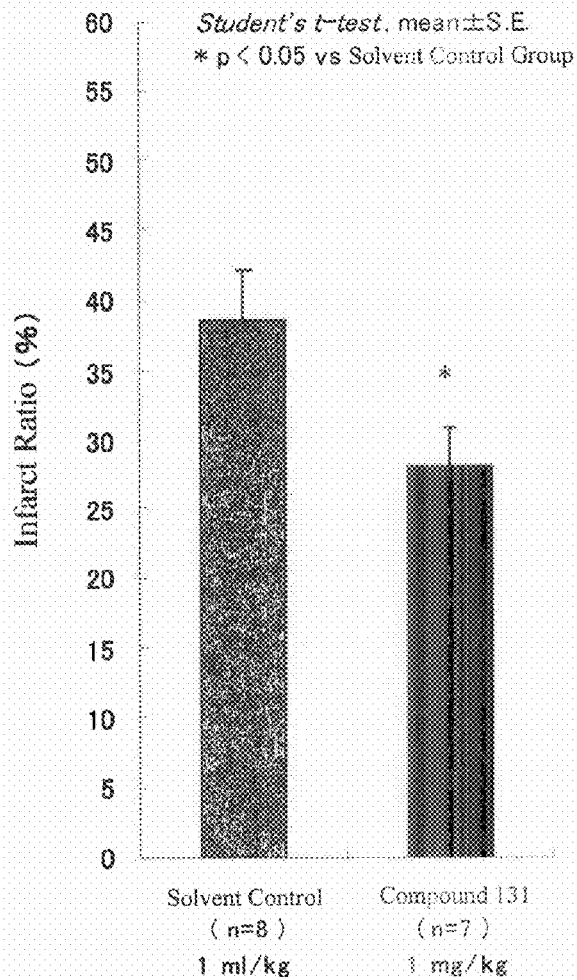

[Figure 5]
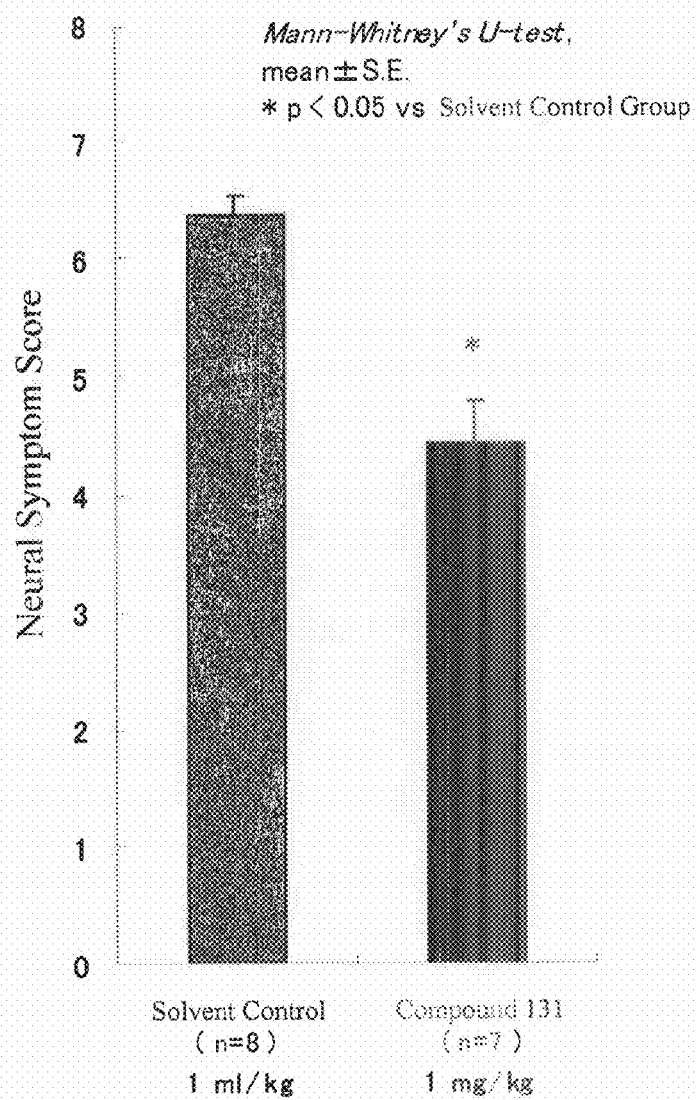

[Figure 6]
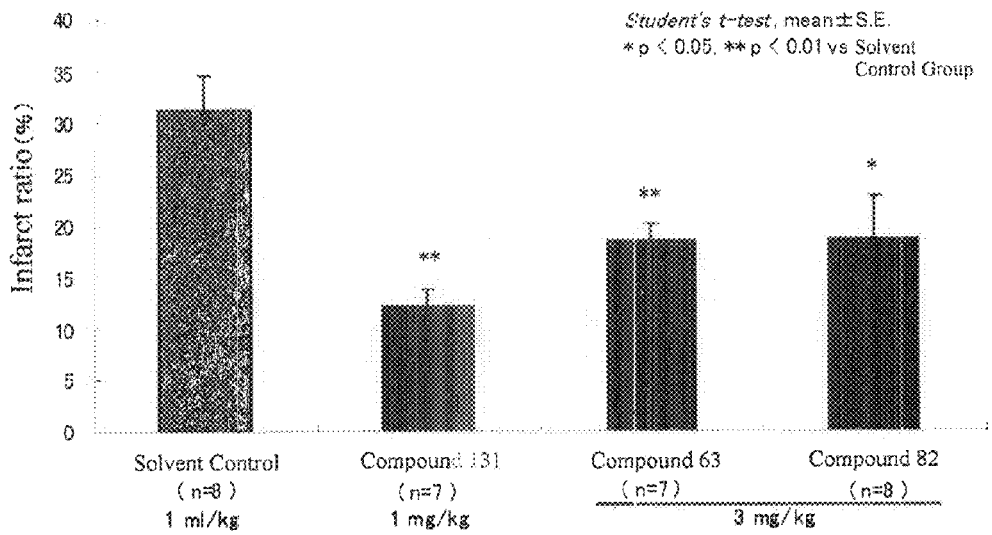
Effect of compound against infarct formation induced by permanent cerebral artery occlusion (infarct ratio)
[Figure 7]
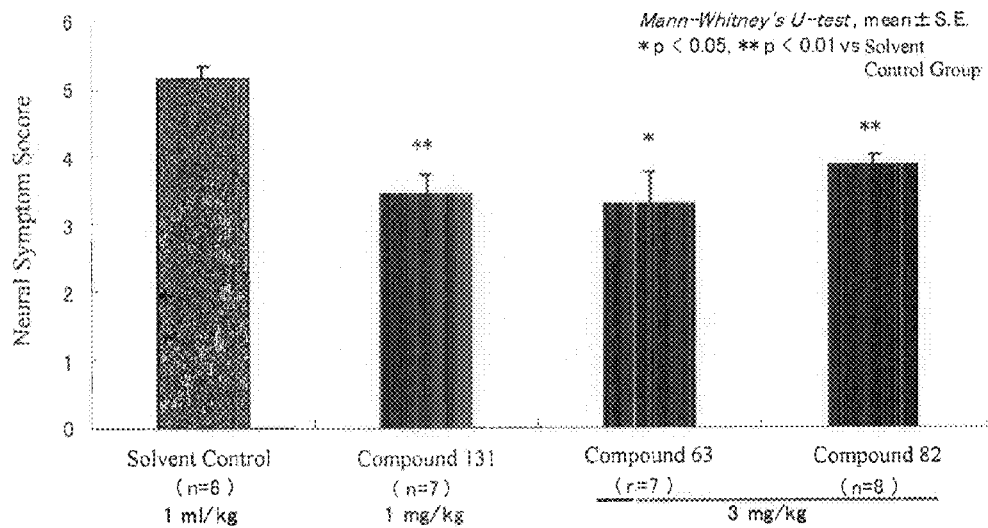
Effect of compound against infarct formation induced by permanent cerebral artery occlusion (neural symptoms)

PYRIMIDINE DERIVATIVE HAVING CELL PROTECTING EFFECT AND USES THEREOF

This application is a National Stage of PCT/JP09/056,723 filed Mar. 31, 2009 and claims the benefit of JP 2008-094365 filed Mar. 31, 2008.

TECHNICAL FIELD

The present invention concerns a novel pyrimidine derivative that is useful as an excellent cell protecting agent, specifically a therapeutic/prophylactic agent against nerve diseases such as ischemic brain diseases or neurodegenerative diseases, or against various diseases for which antioxidant action is effective.

CONVENTIONAL ART

Cell death can be broadly separated into two types: necrotic cell death due to physical causes, and programmed cell death (apoptosis). However, it is thought that there are no essential differences between the two with regard to the causes of their occurrence and their mechanism in various diseases (Non-Patent Documents 1-3), and they are both deeply involved in various diseases. Especially in the diseases of the central nervous system, the suppression of brain cell death, regardless of the type of cell death, has a great influence on the disease state, since function of nerve tissue is hard to recover once it has been lost.

Cerebral tissue is composed of a great number of glial cells including astrocytes, nerve cells, and cerebrovascular cells. Generally, astrocytes have a higher resistance to stress than nerve cells, and they have long been thought to play a role in the differentiation and functional maintenance of nerve cells. However, it has recently been revealed that some astrocytes are more fragile against ischemia than nerve cells (Non-Patent Document 4), and that the cell death of astrocytes occurs prior to nerve cell death in the ischemic core (Non-Patent Documents 5-7). Additionally, many abnormalities of glial cells, including astrocytes, have been reported in various neurodegenerative diseases and neuropsychiatric diseases such as Alzheimer's disease, Parkinson's disease, and amyotrophic lateral sclerosis (Non-Patent Document 8, 9). From these facts, the maintenance of normal functioning of not just nerve cells, but all cerebral cells, including glial cells, is considered to be much more important for the prevention and treatment of nerve diseases such as ischemic brain diseases, neurodegenerative diseases, and psychiatric diseases.

Cerebral infarction is a disease where cerebral blood flow-deficient tissue falls into necrosis or apoptosis. The blood flow-deficiency arises from the obstruction or narrowing of cerebral blood vessels by cerebral arterial sclerosis or by a blood clot which is formed in a vessel outside the brain and carried to the brain. Recently, so-called lifestyle-related diseases such as high blood pressure, heart disease, hyperlipidemia, and diabetes have been increasing in Japan, and the risk of cerebral infarction has been correspondingly growing. Further, in the case of cerebral infarction, since severe after-effects such as cognitive, linguistic, and motor function impairment often becomes a serious problem, development of innovative new treatment that mitigates the after-effects by suppressing the spreading of brain damage is being sought.

However, at present, a truly effective therapeutic means has yet to be discovered. For example, tissue plasminogen activator (tPA) is used as a thrombolytic drug for dissolving the blood clots responsible for a cerebral infarction and restarting blood flow. However, although the use of tPA within 2 to 3 hours of the onset of infarction can significantly suppress brain damage, it is known that its use past 3 hours after the onset, on the contrary, heightens the risk of worsening the brain damage due to cerebral hemorrhage or edema (Non-Patent Document 10). Because of this, the use of tPA against cerebral infarction is limited to within 3 hours of the onset, of the hyperacute stage of cerebral infarction, and the tPA use in the Japanese clinical setting is, therefore, limited to a very small portion of cerebral infarction patients. Accordingly, the creation of a new drug that can expand the therapeutic time window of hyperacute-stage drugs such as tPA is being sought. Additionally, because it is known that reactive oxygen species (free radicals) such as hydrogen peroxide that are generated during cerebral ischemia and recirculation are essentially involved in the exacerbation of brain damage (Non-Patent Document 11), drugs that suppress brain cell death due to free radicals, namely, antioxidant agents, are considered to be effective for the treatment of cerebral infarction. In Japan, the one cerebral protecting agent based upon an antioxidant effect that is commercially available is the free radical scavenger edaravone, but severe side effects such as acute renal failure and hepatic dysfunction have been reported for this medicinal agent. Further, therapeutic cerebral hypothermia is a non-medicinal therapeutic means against cerebral infarction, but this treatment is too hard to be conveniently carried out in many facilities because of difficulty in maintenance controls and infection risk due to the lowering of immunity.

Additionally, it has been known that glutamic acid is excessively released to the extracellular space due to abnormal depolarization in nerve cells during cerebral ischemia, then an abnormal $Ca^{2+}$ influx mediated by glutamate receptors occurs in neighboring nerve cells, and eventually the abnormally elevated $Ca^{2+}$ level leads to nerve cell death (Non-Patent Documents 12, 13). Further, in a large number of diseases of central nervous tissue other than cerebral infarction, abnormalities in glutamatergic neurons, and in synthesis, release, and uptake of glutamic acid have been reported, and the connection between the glutamate system and the disease state has been pointed out (Non-Patent Documents 14-18). Therefore, the inhibition of nerve cell death due to glutamic acid is considered effective for the prevention and treatment of many diseases in the central nervous system including ischemic brain disease. In this context, the development of glutamic acid receptor antagonists and $Ca^{2+}$ channel inhibitors have been attempted, but no such drugs have been created at the present time, so the creation of a new therapeutic agent is being sought.

As described above, extant therapeutic means against nerve diseases such as ischemic brain disease, neurodegenerative disease, or psychiatric disease are not sufficiently effective, so accordingly, the creation of a more effective treatment means is eagerly needed.

[Non-Patent Document 1] Hirsch T et al: The apoptosis-necrosis paradox. Oncogene 15: 1573-1581, 1997

[Non-Patent Document 2] Kroemer G et al: The mitochondrial death/life regulator in apoptosis and necrosis. Annu Rev Physiol 60: 619-642, 1998

[Non-Patent Document 3] Martin L: Neuronal cell death in nervous system development, disease, and injury. Int J Mol Med 7: 455-478, 2001

[Non-Patent Document 4] Lukaszevicz A et al: High sensitivity of protoplasmic cortical astroglia to focal ischemia. J Cereb Blood Flow Metab 22: 289-298, 2002

[Non-Patent Document 5] Garcia J et al: Progression from ischemic injury to infarct following middle cerebral artery occlusion in the rat. Am J Pathol 142: 623-635, 1993

[Non-Patent Document 6] Martin L et al: Hypoxia-ischemia cause abnormalities in glutamate transporters and death of astroglia and neurons in newborn striatum. Ann Neurol 42: 335-348, 1997

[Non-Patent Document 7] Liu D et al: Astrocytic demise precedes delayed neuronal death in focal ischemic rat brain. Mol Brain Res 68: 29-41, 1999

[Non-Patent Document 8] Maragakis N J and Rothstein J D: Mechanisms of disease: astrocytes in neurodegenerative disease. Nat Clin Prac Neurol 2: 679-689, 2006

[Non-Patent Document 9] Cotter D R et al: Glial cell abnormalities in major psychiatric disorders: the evidence and implications. Brain Res Bull 55: 585-595, 2001

[Non-Patent Document 10] Wardlaw J M et al: Systematic review of evidence on thrombolytic therapy for acute ischaemic stroke. Lancet 350: 607-614, 1997

[Non-Patent Document 11] Flamm E et al: Free radicals in cerebral ischemia. Stroke 9: 445-447, 1978

[Non-Patent Document 12] Choi D: Glutamate neurotoxicity and diseases of the nervous system. Neuron 1: 623-634, 1988

[Non-Patent Document 13] Kristian T and Siesjo B: Calcium in ischemic cell death. Stroke 29: 705-718, 1998

[Non-Patent Document 14] Blandini F et al: Glutamate and Parkinson's disease. Mol Neurobiol 12: 73-94, 1996

[Non-Patent Document 15] Farber N B et al: The glutamate synapse in neuropsychiatric disorders. Focus on schizophrenia and Alzheimer's disease. Prog Brain Res 116: 421-437, 1998

[Non-Patent Document 16] Kieburtz K: Antiglutamate therapies in Huntington's disease. J Neural Transm Suppl 55: 97-102, 1999

[Non-Patent Document 17] Kemp J A and McKernan R M: NMDA receptor pathways as drug targets. Nat Neurosci 5 Suppl: 1039-1042, 2002

[Non-Patent Document 18] Van Den Bosch L et al: The role of excitotoxicity in the pathogenesis of amyotrophic lateral sclerosis. Biochem Biophys Acta 1762: 1068-1082, 2006

DISCLOSURE OF THE INVENTION

Problem to be Solved by the Invention

Agents for treating nerve diseases such as ischemic brain diseases, neurodegenerative diseases, or psychiatric diseases are already known, but they all require further improvement with regard to side effects and effectiveness, so the creation of a more effective novel agent is being sought.

Whereby, the problem to be solved by the present invention is to provide an effective cell protecting agent, or a prophylactic/therapeutic agent against various diseases such as nerve diseases.

Means for Solving the Problem

In order to solve said problem, the inventors of the present invention carried out various investigations concerning an agent that is effective for the inhibition of cell damage or cell death. As a result, they found that a novel pyrimidine derivative having a cell protecting action described below, or a pharmaceutically acceptable salt, solvate, hydrate, or prodrug thereof, has an antioxidant action, and additionally has an inhibiting effect against cell damage or cell death, and thereby completed the present invention.

That is, according to the present invention, a pyrimidine derivative, or a pharmaceutically acceptable salt, solvate, hydrate, or prodrug thereof is provided. Said pyrimidine derivative is a compound represented by the following Formula (1a):

[Chemical 1]

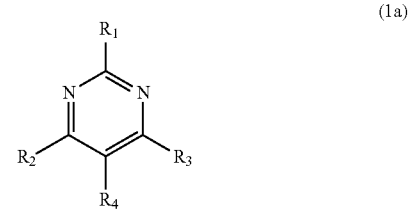

(1a)

In said Formula (1a), $R_1$, $R_2$, and $R_3$ are respectively independently selected from Formula (2a):

[Chemical 2]

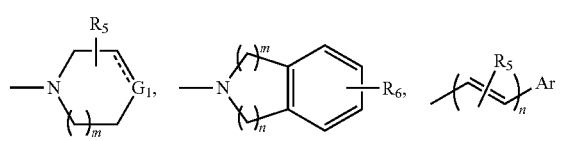

(2a)

or, one of them is an amino group substituted with 1 or 2 of $R_5$, or a phenyl (C1-C6) alkyl group, and the other two are independently selected from said Formula (2a).

Additionally, according to the present invention, a compound is further provided wherein any one of $R_1$, $R_2$, and $R_3$ is Formula (5) in said Formula (2a):

[Chemical 3]

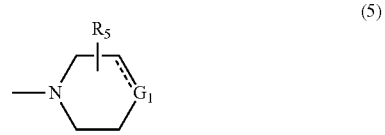

(5)

Additionally, according to the present invention, a compound is further provided wherein $R_2$ and $R_3$ are Formula (5) in said Formula (2a):

[Chemical 4]

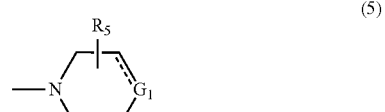

(5)

Additionally, according to the present invention, a compound is further provided wherein $R_1$ is Formula (4) of said Formula (2a):

[Chemical 5]

-continued

(4)

In said Formula (1a), R4 represents a —F, —Cl, —Br, —I, formyl, phenyl, or (C1-C6) alkoxy group. Further, said phenyl group may be substituted with 1 or 2 of $R_6$.

In said Formula (2a), m is 0 or 1. Additionally, n is 1, 2, or 3.

Additionally, in said Formula (2a), $R_5$ represents a —H, carboxyl, (C1-C6) alkyl, (C1-C6) alkoxycarbonyl, (C1-C6) alkoxycarbonylmethyl, amino (C1-C6) alkyl, piperazinyl (C1-C6) alkyl, (C1-C6) alkoxycarbonylpiperazinyl (C1-C6) alkyl, morpholino (C1-C6) alkyl, (C1-C6) alkylpiperizine, (C2-C6) alkenyl, (C2-C6) alkynyl, or phenyl group. Further, the amino group in said amino (C1-C6) alkyl group may be substituted with 1 or 2 (C1-C6) alkyl groups, or 1 (C1-C6) alkoxycarbonyl group. Additionally, said amino (C1-C6) alkyl group may contain a carbonyl group in its carbon chain. Additionally, said phenyl group may be substituted with 1 or 2 of $R_6$.

Additionally, in said Formula (2a), $R_6$ represents a —H, —F, —Cl, —Br, —I, (C1-C6) alkyl, (C1-C6) alkylamino, di (C1-C6) alkylamino, (C1-C6) alkoxy, (C1-C6) alkylthio, (C1-C6) acyl, pyrrolidinyl, piperidino, piperazinyl, (C1-C6) alkoxycarbonyl, (C1-C6) alkoxycarbonylamino, phenyl, benzyl, phenyl (C1-C6) alkyloxy, nitro, amino or hydroxyl group.

Additionally, in said Formula (2a), Ar represents a phenyl, benzyl, pyridyl, pyrimidyl, thienyl, pyrrole, quinolinyl, thiazolyl, benzothiazolyl, thiadiazolyl, imidazolyl, tetrazolyl or pyridazinyl group; or, a condensed ring group wherein 2 or more phenyl, benzyl, pyridyl, pyrimidyl, thienyl, pyrrole, quinolinyl, thiazolyl, benzothiazolyl, thiadiazolyl, imidazolyl, tetrazolyl or pyridazinyl groups are condensed. Further, said phenyl, benzyl, pyridyl, pyrimidyl, thienyl, pyrrole, quinolinyl, thiazolyl, benzothiazolyl, thiadiazolyl, imidazolyl, tetrazolyl or pyridazinyl group; or condensed ring group wherein 2 or more phenyl, benzyl, pyridyl, pyrimidyl, thienyl, pyrrole, quinolinyl, thiazolyl, benzothiazolyl, thiadiazolyl, imidazolyl, tetrazolyl or pyridazinyl groups are condensed; may be substituted with 1 or 2 of $R_6$.

Additionally, in said Formula (2a), $G_1$ is an oxygen atom or a sulfur atom, or it is a carbon atom or nitrogen atom substituted with $R_7$. Further, in cases where said $G_1$ is a carbon atom substituted with $R_7$, this carbon atom may form an unsaturated bond with an adjacent carbon atom.

For example, a carbon atom or nitrogen atom substituted with R7 will have the structure represented by Formula (3):

[Chemical 6]

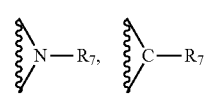
(3)

Additionally, $R_7$ represents a —H, (C1-C6) alkyl, amino (C1-C6) alkyl, (C1-C6) alkylaminocarbonyl, (C1-C6) alkylaminothiocarbonyl, di (C1-C6) alkylaminosulfamoyl, (C1-C6) alkoxycarbonyl, (C1-C6) alkoxycarbonyl (C1-C6) alkyl, carboxy (C1-C6) alkyl, (C1-C6) alkoxycarbonylamino, (C1-C6) alkoxycarbonylamino (C1-C6) alkyl, (C2-C6) alkenyl, (C2-C6) alkynyl, (C3-C6) cycloalkyl, (C1-C6) acyl, nitro, cyano, hydroxyl, amino, phenyl, benzyl, pyridyl, picolyl, pyrimidyl, quinolinyl, thiazolyl, benzothiazolyl, thiadiazolyl, imidazolyl, tetrazolyl or pyridazinyl group. Further, said amino (C1-C6) alkyl group may contain a carbonyl group in its carbon chain. Additionally, said phenyl, benzyl, pyridyl, picolyl, pyrimidyl, quinolinyl, thiazolyl, benzothiazolyl, thiadiazolyl, imidazolyl, tetrazolyl or pyridazinyl group may be substituted with $R_6$.

This is provided that, if in said Formula (1a), any one of $R_1$, $R_2$, or $R_3$ is a phenyl (C1-C6) alkyl group, or is Formula (4):

[Chemical 7]

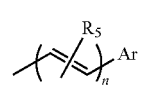
(4)

then $R_4$ is a —F, —Cl, —Br, —I, formyl, nitro, phenyl, (C1-C6) alkyl, (C1-C6) alkoxy, phenyl (C1-C6) alkyl, amino, acetylamino, (C1-C6) alkylamino, di (C1-C6) alkylamino or cyano group. Further, said phenyl group may be substituted with 1 or 2 of $R_6$.

Additionally, according to the present invention, a cell protecting agent comprising said compound, or a pharmaceutically acceptable salt, solvate, hydrate, or prodrug thereof, is provided.

Further, according to the present invention, a cell protecting agent comprising a pyrimidine derivative or a pharmaceutically acceptable salt, solvate, hydrate, or prodrug thereof, is provided. Said pyrimidine derivative is a compound represented by the following Formula (1b):

[Chemical 8]

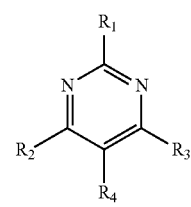
(1b)

In said Formula (1b), $R_1$, $R_2$, and $R_3$ are respectively selected independently from Formula (2b):

[Chemical 9]

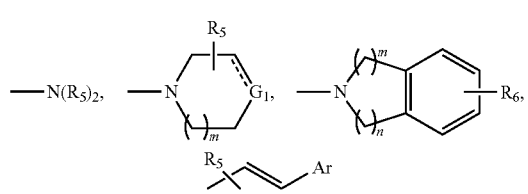
(2b)

In said Formula (1b), $R_4$ represents a —H, benzyl, (C1-C6) alkyl, amino, (C1-C6) alkylamino, di (C1-C6) alkylamino, benzyl or cyano group.

In said Formula (2b), m is 0 or 1. Additionally, n is 1, 2, or 3.

Additionally, in said Formula (2b), $R_5$ represents a —H, (C1-C6) alkyl, (C2-C6) alkenyl, (C2-C6) alkynyl or phenyl group. Further, said phenyl group may be substituted with 1 or 2 of $R_6$.

Additionally, in said Formula (2b), $R_6$ represents a —H, —F, —Cl, —Br, —I, (C1-C6) alkyl, (C1-C6) alkylamino, (C1-C6) alkoxy, (C1-C6) alkylthio, (C1-C6) acyl, pyrrolidinyl, piperidino, piperazinyl, (C1-C6) alkoxycarbonyl, phenyl, benzyl, phenyl (C1-C6) alkyloxy, nitro, amino or hydroxyl group.

Additionally, in said Formula (2b), Ar represents a phenyl, benzyl, pyridyl, pyrimidyl, thienyl, pyrrole, quinolinyl, thiazolyl, benzothiazolyl, thiadiazolyl, imidazolyl, tetrazolyl or pyridazinyl group; or, a condensed ring group wherein 2 or more phenyl, benzyl, pyridyl, pyrimidyl, thienyl, pyrrole, quinolinyl, thiazolyl, benzothiazolyl, thiadiazolyl, imidazolyl, tetrazolyl or pyridazinyl groups are condensed. Further, said phenyl, benzyl, pyridyl, pyrimidyl, thienyl, pyrrole, quinolinyl, thiazolyl, benzothiazolyl, thiadiazolyl, imidazolyl, tetrazolyl or pyridazinyl group; or condensed ring group wherein 2 or more phenyl, benzyl, pyridyl, pyrimidyl, thienyl, pyrrole, quinolinyl, thiazolyl, benzothiazolyl, thiadiazolyl, imidazolyl, tetrazolyl or pyridazinyl groups are condensed; may be substituted with 1 or 2 of $R_6$.

Additionally, in said Formula (2b), $G_1$ is an oxygen atom or a sulfur atom, or it is a carbon atom or nitrogen atom substituted with $R_7$. Further, in cases where said $G_1$ is a carbon atom substituted with $R_7$, this carbon atom may form an unsaturated bond with an adjacent carbon atom.

For example, a carbon atom or nitrogen atom substituted with $R_7$ will have a structure represented by Formula (3):

[Chemical 10]

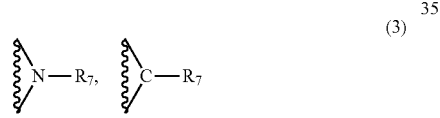

(3)

Additionally, $R_7$ represents a —H, (C1-C6) alkyl, (C2-C6) alkenyl, (C2-C6) alkynyl, (C3-C6) cycloalkyl, (C1-C6) acyl, nitro, cyano or hydroxyl group; or, a phenyl, benzyl, pyridyl, pyrimidyl, quinolinyl, thiazolyl, benzothiazolyl, thiadiazolyl, imidazolyl, tetrazolyl or pyridazinyl group. Further, said phenyl, benzyl, pyridyl, pyrimidyl, quinolinyl, thiazolyl, benzothiazolyl, thiadiazolyl, imidazolyl, tetrazolyl or pyridazinyl group may be substituted with $R_6$.

Additionally, according to the present invention, a brain cell protecting agent comprising any one of said compounds (pyrimidine derivatives), or a pharmaceutically acceptable salt, solvate, hydrate, or prodrug thereof, is also provided.

Further, according to the present invention, a prophylactic agent or a therapeutic agent for ischemic brain disease comprising any one of said compounds (pyrimidine derivatives), or a pharmaceutically acceptable salt, solvate, hydrate, or prodrug thereof, is also provided.

Further, according to the present invention, a prophylactic agent or therapeutic agent for nerve disease, comprising any one of said compounds (pyrimidine derivatives), or a pharmaceutically acceptable salt, solvate, hydrate, or prodrug thereof, is also provided.

Effects of the Invention

The present invention brings about an inhibiting effect against cell damage and the like, because it comprises, as an effective ingredient, a pyrimidine derivative having a particular chemical structure, or a pharmaceutically acceptable salt, solvate, hydrate, or prodrug thereof.

BRIEF EXPLANATION OF THE DRAWINGS

FIG. 3 Graph for explaining the effect of the compound (cerebral infarct ratio) against the formation of infarct induced by transient cerebral ischemia (middle cerebral artery 90 minute occlusion—reperfusion model).

FIG. 4 Graph for explaining the effect of the compound (cerebral infarct ratio) against the formation of infarct induced by transient cerebral ischemia (middle cerebral artery 180 minute occlusion—reperfusion model).

FIG. 5 Graph for explaining the effect of the compound (neural symptoms) against the formation of infarct induced by transient cerebral ischemia (middle cerebral artery 180 minute occlusion—reperfusion model).

FIG. 6 Graph for explaining the effect of the compound (cerebral infarct ratio) against the formation of infarct induced by permanent cerebral vessel occlusion.

FIG. 7 Graph for explaining the effect of the compound (neural symptoms) against the formation of infarct induced by permanent cerebral vessel occlusion.

MODES OF EMBODIMENT OF THE INVENTION

Figure 1:
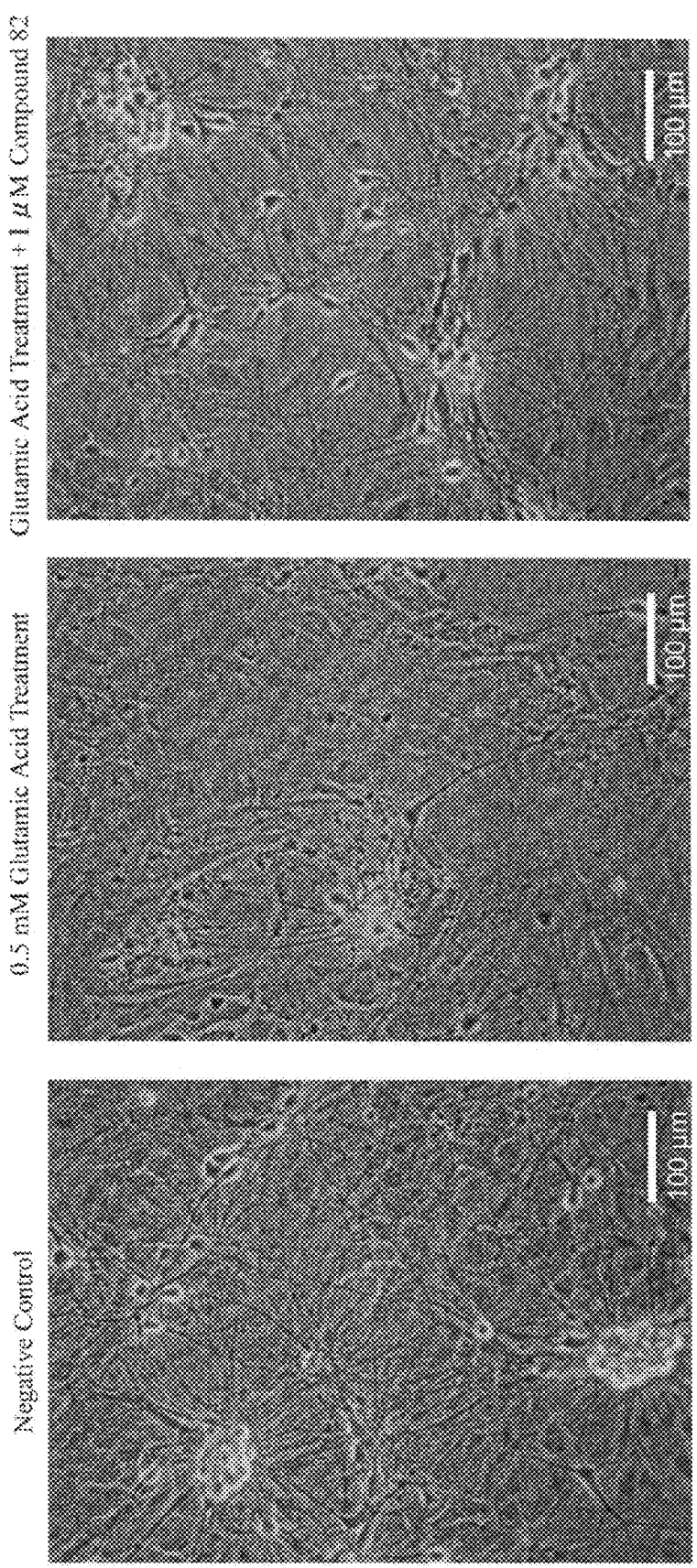
FIG. 1 Microphotograph for explaining the neuronal damage induced by glutamic acid treatment and the protecting action of the compound.

Herebelow, the modes of embodiment of the present invention shall be explained in detail.
[Explanation of Terminology]

In the present specification, the following terms have the meanings indicated below.

The term "halogen" or "halo-" refers to fluorine, chlorine, bromine, or iodine.

The term "hydroxyl" refers to an —OH group.

The term "cyano-" refers to a —CN group.

The term "acetyl" refers to a $CH_3$—(C=O)— group.

The term "amino" refers to a —$NH_2$ group, or a bivalent or trivalent group wherein hydrogen is substituted with another atom.

The term "nitro" refers to a —$NO_2$ group.

The term "formyl" refers to a —(C=O)H group.

The term "carbonyl" refers to a —(C=O)— group that is a bivalent group.

The term "thiocarbonyl" refers to a —(C=S)— group that is a bivalent group.

The terms "alkyl", "alkenyl", and "cycloalkyl" refer not only to univalent groups, but in some cases may refer to bivalent groups or groups with higher valence. For example, when referring to bivalent groups, these terms are respectively used with the same meaning as "alkylene", "alkelene", and "cycloalkylene".

The prefixes on the terms "(Cx-Cy) alkyl", "(Cx-Cy) alkenyl", or "(Cx-Cy) cycloalkyl" refer to groups respectively having, in number, from x to y carbon atoms.

Additionally, regarding arbitrary polyvalent groups, in cases of substitution at sites where single rings or multiple rings can be formed, as long as there are no particular restrictions, those polyvalent groups may form ring structures.

The terms "(C1-C6) alkyl" or "(C1-C6) alkylene" refer to branched or linear saturated hydrocarbon groups having from 1 to 6 carbon atoms, and, for example, include (C1-C3) alkyl, (C1-C4) alkyl, (C1-C6) alkyl, (C2-C6) alkyl, and (C3-C6) alkyl. Examples of representative (C1-C6) alkyl groups are methyl, ethyl, propyl (e.g., propan-1-yl, propan-2-yl (or isopropyl)), butyl (e.g., 2-methylpropan-2-yl (or tert-butyl), butan-1-yl, butan-2-yl), pentyl (e.g., pentan-1-yl, pentan-2-yl, pentan-3-yl), 2-methylbutan-1-yl, 3-methylbutan-1-yl, and hexyl (e.g., hexan-1-yl).

The term "(C2-C6) alkenyl" refers to a linear or branched nonaromatic hydrocarbon group having from 2 to 6 carbon atoms and at least one carbon-carbon double bond, and, for example, include (C2-C3) alkenyl, (C2-C4) alkenyl, (C2-C6) alkenyl, (C3-C6) alkenyl, and (C4-C6) alkenyl. Examples of representative (C2-C6) alkenyl groups are vinyl, 1-propenyl, 2-propenyl, iso-propenyl, 1,3-butadienyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 2-hexenyl, 3-hexenyl, 2,4-hexadienyl, and 5-hexenyl.

The term "(C2-C6) alkynyl" refers to a linear or branched nonaromatic hydrocarbon group having from 2 to 6 carbon atoms and at least one carbon-carbon triple bond, and, for example, includes (C2-C3) alkynyl, (C2-C4) alkynyl, (C2-C6) alkynyl, (C3-C6) alkynyl, and (C4-C6) alkynyl. Examples of representative (C2-C6) alkynyl groups include 2-propynyl, 2-butynyl, and 1,3-hexadien-5-ynyl.

The term "(C3-C6) cycloalkyl" used here refers to a saturated monocyclic carbon ring having from 3 to 6 carbon atoms. Examples of representative (C3-C6) cycloalkyls include cyclopropyl, cyclobutyl, cyclopentyl, and cyclohexyl.

The terms "alkoxy" and "alkyloxy" refer to —O—R— groups where the R is one of said alkyls. Similarly, in cases where the term "Roxy" is used, this refers to —O—R groups that are univalent or bivalent.

The term "(C1-C6) alkoxy" refers to a (C1-C6) alkyl-O— group, and, for example, includes (C1-C3) alkoxy, (C1-C4) alkoxy, (C1-C6) alkoxy, (C2-C6) alkoxy, and (C3-C6) alkoxy. Examples of representative (C1-C6) alkoxys are methoxy, ethoxy, propoxy (e.g., 1-propoxy, 2-propoxy), butoxy (e.g., 1-butoxy, 2-butoxy, 2-methyl-2-propoxy), pentyloxy (e.g., 1-pentyloxy, 2-pentyloxy), and hexyloxy (e.g., 1-hexyloxy, 3-hexyloxy).

Similarly, the term "alkylthio" refers to —S—R groups where the R is one of said alkyls. Similarly, in cases where the term "Rthio" is used, this refers to —S—R groups that are univalent or bivalent.

The term "may be substituted" means that the group being referred to is either unsubstituted, or it is substituted with one or more particular substituent groups. For example, the number of substitutions may be 1, 2, 3, 4, or 5. In cases where the group being referred to is substituted with a plurality of substituent groups, the substituent groups may be the same, or they may be different.

The term "a carbonyl group may be contained in the carbon chain" means that the group being referred to is either unsubstituted, or it contains a carbonyl in the carbon chain comprising said group. For example, the number of contained carbonyls may be 1 or 2. For example, "alkylene groups that may contain a carbonyl group" include alkylene, alkylenecarbonyl, carbonylalkylene, alkylenecarbonylalkylene, and carbonylalkylenecarbonyl groups.

Some of the terms described above may be used several times within a structural formula, and the respective terms may have mutually independent ranges.

Some of the terms described above may be used in combination, and in such cases, the group that is mentioned first becomes a substituent group on the groups that are mentioned later, and the substitution point (adduction point) is on the last portion that is mentioned of the entire group.

[History of the Invention]

Conventionally, it could not be said that extant therapeutic means against nerve diseases such as ischemic brain disease, neurodegenerative disease, and psychiatric disease were sufficiently effective, and therefore, the creation of a more effective treatment means was being sought.

Whereby, the inventors of the present invention carried out various investigations concerning an agent that is effective for the inhibition of cell damage or cell death. As a result, they found that the pyrimidine derivatives and the like having a cell protecting action described below have an excellent antioxidant action, and additionally have an inhibiting effect against cell damage or cell death. That is, the inventors of the present invention found that the pyrimidine derivatives and the like described below may be used as an excellent cell protecting agent, particularly as an inhibitor of brain cell damage or brain cell death, and more specifically as a prophylactic and therapeutic agent against nerve diseases and the like such as ischemic brain disease and neurodegenerative disease, or a prophylactic and therapeutic agent against diseases for which an antioxidant action is effective.

MODES OF EMBODIMENT

Herebelow, the modes of embodiment of the present invention shall be explained.

The pyrimidine derivatives according to the present mode of embodiment, as shown below in Embodiments 1 and 2, is a compound represented by General Formula (1a) or (1b).

Embodiment 1

One mode of embodiment of the present invention is a compound represented by Formula (1a), or a pharmaceutically acceptable salt, solvate, hydrate, or prodrug thereof:

[Chemical 11]

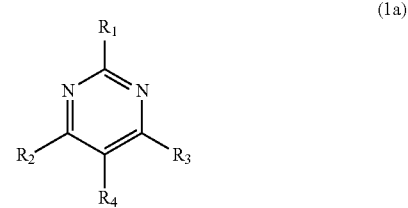

(1a)

wherein $R_1$, $R_2$, and $R_3$ are each selected independently from Formula (2a):

[Chemical 12]

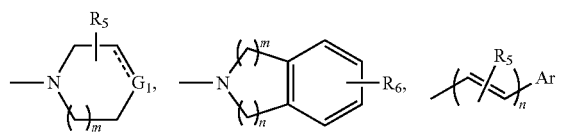

(2a)

wherein m is either 0 or 1; n is 1, 2, or 3;

$R_5$ represents —H, carboxyl, (C1-C6) alkyl, (C1-C6) alkoxycarbonyl, (C1-C6) alkoxycarbonylmethyl, amino (C1-C6) alkyl (said amino group may be substituted with 1 or 2 (C1-C6) alkyl groups; or 1 (C1-C6) alkoxycarbonyl group; additionally, a carbonyl group may be contained in the carbon chain), piperazinyl (C1-C6) alkyl, (C1-C6) alkoxycarbonylpiperazinyl (C1-C6) alkyl, morpholino (C1-C6) alkyl, (C1-C6) alkylpiperizine, (C2-C6) alkenyl, (C2-C6) alkynyl, or phenyl group, wherein said phenyl group may further be substituted with 1 or 2 of $R_6$;

$R_6$ represents —H, —F, —Cl, —Br, —I, (C1-C6) alkyl, (C1-C6) alkylamino, di (C1-C6) alkylamino, (C1-C6) alkoxy, (C1-C6) alkylthio, (C1-C6) acyl, pyrrolidinyl, piperidino, piperazinyl, (C1-C6) alkoxycarbonyl, (C1-C6) alkoxycarbonylamino, phenyl, benzyl, phenyl (C1-C6) alkyloxy, nitro, amino or hydroxyl group;

Ar represents a phenyl, benzyl, pyridyl, pyrimidyl, thienyl, pyrrole, quinolinyl, thiazolyl, benzothiazolyl, thiadiazolyl, imidazolyl, tetrazolyl or pyridazinyl group which may be substituted with 1 or 2 of $R_6$; or a condensed ring group wherein 2 or more phenyl, benzyl, pyridyl, pyrimidyl, thienyl, pyrrole, quinolinyl, thiazolyl, benzothiazolyl, thiadiazolyl, imidazolyl, tetrazolyl or pyridazinyl groups, which may be substituted with 1 or 2 of $R_6$, are condensed;

$G_1$ is an oxygen atom, a sulfur atom, or a carbon atom or nitrogen atom substituted with $R_7$; further, in cases where it is a carbon atom substituted with $R_7$, said carbon atom may form an unsaturated bond with an adjacent carbon atom;

$R_7$ represents —H, (C1-C6) alkyl, amino (C1-C6) alkyl (which may contain a carbonyl group in the carbon chain), (C1-C6) alkylaminocarbonyl, (C1-C6) alkylaminothiocarbonyl, di (C1-C6) alkylaminosulfamoyl, (C1-C6) alkoxycarbonyl, (C1-C6) alkoxycarbonyl (C1-C6) alkyl, carboxy (C1-C6) alkyl, (C1-C6) alkoxycarbonylamino, (C1-C6) alkoxycarbonylamino (C1-C6) alkyl, (C2-C6) alkenyl, (C2-C6) alkynyl, (C3-C6) cycloalkyl, (C1-C6) acyl, nitro, cyano, hydroxyl or amino group; or a phenyl, benzyl, pyridyl, picolyl, pyrimidyl, quinolinyl, thiazolyl, benzothiazolyl, thiadiazolyl, imidazolyl, tetrazolyl or pyridazinyl group, which may be substituted with $R_6$;

or, one of them is an amino group substituted with 1 or 2 of $R_5$, or is a phenyl (C1-C6) alkyl group, and the remaining two are independently selected from said Formula (2a), and $R_4$ represents —F, —Cl, —Br, —I, formyl, phenyl, or (C1-C6) alkoxy group, wherein said phenyl group may be substituted with 1 or 2 of $R_6$, provided that if any one of $R_1$, $R_2$, or $R_3$ is a phenyl (C1-C6) alkyl group, or Formula (4):

[Chemical 13]

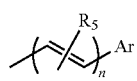

(4)

then $R_4$ is —F, —Cl, —Br, —I, or a formyl, nitro, phenyl, (C1-C6) alkyl, (C1-C6) alkoxy, phenyl (C1-C6) alkyl, amino, acetylamino, (C1-C6) alkylamino, di (C1-C6) alkylamino or cyano group, wherein said phenyl group may be substituted with 1 or 2 of $R_6$.

Additionally, another mode of embodiment of the present invention is a compound described above, or a pharmaceutically acceptable salt, solvate, hydrate, or prodrug thereof, wherein any one of $R_1$, $R_2$, and $R_3$ is Formula (5):

[Chemical 14]

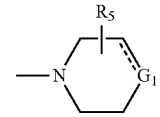

(5)

wherein $G_1$ is an oxygen atom, a sulfur atom, or it may be a carbon atom or nitrogen atom substituted by $R_7$; further, in cases where it is a carbon atom substituted by $R_7$, said carbon atom may form an unsaturated bond with an adjacent carbon atom, $R_7$ represents a —H, (C1-C6) alkyl, amino (C1-C6) alkyl (which may contain a carbonyl group in the carbon chain), (C1-C6) alkylaminocarbonyl, (C1-C6) alkylaminothiocarbonyl, di (C1-C6) alkylaminosulfamoyl, (C1-C6) alkoxycarbonyl, (C1-C6) alkoxycarbonyl (C1-C6) alkyl, carboxy (C1-C6) alkyl, (C1-C6) alkoxycarbonylamino, (C1-C6) alkoxycarbonylamino (C1-C6) alkyl, (C2-C6) alkenyl, (C2-C6) alkynyl, (C3-C6)cycloalkyl, (C1-C6) acyl, nitro, cyano, hydroxyl or amino group; or a phenyl, benzyl, pyridyl, picolyl, pyrimidyl, quinolinyl, thiazolyl, benzothiazolyl, thiadiazolyl, imidazolyl, tetrazolyl or pyridazinyl group, which may be substituted with $R_6$.

Additionally, a further mode of embodiment of the present invention is a compound described above, or a pharmaceutically acceptable salt, solvate, hydrate, or prodrug thereof, wherein $R_2$, and $R_3$ is Formula (5):

[Chemical 15]

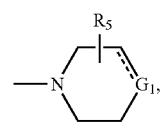

(5)

wherein $G_1$ is an oxygen atom, a sulfur atom, or it may be a carbon atom or nitrogen atom substituted by $R_7$; further, in cases where it is a carbon atom substituted by $R_7$, said carbon atom may form an unsaturated bond with an adjacent carbon atom, and $R_7$ represents a —H, (C1-C6) alkyl, amino (C1-C6) alkyl (which may contain a carbonyl group in the carbon chain), (C1-C6) alkylaminocarbonyl, (C1-C6) alkylaminothiocarbonyl, di (C1-C6) alkylaminosulfamoyl, (C1-C6) alkoxycarbonyl, (C1-C6) alkoxycarbonyl (C1-C6) alkyl, carboxy (C1-C6) alkyl, (C1-C6) alkoxycarbonylamino, (C1-C6) alkoxycarbonylamino (C1-C6) alkyl, (C2-C6) alkenyl, (C2-C6) alkynyl, (C3-C6)cycloalkyl, (C1-C6) acyl, nitro, cyano, hydroxyl or amino group; or a phenyl, benzyl, pyridyl, picolyl, pyrimidyl, quinolinyl, thiazolyl, benzothiazolyl, thiadiazolyl, imidazolyl, tetrazolyl or pyridazinyl group, which may be substituted with $R_6$.

Additionally, a further mode of embodiment of the present invention is a compound described above or a pharmaceutically acceptable salt, solvate, hydrate, or prodrug thereof, wherein $R_1$ is Formula (4):

[Chemical 16]

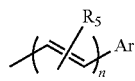

(4)

wherein n is 1, 2, or 3, $R_5$ represents —H, carboxyl, (C1-C6) alkyl, (C1-C6) alkoxycarbonyl, (C1-C6) alkoxycarbonylmethyl, amino (C1-C6) alkyl (said amino group may be substituted by 1 or 2 (C1-C6) alkyl groups, or 1 (C1-C6) alkoxycarbonyl group; additionally, a carbonyl group may be contained in the carbon chain), piperazinyl (C1-C6) alkyl, (C1-C6) alkoxycarbonylpiperazinyl (C1-C6) alkyl, morpholino (C1-C6) alkyl, (C1-C6) alkylpiperizine, (C2-C6) alkenyl, (C2-C6) alkynyl or phenyl group, wherein said phenyl group may be further substituted with 1 or 2 of $R_6$, $R_6$ represents a —H, —F, —Cl, —Br, —I, (C1-C6) alkyl, (C1-C6) alkylamino, di (C1-C6) alkylamino, (C1-C6) alkoxy, (C1-C6) alkylthio, (C1-C6) acyl, pyrrolidinyl, piperidino, piperazinyl, (C1-C6) alkoxycarbonyl, (C1-C6) alkoxycarbonylamino, phenyl, benzyl, phenyl (C1-C6) alkyloxy, nitro, amino or hydroxyl group; and Ar represents a phenyl, benzyl, pyridyl, pyrimidyl, thienyl, pyrrole, quinolinyl, thiazolyl, benzothiazolyl, thiadiazolyl, imidazolyl, tetrazolyl or pyridazinyl group which may be substituted with 1 or 2 of $R_6$; or a condensed ring group wherein 2 or more phenyl, benzyl, pyridyl, pyrimidyl, thienyl, pyrrole, quinolinyl, thiazolyl, benzothiazolyl, thiadiazolyl, imidazolyl, tetrazolyl or pyridazinyl groups, which may be substituted with 1 or 2 of $R_6$, are condensed.

Additionally, in any of the modes of embodiment described above, $R_5$ is more preferably a —H, carboxyl, (C1-C6) alkyl, (C1-C6) alkoxycarbonyl, (C1-C6) alkoxycarbonyl methyl, amino (C1-C6) alkyl (said amino group may be substituted with 1 or 2 (C1-C6) alkyl groups, or 1 (C1-C6) alkoxycarbonyl group, and further, may contain a carbonyl group in its carbon chain), piperazinyl (C1-C6) alkyl, (C1-C6) alkoxycarbonylpiperazinyl (C1-C6) alkyl, morpholino (C1-C6) alkyl, or (C1-C6) alkylpiperidine group.

Additionally, in any of the modes of embodiment described above, $R_6$ is more preferably a —H, —F, —Cl, —Br, —I, (C1-C6) alkyl, (C1-C6) alkylamino, di (C1-C6) alkylamino, (C1-C6) alkoxy, piperidino, piperazinyl, (C1-C6) alkoxycarbonyl, (C1-C6) alkoxycarbonylamino, nitro, amino or hydroxyl group.

Additionally, in any of the modes of embodiment described above, Ar is more preferably a phenyl, benzyl, pyridyl, thienyl or pyrrole group that may be substituted with 1 or 2 of $R_6$; or a condensed ring group wherein 2 or more phenyl, benzyl, pyridyl, thienyl, or pyrrole groups, which may be substituted with 1 or 2 of $R_6$, are condensed.

Additionally, in any of the modes of embodiment described above, $R_7$ is more preferably a —H, (C1-C6) alkyl, amino (C1-C6) alkyl (which may contain a carbonyl group in the carbon chain), di (C1-C6) alkylaminosulfamoyl, (C1-C6) alkoxycarbonyl, (C3-C6) cycloalkyl, nitro, cyano, hydroxyl or amino group; or a phenyl, benzyl or pyridyl group which may be substituted with $R_6$.

Additionally, in any of the modes of embodiment described above, $R_4$ is more preferably —F, —Cl, —Br or —I.

Additionally, in any of the modes of embodiment described above, if any one of $R_2$, or $R_3$ is a phenyl (C1-C6) alkyl group, or Formula (4):

[Chemical 17]

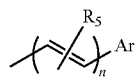

(4)

then $R_4$ is further preferably —F, —Cl, —Br, —I, or a nitro, amino, acetylamino, (C1-C6) alkylamino, di (C1-C6) alkylamino or cyano group, wherein said phenyl group may be substituted with 1 or 2 of $R_6$.

As examples of the pyrimidine derivatives in said Embodiment 1, the following compounds may be given, but the pyrimidine derivatives of the present invention are not restricted to these compounds.

4,6-dimorpholino-5-phenyl-2-(4-phenylpiperazin-1-yl)pyrimidine (Compound 46)

2,4-dimorpholino-5-phenyl-2-(4-phenylpiperazin-1-yl)pyrimidine (Compound 47)

5-methoxy-2,4-dimorpholino-2-(4-phenylpiperazin-1-yl) pyrimidine (Compound 50)

5-acetylamino-2-[2-(4-methoxyphenyl)vinyl]-4,6-dimorpholinopyrimidine (Compound 79)

5-fluoro-4,6-dimorpholino-2-(4-phenylpiperazin-1-yl)pyrimidine (Compound 82)

5-fluoro-2,4-dimorpholino-2-(4-phenylpiperazin-1-yl)pyrimidine (Compound 83)

4-dimethylamino-5-fluoro-6-morpholino-2-(4-phenylpiperazin-1-yl)pyrimidine (Compound 84)

2-dimethylamino-5-fluoro-4-morpholino-6-(4-phenylpiperazin-1-yl)pyrimidine (Compound 85)

4-(4-benzylpiperidin-1-yl)-2-dimethylamino-5-fluoro-6-morpholinopyrimidine (Compound 86)

5-fluoro-4-(3,4-dihydro-1H-isoquinolin-2-yl)-2,6-dimorpholinopyrimidine (Compound 87)

4-(N-ethyl-N-phenylamino)-5-fluoro-2,6-dimorpholinopyrimidine (Compound 88)

5-fluoro-2-(isoindolin-2-yl)-4,6-dimorpholinopyrimidine (Compound 89)

4-(4-benzylpiperazin-1-yl)-5-fluoro-2,6-dimorpholinopyrimidine (Compound 90)

2-dimethylamino-5-fluoro-4-morpholino-6-[4-(pyridin-2-yl)piperazin-1-yl]pyrimidine (Compound 91)

5-fluoro-4,6-dimorpholino-2-[4-(pyrimidin-2-yl)piperazin-1-yl]pyrimidine (Compound 92)

5-fluoro-4,6-dimorpholino-2-(3-phenylpiperazin-1-yl)pyrimidine (Compound 93)

5-fluoro-2,4-dimorpholino-6-(3-phenylpiperazin-1-yl)pyrimidine (Compound 94)

5-fluoro-2,4-dimorpholino-6-[4-(4-nitrophenyl)piperazin-1-yl]pyrimidine (Compound 95)

5-fluoro-2-[4-(4-fluorophenyl)piperazin-1-yl]-4,6-dimorpholinopyrimidine (Compound 96)

5-fluoro-4-[4-(4-fluorophenyl)piperazin-1-yl]-2,6-dimorpholinopyrimidine (Compound 97)

5-fluoro-2-[4-(4-methylphenyl)piperazin-1-yl]-4,6-dimorpholinopyrimidine (Compound 98)

5-fluoro-4-[4-(4-methylphenyl)piperazin-1-yl]-2,6-dimorpholinopyrimidine (Compound 99)

2-[4-(4-acetylphenyl)piperazin-1-yl]-5-fluoro-4,6-dimorpholinopyrimidine (Compound 100)

4-[4-(4-acetylphenyl)piperazin-1-yl]-5-fluoro-2,6-dimorpholinopyrimidine (Compound 101)

2-[4-(2-chlorophenyl)piperazin-1-yl]-5-fluoro-4,6-dimorpholinopyrimidine (Compound 102)

2-[4-(2-ethoxyphenyl)piperazin-1-yl]-5-fluoro-4,6-dimorpholinopyrimidine (Compound 103)
5-fluoro-2-[4-(2-methylphenyl)piperazin-1-yl]-4,6-dimorpholinopyrimidine (Compound 104)
5-fluoro-4,6-dimorpholino-2-[4-(2,3-xylyl)piperazin-1-yl]pyrimidine (Compound 105)
5-fluoro-2-[4-(2-fluorophenyl)piperazin-1-yl]-4,6-dimorpholinopyrimidine (Compound 106)
5-fluoro-2-[4-(4-hydroxyphenyl)piperazin-1-yl]-4,6-dimorpholinopyrimidine (Compound 107)
5-fluoro-2-[4-(2-methoxyphenyl)piperazin-1-yl]-4,6-dimorpholinopyrimidine (Compound 108)
2-[4-(4-chlorophenyl)piperazin-1-yl]-5-fluoro-4,6-dimorpholinopyrimidine (Compound 109)
6-[4-(2-chlorophenyl)piperazin-1-yl]-2-dimethylamino-5-fluoro-4-morpholinopyrimidine (Compound 110)
2-dimethylamino-5-fluoro-4-[4-(2-methoxyphenyl)piperazin-1-yl]-6-morpholinopyrimidine (Compound 111)
2-dimethylamino-5-fluoro-4-[4-(2-fluorophenyl)piperazin-1-yl]-6-morpholinopyrimidine (Compound 112)
4-[4-(4-chlorophenyl)piperazin-1-yl]-2-dimethylamino-5-fluoro-6-morpholinopyrimidine (Compound 113)
2-(4-cyano-4-phenylpiperidin-1-yl)-5-fluoro-4,6-dimorpholinopyrimidine (Compound 114)
4-(4-cyano-4-phenylpiperidin-1-yl)-5-fluoro-2,6-dimorpholinopyrimidine (Compound 115)
5-fluoro-2-(4-hydroxy-4-phenylpiperidin-1-yl)-4,6-dimorpholinopyrimidine (Compound 116)
5-fluoro-4-(4-hydroxy-4-phenylpiperidin-1-yl)-2,6-dimorpholinopyrimidine (Compound 117)
2-(4-acetyl-4-phenylpiperidin-1-yl)-5-fluoro-4,6-dimorpholinopyrimidine (Compound 118)
4-(4-acetyl-4-phenylpiperidin-1-yl)-5-fluoro-2,6-dimorpholinopyrimidine (Compound 119)
5-fluoro-4,6-dimorpholino-2-(4-phenyl-1,2,5,6-tetrahydropyridin-1-yl)pyrimidine (Compound 120)
5-fluoro-2,4-dimorpholino-6-(4-phenyl-1,2,5,6-tetrahydropyridin-1-yl)pyrimidine (Compound 121)
5-fluoro-4,6-dimorpholino-2-(1,2,3,4-tetrahydro-2H-isoquinolin-2-yl)pyrimidine (Compound 122)
2-(4-cyclohexylpiperazin-1-yl)-5-fluoro-4,6-dimorpholinopyrimidine (Compound 123)
4-(4-cyclohexylpiperazin-1-yl)-5-fluoro-2,6-dimorpholinopyrimidine (Compound 124)
5-fluoro-4-[4-(2-fluorophenyl)piperazin-1-yl]-6-morpholino-2-(4-phenylpiperazin-1-yl)pyrimidine (Compound 125)
2,4-bis[4-(2-fluorophenyl)piperazin-1-yl]-5-fluoro-6-morpholinopyrimidine (Compound 126)
5-fluoro-2-[4-(2-fluorophenyl)piperazin-1-yl]-4-[4-(2-methylphenyl)piperazin-1-yl]-6-morpholinopyrimidine (Compound 127)
5-fluoro-4-morpholino-6-(4-phenylpiperazin-1-yl)-2-[4-(2-methylphenylpiperazin-1-yl]pyrimidine (Compound 128)
2,4-bis[4-(2-methylphenyl)piperazin-1-yl]-5-fluoro-6-morpholinopyrimidine (Compound 129)
5-chloro-4,6-dimorpholino-2-(4-phenylpiperazin-1-yl)pyrimidine (Compound 130)
5-amino-2-[2-(4-methoxyphenyl)vinyl]-4,6-dimorpholinopyrimidine (Compound 131)
5-amino-4,6-dimorpholino-2-[2-(2-thienyl)vinyl]pyrimidine (Compound 132)
5-amino-2-[2-(4-methylthiopheno[1,2-b]pyrrol-5-yl)vinyl]-4,6-dimorpholinopyrimidine (Compound 133)
5-amino-4,6-dimorpholino-2-[2-(pyridin-4-yl)vinyl]pyrimidine (Compound 134)
5-amino-2-[2-(4-fluorophenyl)vinyl]-4,6-dimorpholinopyrimidine (Compound 135)
5-amino-4,6-dimorpholino-2-[2-(4-piperidin-1-ylphenyl)vinyl]pyrimidine (Compound 136)
5-amino-2-[2-(2-methylphenyl)vinyl]-4,6-dimorpholinopyrimidine (Compound 137)
5-amino-4-dimethylamino-2-[2-(4-methoxyphenyl)vinyl]-6-morpholinopyrimidine (Compound 138)
5-amino-2-[2-(4-methoxyphenyl)vinyl]-4-methylamino-6-morpholinopyrimidine (Compound 139)
5-formyl-4,6-dimorpholino-2-(4-phenylpiperazin-1-yl)pyrimidine (Compound 142)
5-amino-2-[4-(4-diethylaminophenyl)butan-1,3-dienyl]-4,6-dimorpholinopyrimidine (Compound 144)
5-amino-2-[4-(4-diethylaminophenyl)butyl]-4,6-dimorpholinopyrimidine (Compound 145)
4-[4-(4-aminophenyl)piperazin-1-yl]-5-fluoro-2,6-dimorpholinopyrimidine (Compound 146)
5-fluoro-4-[4-(4-methylphenyl)piperazin-1-yl]-6-morpholino-2-(1-piperazinyl)pyrimidine (Compound 149)
2-[4-(tert-butoxycarbonyl)piperazin-1-yl]-5-fluoro-4-[4-(4-methylphenyl)piperazin-1-yl]-6-morpholinopyrimidine (Compound 150)
5-fluoro-4-[4-(4-methylphenyl)piperazin-1-yl]-2-(4-methylpiperazin-1-yl)-6-morpholinopyrimidine (Compound 151)
5-fluoro-2-[4-(4-methylphenyl)piperazin-1-yl]-4-morpholino-6-(1-piperazinyl)pyrimidine (Compound 152)
4-[4-(tert-butoxycarbonyl)piperazin-1-yl]-5-fluoro-2-[4-(4-methylphenyl)piperazin-1-yl]-6-morpholinopyrimidine (Compound 153)
5-fluoro-2-[4-(4-methylphenyl)piperazin-1-yl]-4-(4-methylpiperazin-1-yl)-6-morpholinopyrimidine (Compound 154)
5-fluoro-4-[4-(4-methylphenyl)piperazin-1-yl]-6-(4-methylpiperazin-1-yl)-2-morpholinopyrimidine (Compound 155)
2-[4-(2-aminoethyl)piperazin-1-yl]-5-fluoro-4-[4-(4-methylphenyl)piperazin-1-yl]-6-morpholinopyrimidine (Compound 156)
5-fluoro-2-{4-[2-(tert-butoxycarbonylamino)ethyl]piperazin-1-yl}-4-[4-(4-methylphenyl)piperazin-1-yl]-6-morpholinopyrimidine (Compound 157)
5-fluoro-4-[4-(4-methylphenyl)piperazin-1-yl]-6-morpholino-2-[2-(piperazin-1-yl)-ethylamino]pyrimidine (Compound 158)
2-[2-(4-tert-butoxycarbonylpiperazin-1-yl)ethylamino]-5-fluoro-4-[4-(4-methylphenyl)piperazin-1-yl]-6-morpholinopyrimidine (Compound 159)
5-fluoro-4-[4-(4-methylphenyl)piperazin-1-yl]-2-morpholino-6-(2-morpholinoethylamino)pyrimidine (Compound 160)
4-[4-(tert-butoxycarbonyl)piperazin-1-yl]-5-fluoro-6-morpholino-2-[4-(2-pyridyl)piperazin-1-yl]pyrimidine (Compound 161)
5-fluoro-4-morpholino-6-(1-piperazinyl)-2-[4-(2-pyridyl)piperazin-1-yl]pyrimidine (Compound 162)
5-fluoro-4,6-dimorpholino-2-[4-(2-pyridyl)piperazin-1-yl]pyrimidine (Compound 163)
5-fluoro-2,4-dimorpholino-6-[4-(2-pyridyl)piperazin-1-yl]pyrimidine (Compound 164)
5-fluoro-4-(4-methylpiperazin-1-yl)-6-morpholino-2-[4-(2-pyridyl)piperazin-1-yl]pyrimidine (Compound 166)
5-fluoro-4-(4-methylpiperazin-1-yl)-6-morpholino-2-(1,2,3,4-tetrahydro-1H-quinolin-1-yl)pyrimidine (Compound 167)

4-[4-(tert-butoxycarbonyl)piperazin-1-yl]-5-fluoro-6-morpholino-2-(1,2,3,4-tetrahydro-1H-quinolin-1-yl)pyrimidine (Compound 168)

5-fluoro-2-(1-piperazinyl)-4-morpholino-6-(1,2,3,4-tetrahydro-1H-quinolin-1-yl)pyrimidine (Compound 169)

5-amino-2-[2-(4-methoxyphenyl)vinyl]-4-morpholino-6-(1-piperazinyl)pyrimidine (Compound 170)

5-fluoro-4-(4-methylpiperazin-1-yl)-2-morpholino-6-(4-phenylpiperazin-1-yl)pyrimidine (Compound 171)

5-amino-2-[2-(4-methoxyphenyl)vinyl]-4-(4-methylpiperazin-1-yl)-6-morpholinopyrimidine (Compound 172)

5-amino-2-[2-(4-methoxyphenyl)vinyl]-4-morpholino-6-[2-(1-piperazinyl)ethylamino]pyrimidine (Compound 173)

5-amino-4-(2-aminoethylamino)-2-[2-(4-methoxyphenyl)vinyl]-6-morpholinopyrimidine (Compound 174)

5-amino-2-[2-(4-methoxyphenyl)vinyl]-4-[4-(2-dimethylaminoethyl-piperazin-1-yl)]-6-morpholinopyrimidine (Compound 175)

5-amino-4-(4-aminomethylcarbonylpiperazin-1-yl)-2-[2-(4-methoxyphenyl)vinyl]-6-morpholinopyrimidine (Compound 176)

2-(4-tert-butoxycarbonylpiperazin-1-yl)-5-fluoro-4-morpholino-6-[4-(2,3-xylyl)piperazin-1-yl]pyrimidine (Compound 177)

5-fluoro-4-morpholino-2-(1-piperazinyl)-6-[4-(2,3-xylyl)piperazin-1-yl]pyrimidine (Compound 178)

4-(4-tert-butoxycarbonylpiperazin-1-yl)-5-fluoro-6-morpholino-2-[4-(2,3-xylyl)piperazin-1-yl]pyrimidine (Compound 179)

5-fluoro-4-morpholino-6-(1-piperazinyl)-2-[4-(2,3-xylyl)piperazin-1-yl]pyrimidine (Compound 180)

4-(4-tert-butoxycarbonylpiperazin-1-yl)-5-fluoro-2-[4-(2-fluorophenyl)piperazin-1-yl]-6-morpholinopyrimidine (Compound 181)

5-fluoro-2-[4-(2-fluorophenyl)piperazin-1-yl]-4-morpholino-6-(1-piperazinyl)pyrimidine (Compound 182)

5-fluoro-2-(4-methylpiperazin-1-yl)-4-morpholino-6-[4-(2,3-xylyl)piperazin-1-yl]pyrimidine (Compound 183)

5-fluoro-4-(4-methylpiperazin-1-yl)-6-morpholino-2-[4-(2,3-xylyl)piperazin-1-yl]pyrimidine (Compound 184)

5-fluoro-2-[4-(2-fluorophenyl)piperazin-1-yl]-4-(4-methylpiperazin-1-yl)-6-morpholinopyrimidine (Compound 185)

5-fluoro-4-(4-methylpiperazin-1-yl)-2-morpholino-6-[4-(2,3-xylyl)piperazin-1-yl]-pyrimidine (Compound 186)

2-[4-(2-chlorophenyl)piperazin-1-yl]-5-fluoro-6-(4-methylpiperazin-1-yl)-4-morpholinopyrimidine (Compound 187)

4-(4-tert-butoxycarbonylpiperazin-1-yl)-2-[4-(2-chlorophenyl)piperazin-1-yl]-5-fluoro-6-morpholinopyrimidine (Compound 188)

2-[4-(2-chlorophenyl)piperazin-1-yl]-5-fluoro-4-morpholino-6-(1-piperazinyl)pyrimidine (Compound 189)

2-[4-(2-ethoxyphenyl)piperazin-1-yl]-5-fluoro-4-(4-methylpiperazin-1-yl)-6-morpholinopyrimidine (Compound 190)

5-fluoro-4-morpholino-2-[4-(4-pyridinylmethyl)piperazin-1-yl]-6-[4-(2,3-xylyl)piperazin-1-yl]-pyrimidine (Compound 191)

5-fluoro-2-[4-(4-dimethylaminobenzyl)piperazin-1-yl]-4-morpholino-6-[4-(2,3-xylyl)piperazin-1-yl]pyrimidine (Compound 192)

2-[4-(4-tert-butoxycarbonylaminobenzyl)piperazin-1-yl]-5-fluoro-4-morpholino-6-[4-(2,3-xylyl)piperazin-1-yl]pyrimidine (Compound 193)

2-[4-(4-aminobenzyl)piperazin-1-yl]-5-fluoro-4-morpholino-6-[4-(2,3-xylyl)piperazin-1-yl]pyrimidine (Compound 194)

5-amino-4-(4-tert-butoxycarbonylaminopiperidin-1-yl)-2-[2-(4-methoxyphenyl)vinyl]-6-morpholinopyrimidine (Compound 195)

5-amino-4-(4-aminopiperidin-1-yl)-2-[2-(4-methoxyphenyl)vinyl]-6-morpholinopyrimidine (Compound 196)

5-amino-4-(4-tert-butoxycarbonylmethylamino)-2-[2-(4-methoxyphenyl)vinyl]-6-morpholinopyrimidine (Compound 197)

5-amino-2-[2-(4-methoxyphenyl)vinyl]-4-[N-methyl-N-(1-methylpiperidin-4-yl)amino]-6-morpholinopyrimidine (Compound 198)

5-amino-2-[2-(4-methoxyphenyl)ethyl]-4-(1-piperazinyl)-6-morpholinopyrimidine (Compound 199)

5-amino-4-[4-(carboxymethyl)piperazin-1-yl]-2-[2-(4-methoxyphenyl)vinyl]-6-morpholinopyrimidine (Compound 200)

4-amino-2-[2-(4-methoxyphenyl)vinyl]-6-morpholyl-5-nitropyrimidine (Compound 201)

4,5-diamino-2-[2-(4-methoxyphenyl)vinyl]-6-morpholinopyrimidine (Compound 202)

5-amino-4-[4(3-aminopropionyl)piperazin-1-yl]-6-morpholino-2-[2-(4-methoxyphenyl)vinyl]pyrimidine (Compound 203)

5-fluoro-4-(4-methylpiperazin-1-yl)-6-morpholino-2-[4-(4-pyridinylmethyl)piperazin-1-yl]pyrimidine (Compound 204)

5-amino-2-[2-(4-methoxyphenyl)vinyl]-4-(4-dimethylthiocarbamoylpiperazin-1-yl)-6-morpholinopyrimidine (Compound 205)

5-amino-4-carbamoylmethylamino-2-[2-(4-methoxyphenyl)vinyl]-6-morpholinopyrimidine (Compound 206)

5-amino-2-[2-(4-methoxyphenyl)vinyl]-4-morpholino-6-(2-morpholinoethylamino)pyrimidine (Compound 207)

5-amino-2-[2-(4-methoxyphenyl)vinyl]-4-(1-piperazinyl)-6-[2-(1-piperazinyl)ethylamino)pyrimidine (Compound 208)

5-amino-4-(3-ethoxycarbonylthiomorpholin-4-yl)-2-[2-(4-methoxyphenyl)vinyl]-6-morpholinopyrimidine (Compound 209)

5-amino-4-dimethylamino-2-[2-(4-methoxyphenyl)vinyl]-6-(1-piperazinyl)pyrimidine (Compound 210)

5-amino-2-[2-(4-methoxyphenyl)vinyl]-4-(4-methylpiperazin-1-yl)-6-(1-piperazinyl)pyrimidine (Compound 211)

5-amino-4-(4-tert-butoxycarbonylmethylpiperazin-1-yl)-2-[2-(4-methoxyphenyl)vinyl]-6-morpholinopyrimidine (Compound 212)

4-(4-acetylpiperazin-1-yl)-5-amino-2-[2-(4-methoxyphenyl)vinyl]-6-(piperazin-1-yl)pyrimidine (Compound 213)

5-amino-4-(4-dimethylsulfamoylpiperazin-1-yl)-2-[2-(4-methoxyphenyl)ethyl]-6-morpholinopyrimidine (Compound 214)

5-amino-4-(4-dimethylsulfamoylpiperazin-1-yl)-2-[2-(4-methoxyphenyl)vinyl]-6-morpholinopyrimidine (Compound 215)

5-fluoro-2-[2-(4-methoxyphenyl)vinyl]-4,6-dimorpholinopyrimidine (Compound 216)

Embodiment 2

A different embodiment of the present invention is a cell protecting agent comprising a compound represented by Formula (1b), or a pharmaceutically acceptable salt, solvate, hydrate, or prodrug thereof:

[Chemical 18]

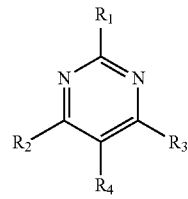
(1b)

wherein $R_1$, $R_2$, and $R_3$ are each selected independently from Formula (2b):

[Chemical 19]

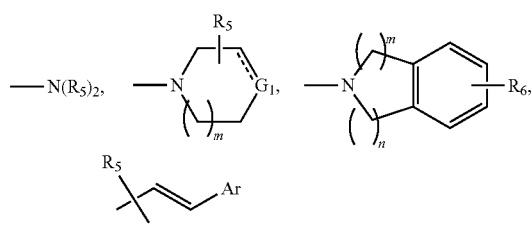
(2b)

wherein m is either 0 or 1; n is 1, 2, or 3;

$R_5$ represents a —H, (C1-C6) alkyl, (C2-C6) alkenyl, (C2-C6) alkynyl or phenyl group, wherein said phenyl group may be further substituted with 1 or 2 of $R_6$;

$R_6$ represents a —H, —F, —Cl, —Br, —I, (C1-C6) alkyl, (C1-C6) alkylamino, (C1-C6) alkoxy, (C1-C6) alkylthio, (C1-C6) acyl, pyrrolidinyl, piperidino, piperazinyl, (C1-C6) alkoxycarbonyl, phenyl, benzyl, phenyl (C1-C6) alkyloxy, nitro, amino or hydroxyl group;

Ar represents a phenyl, benzyl, pyridyl, pyrimidyl, thienyl, pyrrole, quinolinyl, thiazolyl, benzothiazolyl, thiadiazolyl, imidazolyl, tetrazolyl or pyridazinyl group which may be substituted with 1 or 2 of $R_6$; or a condensed ring group wherein 2 or more phenyl, benzyl, pyridyl, pyrimidyl, thienyl, pyrrole, quinolinyl, thiazolyl, benzothiazolyl, thiadiazolyl, imidazolyl, tetrazolyl or pyridazinyl groups, which may be substituted with 1 or 2 of $R_6$, are condensed $G_1$ is an oxygen atom, a sulfur atom, or a carbon atom or nitrogen atom substituted with $R_7$; further, in cases where it is a carbon atom substituted with $R_7$, said carbon atom may form an unsaturated bond with an adjacent carbon atom; and $R_7$ represents a —H, (C1-C6) alkyl, (C2-C6) alkenyl, (C2-C6) alkynyl, (C3-C6) cycloalkyl, (C1-C6) acyl, nitro, cyano or hydroxyl group; or a phenyl, benzyl, pyridyl, pyrimidyl, quinolinyl, thiazolyl, benzothiazolyl, thiadiazolyl, imidazolyl, tetrazolyl or pyridazinyl group, which may be substituted with $R_6$, and $R_4$ represents a —H, benzyl, (C1-C6) alkyl, amino, (C1-C6) alkylamino, di (C1-C6) alkylamino, benzyl or cyano group.

As examples of the pyrimidine derivatives of said Embodiment 2, the following compounds may be given, but the pyrimidine derivatives of the present invention are not restricted to these compounds.

4,6-dimorpholino-2-(4-phenylpiperazin-1-yl)pyrimidine (Compound 1)
4-dimethylamino-6-morpholino-2-(4-phenylpiperazin-1-yl)pyrimidine (Compound 2)
2,4-dimorpholino-6-(4-phenylpiperazin-1-yl)pyrimidine (Compound 3)
2-(4-benzylpiperidin-1-yl)-4,6-dimorpholinopyrimidine (Compound 4)
4-(4-benzylpiperidin-1-yl)-2,6-dimorpholinopyrimidine (Compound 5)
4,6-dimorpholino-2-(1,2,3,4-tetrahydro-2H-isoquinolin-2-yl)pyrimidine (Compound 6)
2-(6-fluoro-2-methyl-1,2,3,4-tetrahydroquinolin-1-yl)-4,6-dimorpholinopyrimidine (Compound 7)
4,6-dimorpholino-2-(1,2,3,4-tetrahydroquinolin-1-yl)pyrimidine (Compound 8)
2,4-dimorpholino-6-(1,2,3,4-tetrahydroquinolin-1-yl)pyrimidine (Compound 9)
2-(isoindolin-2-yl)-4,6-dimorpholinopyrimidine (Compound 10)
2-(4-benzylpiperazin-1-yl)-4,6-dimorpholinopyrimidine (Compound 11)
4,6-dimorpholino-2-[4-(pyridin-2-yl)piperazin-1-yl]pyrimidine (Compound 12)
2,4-dimorpholino-6-[4-(pyridin-2-yl)piperazin)-1-yl]pyrimidine (Compound 13)
4,6-dimorpholino-2-[4-(pyrimidin-2-yl)piperazin-1-yl]pyrimidine (Compound 14)
2,4-dimorpholino-6-[4-(pyrimidin-2-yl)piperazin-1-yl]pyrimidine (Compound 15)
4,6-dimorpholino-2-(3-phenylpiperazin-1-yl)pyrimidine (Compound 16)
2,4-dimorpholino-6-(3-phenylpiperazin-1-yl)pyrimidine (Compound 17)
4,6-dimorpholino-2-(4-nitrophenylpiperazin-1-yl)pyrimidine (Compound 18)
2,4-dimorpholino-6-(4-nitrophenylpiperazin-1-yl)pyrimidine (Compound 19)
2-[4-(4-fluorophenyl)piperazin-1-yl]-4,6-dimorpholinopyrimidine (Compound 20)
4-[4-(4-fluorophenyl)piperazin-1-yl]-2,6-dimorpholinopyrimidine (Compound 21)
2-[4-(4-methylphenyl)piperazin-1-yl]-4,6-dimorpholinopyrimidine (Compound 22)
4-[4-(4-methylphenyl)piperazin-1-yl]-2,6-dimorpholinopyrimidine (Compound 23)
2-[4-(4-acetylphenyl)piperazin-1-yl]-4,6-dimorpholinopyrimidine (Compound 24)
4-[4-(4-acetylphenyl)piperazin-1-yl]-2,6-dimorpholinopyrimidine (Compound 25)
2-[4-(2-chlorophenyl)piperazin-1-yl]-4,6-dimorpholinopyrimidine (Compound 26)
2-[4-(2-ethoxyphenyl)piperazin-1-yl]-4,6-dimorpholinopyrimidine (Compound 27)
2-[4-(2-methylphenyl)piperazin-1-yl]-4,6-dimorpholinopyrimidine (Compound 28)
4,6-dimorpholino-2-[4-(2,3-xylyl)piperazin-1-yl]pyrimidine (Compound 29)
2-[4-(4-hydroxyphenyl)piperazin-1-yl]-4,6-dimorpholinopyrimidine (Compound 30)
2-[4-(2-fluorophenyl)piperazin-1-yl]-4,6-dimorpholinopyrimidine (Compound 31)
2-[4-(2-methoxyphenyl)piperazin-1-yl]-4,6-dimorpholinopyrimidine (Compound 32)
2-[4-(2-chlorophenyl)piperazin-1-yl]-4,6-dimorpholinopyrimidine (Compound 33)
2-(4-cyano-4-phenylpiperidin-1-yl)-4,6-dimorpholinopyrimidine (Compound 34)

4-(4-cyano-4-phenylpiperidin-1-yl)-2,6-dimorpholinopyrimidine (Compound 35)
2-(4-hydroxy-4-phenylpiperidin-1-yl)-4,6-dimorpholinopyrimidine (Compound 36)
4-(4-hydroxy-4-phenylpiperidin-1-yl)-2,6-dimorpholinopyrimidine (Compound 37)
2-(4-acetyl-4-phenylpiperidin-1-yl)-4,6-dimorpholinopyrimidine (Compound 38)
4-(4-acetyl-4-phenylpiperidin-1-yl)-2,6-dimorpholinopyrimidine (Compound 39)
4,6-dimorpholino-2-[4-phenyl(1,2,5,6-tetrahydropyridin-1-yl)]pyrimidine (Compound 40)
2,4-dimorpholino-6-[4-phenyl(1,2,5,6-tetrahydropyridin-1-yl)]pyrimidine (Compound 41)
2-[4-(4-cyclohexyl)piperazin-1-yl]-4,6-dimorpholinopyrimidine (Compound 42)
4-[4-(4-cyclohexyl)piperazin-1-yl]-2,6-dimorpholinopyrimidine (Compound 43)
5-methyl-4,6-dimorpholino-2-(4-phenylpiperazin-1-yl)pyrimidine (Compound 44)
5-methyl-2,4-dimorpholino-6-(4-phenylpiperazin-1-yl)pyrimidine (Compound 45)
5-benzyl-4,6-dimorpholino-2-(4-phenylpiperazin-1-yl)pyrimidine (Compound 48)
5-benzyl-2,4-dimorpholino-6-(4-phenylpiperazin-1-yl)pyrimidine (Compound 49)
2-(4-benzylpiperazin-1-yl)-4-dimethylamino-6-morpholinopyrimidine (Compound 51)
4-morpholino-2-(4-phenylpiperazin-1-yl)-6-(piperazin-1-yl)pyrimidine (Compound 52)
4-(4-formylpiperazin-1-yl)-6-morpholino-2-(4-phenylpiperazin-1-yl)pyrimidine (Compound 53)
4-(4-acetylpiperazin-1-yl)-6-morpholino-2-(4-phenylpiperazin-1-yl)pyrimidine (Compound 54)
6-dibutylamino-4-morpholino-2-(4-phenylpiperazin-1-yl)pyrimidine (Compound 55)
4-morpholino-2-(4-phenylpiperazin-1-yl)-6-propylaminopyrimidine (Compound 56)
2,4-bis(4-phenyl)piperazin-1-yl)-6-morpholinopyrimidine (Compound 57)
4-[4-(2-fluorophenyl)piperazin-1-yl]-6-morpholino-2-(4-phenylpiperazin-1-yl)pyrimidine (Compound 58)
2,4-bis[4-(2-fluorophenyl)piperazin-1-yl]-6-morpholinopyrimidine (Compound 59)
2-[4-(2-fluorophenyl)piperazin-1-yl]-4-[4-(2-methylphenyl)piperazin-1-yl]-6-morpholinopyrimidine (Compound 60)
2-[4-(2-methylphenyl)piperazin-1-yl]-6-morpholino-4-(4-phenylpiperazin-1-yl)pyrimidine (Compound 61)
2,4-bis[4-(2-methylphenyl)piperazin-1-yl]-6-morpholinopyrimidine (Compound 62)
5-amino-4,6-dimorpholino-2-(4-phenylpiperazin-1-yl)pyrimidine (Compound 63)
5-amino-2,4-dimorpholino-6-(4-phenylpiperazin-1-yl)pyrimidine (Compound 64)
5-amino-4-dimethylamino-6-morpholino-2-(4-phenylpiperazin-1-yl)pyrimidine (Compound 65)
5-amino-2-(4-benzylpiperidin-1-yl)-4,6-dimorpholinopyrimidine (Compound 66)
5-amino-4-(4-benzylpiperidin-1-yl)-2,6-dimorpholinopyrimidine (Compound 67)
5-amino-2-(4-benzylpiperidin-1-yl)-4-dimethylamino-6-morpholinopyrimidine (Compound 68)
5-amino-2-(4-benzylpiperidin-1-yl)-4-dimethylamino-6-thiomorpholinopyrimidine (Compound 69)
5-amino-4,6-dimorpholino-2-(1,2,3,4-tetrahydro-1H-isoquinolin-2-yl)pyrimidine (Compound 70)
5-amino-2-(6-fluoro-2-methyl-1,2,3,4-tetrahydroquinolin-1-yl)-4,6-dimorpholinopyrimidine (Compound 71)
5-amino-2-(1,2,3,4-tetrahydroquinolin-1-yl)-4,6-dimorpholinopyrimidine (Compound 72)
5-amino-2-(4-benzylpiperazin-1-yl)-4,6-dimorpholinopyrimidine (Compound 73)
5-amino-2-(4-benzylpiperazin-1-yl)-4-dimethylamino-6-morpholinopyrimidine (Compound 74)
5-amino-4,6-dimorpholino-2-[4-(pyridin-2-yl)piperazin-1-yl]pyrimidine (Compound 75)
5-amino-2-(4-methylpiperazin-1-yl)-4,6-dimorpholinopyrimidine (Compound 76)
5-acetylamino-4,6-dimorpholino-2-(4-phenylpiperazin-1-yl)pyrimidine (Compound 77)
5-acetylamino-4-(4-benzylpiperidin-1-yl)-2,6-dimorpholinopyrimidine (Compound 78)
5-ethylamino-4,6-dimorpholino-2-(4-phenylpiperazin-1-yl)pyrimidine (Compound 80)
4-(4-benzylpiperazin-1-yl)-5-ethylamino-2,6-dimorpholinopyrimidine (Compound 81)
5-amino-4,6-bis(dimethylamino)-2-[2-(4-methoxyphenyl)vinyl]pyrimidine (Compound 140)
5-dimethylamino-4,6-dimorpholino-2-(4-phenylpiperazin-1-yl)pyrimidine (Compound 141)
6-dimethylamino-2-methyl-4-morpholino-5-nitropyrimidine (Compound 143)
4-(4-methylpiperazin-1-yl)-2-morpholino-6-(1,2,3,4-tetrahydro-2H-isoquinolin-2-yl)pyrimidine (Compound 165)

[Further Modes of the Present Invention]

As compounds of the present invention (pyrimidine derivatives), said Embodiments 1 or 2, or compounds having a more concrete structure, or particular compounds, included therein, may be used. Similarly, the following descriptions include said Embodiments 1 or 2, or compounds having a more concrete structure, or particular compounds (pyrimidine derivatives), included therein.

Said pyrimidine derivatives shall, in cases where they have asymmetric carbon atoms in their structure, be taken to include all asymmetric carbon atom derived isomers and mixtures thereof (racemic mixtures).

Methods of preparing, separating, and isolating the desired stereoisomers from racemic mixtures or nonracemic mixtures are publicly known to those skilled in the art; for example, preparation of diastereoisomer salts or complexes that are separable by crystallization; for example, preparation of diastereoisomers that are separable by crystallization, or gas-liquid or liquid chromatography; selective reaction of one optical isomer using an optical isomer specific reagent, for example oxidation or reduction with oxygen followed by separation of optical isomers; or separation by gas-liquid or liquid chromatography in a chiral environment (e.g., in the presence of chiral supports such as bound chiral ligand bound silica or a chiral solvent).

Further, said pyrimidine derivatives may, for example, be in a form dissolved in a pharmaceutically acceptable solvent such as water or ethanol. Generally, it may be thought that the dissolved form is equivalent to the undissolved form, with regard to the aims of the present invention.

Further, said pyrimidine derivatives may be in the form of a hydrate, a solvate, or a pharmaceutically acceptable salt (acid addition salt or base addition salt). "Pharmaceutically acceptable salt" refers to a salt that can be accepted pharmaceutically, and can carry out the desired pharmacological activity of the parent compound. Pharmaceutically acceptable salts are understood as being nontoxic or as being within a range of toxicity that is applicable to the human body.

Further information regarding suitable pharmaceutically acceptable salts is well-known in said technical area, as described in *Remington's Pharmaceutical Sciences*, 17$^{th}$ ed., Mack Publishing Company, Easton, Pa., 1985, or "Pharmaceutical Salts", *J. Pharm. Sci.*, 1977; 66: 1-19, incorporated herein by reference.

Examples of pharmaceutically acceptable acid addition salts are salts that are formed by the addition of, for example, inorganic acids such as hydrochloric acid, hydrobromic acid, sulfuric acid, nitric acid, and phosphoric acid; or organic acids such as acetic acid, trifluoroacetic acid, propionic acid, hexanoic acid, cyclopentane propionic acid, glycolic acid, pyruvic acid, lactic acid, oxalic acid, maleic acid, malonic acid, succinic acid, fumaric acid, malic acid, tartaric acid, citric acid, benzoic acid, cinnamic acid, 3-(4-hydroxybenzoyl)benzoic acid, mandelic acid, methane sulfonic acid, ethane sulfonic acid, 1,2-ethane disulfonic acid, 2-hydroxy ethane sulfonic acid, benzene sulfonic acid, 4-chlorobenzene sulfonic acid, 2-naphthalene sulfonic acid, 4-toluene sulfonic acid, camphor sulfonic acid, glucoheptonic acid, 4,4'-methylene bis-(3-hydroxy-2-ene-1-carboxylic acid), 3-phenyl propionic acid, trimethyl acetic acid, tert-butyl acetic acid, lauryl sulfuric acid, gluconic acid, glutamic acid, hydroxy naphthoic acid, stearic acid, muconic acid, and salicylic acid.

Examples of pharmaceutically acceptable base addition salts include salts wherein the acidic proton that is in the parent compound is replaced by a metallic ion such as salts of sodium, potassium, lithium, ammonium, calcium, magnesium, iron, zinc, copper, manganese, and aluminum. Further, for example, salts derived from organic bases such as primary, secondary, and tertiary amines, substituted amines, and cyclic amines are also included. Examples of organic bases are isopropylamine, trimethylamine, diethylamine, triethylamine, tripropylamine, ethanolamine, 2-dimethylamino ethanol, dicyclohexylamine, lysine, arginine, histidine, caffeine, procaine, hydrabamine, choline, betaine, ethylenediamine, glucosamine, methyl glucamine, theobromine, purine, piperazine, piperizine, N-ethylpiperizine, tromethamine, N-methyl glucamine, and polyamine resin. Representative organic bases are, for example, isopropylamine, diethylamine, ethanolamine, trimethylamine, dicyclohexylamine, choline, and caffeine.

Examples of solvates include organic solvates such as, for example, dimethylsulfoxide solvates, dimethylformamide solvates, or alcohol solvates such as ethanol solvates, methanol solvates, or n-propyl alcohol solvates.

Additionally, said pyrimidine derivatives, or pharmaceutically acceptable salts, solvates, or hydrates thereof, may exist as amorphous bodies. Generally, with regard to many organic compounds and salts thereof, it is known that various crystal polymorphs exist, and a variety of crystal polymorphs can be produced by many different methods that are publicly known in said technical area. Concretely, for example, various crystal polymorphs including amorphous bodies can be produced by the fusion method, or an extruder. Additionally, amorphous bodies may also be provided in the form of a solid dispersion including an excipient.

Additionally, said pyrimidine derivatives, or pharmaceutically acceptable salts, solvates, or hydrates thereof, may take the form of prodrugs. Prodrugs refer to compounds that produce a parent compound by transforming in vivo, such as by hydrolysis in the bloodstream. General examples are not restricted to the following, but include esters and amide forms of compounds having a carboxyl group, and similarly, amide forms of compounds having an amino group. Examples of pharmaceutically acceptable esters are not restricted to the following, but include alkyl esters (e.g., having from 1 to 6 carbon atoms) wherein the alkyl group is linear or branched. Acceptable esters include, for example, cycloalkyl esters, and aryl alkyl esters such as benzyl. Examples of pharmaceutically acceptable amides are not restricted to the following, but include primary amides, and secondary and tertiary alkyl amides (e.g., having from 1 to 6 carbon atoms). These amides and esters can be prepared in accordance with well-known methods in said technical area.

Additionally, other prodrugs may also be prepared in accordance with well-known methods in said technical area. Generally, according to these methods, an appropriate functional group of the compound is modified. These modified functional groups can re-form the original functional group by a predetermined manipulation or an in vivo transformation. Details regarding prodrugs are well-known in said technical area, as described in T. Higuchi and V. Stella, "Pro-drugs as Novel Delivery Systems", Vol. 14 of the A.C.S. Symposium Series, and *Bioreversible Carriers in Drug Design*, ed. Edward B. Roche, American Pharmaceutical Association and Pergamon Press, 1987, incorporated herein by reference.

Modes of embodiment of said pyrimidine derivatives, or pharmaceutically acceptable salts, solvates, or hydrates thereof include N-oxide derivatives and protective derivatives of said pyrimidine derivatives. For example, in cases where said pyrimidine derivatives contain nitrogen atoms that can be oxidized, the nitrogen atoms can be transformed into N-oxides by methods that are well-known in said technical area. For example, in cases where said pyrimidine derivatives contain groups that contain hydroxy, carboxy, or nitrogen atoms, these groups can be protected by an appropriate protective group. Disclosures of representative examples of appropriate protective groups are described in T. W. Greene, *Protective Groups in Organic Synthesis*, John Wiley & Sons, Inc. 1991, incorporated herein by reference. Protective derivatives of said pyrimidine derivatives may also be prepared by methods that are well-known in said technical area.

As long as it is not particularly restricted, and no inconsistency arises, the term "pyrimidine derivatives and the like" in the present specification shall be used as a generic term that includes all of the various forms described above that said pyrimidine derivatives may take.

Other modes of embodiment of the present invention are compositions, pharmaceutical compositions, formulations, medicaments, and agents including said pyrimidine derivatives and the like. Said compositions, pharmaceutical compositions, formulations, medicaments, and agents may contain, in addition to said pyrimidine derivatives and the like, pharmaceutically acceptable pharmaceutical aids, diluents, and/or a carrier. Further, said compositions, pharmaceutical compositions, formulations, medicaments, and agents may also contain other medicinal products or agents. When said compositions, pharmaceutical compositions, formulations, medicaments, and agents are administered, it is desirable for them to contain an effective amount of pyrimidine derivatives and the like.

Said compositions, pharmaceutical compositions, formulations, medicaments, and agents may be administered orally or parenterally, and as examples of forms of oral administration, pills, fine grain agents, coated pills, powder medicine, granulated agents, capsules (e.g., hard gelatin capsules, soft gelatin capsules), microcapsules, syrups, and the like may be used. Additionally, as examples of forms of parenteral administration, injectable agents (including freeze dried agents for injection that are dissolved at the time of use), and suppositories may be used. Additionally, it may be prepared as a liposomal agent. Further, it may be used as a liquid agent wherein said pyrimidine derivatives and the like are predispersed in a pharmaceutically acceptable solvent, and in this case, for example, it can be used as a syrup for oral administration or as an injectable agent for parenteral administration (including freeze dried agents for injection that are dissolved at the time of use).

Additionally, said compositions, pharmaceutical compositions, formulations, medicaments, and agents may be administered as, for example, solutions, suspensions, emulsions, microemulsions, multiphase emulsions, foams, topical medicines, pastes, plasters, ointments, coated pills, rinses, rectal capsules, drops, gels, sprays, powders, aerosols, inhalants, eye drops, ophthalmic ointments, ophthalmic rinses, infusion solutions, or grafts.

Pharmaceutical aids and/or carriers (excipients) may be used in the preparation of said compositions, pharmaceutical compositions, formulations, medicaments, and agents. As pharmaceutical aids, for example, colorants, sweetening agents, flavoring agents, binding agents, adsorption agents, lubricants, disintegrants, softening agents, suspending agents, emulsifying agents, preservative agents, antioxidants, surfactants, stabilizing agents, pH adjusting agents, dispersing agents, isotonic agents, wetting agents, dissolving agents, solubilization agents, and/or absorption promoters may be used. These various forms may be prepared according to the conventional methods, and may be prepared aseptically.

Additionally, in said forms of administration, depending upon the conditions of use, a functional coating such as an enteric coating may further be provided. In cases of administration in a solid form, for example, preparation can be done using coatings such as enteric coatings and shells. Additionally, such forms of administration can be made to release compounds to a certain portion of the intestinal tract in a delayed manner. Representative examples of appropriate embedding compositions are, for example, polymer substances and wax. Additionally, it may be put in the form of a microcapsule along with an excipient.

Examples of said excipients (carriers) are crystalline cellulose, sugars (e.g., glucose, sucrose, lactose, D-mannitol, D-sorbitol), starches (e.g., corn starch, potato starch, wheat starch, rice starch), magnesium silicate, sodium hydrogenphosphate, calcium hydrogenphosphate, sodium citrate, and talc.

Examples of said disintegrants are sodium carbonate, calcium carbonate, gum arabic, starches (e.g., corn starch, potato starch, wheat starch, tapioca starch, rice starch), agar, alginic acid, silicate complex, traganth, crystalline cellulose, low substituted hydroxypropyl cellulose, croscarmellose sodium, carmellose calcium, carmellose sodium, and sodium carboxymethyl starch.

Examples of said binding agents are cellulose derivatives, starch, alginates, gelatin, polyvinyl pyrrolidone, sucrose, and acacia gum.

Examples of said wetting agents are glycerol, cetyl alcohol, glycerol monostearate, magnesium stearate, talc, calcium stearate, solid polyethylene glycol, and sodium lauryl sulfate.

Examples of said absorption promoters are quaternary ammonium compounds and the like.

Examples of said adsorption agents are kaolin and bentonite.

Examples of said lubricants are carnauba wax, hydrogenated oil, magnesium stearate, calcium stearate, sodium hydrogenphosphate, calcium hydrogenphosphate, and white beeswax.

Examples of said preservative agents are paraben, chlorobutanol, phenol, and sorbic acid.

Examples of said isotonic agents are sugars and sodium chloride.

Examples of said suspending agents are ethoxylated isostearyl alcohols, polyoxyethylene sorbitol and sorbitan ester, microcrystalline cellulose, aluminum metahydroxide, bentonite, agar, and tragacanth.

Examples of said dissolving agents are ethanol, dilute hydrochloric acid, sodium hydroxide, sodium hydrogen carbonate, olive oil, squalene, squalane, normal saline solution, injection solvent, canola oil, glucose, propylene glycol, polysorbate, and macrogol.

Examples of said solubilization agents are, in addition to said dissolving agents, L-arginine, alpha-cyclodextrin, beta-cyclodextrin, D-sorbitol, soybean oil, urea, sucrose, hydroxypropylcellulose, hypromellose, povidone, and D-mannitol.

Additionally, as agents that delay the absorption of injectable agents, for example, aluminum monostearate and gelatin and the like may be used.

The examples of said pharmaceutical aids are merely illustrative, and various pharmaceutical aids that are well-known in said technical area may be used, as long as they provide the desired effect.

Among the liquid dosage forms for oral administration of said compositions, pharmaceutical compositions, formulations, medicaments, and agents are included pharmaceutically acceptable emulsions, solutions, suspensions, syrups, and elixirs. Such dosage forms are generally prepared, for example, by dissolving or dispersing said pyrimidine derivatives and the like in carriers, for example, distilled water, normal saline solution, aqueous dextrose, glycerol, and ethanol; for example, dissolving agents and emulsifying agents such as ethyl alcohol, isopropyl alcohol, ethyl carbonate, ethyl acetate, benzyl alcohol, benzyl benzoate, propylene glycol, 1,3-butylene glycol, and dimethylformamide; for example, oils such as cotton seed oil, peanut oil, corn germ oil, olive oil, castor oil, sesame oil, glycerol, the oil like the fatty acid ester oil of the tetrahydrofurfuryl alcohol, polyethylene glycol, and sorbitan fatty acid ester oil; or mixtures of these substances, and forming solutions or suspensions.

Dosage forms of said compositions, pharmaceutical compositions, formulations, medicaments, and agents that are appropriate for injection may be prepared by using a physiologically acceptable aqueous or nonaqueous sterile solution, dispersion liquid, suspension, or emulsion, a sterile injection solution and/or a sterile powder that is reconstituted into a dispersion liquid. Representative examples of appropriate aqueous or nonaqueous carriers, diluted solutions, solvents, or vehicles are distilled water, ethanol, polyols (e.g., propylene glycol, polyethylene glycol, and glycerol), appropriate mixtures thereof, plant-derived oils (e.g., olive oil), and injectable organic esters such as ethyl oleate. These aqueous or nonaqueous carriers, diluted solutions, solvents or vehicles, may contain appropriate salts, pH adjusters, and the like, as in normal saline solution.

Dosage forms of said compositions, pharmaceutical compositions, formulations, medicaments, and agents that are appropriate for rectal administration may be prepared, for example, as a suppository using an appropriate carrier (excipient). The excipient is preferably a non-stimulating excipient, and examples are cocoa butter, polyethylene glycol, or suppository waxes that are in a solid form at normal temperatures, but are in liquid form at body temperature, and dissolve in appropriate body cavities, and release the active ingredient.

Dosage forms of the compounds of the present invention appropriate for local application include ointments, powders, sprays, and inhalants. The active ingredients are mixed under sterile conditions with a pharmaceutically acceptable carrier, and if needed, arbitrary preservative agents, buffers, or spraying agents. It can be thought that ophthalmic preparations, opthalmic ointments, powders, and solutions are included in the scope of this invention.

Methods for preparation in said dosage forms are well-known in said technical area, and, for example, are described in *Remington's Pharmaceutical Sciences,* 18th Ed., (Mack Publishing Company, Easton, Pa., 1990), incorporated herein by reference.

In cases where said pyrimidine derivatives and the like are applied to mammals, particularly humans, an arbitrary dosage form appropriate for the desired delivery route can be used, and delivery can be done through routes such as oral, dermal, intradermal, intrabronchial, intranasal, intra-arterial, intravenous, intramuscular, subcutaneous, intraperitoneal, transvagina, transrectal, sublingual, intracranial, epidural, intratracheal, intraocular, and other local sites.

Including cases of prophylactic use, one example of a preferable route of administration is oral administration, as the dosage is adjustable in accordance with the severity of the targeted disease state, and the quality of life of the user can be made high.

Said pyrimidine derivatives and the like have an excellent antioxidant action, and provide an excellent inhibiting effect against cell damage and cell death. Accordingly, said pyrimidine derivatives and the like may be used as prophylactic agents or therapeutic agents for diseases against which antioxidant action, or inhibiting action against cell damage and cell death are effective. For example, said pyrimidine derivatives and the like may be used as a cell protecting agent, particularly a brain cell protecting agent that is effective against brain disorders that last for a long time, such as ischemia, or as a prophylactic/therapeutic agent against nerve diseases such as ischemic brain disease, neurodegenerative disease, or psychiatric disease.

Additionally, said pyrimidine derivatives and the like have, in addition to or independently of an antioxidant action, an excellent cell protecting action that protects cells against cell death or cell damage. Accordingly, one mode of embodiment of the present invention is a cell protecting agent containing said pyrimidine derivatives and the like (e.g., the compounds of Embodiment 1 or 2, or pharmaceutically acceptable salts, solvates, hydrates, or prodrugs thereof or the like); or, a method for protecting cells (including contact with cells) using said pyrimidine derivatives and the like (e.g., the compounds of Embodiment 1 or 2, or pharmaceutically acceptable salts, solvates, hydrates, or prodrugs thereof or the like).

Further, since said pyrimidine derivatives and the like are effective for brain cells, they can suitably be used for brain cells. That is, a further mode of embodiment of the present invention is a brain cell protecting agent (inhibiting agent against brain cell damage or brain cell death) containing said pyrimidine derivatives and the like (e.g., the compounds of Embodiment 1 or 2, or pharmaceutically acceptable salts, solvates, hydrates, or prodrugs thereof or the like); or a method (including contact with cells) for protecting brain cells (method for suppressing damage or death of brain cells) using said pyrimidine derivatives and the like (e.g., the compounds of Embodiment 1 or 2, or pharmaceutically acceptable salts, solvates, hydrates, or prodrugs thereof or the like).

Further, forms of cell death include necrotic cell death and apoptosis, but with regard to the inhibiting effect of said compound against cell damage or cell death, the manner of cell death does not matter.

Additionally, brain cells include cerebral nerve cells and astrocytes, and stimulants of brain cell damage and brain cell death include hydrogen peroxide (oxidative stress) and glutamic acid.

Additionally, it can be used for treatment of the various cells (including brain cells and nerve cells) both in vitro and in vivo.

Further, said pyrimidine derivatives and the like may be used as prophylactic agents/therapeutic agents against diseases for which antioxidant action or inhibiting action against cell damage and cell death is effective, and by administering said pyrimidine derivatives and the like into mammals, prevention and treatment against diseases for which antioxidant action or inhibiting action against cell damage and cell death is effective can be carried out. Diseases for which antioxidant action or inhibiting action against cell damage and cell death is effective, and/or diseases for which said pyrimidine derivatives and the like are therapeutically effective, are not particularly restricted, but examples are nerve diseases such as ischemic brain disease, neurodegenerative disease, or psychiatric disease, or diseases of peripheral tissues such as heart disease, liver disease, kidney disease, and pancreatic disease. In particular, it may be used suitably against ischemic brain disease or nerve disease.

That is, other modes of embodiment of the present invention are prophylactic agents or therapeutic agents against ischemic brain disease, containing said pyrimidine derivatives and the like (e.g., the compounds of Embodiment 1 or 2, or pharmaceutically acceptable salts, solvates, hydrates, or prodrugs thereof or the like); or, methods of prevention or methods of therapy against ischemic brain disease, including the administration to mammals of said pyrimidine derivatives and the like (e.g., the compounds of Embodiment 1 or 2, or pharmaceutically acceptable salts, solvates, hydrates, or prodrugs thereof or the like). Additionally, other modes of embodiment of the present invention are prophylactic agents or therapeutic agents against nerve disease, containing said pyrimidine derivatives and the like (e.g., the compounds of Embodiment 1 or 2, or pharmaceutically acceptable salts, solvates, hydrates, or prodrugs thereof or the like); or, methods of prevention or methods of therapy against nerve disease, including the administration to mammals of said pyrimidine derivatives and the like (e.g., the compounds of Embodiment 1 or 2, or pharmaceutically acceptable salts, solvates, hydrates, or prodrugs thereof or the like).

Ischemic brain diseases include, for example, cerebral infarction, cerebral hemorrhage, intracranial hemorrhage, subarachnoid hemorrhage, hypertensive brain disease, cerebral embolism, or transient cerebral ischemic attack. In one mode of embodiment of the present invention, the ischemic brain disease is cerebral infarction. Additionally, in another mode of embodiment, the ischemic brain disease is transient cerebral ischemic attack. Additionally, in another mode of embodiment, it is intracranial hemorrhage, cerebral hemorrhage, subarachnoid hemorrhage, hypertensive brain disease, or cerebral embolism.

Nerve diseases include, for example, Alzheimer's disease, head trauma, spinal cord injury, cerebral palsy, Huntington's disease, Pick's disease, Down's syndrome, Parkinson's disease, Creutzfeldt-Jakob disease, AIDS encephalopathy, multiple sclerosis, amyotrophic lateral sclerosis, cerebellar ataxia, epilepsy, glaucoma, depression, and integration disorder syndrome. That is, in one mode of embodiment of the present invention, the nerve diseases are Alzheimer's disease, head trauma, spinal cord injury, cerebral palsy, Huntington's disease, Pick's disease, Down's syndrome, Parkinson's disease, Creutzfeldt-Jakob disease, AIDS encephalopathy, multiple sclerosis, amyotrophic lateral sclerosis, cerebellar ataxia, epilepsy, glaucoma, depression, and integration disorder syndrome.

Heart diseases include, for example, angina, myocardial infarction, and cardiac failure. Liver diseases include, for example, hepatitis, hepatic cirrhosis, and hepatic failure. Kidney diseases include, for example, renal infarction, nephritis, and renal failure. Pancreatic diseases include, for example, pancreatitis.

A concrete example of a brain cell protecting agent using said pyrimidine derivatives and the like is a brain cell protecting agent against transient focal cerebral ischemia, or a brain cell protecting agent against permanent cerebral artery occluded cerebral infarction. Said pyrimidine derivatives and the like have cerebral infarct area reducing effects or neurological symptom improving effects against transient focal cerebral ischemia and/or permanent cerebral artery occluded cerebral infarction, and may be used suitably as a brain cell protecting agent against transient focal cerebral ischemia and/or permanent cerebral artery occluded cerebral infarction.

Further, said pyrimidine derivatives and the like may be used as an ischemic brain disease therapeutic agent and/or an ischemic brain disease prophylactic agent. Said pyrimidine derivatives and the like have cerebral infarct area reducing effects or neurological symptom improving effects against transient focal cerebral ischemia, and may be used suitably as an ischemic brain disease therapeutic agent and/or an ischemic brain disease prophylactic agent.

An appropriate dosing regimen may be determined based upon well-known technical knowledge, information provided in the present specification, and experience regarding individual subjects that are being treated. Normally, it is preferable for said pyrimidine derivatives and the like to be administered at concentrations for which effective results can be obtained without giving rise to dangerous or damaging side effects.

"Effective amount" includes the therapeutically effective amount of the pyrimidine derivatives of the present invention for improving the symptoms of the disease in cases of administration in a therapeutic subject, and the prophylactically effective amount of the pyrimidine derivatives of the present invention for preventing the arising of a disease state in cases of administration in a prophylactic subject. The effective amount of said pyrimidine derivatives and the like can vary depending upon a diversity of factors, including the level of activity, metabolic stability, duration of action, elimination rate, and delivery mode (dosage form) of the respective compounds, in addition to administration time, age, weight, general state of health, sex, and daily food and drink of the therapeutic subject, the combination of agents at the time of administration (drug interactions), and severity of symptoms of the subject. The effective amount can be determined conventionally by considering well-known information in said technical area and the present disclosure. A dosage that is divided into portions may be administered daily (e.g., 2 to 4 dosage portions per day), or a single dose may be administered. Additionally, administration can be done on a daily, weekly, or monthly basis.

Said pyrimidine derivatives and the like can, for example, be administered to patients in a dosage within a range of 0.001 to 6000 mg daily. In cases where it is used as an oral agent, the dosage of the effective ingredient will differ depending upon the symptoms, age, and weight of the patient, but as one example, for an adult weighing 60 kg, 60 to 6000 mg as a daily dosage may be administered once, or 2 to 3 times, or divided into more portions. Additionally, in cases where it is used as a injectable agent, the dose of the effective ingredient will differ depending upon the symptoms, age, and weight of the patient, but as one example, for an adult weighing 60 kg, 6 to 600 mg as a daily dosage may be administered once, or 2 to 3 times, or divided into more portions. Additionally, in cases of eye drops or if the aim is inhalation into the lungs or nasal passage, there will be differences depending upon the symptoms of the patient, but 1 to 1000 milligram as a daily dosage for an adult can be administered once, or 2 to 3 times, or divided into more portions. Further, in cases where it is used as a prophylactic agent, the dosage of the effective component will differ depending upon the symptoms, age, and weight of the patient, but as one example, for an adult weighing 60 kg, 0.001 to 6000 mg as a daily dosage may be administered once, or 2 to 3 times, or divided into more portions.

In cases where preparation is done in fixed dosages, pyrimidine derivatives and the like may be used within said dosage ranges. Additionally, as combination drugs, pyrimidine derivatives and the like within said dosage ranges, and other medically active agents within an approved dosage range may be used. In cases where a combination drug is not appropriate, the pyrimidine derivatives and the like may be used in succession with other medically active agents within an approved dosage range.

Mammals and other animals, particularly humans, are included in "(therapeutic/prophylactic) subjects" or "patients". Therefore, the present method may be applied to both treatment of humans and for veterinary purposes. Preferably, the "(therapeutic/prophylactic) subjects" or "patients" are humans.

Here, "treat" or "therapeutic" with regard to diseases, abnormalities, or syndromes includes at least one of (i) the inhibition of a disease state (or the progression of a disease); or (ii) the alleviation of a disease state (or the regression of a disease state). Preferably, it is (ii). Details concerning therapy can be confirmed by the normal experiments, investigations, and the like by specialists in said technical area.

Additionally, here, "prevent" or "prophylactic" with regard to diseases, abnormalities, or syndromes includes cases where some subject is prone to fall into a disease state, but is not diagnosed as having that disease, and the coming about of the disease state in the subject is prevented. Details regarding prevention can be confirmed by the normal experiments, investigations, and the like by specialists in said technical area.

Modes of embodiment of the present invention have been described above, but these are mere examples of the present invention, and various constitutions other than those given above may be utilized. For example, in said modes of embodiment, the explanations focused on uses as a cell protecting agent and medicinal uses as a therapeutic agent, but the intent is not to make a restriction to medicinal uses in particular. A wide range of uses is envisioned for the present invention, other than medicinal uses, for example, animal medicaments, diagnostic agents, test reagents, additive agents for processing livestock food products, additive agents for processing aquatic food products, and cell protecting agents for manufacturing and storing of artificial organs for artificial organ implantation, and there is no intent to exclude such uses.

EXAMPLE

Herebelow, the present invention shall be explained concretely by way of examples, but these are respectively examples, and the present invention is not restricted to them. Further, the commercial reagents mentioned in the examples were used in accordance with the usage instructions of the manufacturer, or conventional methods, as long as there are no statements to the contrary.

[General Manufacturing Procedure]

With regard to production procedures of the compounds of the present mode of embodiment represented by General Formula (1a) or (1b), Regioisomers (V) and (VIII) can be produced by reacting amines (A-H, B-H, C-H) in order, as shown in the Reaction Formula (6) given below.

[Chemical 20]

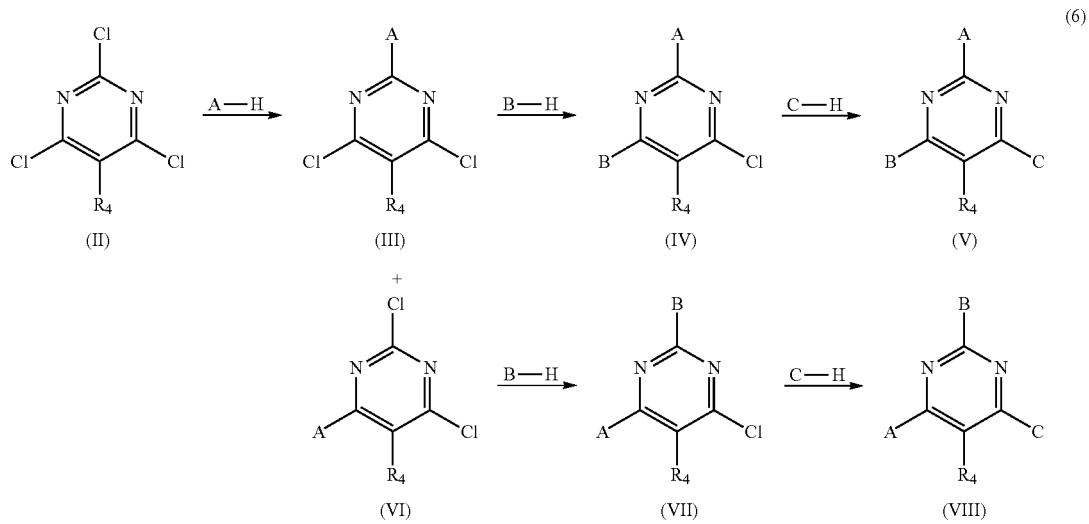

Here, by changing the order in which amines are added, the 3 types of regioisomers (IX), (X), and (XI) in the General Formula (7) given below may respectively be synthesized.

[Chemical 21]

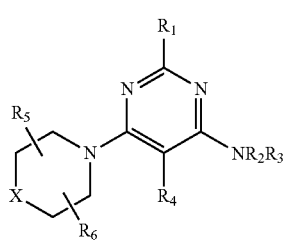

(IX)

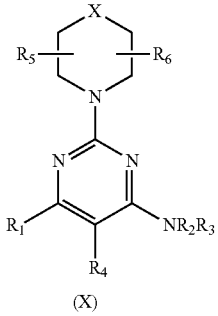

(X)

-continued

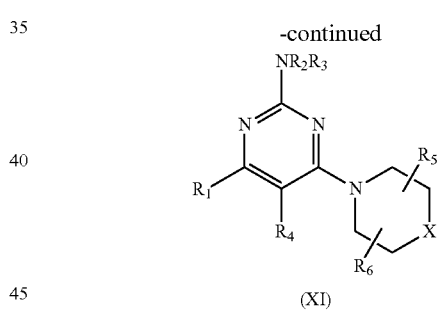

(XI)

With regard to the introduction of a substituent group in position 5 with respect to each of the regioisomers given above, the introduction can be done conveniently by using the conventional method as shown in Reaction Formula (8) given below.

[Chemical 22]

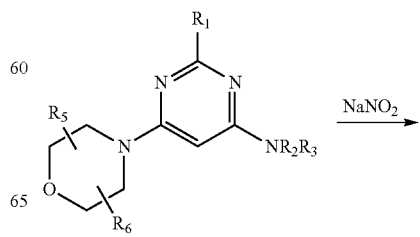

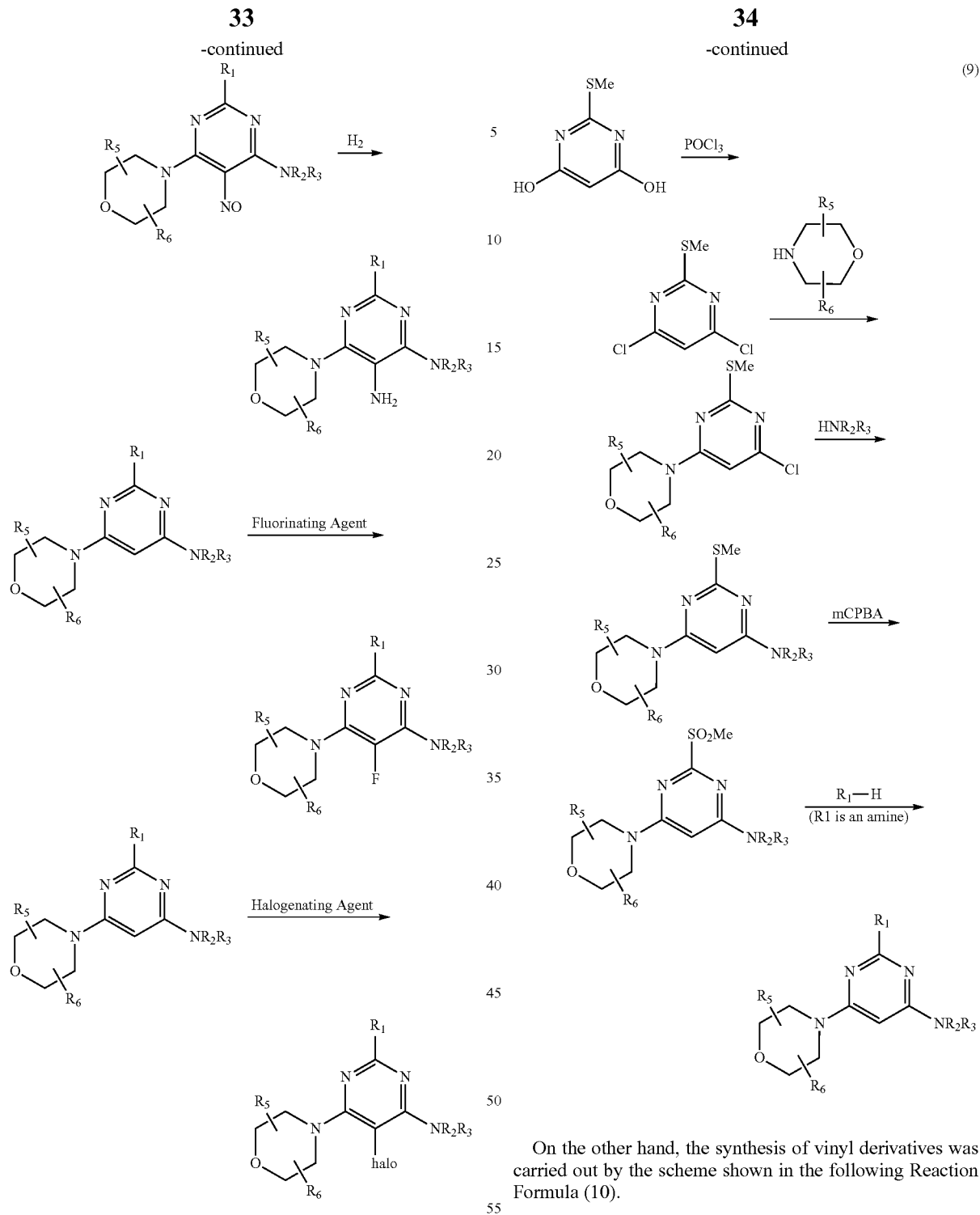

Additionally, since the two regioisomers (III) and (VI) are generated by the reaction of said regioisomer (II) and the amine (A-H), in order to determine the substitution position of the amine, confirmation is done by synthesizing pyrimidine derivatives by a synthesis method due to another scheme, as shown in the following Reaction Formula (9).

[Chemical 23]

On the other hand, the synthesis of vinyl derivatives was carried out by the scheme shown in the following Reaction Formula (10).

[Chemical 24]

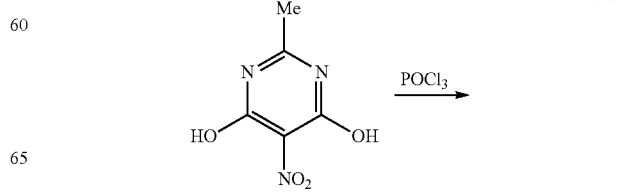

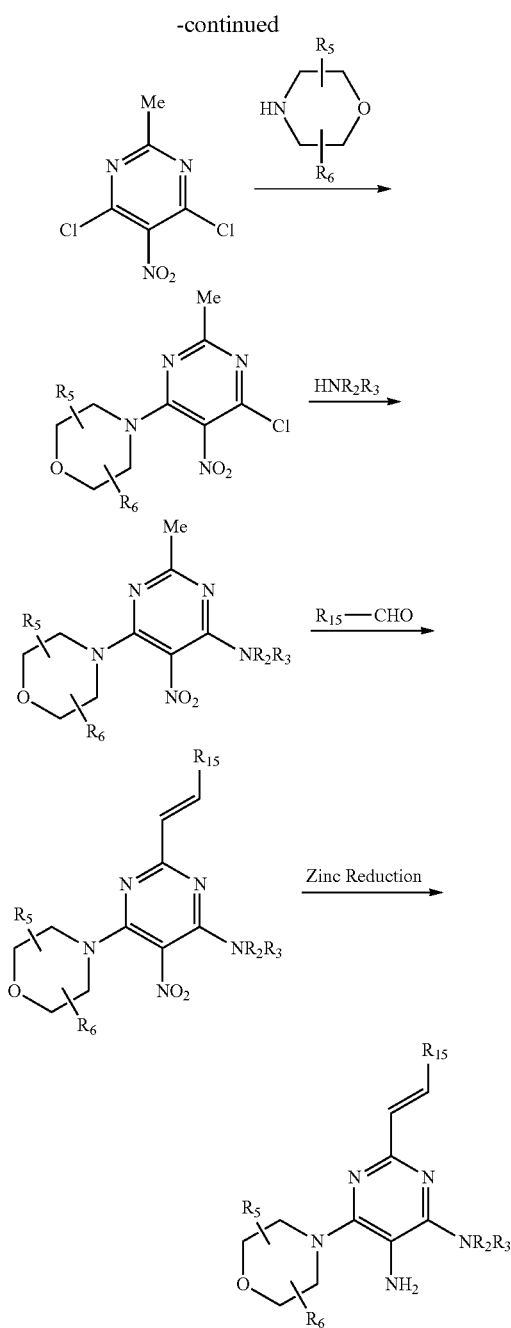

That is, in order to produce the compound of the present mode of embodiment represented by said General Formula (1a) or (1b), a portion of the explanation shall be repeated, but as explained in said Reaction Formula (6), trichloropyrimidine derivatives are reacted with from an equivalent amount to an excess of amine (A-H) at from −15 degrees Celsius to room temperature for 1 to 24 hours, preferably reacting at room temperature for 24 hours, and dichloropyrimidine derivatives are thereby obtained. Next, by reacting with an equivalent amount to an excess of amine (B-H) at from 0 degrees Celsius to 100 degrees Celsius for 1 to 24 hours, monochloropyrimidine derivatives are obtained. Further, by reacting with an equivalent amount to an excess of amine (C-H) at from room temperature to 100 degrees Celsius for 1 to 24 hours, the targeted pyrimidine derivative is obtained.

Further, by changing the order in which the amines are added during this time, the three types of regioisomers of said General Formula (7) can be created.

In these reactions, reactions are carried out as needed in a solvent, or under the presence of a hydrogen chloride scavenger. As hydrogen chloride scavengers, for example, sodium hydroxide, potassium hydroxide, sodium carbonate, potassium carbonate, triethylamine, or pyridine and the like may be used, and as solvents, acetone, toluene, hexane, xylene, dioxane, tetrahydrofuran or dichloroethane, N,N-dimethylformamide (DMF), and the like can be used. The present reaction may be carried out using a base as the solvent mentioned above. Additionally, in cases where the amine has a low boiling point, it is desirable for it to be carried out in a heated sealed tube.

Next, in cases where an amino group is to be introduced at position 5 of the pyrimidine ring, as shown in said Reaction Formula (8), after reacting a 5-unsubstituted pyrimidine derivative with 1 to 2 moles of sodium nitrite in an acetic acid or water-acetic acid mixture solvent at 0 degrees Celsius to room temperature for 5 minutes to 5 hours, this is reduced and the 5-amino form of General Formula (1a) or (1b) is obtained. In cases where hydrogenation is done using palladium carbon as a reducing agent, this is carried out with ethyl acetate, acetic acid, acetic acid-anhydrous acetic acid, ethanol, methanol, DMF, or methyl cellosolve as the solvent, at room temperature to 100 degrees Celsius, at 1 to 5 atmospheres, and for 0.5 to 48 hours. In cases where hydrosulfite sodium or sodium borohydride or the like are used as the reducing agent, this is carried out with methanol, ethanol, or a mixture thereof with water as the solvent, by reacting for 0.5 to 24 hours at room temperature to 100 degrees Celsius, with 1 to 10 moles of the reducing agent. The 5-amino derivative can be transformed into an amide or an alkylamino group by acylation or by further reduction.

In cases where a fluorine atom is to be introduced at position 5 of the pyrimidine ring, as shown in said Reaction Formula (9), a fluorinating agent DAST or BAST is added to an organic solvent (preferably a halogen based solvent) containing a 5-unsubstituted pyrimidine derivative, reacting for 1 to 24 hours at −78 degrees Celsius to room temperature, preferably reacting for 1 hour at −15 degrees Celsius, and a 5-fluoro pyrimidine derivative is obtained. In cases where a halogen atom is to be introduced at position 5 of the pyrimidine ring, as shown in Reaction Formula (8), a halogenating agent (NCS, NBS, and a radical intiator added as needed) is added to an organic solvent (preferably a halogen based solvent) containing a 5-unsubstituted pyrimidine derivative, reacting for 1 to 24 hours at −15 degrees Celsius to reflux temperature, preferably reacting for 1 hour at 100 degrees Celsius, and a pyrimidine derivative that is halogenated at position 5 is obtained.

In order to synthesize a pyrimidine derivative by a synthesis method using a different scheme for determining the substitution position of the amine, as shown in said Reaction Formula (9), with 4,6-dihydroxy-2-methylthiopyrimidine as the starting material, and by either reacting at a temperature of from room temperature to 100 degrees Celsius for 1 to 2 hours, using an excess of hydrogenation agent as a solvent, or by reacting 2 to 3 moles of a hydrogenation agent in a basic solvent such as dimethyl aniline or diethyl aniline, 4,6-dichloro-2-methylthiopyrimidine is obtained. Next, by reacting at 0 degrees Celsius to 100 degrees Celsius for 1 to 24 hours with an equivalent amount or an excess of an amine, a monochloropyrimidine derivative is obtained. Further, by reacting at room temperature to 100 degrees Celsius for 1 to 24 hours with an equivalent amount or an excess of an amine, the target 4,6-2-amino substituted pyrimidine derivative is obtained.

Next, in an organic solvent, preferably a halogen based solvent, an oxidizing agent (e.g., meta-chloroperoxybenzoic acid (mCPBA) or hydrogen peroxide or the like) is added, and by reacting for 1 to 24 hours at −15 degrees Celsius to 60 degrees Celsius, preferably reacting for 1 hour at −15 degrees Celsius, a sulfone derivative is obtained. Further, along with from an equivalent amount to an excess of amine, an organic solvent is added as needed, and by reacting from 1 to 24 hours at room temperature to reflux temperature, preferably reacting for 6 hours at 100 degrees Celsius, a pyrimidine derivative wherein position 1 is substituted with an amino group is obtained. In this reaction, the reaction is carried out as needed in a solvent, or under the presence of a hydrogen chloride scavenger. As hydrogen chloride scavengers, for example, sodium hydroxide, potassium hydroxide, sodium carbonate, potassium carbonate, triethylamine, or pyridine and the like may be used, and as solvents, acetone, toluene, hexane, xylene, dioxane, tetrahydrofuran or dichloroethane, N,N-dimethylformamide (DMF), and the like can be used. The present reaction may be carried out using a base as the solvent mentioned above. Additionally, in cases where the amine has a low boiling point, it is desirable for it to be carried out in a heated sealed tube.

For vinyl derivatives, as shown in said Reaction Formula (10), with 4,6-dihydroxy-5-nitro-2-methylpyrimidine as the starting material, similarly to the compounds described above, after chlorination, and 2 amino groups are introduced, reacting for 1 to 24 hours at room temperature to reflux temperature, preferably reacting for 6 hours at 100 degrees Celsius under the presence of an aromatic, a heterocyclic aldehyde, piperidine, or a base, and a 2-vinylpyrimidine derivative is obtained. Further, by carrying out zinc reduction, nitro groups were transformed into amino groups. As shown above, the amino group at position 5 was transformed into a different substituent group as needed.

Further, the products obtained in each of said procedures can, according to need, be separated and refined by conventional methods, for example, extraction, concentration, neutralization, filtering, recrystallization, column chromatography, and the like.

Example 1

4,6-dimorpholino-2-(4-phenylpiperazin-1-yl)pyrimidine (Compound 1)

(1-1) Synthesis of 4,6-dichloro-2-(4-phenylpiperazin-1-yl)pyrimidine and 2,4-dichloro-6-(4-phenylpiperazin-1-yl)pyrimidine (See Reaction Formula (11) below)

[Chemical 25]

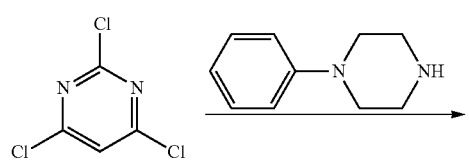

(11)

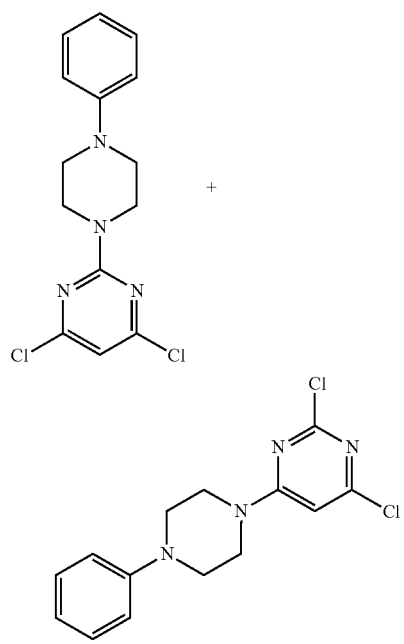

The synthesis method shall be explained concretely following the order below. 2,4,6-trichloropyrimidine (20 ml, 165 mmol) and triethylamine (27.7 ml) were dissolved in ether (200 ml), and phenylpiperadine (25.2 ml, 165 mmol) was added under ice cooling. After approximately 1 hour of agitation at room temperature, water was added, and extraction was carried out 2 times with ether. After washing the ether layer with saturated saline, drying was done with $MgSO_4$, and the solvent was distilled away under reduced pressure. Purification was done by silica gel chromatography (hexane:ethyl acetate=19:1), and 17.6 g (34% yield) of 4,6-dichloro-2-(4-phenylpiperazin-1-yl)pyrimidine was obtained. NMR data for the obtained 4,6-dichloro-2-(4-phenylpiperazin-1-yl)pyrimidine is shown below.

NMR ($CDCl_3$) δ: 3.23 (4H, m), 3.99 (4H, m), 6.56 (1H, s), 6.95 (3H, m), 7.27 (2H, m)

Further, a silica gel chromatography column was eluted with a different solvent (hexane:ethyl acetate=4:1), and 30 g (59% yield) of 2,4-dichloro-6-(4-phenylpiperazin-1-yl)pyrimidine was obtained. NMR data for the obtained 2,4-dichloro-6-(4-phenylpiperazin-1-yl)pyrimidine is shown below.

NMR ($CDCl_3$) δ: 3.25-3.29 (4H, m), 3.83 (4H, m), 6.47 (1H, s), 6.90-6.96 (3H, m), 7.26-7.33 (2H, m).

(1-2) Synthesis of 4,6-dimorpholino-2-(4-phenylpiperazin-1-yl)pyrimidine (Compound 1)

(See Reaction Formula (12) below)

[Chemical 26]

The synthesis method shall be explained concretely following the order below. Morpholine (30 ml, 340 mmol) was added to 4,6-dichloro-2-phenylpiperazino pyrimidine (5.3 g, 17.1 mmol) under ice cooling, and was agitated at 100 degrees Celsius overnight. After cooling to room temperature, water was added and extraction was carried out 2 times with ethyl acetate. The organic layer was washed with saturated saline, next, drying was done with MgSO$_4$, and the solvent was distilled away under reduced pressure. The residue was recrystallized by water-ethanol, and 5.6 g (80%) of 4,6-dimorpholino-2-(4-phenylpiperazin-1-yl)pyrimidine was obtained. The melting point measurement result, the MS measurement result, and the NMR data for the obtained Compound 1 are shown below.

Melting Point: 182-184 degrees C.,

MS m/z: 410 (M$^+$),

NMR (CDCl$_3$) δ: 3.21 (4H, m), 3.51 (8H, m), 3.77 (8H, m), 4.12 (4H, m), 5.09 (1H, s), 6.85-7.31 (5H, m).

Example 2

4-dimethylamino-6-morpholino-2-(4-phenylpiperazin-1-yl)pyrimidine (Compound 2)

Using a similar method to that for Example 1, a pyrimidine derivative having different substituent groups at positions 2, 4, and 6 was synthesized (See Reaction Formula (13) below).

[Chemical 27]

The synthesis method shall be explained concretely following the order below. 50% dimethylamine aqueous solution (2.9 ml) was added to a solution of 4,6-dichloro-2-(4-phenylpiperazin-1-yl)pyrimidine (1.01 g, 3.26 mmol) in tetrahydrofuran (10 ml) solution, and this was agitated overnight at room temperature. Water was added and extraction was carried out 2 times with ethyl acetate. After washing the organic layer in saturated saline, drying was done with MgSO$_4$, the solvent was distilled away under reduced pressure, and a 4-chloro-6-dimethylamino-2-(4-phenylpiperazin-1-yl)pyrimidine powder was obtained. This powder was used in the next reaction without separation and refinement. Morpholine (6.0 ml) was added to this powder, and this was agitated at 100 degrees Celsius overnight. After cooling, water was added and extraction was carried out 2 times with dichloromethane. The organic layer was washed with saturated saline, drying was done with MgSO$_4$, and the solvent was distilled away under reduced pressure. The residue was washed with ether, and 810 mg (two step yield: 70%) of coarse crystals of 6-dimethylamino-4-morpholino-2-(4-phenylpiperazin-1-yl)pyrimidine was obtained. The melting point measurement result, the MS measurement result, and the NMR data for the obtained Compound 2 are shown below.

Melting Point: 149 degrees C.,
MS m/z: 236, 368 (M+),
NMR (CDCl$_3$) δ: 3.04 (6H, s), 3.21 (4H, m), 3.50 (4H, m), 3.78 (4H, m), 3.90 (4H, m), 5.00 (1H, s), 6.84-6.98 (3H, m), 7.25-7.31 (2H, m).

Example 3

Using a similar method to that for Examples 1 and 2, the following compounds were produced from corresponding starting materials (Compounds 3 to 50).

2,4-dimorpholino-6-(4-phenylpiperazin-1-yl)pyrimidine (Compound 3)

(See Formula (14) below)
The NMR data for the obtained Compound 3 are shown below.

[Chemical 28]

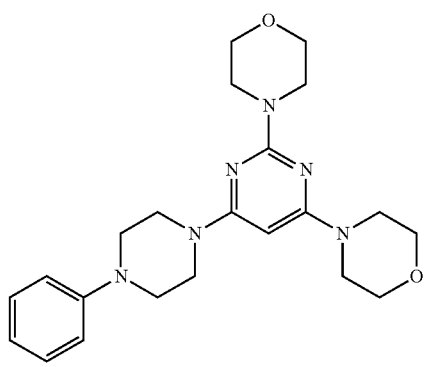

(14)

NMR (CDCl$_3$) δ: 3.24 (4H, m), 3.50 (4H, m), 3.73 (16H, m), 5.15 (1H, s), 6.86-6.97 (3H, m), 7.26-7.31 (2H, m).

2-(4-benzylpiperidin-1-yl)-4,6-dimorpholinopyrimidine (Compound 4)

(See Formula (15) below)
The NMR data for the obtained Compound 4 are shown below.

[Chemical 29]

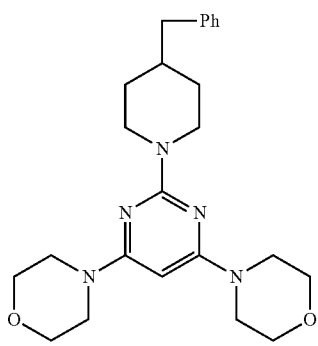

(15)

NMR (CDCl$_3$) δ: 1.10-1.30 (2H, m), 1.60-1.80 (3H, m), 2.55 (2H, d), 2.70 (2H, m), 3.48 (8H, m), 3.75 (8H, m), 4.64 (2H, m), 5.04 (1H, s), 7.10-7.31 (5H, m).

4-(4-benzylpiperidin-1-yl)-2,6-dimorpholinopyrimidine (Compound 5)

(See Formula (16) below)
The NMR data for the obtained Compound 5 are shown below.

[Chemical 30]

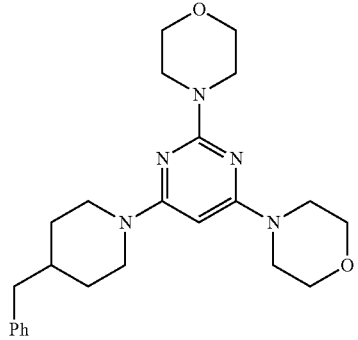

(16)

NMR (CDCl$_3$) δ: 1.20 (2H, m), 1.60-1.80 (3H, m), 2.54 (2H, d), 2.71 (2H, m), 3.47 (4H, m), 3.67-3.77 (12H, m), 4.25 (2H, m), 5.11 (1H, s), 7.10-7.30 (5H, m).

4,6-dimorpholino-2-(1,2,3,4-tetrahydro-2H-isoquinolin-2-yl)pyrimidine (Compound 6)

(See Formula (17) below)
The NMR data for the obtained Compound 6 are shown below.

[Chemical 31]

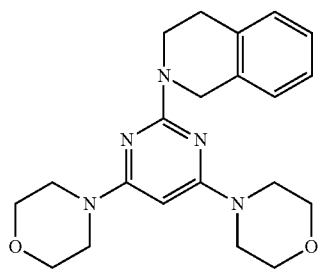

(17)

NMR (CDCl$_3$) δ: 2.88 (2H, m), 3.52 (8H, m), 3.78 (8H, m), 3.99 (2H, m), 4.86 (2H, s), 5.08 (1H, s), 7.16 (4H, m).

2-(6-fluoro-2-methyl-1,2,3,4-tetrahydroquinolin-1-yl)-4,6-dimorpholinopyrimidine (Compound 7)

(See Formula (18) below)
The NMR data for the obtained Compound 7 are shown below.

[Chemical 32]

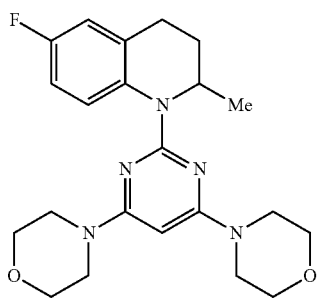

(18)

NMR (CDCl$_3$) δ: 1.20 (3H, d, J=6.4 Hz), 1.57 (1H, m), 2.22 (1H, m), 2.64 (2H, m), 3.47 (8H, m), 3.75 (8H, m), 5.04 (1H, m), 5.17 (1H, s), 6.78 (2H, m), 7.63 (1H, m).

4,6-dimorpholino-2-(1,2,3,4-tetrahydroquinolin-1-yl) pyrimidine (Compound 8)

(See Formula (19) below)

The NMR data for the obtained Compound 8 are shown below.

[Chemical 33]

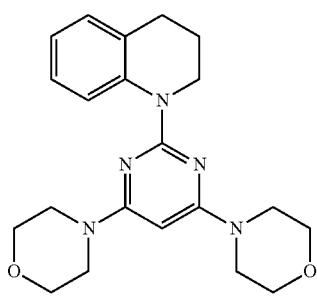

(19)

NMR (CDCl$_3$) δ: 1.98 (2H, m), 2.77 (2H, m), 3.49 (8H, m), 3.75 (8H, m), 4.00 (2H, m), 5.19 (1H, s), 6.91 (1H, m), 7.09 (2H, m), 7.80 (1H, m).

2,4-dimorpholino-6-(1,2,3,4-tetrahydroquinolin-1-yl) pyrimidine (Compound 9)

(See Formula (20) below)

The NMR data for the obtained Compound 9 are shown below.

[Chemical 34]

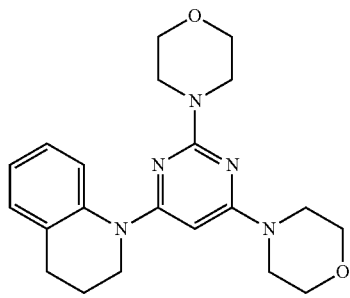

(20)

NMR (CDCl$_3$) δ: 1.92 (2H, m), 2.76 (2H, m), 3.43 (4H, m), 3.72 (4H, m), 3.74 (8H, s), 3.92 (2H, m), 5.62 (1H, s), 6.93 (1H, m), 7.12 (2H, m), 7.40 (1H, m).

2-(isoindolin-2-yl)-4,6-dimorpholinopyrimidine (Compound 10)

(See Formula (21) below)

The melting point measurement result, the MS measurement result, and the NMR data for the obtained Compound 10 are shown below.

[Chemical 35]

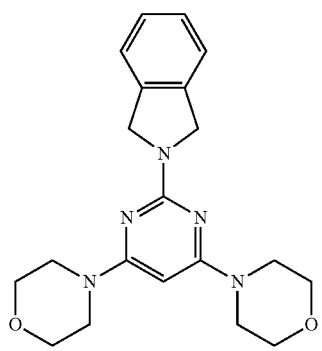

(21)

Melting Point: 194.0-198.0 degrees C.

MS m/z: 367 (M$^+$),

NMR (CDCl$_3$) δ: 3.55 (8H, t, J=4.9 Hz), 3.77 (8H, t, J=4.9 Hz), 4.83 (4H, s), 5.10 (1H, s), 7.20-7.30 (4H, m).

2-(4-benzylpiperazin-1-yl)-4,6-dimorpholinopyrimidine (Compound 11)

(See Formula (22) below)

The NMR data for the obtained Compound 11 are shown below.

[Chemical 36]

-continued (22)

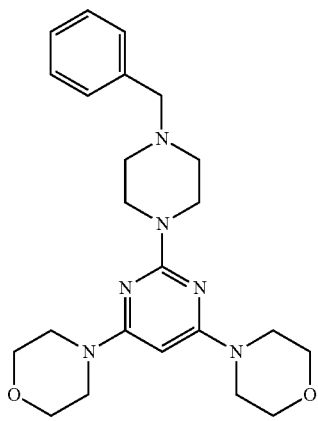

NMR (CDCl$_3$) δ: 2.46 (4H, t, J=5.1 Hz), 3.47 (8H, t, J=4.7 Hz), 3.53 (2H, s), 3.72-3.77 (12H, m), 5.05 (1H, s), 7.23-7.36 (5H, m).

4,6-dimorpholino-2-[4-(pyridin-2-yl)piperazin-1-yl]pyrimidine (Compound 12)

(See Formula (23) below)
The NMR data for the obtained Compound 12 are shown below.

[Chemical 37]

(23)

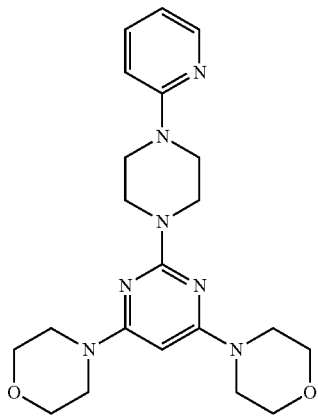

NMR (CDCl$_3$) δ: 3.53 (8H, m), 3.59 (4H, m), 3.77 (8H, m), 3.85 (4H, m), 5.09 (1H, s), 6.61-6.68 (2H, m), 7.50 (1H, m), 8.21 (1H, m).

2,4-dimorpholino-6-[4-(pyridin-2-yl)piperazin-1-yl]pyrimidine (Compound 13)

(See Formula (24) below)
The NMR data for the obtained Compound 13 are shown below.

[Chemical 38]

-continued (24)

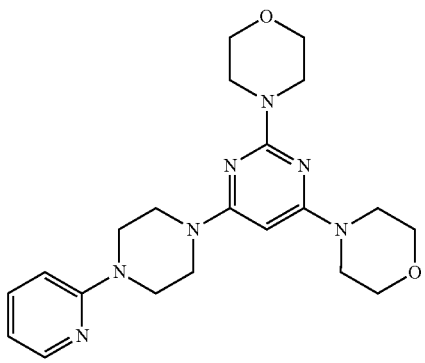

NMR (CDCl$_3$) δ: 3.50-3.87 (24H, m), 5.14 (1H, s), 6.65 (2H, m), 7.50 (1H, m), 8.21 (1H, m).

4,6-dimorpholino-2-[4-(pyrimidin-2-yl)piperazin-1-yl]pyrimidine (Compound 14)

(See Formula (25) below)
The melting point measurement result, the MS measurement result, and the NMR data for the obtained Compound 14 are shown below.

[Chemical 39]

(25)

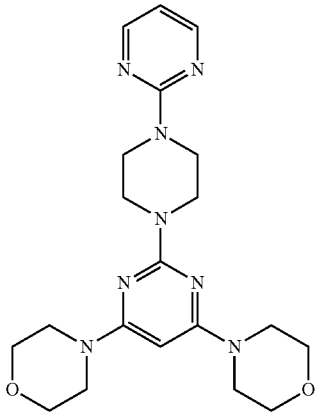

Melting Point: 212.0-215.0 degrees C.,
MS m/z: 412 (M$^+$),
NMR (CDCl$_3$) δ: 3.52 (8H, t, J=4.9 Hz), 3.75-3.90 (16H, m), 5.10 (1H, s), 6.50 (1H, t, J=4.7 Hz), 8.33 (2H, d, J=4.7 Hz).

2,4-dimorpholino-6-[4-(pyrimidin-2-yl)piperazin-1-yl]pyrimidine (Compound 15)

(See Formula (26) below)
The MS measurement result, and the NMR data for the obtained Compound 15 are shown below.

[Chemical 40]

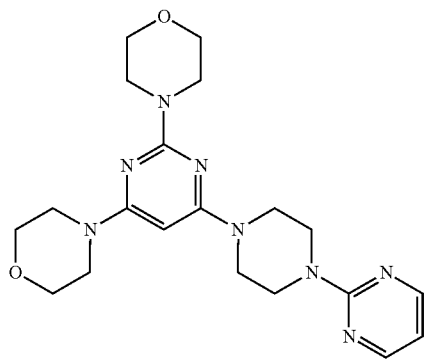

(26)

MS m/z: 412 (M+),

NMR (CDCl$_3$) δ: 3.51 (4H, t, J=4.9 Hz), 3.60-3.95 (20H, m), 5.12 (1H, s), 6.52 (1H, t, J=4.7 Hz), 8.33 (2H, d, J=4.7 Hz).

4,6-dimorpholino-2-(3-phenylpiperazin-1-yl)pyrimidine (Compound 16)

(See Formula (27) below)
The melting point measurement result, the MS measurement result, and the NMR data for the obtained Compound 16 are shown below.

[Chemical 41]

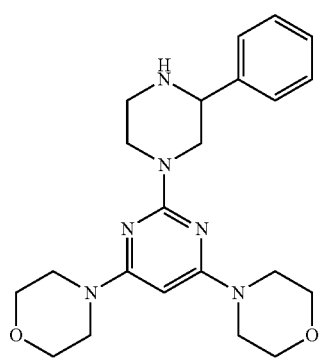

(27)

Melting Point: 100.0-104.0 degrees C.,
MS m/z: 410 (M+),

NMR (CDCl$_3$) δ: 2.80 (1H, dd, J=13.1, 10.6 Hz), 2.97 (2H, d, J=10.6 Hz), 3.13 (1H, d, J=8.2 Hz), 3.47 (8H, t, J=4.7 Hz), 3.75 (10H, t, J=4.7 Hz), 4.64 (2H, d, J=10.6 Hz), 5.06 (1H, s), 7.25-7.45 (5H, m).

2,4-dimorpholino-6-(3-phenylpiperazin-1-yl)pyrimidine (Compound 17)

(See Formula (28) below)
The melting point measurement result, the MS measurement result, and the NMR data for the obtained Compound 17 are shown below.

[Chemical 42]

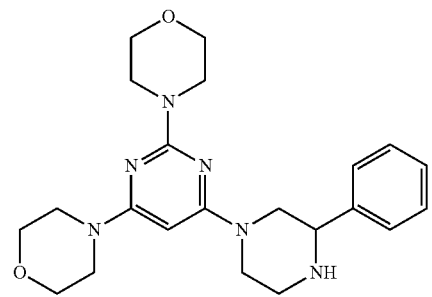

(28)

Melting Point: 181.0-185.0 degrees C.,
MS m/z: 410 (M+),

NMR (CDCl$_3$) δ: 2.78 (1H, dd, J=13.1, 10.6 Hz), 2.90-3.00 (2H, m), 3.10-3.20 (1H, m), 3.46 (4H, t, J=4.7 Hz), 3.64-85 (14H, m), 4.21 (2H, t, J=13.5 Hz), 5.10 (1H, s), 7.25-7.45 (5H, m).

4,6-dimorpholino-2-(4-nitrophenylpiperazin-1-yl)pyrimidine (Compound 18)

(See Formula (29) below)
The NMR data for the obtained Compound 18 are shown below.

[Chemical 43]

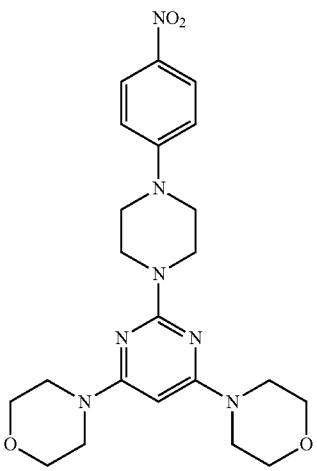

(29)

NMR (CDCl$_3$) δ: 3.49 (12H, m), 3.77 (8H, m), 3.91 (4H, m), 5.11 (1H, s), 6.82 (2H, d, J=9.5 Hz), 8.16 (2H, d, J=9.5 Hz).

2,4-dimorpholino-6-(4-nitrophenylpiperazin-1-yl)pyrimidine (Compound 19)

(See Formula (30) below)
The NMR data for the obtained Compound 19 are shown below.

[Chemical 44]

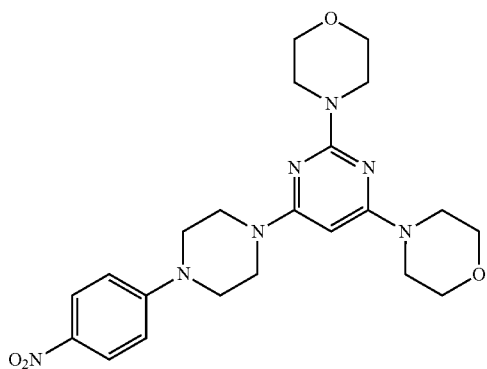

(30)

NMR (CDCl₃) δ: 3.52 (8H, m), 3.75 (16H, m), 5.11 (1H, s), 6.80 (2H, d, J=9.4 Hz), 8.16 (2H, d, J=9.4 Hz).

2-[4-(4-fluorophenyl)piperazin-1-yl]-4,6-dimorpholinopyrimidine (Compound 20)

(See Formula (31) below)
The melting point measurement result, the MS measurement result, and the NMR data for the obtained Compound 20 are shown below.

[Chemical 45]

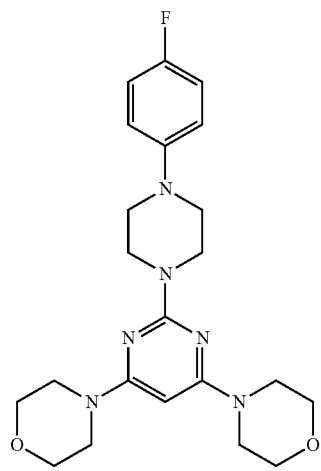

(31)

Melting Point: 196.0-199.0 degrees C.,
MS m/z: 428 (M⁺),
NMR (CDCl₃) δ: 3.12 (4H, t, J=5.0 Hz), 3.51 (8H, t, J=4.9 Hz), 3.77 (8H, t, J=4.9 Hz), 3.88 (4H, t, J=5.0 Hz), 5.09 (1H, s), 6.85-7.00 (4H, m).

4-[4-(4-fluorophenyl)piperazin-1-yl]-2,6-dimorpholinopyrimidine (Compound 21)

(See Formula (32) below)
The melting point measurement result, the MS measurement result, and the NMR data for the obtained Compound 21 are shown below.

[Chemical 46]

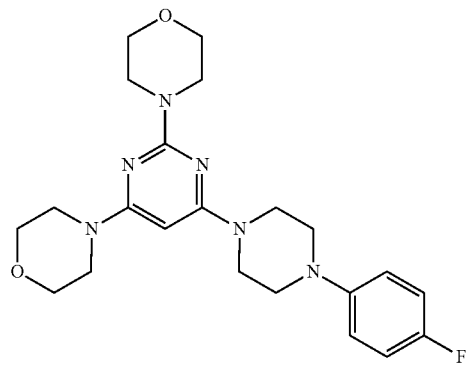

(32)

Melting Point: 215.0-218.0 degrees C.,
MS m/z: 428 (M⁺),
NMR (CDCl₃) δ: 3.15 (4H, t, J=5.0 Hz), 3.51 (4H, t, J=5.0 Hz), 3.65-3.80 (16H, m), 5.13 (1H, s), 6.85-7.05 (4H, m).

2-[4-(4-methylphenyl)piperazin-1-yl]-4,6-dimorpholinopyrimidine (Compound 22)

(See Formula (33) below)
The melting point measurement result, the MS measurement result, and the NMR data for the obtained Compound 22 are shown below.

[Chemical 47]

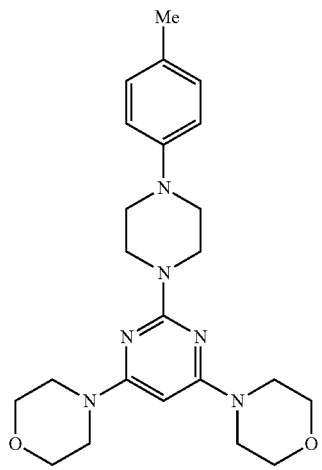

(33)

Melting Point: 191.0-194.0 degrees C.,
MS m/z: 424 (M⁺),
NMR (CDCl₃) δ: 2.28 (3H, s), 3.21 (4H, t, J=5.0 Hz), 3.51 (8H, t, J=4.9 Hz), 3.77 (8H, t, J=4.9 Hz), 3.88 (4H, t, J=5.0 Hz), 5.09 (1H, s), 6.89 (2H, d, J=8.6 Hz), 7.09 (2H, d, J=8.6 Hz).

4-[4-(4-methylphenyl)piperazin-1-yl]-2,6-dimorpholinopyrimidine (Compound 23)

(See Formula (34) below)
The melting point measurement result, the MS measurement result, and the NMR data for the obtained Compound 23 are shown below.

[Chemical 48]

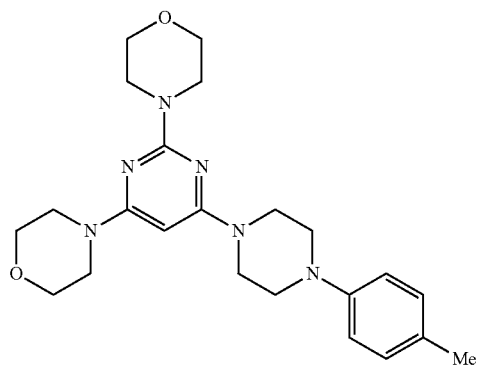

(34)

Melting Point: 219.0-222.0 degrees C.,
MS m/z: 428 (M+),
NMR (CDCl₃) δ: 2.28 (3H, s), 3.18 (4H, t, J=5.0 Hz), 3.48 (4H, t, J=5.0 Hz), 3.65-3.80 (16H, m), 5.16 (1H, s), 6.91 (2H, d, J=8.6 Hz), 7.10 (2H, d, J=8.6 Hz).

2-[4-(4-acetylphenyl)piperazin-1-yl]-4,6-dimorpholinopyrimidine (Compound 24)

(See Formula (35) below)
The melting point measurement result, the MS measurement result, and the NMR data for the obtained Compound 24 are shown below.

[Chemical 49]

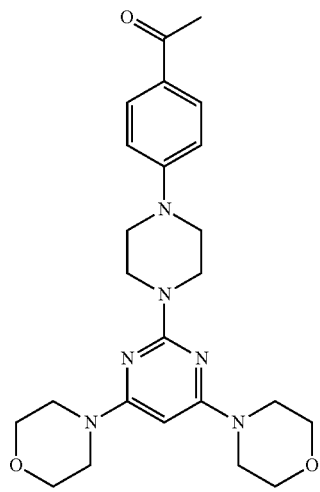

(35)

Melting Point: 162.0-166.0 degrees C.,
MS m/z: 452 (M+),
NMR (CDCl₃) δ: 2.53 (3H, s), 3.40 (4H, t, J=5.0 Hz), 3.51 (8H, t, J=4.9 Hz), 3.76 (8H, t, J=4.9 Hz), 3.89 (4H, t, J=5.0 Hz), 5.10 (1H, s), 6.89 (2H, d, J=9.1 Hz), 7.89 (2H, d, J=9.1 Hz).

4-[4-(4-acetylphenyl)piperazin-1-yl]-2,6-dimorpholinopyrimidine (Compound 25)

(See Formula (36) below)
The melting point measurement result, the MS measurement result, and the NMR data for the obtained Compound 25 are shown below.

[Chemical 50]

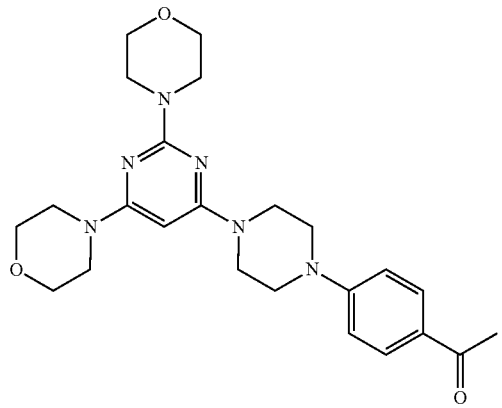

(36)

Melting Point: 198.0-201.0 degrees C.,
MS m/z: 452 (M+),
NMR (CDCl₃) δ: 2.53 (3H, s), 3.45 (4H, t, J=5.0 Hz), 3.49 (4H, t, J=5.0 Hz), 3.65-3.80 (16H, m), 5.12 (1H, s), 6.88 (2H, d, J=8.9 Hz), 7.90 (2H, d, J=8.9 Hz).

2-[4-(2-chlorophenyl)piperazin-1-yl]-4,6-dimorpholinopyrimidine (Compound 26)

(See Formula (37) below)
The melting point measurement result, the MS measurement result, and the NMR data for the obtained Compound 26 are shown below.

[Chemical 51]

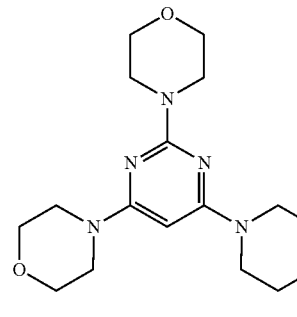

(37)

Melting Point: 156 degrees C.,
MS m/z: 444 (M+),
NMR (CDCl₃) δ: 3.07 (4H, t, J=5.0 Hz), 3.52 (8H, t, J=4.8 Hz), 3.77 (8H, t, J=4.8 Hz), 3.91 (4H, t, J=5.0 Hz), 5.09 (1H, s), 6.96-7.06 (2H, m), 7.20-7.23 (1H, m), 7.38 (1H, dd, J=1.5, 7.9 Hz).

2-[4-(2-ethoxyphenyl)piperazin-1-yl]-4,6-dimorpholinopyrimidine (Compound 27)

(See Formula (38) below)
The melting point measurement result, the MS measurement result, and the NMR data for the obtained Compound 27 are shown below.

[Chemical 52]

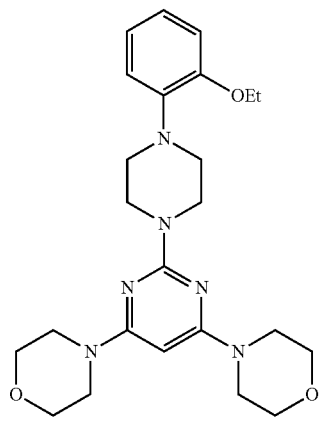
(38)

Melting Point: 184 degrees C.,
MS m/z: 454 (M$^+$),
NMR (CDCl$_3$) δ: 1.48 (3H, t, J=7.0 Hz), 3.11 (4H, t, J=4.9 Hz), 3.52 (8H, t, J=4.8 Hz), 3.77 (8H, t, J=4.8 Hz), 3.91 (4H, t, J=4.9 Hz), 4.09 (2H, q, J=7.0 Hz), 5.09 (1H, s), 6.86-7.98 (4H, m).

2-[4-(2-methylphenyl)piperazin-1-yl]-4,6-dimorpholino-pyrimidine (Compound 28)

(See Formula (39) below)
The melting point measurement result, the MS measurement result, and the NMR data for the obtained Compound 28 are shown below.

[Chemical 53]

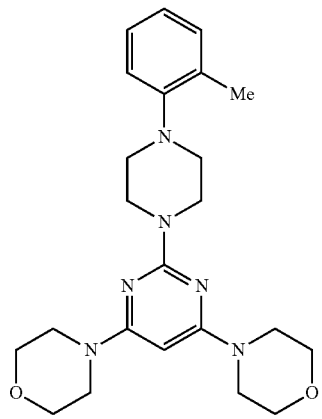
(39)

Melting Point: 149 degrees C.,
MS m/z: 424 (M$^+$),
NMR (CDCl$_3$) δ: 2.35 (3H, s), 2.93 (4H, t, J=4.9 Hz), 3.52 (8H, t, J=4.9 Hz), 3.76 (8H, q, J=4.9 Hz), 3.87 (4H, t, J=4.9 Hz), 5.09 (1H, s), 6.97-7.02 (2H, m), 7.16-7.19 (2H, m).

4,6-dimorpholino-2-[4-(2,3-xylyl)piperazin-1-yl]pyrimidine (Compound 29)

(See Formula (40) below)
The melting point measurement result, the MS measurement result, and the NMR data for the obtained Compound 29 are shown below.

[Chemical 54]

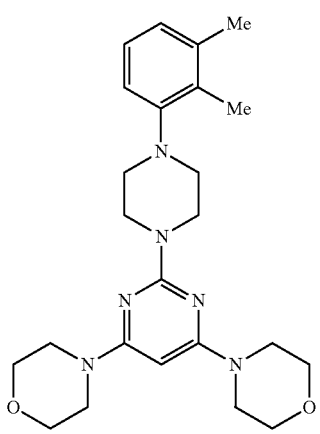
(40)

Melting Point: 141 degrees C.,
MS m/z: 438 (M$^+$),
NMR (CDCl$_3$) δ: 2.27 (3H, s), 2.28 (3H, s), 2.90 (4H, t, J=4.7 Hz), 3.51 (8H, t, J=4.9 Hz), 3.73-3.82 (12H, m), 5.09 (1H, s), 6.88-6.91 (2H, m), 7.08 (1H, t, J=7.8 Hz).

2-[4-(4-hydroxyphenyl)piperazin-1-yl]-4,6-dimorpholinopyrimidine (Compound 30)

(See Formula (41) below)
The melting point measurement result, the MS measurement result, and the NMR data for the obtained Compound 30 are shown below.

[Chemical 55]

(41)

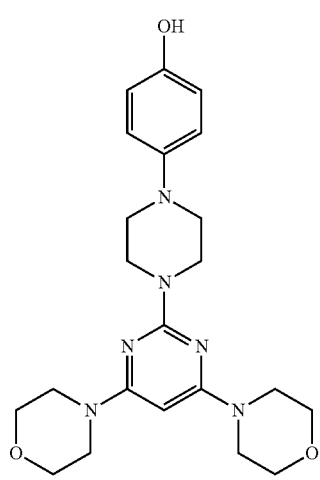

Melting Point: 113 degrees C.,
MS m/z: 426 (M+),
NMR (CDCl$_3$) δ: 3.07 (4H, t, J=5.1 Hz), 3.51 (8H, t, J=4.8 Hz), 3.77 (8H, t, J=4.8 Hz), 3.88 (4H, t, J=5.1 Hz), 5.09 (1H, s), 6.77 (2H, d, J=8.9 Hz), 6.89 (2H, d, J=8.9 Hz).

2-[4-(2-fluorophenyl)piperazin-1-yl]-4,6-dimorpholinopyrimidine (Compound 31)

(See Formula (42) below)
The melting point measurement result, the MS measurement result, and the NMR data for the obtained Compound 31 are shown below.

[Chemical 56]

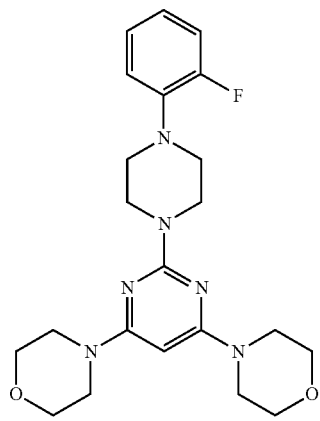

(42)

Melting Point: 148 degrees C.,
MS m/z: 428 (M+),
NMR (CDCl$_3$) δ: 3.10 (4H, t, J=4.9 Hz), 3.51 (8H, t, J=4.9 Hz), 3.77 (8H, t, J=4.9 Hz), 3.90 (4H, t, J=4.9 Hz), 5.09 (1H, s), 6.91-7.09 (4H, m).

2-[4-(2-methoxyphenyl)piperazin-1-yl]-4,6-dimorpholinopyrimidine (Compound 32)

(See Formula (43) below)
The melting point measurement result, the MS measurement result, and the NMR data for the obtained Compound 32 are shown below.

[Chemical 57]

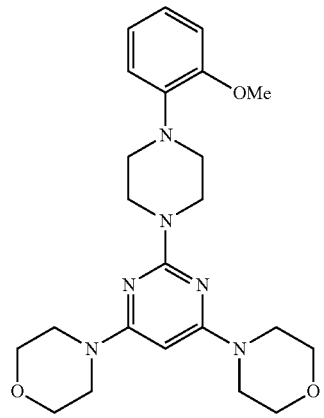

(43)

Melting Point: 214 degrees C.,
MS m/z: 440 (M+),
NMR (CDCl$_3$) δ: 3.08 (4H, t, J=4.9 Hz), 3.51 (8H, t, J=4.9 Hz), 3.77 (8H, t, J=4.9 Hz), 3.89 (3H, s), 3.92 (4H, t, J=4.9 Hz), 5.09 (1H, s), 6.87-7.05 (4H, m).

2-[4-(4-chlorophenyl)piperazin-1-yl]-4,6-dimorpholinopyrimidine (Compound 33)

(See Formula (44) below)
The melting point measurement result, the MS measurement result, and the NMR data for the obtained Compound 33 are shown below.

[Chemical 58]

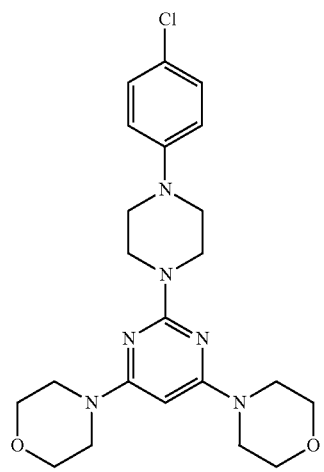

(44)

Melting Point: 213 degrees C.,
MS m/z: 444 (M+),
NMR (CDCl$_3$) δ: 3.16 (4H, t, J=5.0 Hz), 3.51 (8H, t, J=4.8 Hz), 3.77 (8H, t, J=4.8 Hz), 3.88 (4H, t, J=5.0 Hz), 5.09 (1H, s), 6.87 (2H, d, J=8.9 Hz), 7.22 (2H, d, J=8.9 Hz).

2-(4-cyano-4-phenylpiperidin-1-yl)-4,6-dimorpholinopyrimidine (Compound 34)

(See Formula (45) below)

The NMR data for the obtained Compound 34 are shown below.

[Chemical 59]

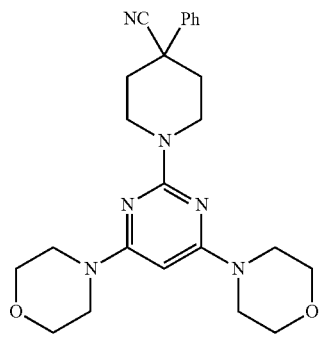

(45)

NMR (CDCl$_3$) δ: 1.95-2.15 (4H, m), 3.25 (2H, m), 3.50 (8H, m), 3.82 (8H, m), 4.90 (2H, m), 5.10 (1H, s), 7.26-7.50 (5H, m).

4-(4-cyano-4-phenylpiperidin-1-yl)-2,6-dimorpholinopyrimidine (Compound 35)

(See Formula (46) below)
The NMR data for the obtained Compound 35 are shown below.

[Chemical 60]

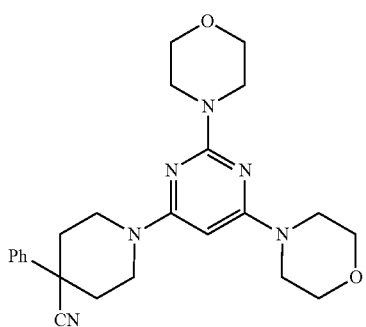

(46)

NMR (CDCl$_3$) δ: 2.00-2.16 (4H, m), 3.32 (2H, m), 3.51 (4H, m), 3.72 (12H, m), 4.47 (2H, m), 5.18 (1H, s), 7.31-7.50 (5H, m).

2-(4-hydroxy-4-phenylpiperidin-1-yl)-4,6-dimorpholinopyrimidine (Compound 36)

(See Formula (47) below)
The melting point measurement result, the MS measurement result, and the NMR data for the obtained Compound 36 are shown below.

[Chemical 61]

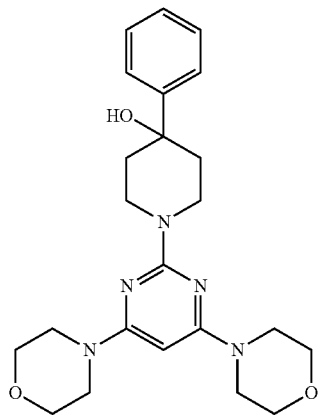

(47)

Melting Point: 157.0-159.0 degrees C.,
MS m/z: 425 (M$^+$),
NMR (CDCl$_3$) δ: 1.74 (2H, d, J=12.2 Hz), 2.06 (2H, dd, J=18.8, 6.6 Hz), 3.28 (2H, dd, J=12.9, 2.5 Hz), 3.53 (8H, t, J=5.0 Hz), 3.71 (8H, t, J=4.7 Hz), 4.62 (2H, d, J=13.0 Hz), 5.06 (1H, s), 7.26 (1H, m), 7.34 (2H, t, J=7.4 Hz), 7.48 (2H, d, J=7.4 Hz).

4-(4-hydroxy-4-phenylpiperidin-1-yl)-2,6-dimorpholinopyrimidine (Compound 37)

(See Formula (48) below)
The melting point measurement result, the MS measurement result, and the NMR data for the obtained Compound 37 are shown below.

[Chemical 62]

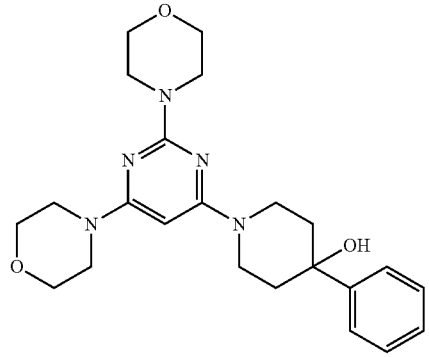

(48)

Melting Point: 189.0-192.0 degrees C.,
MS m/z: 425 (M$^+$),
NMR (CDCl$_3$) δ: 1.76 (2H, d, J=12.0 Hz), 2.07 (2H, dd, J=18.8, 6.6 Hz), 3.31 (2H, dd, J=12.9, 2.5 Hz), 3.48 (4H, t, J=5.0 Hz), 3.74 (12H, m), 4.22 (2H, d, J=13.2 Hz), 5.12 (1H, s), 7.28 (1H, t, J=7.2 Hz), 7.34 (2H, t, J=7.4 Hz), 7.46 (2H, d, J=7.4 Hz).

2-(4-acetyl-4-phenylpiperidin-1-yl)-4,6-dimorpholinopyrimidine (Compound 38)

(See Formula (49) below)
The melting point measurement result, the MS measurement result, and the NMR data for the obtained Compound 38 are shown below.

[Chemical 63]

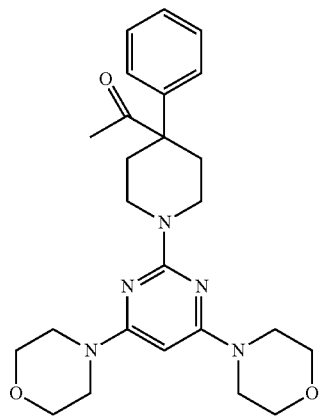

(49)

Melting Point: 115.0-118.0 degrees C.,
MS m/z: 451 (M⁺),
NMR (CDCl$_3$) δ: 1.95 (3H, s), 2.00-2.10 (2H, m), 2.42 (2H, d, J=14.0 Hz), 3.20-3.30 (2H, m), 3.49 (8H, t, J=4.9 Hz), 3.76 (8H, t, J=4.9 Hz), 4.15-4.25 (2H, m), 5.05 (1H, s), 7.25-7.40 (5H, m).

4-(4-acetyl-4-phenylpiperidin-1-yl)-2,6-dimorpholinopyrimidine (Compound 39)

(See Formula (50) below)
The melting point measurement result, the MS measurement result, and the NMR data for the obtained Compound 39 are shown below.

[Chemical 64]

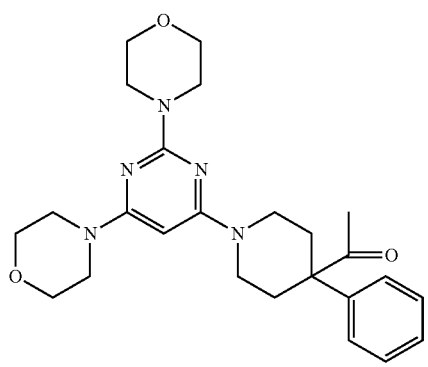

(50)

Melting Point: 146.0-147.0 degrees C.,
MS m/z: 451 (M⁺),
NMR (CDCl$_3$) δ: 1.94 (3H, s), 2.00-2.10 (2H, m), 2.44 (2H, d, J=14.0 Hz), 3.20-3.30 (2H, m), 3.48 (4H, t, J=4.9 Hz), 3.70-3.80 (12H, m), 3.90-4.00 (2H, m), 5.12 (1H, s), 7.25-7.40 (5H, m).

4,6-dimorpholino-2-[4-phenyl (1,2,5,6-tetrahydropyridin-1-yl)]pyrimidine (Compound 40)

(See Formula (51) below)
The melting point measurement result, the MS measurement result, and the NMR data for the obtained Compound 40 are shown below.

[Chemical 65]

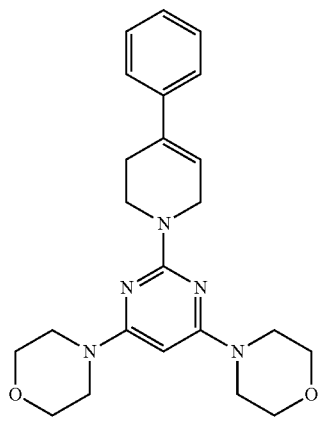

(51)

Melting Point: 157.0-160.0 degrees C.,
MS m/z: 407 (M⁺),
NMR (CDCl$_3$) δ: 2.57 (2H, brs), 3.51 (8H, t, J=4.8 Hz), 3.76 (8H, t, J=4.8 Hz), 3.97 (2H, t, J=5.7 Hz), 4.33 (2H, brs), 5.07 (1H, s), 6.12 (1H, brs), 7.25-7.40 (5H, m).

2,4-dimorpholino-6-[4-phenyl (1,2,5,6-tetrahydropyridin-1-yl)]pyrimidine (Compound 41)

(See Formula (52) below)
The melting point measurement result, the MS measurement result, and the NMR data for the obtained Compound 41 are shown below.

[Chemical 66]

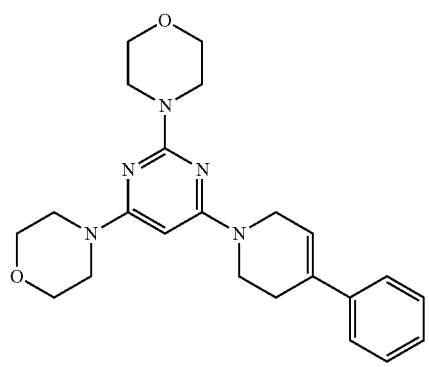

(52)

Melting Point: 165.0-168.0 degrees C.,
MS m/z: 407 (M⁺),
NMR (CDCl$_3$) δ: 2.62 (2H, brs), 3.54 (4H, t, J=4.8 Hz), 3.61 (14H, t, J=4.8 Hz), 4.22 (2H, brs), 6.09 (1H, brs), 5.11 (1H, s), 7.25-7.40 (5H, m).

2-[4-(4-cyclohexyl)piperazin-1-yl]-4,6-dimorpholinopyrimidine (Compound 42)

(See Formula (53) below)
The melting point measurement result, the MS measurement result, and the NMR data for the obtained Compound 42 are shown below.

[Chemical 67]

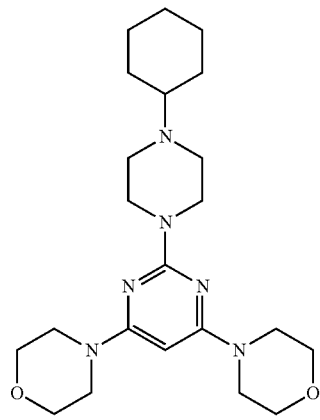

(53)

Melting Point: 171.0-174.0 degrees C.,
MS m/z: 416 (M+),
NMR (CDCl$_3$) δ: 1.15-1.25 (4H, m), 1.60-1.70 (2H, m), 1.75-1.95 (4H, m), 2.27 (1H, brs), 2.58 (4H, t, J=5.0 Hz), 3.49 (8H, t, J=5.0 Hz), 3.74 (12H, t, J=5.0 Hz), 5.06 (1H, s).

4-[4-(4-cyclohexyl)piperazin-1-yl]-2,6-dimorpholinopyrimidine (Compound 43)

(See Formula (54) below)
The melting point measurement result, the MS measurement result, and the NMR data for the obtained Compound 43 are shown below.

[Chemical 68]

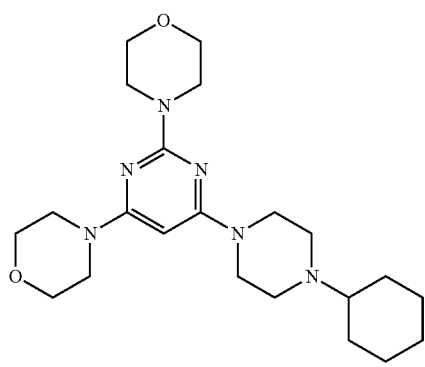

(54)

Melting Point: 144.0-147.0 degrees C.,
MS m/z: 416 (M+),
NMR (CDCl$_3$) δ: 1.15-1.25 (4H, m), 1.60-1.70 (2H, m), 1.80-1.95 (4H, m), 2.28 (1H, brs), 2.61 (4H, t, J=5.0 Hz), 3.50 (8H, t, J=5.0 Hz), 3.74 (12H, t, J=5.7 Hz), 5.10 (1H, s).

5-methyl-4,6-dimorpholino-2-(4-phenylpiperazin-1-yl)pyrimidine (Compound 44)

(See Formula (55) below)
The melting point measurement result, the MS measurement result, and the NMR data for the obtained Compound 44 are shown below.

[Chemical 69]

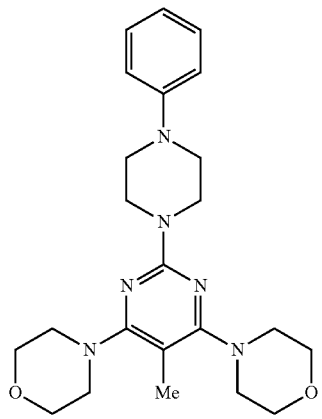

(55)

Melting Point: 99.0-102.0 degrees C.,
MS m/z: 424 (M+),
NMR (CDCl$_3$) δ: 2.00 (3H, s), 3.22 (4H, t, J=5.1 Hz), 3.30 (8H, t, J=4.6 Hz), 3.79 (8H, t, J=4.6 Hz), 3.88 (4H, t, J=5.1 Hz), 6.88 (1H, t, J=7.3 Hz), 6.97 (2H, d, J=7.3 Hz), 7.30 (2H, d, J=7.3 Hz).

5-methyl-2,4-dimorpholino-6-(4-phenylpiperazin-1-yl)pyrimidine (Compound 45)

(See Formula (58) below)
The melting point measurement result, the MS measurement result, and the NMR data for the obtained Compound 45 are shown below.

[Chemical 70]

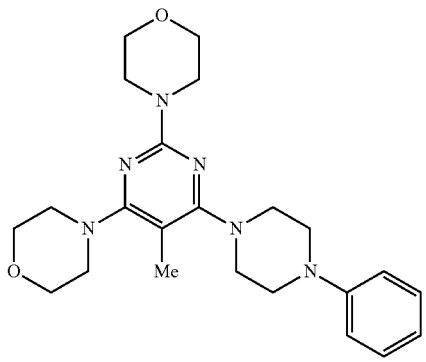

(56)

Melting Point: 149.0-152.0 degrees C.,
MS m/z: 424 (M+),
NMR (CDCl$_3$) δ: 2.03 (3H, s), 3.25-3.32 (8H, m), 3.48 (4H, t, J=4.6 Hz), 3.70-3.80 (12H, m), 6.88 (1H, t, J=7.3 Hz), 6.96 (2H, d, J=7.3 Hz), 7.26 (2H, d, J=7.3 Hz).

4,6-dimorpholino-5-phenyl-2-(4-phenylpiperazin-1-yl)pyrimidine (Compound 46)

(See Formula (57) below)
The melting point measurement result, the MS measurement result, and the NMR data for the obtained Compound 46 are shown below.

[Chemical 71]

(57)

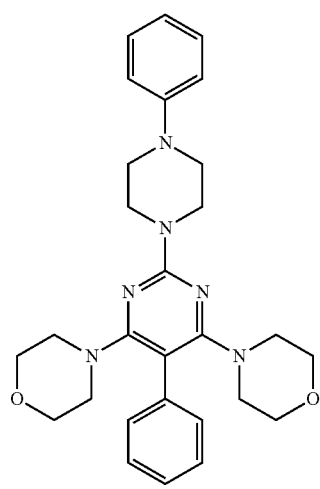

Melting Point: 163.0-165.0 degrees C.,
MS m/z: 486 (M+),
NMR (CDCl$_3$) δ: 2.97 (8H, t, J=4.6 Hz), 3.25 (4H, t, J=5.1 Hz), 3.50 (8H, t, J=4.6 Hz), 3.95 (4H, t, J=5.1 Hz), 6.89 (1H, t, J=7.3 Hz), 6.99 (2H, d, J=7.8 Hz), 7.21 (1H, d, J=7.3 Hz), 7.30-7.40 (6H, m).

2,4-dimorpholino-5-phenyl-6-(4-phenylpiperazin-1-yl)pyrimidine (Compound 47)

(See Formula (58) below)
The melting point measurement result, the MS measurement result, and the NMR data for the obtained Compound 47 are shown below.

[Chemical 72]

(58)

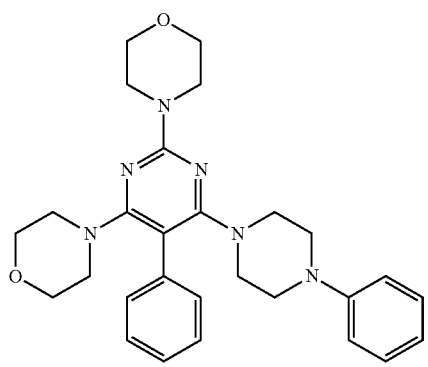

Melting Point: 203.0-206.0 degrees C.,
MS m/z: 486 (M+),
NMR (CDCl$_3$) δ: 2.97 (8H, t, J=5.1 Hz), 3.14 (4H, t, J=5.1 Hz), 3.49 (4H, t, J=4.6 Hz), 3.77 (8H, s), 6.80-6.90 (4H, m), 7.21 (2H, t, J=7.3 Hz), 7.36 (2H, t, J=7.8 Hz), 7.42 (2H, d, J=7.3 Hz).

5-benzyl-4,6-dimorpholino-2-(4-phenylpiperazin-1-yl)pyrimidine (Compound 48)

(See Formula (59) below)

The melting point measurement result, the MS measurement result, and the NMR data for the obtained Compound 48 are shown below.

[Chemical 73]

(59)

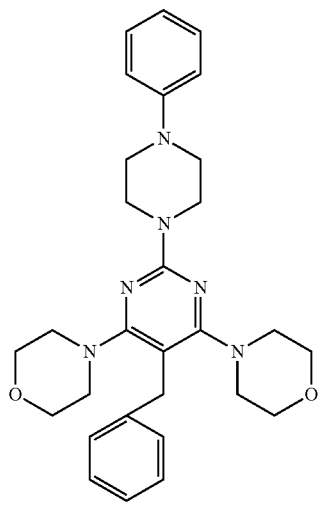

Melting Point: 141.0-144.0 degrees C.,
MS m/z: 500 (M+),
NMR (CDCl$_3$) δ: 3.25-3.20 (12H, m), 3.53 (8H, t, J=4.7 Hz), 3.89 (2H, s), 3.91 (4H, t, J=4.6 Hz), 6.89 (1H, t, J=7.3 Hz), 6.99 (2H, d, J=7.8 Hz), 7.10-7.35 (7H, m).

5-benzyl-2,4-dimorpholino-6-(4-phenylpiperazin-1-yl)pyrimidine (Compound 49)

(See Formula (60) below)
The melting point measurement result, the MS measurement result, and the NMR data for the obtained Compound 49 are shown below.

[Chemical 74]

(60)

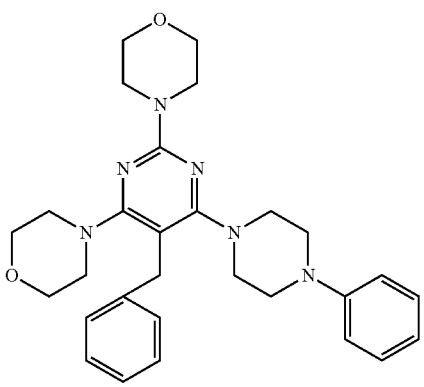

Melting Point: 162.0-165.0 degrees C.,
MS m/z: 500 (M+),
NMR (CDCl$_3$) δ: 3.06 (4H, t, J=4.9 Hz), 3.20 (4H, t, J=4.6 Hz), 3.36 (4H, t, J=4.9 Hz), 3.51 (4H, t, J=4.6 Hz), 3.75 (8H, m), 3.91 (2H, s), 6.86 (3H, t, J=7.3 Hz), 6.99 (2H, d, J=7.8 Hz), 7.10-7.30 (5H, m).

5-methoxy-2,4-dimorpholino-6-(4-phenylpiperazin-1-yl)pyrimidine (Compound 50)

(See Formula (61) below)
The melting point measurement result, the MS measurement result, and the NMR data for the obtained Compound 50 are shown below.

[Chemical 75]

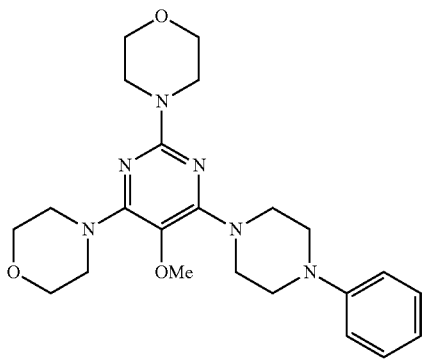

(61)

Melting Point: 118.0-120.0 degrees C.,
MS m/z: 440 (M+),
NMR (CDCl$_3$) δ: 3.25 (4H, t, J=4.9 Hz), 3.54 (3H, s), 3.55-3.70 (8H, m), 3.70-3.80 (12H, m), 6.87 (1H, t, J=7.8 Hz), 6.96 (2H, d, J=7.8 Hz), 7.30 (2H, d, J=7.8 Hz).

Example 4

Using a similar method to that for Example 1, by reacting with amines 3 times, the following compounds were produced from corresponding starting materials (Compounds 51-62).

2-(4-benzylpiperazin-1-yl)-6-dimethylamino-4-morpholinopyrimidine (Compound 51)

(See Formula (62) below)
The NMR data for the obtained Compound 51 are shown below.

[Chemical 76]

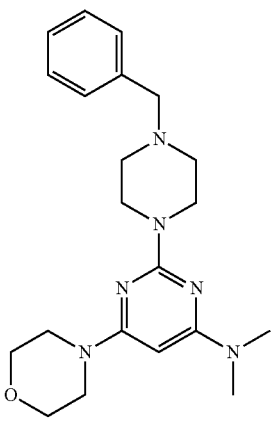

(62)

NMR (CDCl$_3$) δ: 2.46 (4H, t, J=5.0 Hz), 3.00 (6H, s), 3.47 (4H, t, J=4.7 Hz), 3.53 (2H, s), 3.73-3.77 (8H, m), 4.97 (1H, s), 7.25-7.36 (5H, m).

4-morpholino-2-(4-phenylpiperazin-1-yl)-6-(piperazin-1-yl)pyrimidine (Compound 52)

(See Formula (63) below)
The melting point measurement result, the MS measurement result, and the NMR data for the obtained Compound 52 are shown below.

[Chemical 77]

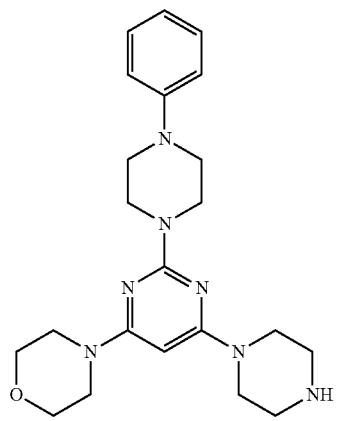

(63)

Melting Point: 149-150 degrees C.,
MS m/z: 409 (M+),
NMR (CDCl$_3$) δ: 2.93 (4H, t, J=5.0 Hz), 3.21 (4H, t, J=5.1 Hz), 3.50-3.52 (8H, m), 3.77 (4H, t, J=4.8 Hz), 3.89 (4H, t, J=5.1 Hz), 5.10 (1H, s), 6.87 (1H, t, J=7.3 Hz), 6.97 (2H, d, J=7.9 Hz), 7.25-7.31 (2H, m).

4-(4-formylpiperazin-1-yl)-6-morpholino-2-(4-phenylpiperazin-1-yl)pyrimidine (Compound 53)

(See Formula (64) below)
The melting point measurement result, the MS measurement result, and the NMR data for the obtained Compound 53 are shown below.

[Chemical 78]

-continued

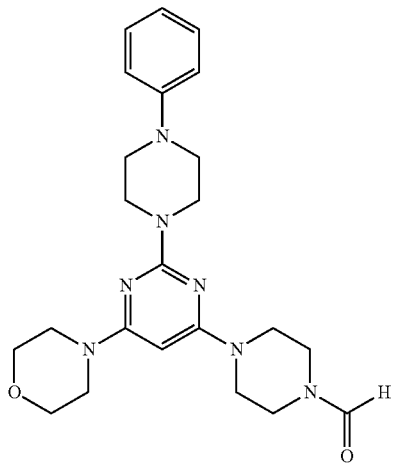

(64)

Melting Point: 171-172 degrees C.,
MS m/z: 437 (M⁺),
NMR (CDCl$_3$) δ: 3.22 (4H, t, J=5.1 Hz), 3.43-3.45 (2H, m), 3.52-3.53 (6H, m), 3.62-3.64 (4H, m), 3.78 (4H, t, J=4.9 Hz), 3.89 (4H, t, J=5.1 Hz), 5.12 (1H, s), 6.88 (1H, t, J=7.3 Hz), 6.97 (2H, d, J=7.8 Hz), 7.27-7.30 (2H, m), 8.12 (1H, s).

4-(4-acetylpiperazin-1-yl)-6-morpholino-2-(4-phenylpiperazin-1-yl)pyrimidine (Compound 54)

(See Formula (65) below)
The melting point measurement result, the MS measurement result, and the NMR data for the obtained Compound 54 are shown below.

[Chemical 79]

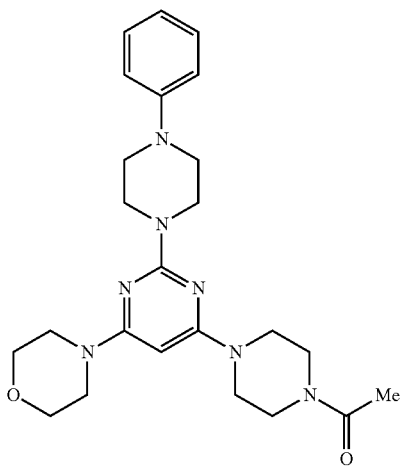

(65)

Melting Point: 171-172 degrees C.,
MS m/z: 451 (M⁺),
NMR (CDCl$_3$) δ: 2.14 (3H, s), 3.21 (4H, t, J=5.0 Hz), 3.48-3.56 (8H, m), 3.66-3.71 (4H, m), 3.78 (4H, t, J=4.9 Hz), 3.89 (4H, t, J=5.0 Hz), 5.10 (1H, s), 6.88 (1H, t, J=7.4 Hz), 6.97 (2H, d, J=7.9 Hz), 7.27-7.30 (2H, m).

6-dibutylamino-4-morpholino-2-(4-phenylpiperazin-1-yl)pyrimidine (Compound 55)

(See Formula (66) below)

The melting point measurement result, the MS measurement result, and the NMR data for the obtained Compound 55 are shown below.

[Chemical 80]

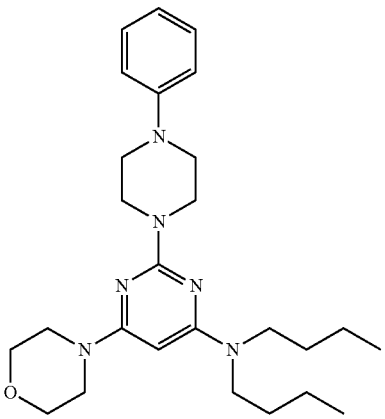

(66)

Melting Point: 84-85 degrees C.,
MS m/z: 452 (M⁺),
NMR (CDCl$_3$) δ: 0.93 (6H, t, J=7.3 Hz), 1.31-1.36 (4H, m), 1.51-1.62 (4H, m), 3.21 (4H, t, J=5.1 Hz), 3.38 (4H, t, J=7.4 Hz), 3.48 (4H, t, J=4.9 Hz), 3.78 (4H, t, J=4.8 Hz), 3.88 (4H, t, J=5.0 Hz), 4.98 (1H, s), 6.87 (1H, t, J=7.3 Hz), 6.97 (2H, d, J=7.9 Hz), 7.25-7.31 (2H, m).

4-morpholino-2-(4-phenylpiperazin-1-yl)-6-propylaminopyrimidine (Compound 56)

(See Formula (67) below)
The MS measurement result, and the NMR data for the obtained Compound 56 are shown below.

[Chemical 81]

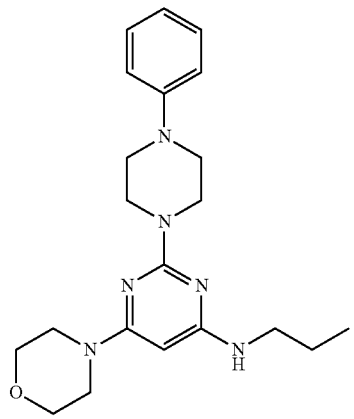

(67)

MS m/z: 382 (M⁺),
NMR (CDCl$_3$) δ: b: 0.98 (3H, t, J=7.3 Hz), 1.62 (2H, dd, J=3.6, 7.2 Hz), 3.13-3.22 (6H, m), 3.49-3.56 (5H, m), 3.77 (4H, t, J=4.9 Hz), 3.88 (4H, t, J=5.1 Hz), 4.94 (1H, s), 6.87 (1H, t, J=7.3 Hz), 6.97 (2H, d, J=7.9 Hz), 7.25-7.31 (2H, m).

2,4-bis(4-phenylpiperazin-1-yl)-6-morpholinopyrimidine (Compound 57)

(See Formula (68) below)
The NMR data for the obtained Compound 57 are shown below.

[Chemical 82]

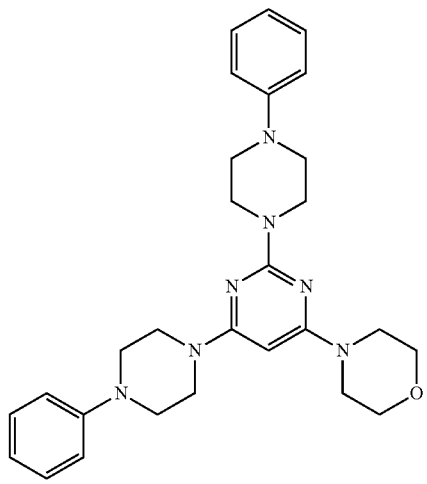

(68)

NMR (CDCl$_3$) δ: 3.24 (8H, m), 3.52 (4H, m), 3.72 (4H, m), 3.78 (4H, m), 3.91 (4H, m), 5.16 (1H, s), 6.85-6.99 (6H, m), 7.26-7.32 (4H, m).

4-[4-(2-fluorophenyl)piperazin-1-yl]-6-morpholino-2-(4-phenylpiperazin-1-yl)pyrimidine (Compound 58)

(See Formula (69) below)
The melting point measurement result, the MS measurement result, and the NMR data for the obtained Compound 58 are shown below.

[Chemical 83]

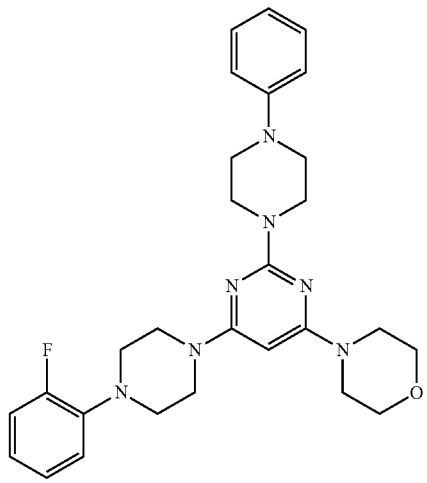

(69)

Melting Point: 90-91 degrees C.,

MS m/z: 503 (M$^+$),

NMR (CDCl$_3$) δ: 3.15 (4H, t, J=4.6 Hz), 3.22 (4H, t, J=5.2 Hz), 3.53 (4H, t, J=4.8 Hz), 3.75 (8H, m), 3.91 (4H, t, J=4.9 Hz), 5.17 (1H, s), 6.90-7.04 (7H, m), 7.27-7.30 (2H, m).

2,4-bis[4-(2-fluorophenyl)piperazin-1-yl]-6-morpholinopyrimidine (Compound 59)

(See Formula (70) below)
The melting point measurement result, the MS measurement result, and the NMR data for the obtained Compound 59 are shown below.

[Chemical 84]

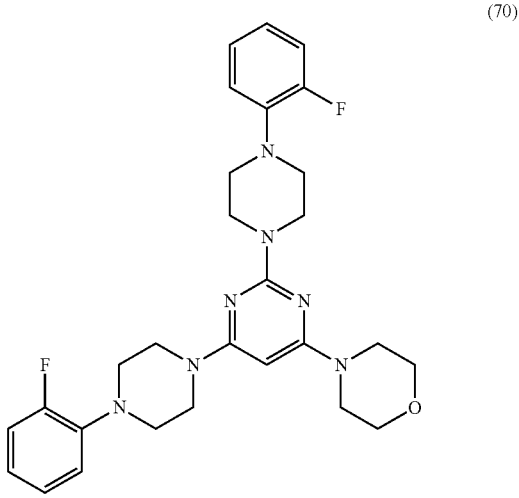

(70)

Melting Point: 98-99 degrees C.,

MS m/z: 521 (M$^+$),

NMR (CDCl$_3$) δ: 3.11-3.15 (8H, m), 3.53 (4H, t, J=4.9 Hz), 3.75 (8H, m), 3.93 (4H, t, J=4.9 Hz), 5.17 (1H, s), 6.94-7.11 (8H, m).

2-[4-(2-fluorophenyl)piperazin-1-yl]-4-[4-(2-methylphenyl)piperazin-1-yl]-6-morpholinopyrimidine (Compound 60)

(See Formula (71) below)
The melting point measurement result, the MS measurement result, and the NMR data for the obtained Compound 60 are shown below.

[Chemical 85]

71
-continued (71)

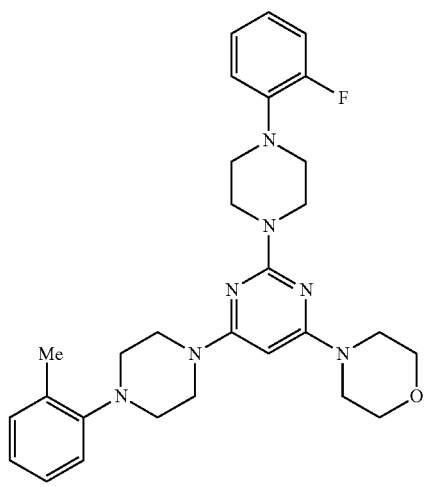

Melting Point: 98-99 degrees C.,
MS Ms m/z: 517 (M+),
NMR (CDCl$_3$) δ: 2.35 (3H, s), 2.97 (4H, t, J=5.1 Hz), 3.12 (4H, t, J=4.9 Hz), 3.53 (4H, t, J=4.8 Hz), 3.69 (4H, t, J=4.6 Hz), 3.78 (4H, t, J=4.8 Hz), 3.93 (4H, t, J=4.9 Hz), 5.17 (1H, s), 6.97-7.05 (6H, m), 7.17-7.20 (2H, m).

2-[4-(2-methylphenyl)piperazin-1-yl]-6-morpholino-4-(4-phenylpiperazin-1-yl)pyrimidine (Compound 61)

(See Formula (72) below)
The melting point measurement result, the MS measurement result, and the NMR data for the obtained Compound 61 are shown below.

[Chemical 86]

(72)

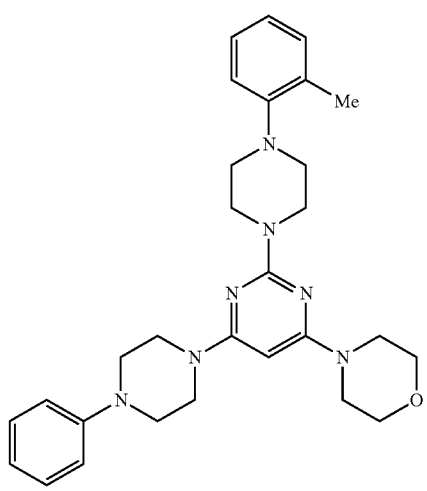

Melting Point: 93-94 degrees C.,
MS m/z: 499 (M+),
NMR (CDCl$_3$) δ: 2.36 (3H, s), 2.95 (4H, t, J=4.9 Hz), 3.26 (4H, t, J=4.9 Hz), 3.53 (4H, t, J=4.7 Hz), 3.72 (4H, t, J=5.0 Hz), 3.78 (4H, t, J=4.8 Hz), 3.89 (4H, t, J=4.9 Hz), 5.16 (1H, s), 6.92-6.99 (6H, m), 7.18-7.29 (3H, m).

72

2,4-bis[4-(2-methylphenyl)piperazin-1-yl]-6-morpholinopyrimidine (Compound 62)

(See Formula (73) below)
The melting point measurement result, the MS measurement result, and the NMR data for the obtained Compound 62 are shown below.

[Chemical 87]

(73)

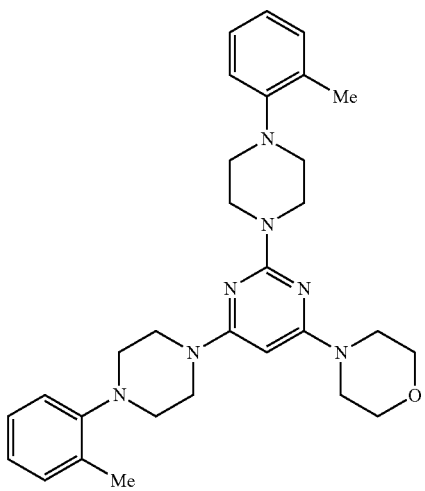

Melting Point: 98-99 degrees C.,
MS m/z: 513 (M+),
NMR (CDCl$_3$) δ: 2.35 (3H, s), 2.36 (3H, s), 2.96 (8H, t, J=8.7 Hz), 3.53 (4H, t, J=4.7 Hz), 3.69 (4H, t, J=4.9 Hz), 3.78 (4H, t, J=4.9 Hz), 3.89 (4H, t, J=4.6 Hz), 5.17 (1H, s), 7.00-7.03 (4H, m), 7.17-7.20 (4H, m).

Example 5

Synthesis of 5-amino-4,6-dimorpholino-2-(4-phenylpiperazin-1-yl)pyrimidine (Compound 63)

(See Reaction Formula (74) below)

[Chemical 88]

(74)

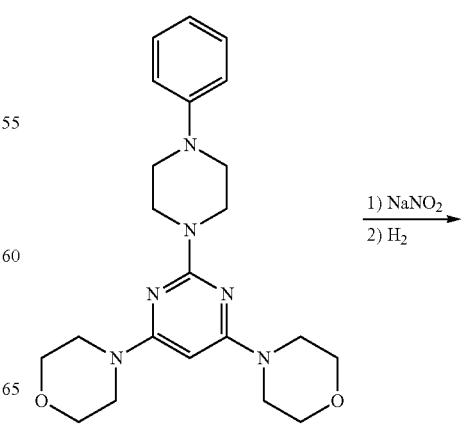

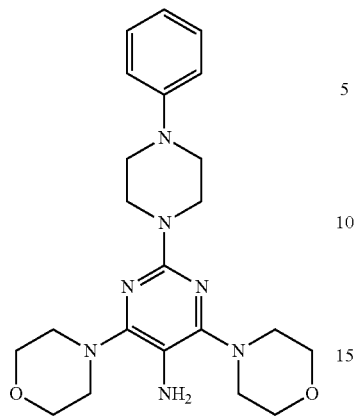

The synthesis method shall be explained concretely, and in order, below. 4,6-dimorpholino-2-(4-phenylpiperazin-1-yl)pyrimidine (3.0 g, 7.31 mmol) was dissolved in acetic acid (20 ml), an aqueous solution (1 ml) of sodium nitrite (605 mg, 8.78 mmol) was dripped in under water cooling, and agitation was done for 30 minutes at room temperature. After adjusting the pH to approximately 4.0 with a 2N NaOH aqueous solution, extraction was carried out 2 times using dichloromethane. After washing with water, drying was done with $MgSO_4$, and the solvent was distilled away under reduced pressure. The residue was dissolved in a methanol (40 ml)-ethyl acetate (40 ml) mixture solvent, 300 mg of Pd/C was added, and catalytic hydrogenation was done for 2 hours under atmospheric pressure. The Pd/C was filtered using celite, and the filtered liquid was distilled away under reduced pressure. The residue was washed with ether, and 1.63 g (52% yield) of 5-amino-4,6-dimorpholino-2-(4-phenylpiperazin-1-yl)pyrimidine was obtained. The melting point measurement result, the MS measurement result, and the NMR data for the obtained Compound 63 are shown below.

Melting Point: 185-186 degrees C.,

MS m/z: 425 ($M^+$),

NMR ($CDCl_3$) δ: 2.96 (2H, bs), 3.20-3.31 (12H, m), 3.78-3.83 (12H, m), 6.85-7.31 (5H, m).

Example 6

Using a similar method to that for Example 5, the following compounds were produced from corresponding starting materials (Compounds 64-76).

5-amino-2,4-dimorpholino-6-(4-phenylpiperazin-1-yl)pyrimidine (Compound 64)

(See Formula (75) below)

The NMR data for the obtained Compound 64 are shown below.

[Chemical 89]

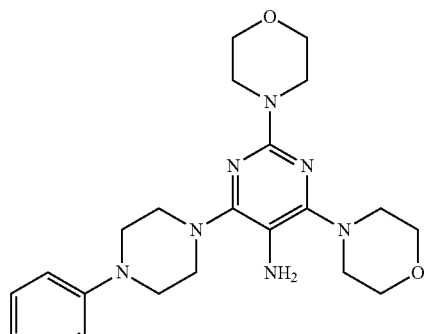

NMR ($CDCl_3$) δ: 2.99 (2H, s), 3.29 (8H, m), 3.45 (4H, m), 3.64 (4H, m), 3.75-3.83 (8H, m), 6.85-6.99 (3H, m), 7.25-7.32 (2H, m).

5-amino-4-dimethylamino-6-morpholino-2-(4-phenylpiperazin-1-yl)pyrimidine (Compound 65)

(See Formula (76) below)

The NMR data for the obtained Compound 65 are shown below.

[Chemical 90]

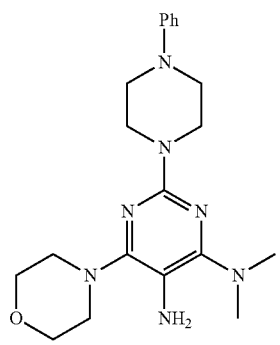

NMR ($CDCl_3$) δ: 2.88 (6H, s), 2.95 (2H, brs), 3.22-3.00 (8H, m), 3.80-3.83 (8H, m), 6.87 (1H, t, J=7.3 Hz), 6.99 (2H, dd, J=0.9, 8.83 Hz), 7.28-7.31 (2H, m).

5-amino-2-(4-benzylpiperidin-1-yl)-4,6-dimorpholinopyrimidine (Compound 66)

(See Formula (77) below)

The NMR data for the obtained Compound 66 are shown below.

[Chemical 91]

(77)

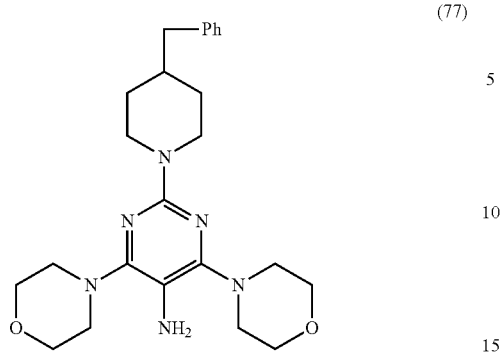

NMR (CDCl₃) δ: 1.19 (2H, m), 1.69 (3H, m), 2.90 (2H, s), 2.53-2.72 (4H, m), 3.26 (8H, m), 3.79 (8H, m), 4.56 (2H, m), 7.20-7.31 (5H, m).

5-amino-4-(4-benzylpiperidin-1-yl)-2,6-dimorpholinopyrimidine (Compound 67)

(See Formula (78) below)

The NMR data for the obtained Compound 67 are shown below.

[Chemical 92]

(78)

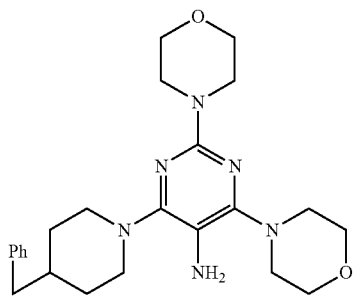

NMR (CDCl₃) δ: 1.32 (2H, m), 1.72 (3H, m), 2.57-2.72 (4H, m), 2.93 (2H, s), 3.26 (4H, m), 3.60 (4H, m), 3.57-3.81 (10H, m), 7.14-7.29 (5H, m).

5-amino-2-(4-benzylpiperidin-1-yl)-4-dimethylamino-6-morpholinopyrimidine (Compound 68)

(See Formula (79) below)

The NMR data for the obtained Compound 68 are shown below.

[Chemical 93]

(79)

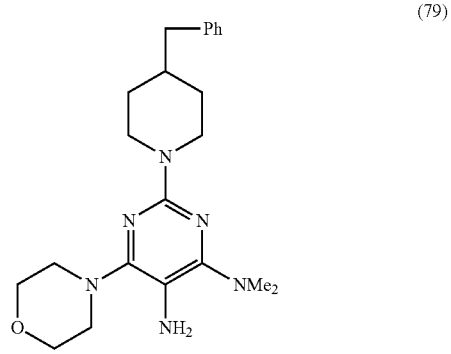

NMR (CDCl₃) δ: 1.20-1.69 (5H, m), 2.53-2.80 (4H, m), 2.84 (8H, brs), 3.25 (4H, m), 3.80 (4H, m), 4.58 (2H, m), 7.14-7.31 (5H, m).

5-amino-2-(4-benzylpiperidin-1-yl)-4-dimethylamino-6-thiomorpholinopyrimidine (Compound 69)

(See Formula (80) below)

The NMR data for the obtained Compound 69 are shown below.

[Chemical 94]

(80)

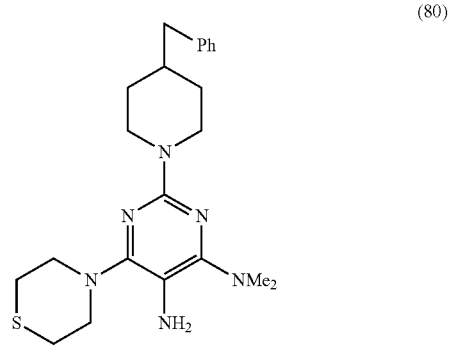

NMR (CDCl₃) δ: 1.20 (2H, m), 1.56-1.74 (5H, m), 2.53-2.80 (4H, m), 2.74 (4H, m), 2.84 (6H, s), 3.52 (4H, m), 4.56 (2H, m), 7.14-7.31 (5H, m).

5-amino-4,6-dimorpholino-2-(1,2,3,4-tetrahydro-1H-isoquinolin-2-yl)pyrimidine (Compound 70)

(See Formula (81) below)

The NMR data for the obtained Compound 70 are shown below.

[Chemical 95]

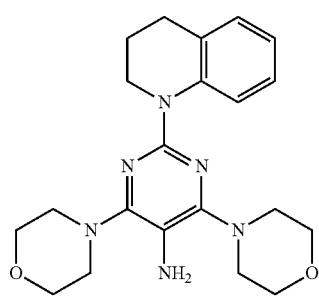

(81)

NMR (CDCl$_3$) δ: 2.91 (4H, m), 3.30 (8H, m), 3.82 (8H, m), 3.95 (2H, m), 4.81 (2H, s), 7.12-7.18 (4H, m).

5-amino-2-(6-fluoro-2-methyl-1,2,3,4-tetrahydro-quinolin-1-yl)-4,6-dimorpholinopyrimidine (Compound 71)

(See Formula (82) below)

The NMR data for the obtained Compound 71 are shown below.

[Chemical 96]

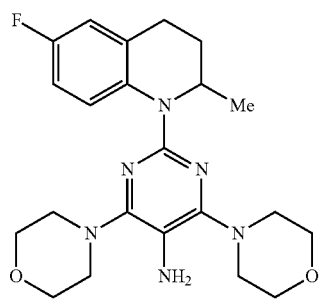

(82)

NMR (CDCl$_3$) δ: 1.21 (3H, d, J=6.43 Hz), 1.66 (1H, m), 2.23 (1H, m), 2.67 (2H, m), 3.02 (2H, s), 3.25 (8H, m), 3.80 (8H, m), 5.00 (1H, m), 6.77 (2H, m), 7.67 (1H, m).

5-amino-4,6-dimorpholino-2-(1,2,3,4-tetrahydro-quinolin-1-yl)pyrimidine (Compound 72)

(See Formula (83) below)

The NMR data for the obtained Compound 72 are shown below.

[Chemical 97]

(83)

NMR (CDCl$_3$) δ: 1.96 (2H, m), 2.78 (2H, m), 3.04 (2H, s), 3.28 (8H, m), 3.81 (8H, m), 3.97 (2H, m), 6.90 (1H, m), 7.06 (2H, m), 7.87 (1H, m).

5-amino-2-(4-benzyl piperazin-1-yl)-4,6-dimorpholinopyrimidine (Compound 73)

(See Formula (84) below)

The NMR data for the obtained Compound 73 are shown below.

[Chemical 98]

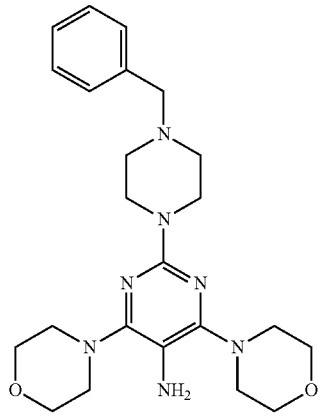

(84)

NMR (CDCl$_3$) δ: 2.48 (4H, t, J=5.0 Hz), 2.92 (2H, brs), 3.25 (8H, t, J=4.6 Hz), 3.54 (2H, s), 3.65 (4H, t, J=5.0 Hz), 3.79 (8H, t, J=4.6 Hz), 7.24-7.33 (5H, m).

5-amino-2-(4-benzylpiperazin-1-yl)-6-dimethylamino-4-morpholinopyrimidine (Compound 74)

(See Formula (85) below)

The NMR data for the obtained Compound 74 are shown below.

[Chemical 99]

-continued (85)

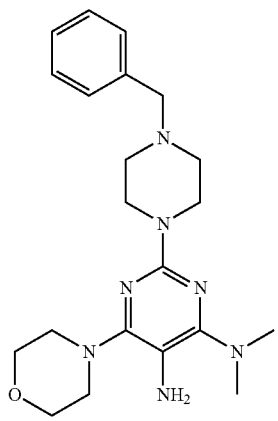

NMR (CDCl$_3$) δ: 2.48 (4H, t, J=5.0 Hz), 2.84 (6H, s), 2.92 (2H, brs), 3.25 (4H, t, J=4.7 Hz), 3.55 (2H, s), 3.66 (4H, t, J=4.7 Hz), 3.79 (4H, t, J=5.0 Hz), 7.24-7.34 (5H, m).

5-amino-4,6-dimorpholino-2-[4-(pyridin-2-yl)-piperazin-1-yl]pyrimidine (Compound 75)

(See Formula (86) below)
The NMR data for the obtained Compound 75 are shown below.

[Chemical 100]

(86)

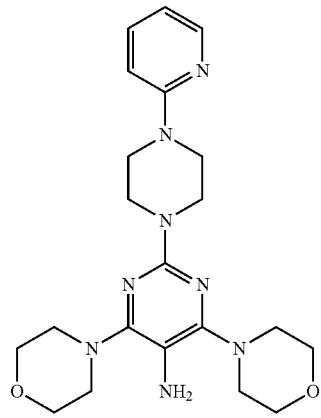

NMR (CDCl$_3$) δ: 2.95 (2H, s), 3.28 (8H, m), 3.60 (4H, s), 3.75-3.83 (12H, m), 6.60-6.70 (2H, m), 7.49 (1H, m), 8.22 (1H, m).

5-amino-2-(4-methylpiperazin-1-yl)-4,6-dimorpholinopyrimidine (Compound 76)

(See Formula (87) below)
The NMR data for the obtained Compound 76 are shown below.

[Chemical 101]

-continued (87)

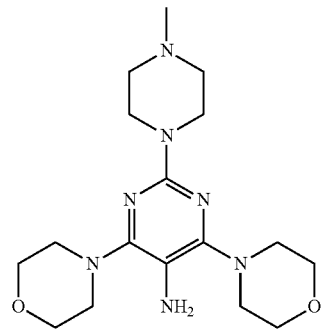

NMR (CDCl$_3$) δ: 2.33 (3H, s), 2.45 (4H, t, J=5.0 Hz), 2.93 (2H, brs), 3.27 (8H, t, J=4.7 Hz), 3.67 (4H, t, J=5.0 Hz), 3.80 (8H, t, J=4.7 Hz).

Example 7

Synthesis of 5-acetylamino-4,6-dimorpholino-2-(4-phenylpiperazin-1-yl)pyrimidine (Compound 77)

(See Reaction Formula (88) below)

[Chemical 102]

(88)

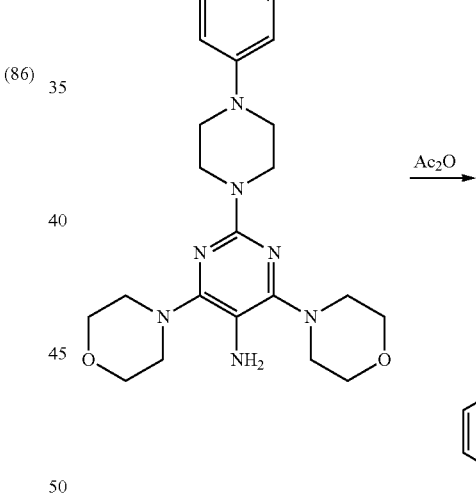

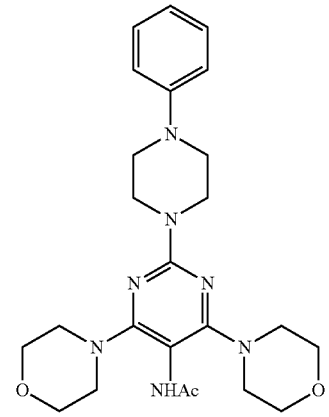

The synthesis method shall be explained concretely, and in order, below. A solution of 5-amino-2-(4-phenylpiperazin-1-yl)-4,6-dimorpholinopyrimidine (700 mg, 1.64 mmol), acetic anhydride (5 ml), and pyridine (a few drops) was agitated for 1 hour at 60 degrees Celsius. The deposited solid was captured by filtering, washed with ether, and 330 mg of 5-acetylamino-4,6-dimorpholino-2-(4-phenylpiperazin-1-yl)pyrimidine was obtained (43% yield). The melting point measurement result, the MS measurement result, and the NMR data for the obtained Compound 77 are shown below.

Melting Point: 229-230 degrees C.,

MS m/z: 335, 467 (M+),

NMR (CDCl$_3$) δ: 1.78 (3H, s), 3.18-3.91 (24H, m), 6.25 (1H, s), 6.87-7.32 (5H, m).

Example 8

Using a similar method to that for Example 7, the following Compounds 78 and 79 were produced from corresponding starting materials.

5-acetylamino-4-(4-benzylpiperidin-1-yl)-2,6-dimorpholinopyrimidine (Compound 78)

(See Formula (89) below)
The NMR data for the obtained Compound 78 are shown below.

[Chemical 103]

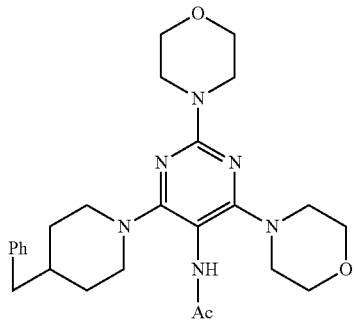

(89)

NMR (CDCl$_3$) δ: 1.25 (2H, m), 1.56-1.72 (3H, m), 1.73 (3H, s), 2.52 (2H, m), 2.72 (2H, m), 3.34 (4H, m), 3.71 (12H, m), 3.90 (2H, m), 6.30 (1H, s), 7.21-7.31 (5H, m).

5-acetylamino-2-[2-(4-methoxyphenyl)vinyl]-4,6-dimorpholinopyrimidine (Compound 79)

(See Formula (90) below)
The melting point measurement result, the MS measurement result, and the NMR data for the obtained Compound 79 are shown below.

[Chemical 104]

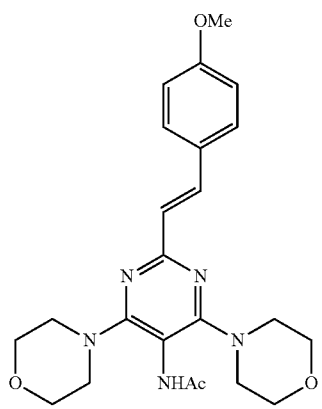

(90)

Melting Point: 189.0-191.0 degrees C.,

MS m/z: 439 (M+),

NMR (CDCl$_3$) δ: 1.82+2.17 (3H, s), 3.30-3.70 (8H, m), 3.70-3.80 (8H, m), 3.84 (3H, s), 6.27+6.59 (1H, brs), 6.85 (1H, d, J=15.5 Hz), 6.91 (2H, d, J=8.7 Hz), 7.54 (2H, d, J=8.6 Hz), 7.78 (1H, d, J=15.5 Hz).

Example 9

Synthesis of 5-ethylamino-4,6-dimorpholino-2-(4-phenylpiperazin-1-yl)pyrimidine (Compound 80)

(See Reaction Formula (91) below)

[Chemical 105]

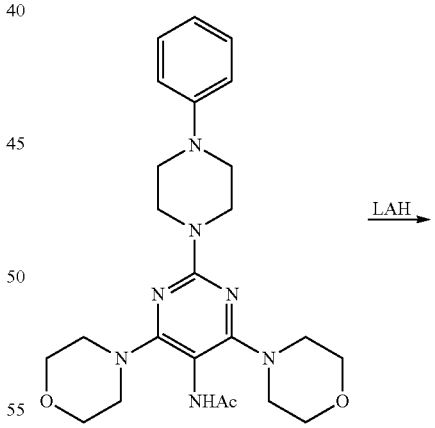

(91)

83
-continued

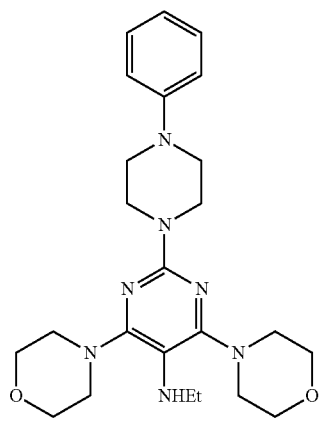

The synthesis method shall be explained concretely, and in order, below. LiAlH₄ was dispersed in dry THF (50 ml), and next, 5-acetylamino-4,6-dimorpholino-2-(4-phenylpiperazin-1-yl)pyrimidine (150 mg, 0.32 mmol) was added, and refluxed for approximately 3 hours under heat. Water was added, and the precipitated solid was removed by celite filtering, and the filtered liquid was extracted 2 times with ethyl acetate. After washing the organic layer with saturated saline, drying was done with MgSO₄, and the solvent was distilled away under reduced pressure. Purification was done by silica gel chromatography (hexane:ethyl acetate=3:1), and 50 mg of 4,6-dimorpholino-5-ethylamino-2-phenylpiperazinopyrimidine (yield 34%) was obtained. The melting point measurement result, the MS measurement result, and the NMR data for the obtained Compound 80 are shown below.

Melting Point: 100-104 degrees C.,

MS m/z: 453 (M⁺),

NMR (CDCl₃) δ: 1.07 (3H, t, J=7.1 Hz), 2.88 (2H, q, J=7.1 Hz), 3.21-3.33 (12H, m), 3.78-3.83 (12H, m), 6.87-7.31 (5H, m).

Example 10

Using a similar method to that for Example 9, the following compounds were produced from corresponding starting materials.

4-(4-benzylpiperazin-1-yl)-5-ethylamino-2,6-dimorpholinopyrimidine (Compound 81)

(See Formula (92) below)

The NMR data for the obtained Compound 81 are shown below.

[Chemical 106]

84
-continued (92)

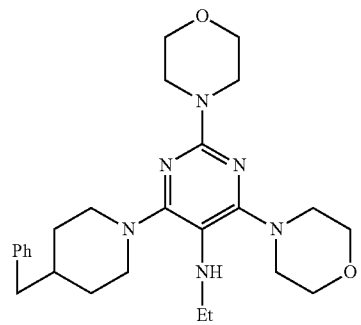

NMR (CDCl₃) δ: 1.06 (3H, t, J=7.1 Hz), 1.35 (1H, m), 1.70 (2H, m), 2.57 (2H, m), 2.67 (2H, m), 2.87 (2H, q, J=7.1 Hz), 3.25 (1H, bs), 3.35 (4H, m), 3.59-3.79 (16H, m), 7.14-7.31 (5H, m).

Example 11

Synthesis of 5-fluoro-4,6-dimorpholino-2-(4-phenylpiperazin-1-yl)pyrimidine (Compound 82)

(See Reaction Formula (93) below)

[Chemical 107]

(93)

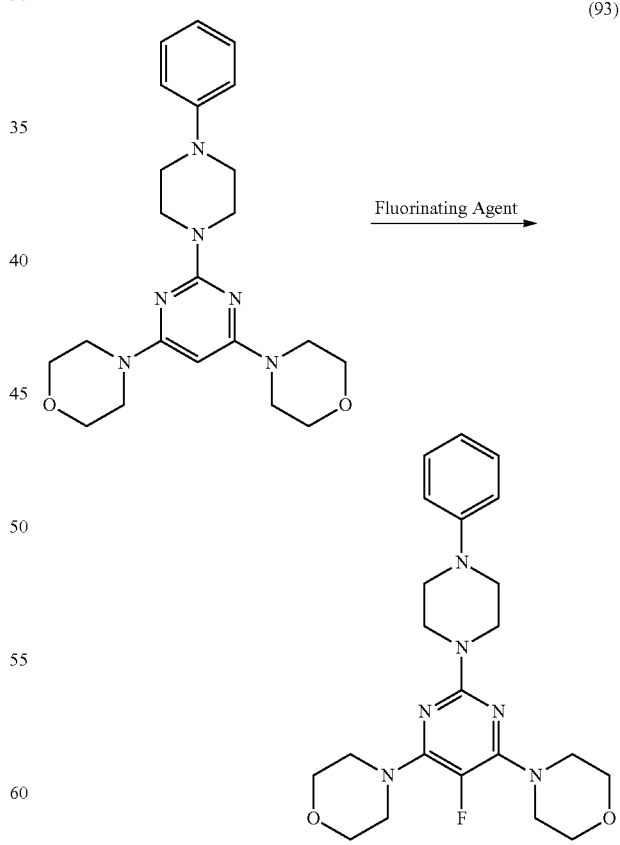

The synthesis method shall be explained concretely, and in order, below. 4,6-dimorpholino-2-(4-phenylpiperazin-1-yl)pyrimidine (380 mg, 0.926 mmol) was dissolved in dichloromethane (5 ml), and N-fluoro-2,4,6-trimethylpyridinium triflate (402 mg, 1.39 mmol) was added. After agitation for 30 minutes at room temperature, water was added and extraction was done with dichloromethane. After washing the organic layer with saturated saline, drying was done with MgSO₄, and the solvent was distilled away under reduced pressure. Purification was done by silica gel chromatography (hexane:ethyl acetate=4:1), and 122 mg of 4,6-dimorpholino-5-fluoro-2-(4-phenylpiperazin-1-yl)pyrimidine was obtained (yield 31%). The melting point measurement result, the MS measurement result, and the NMR data for the obtained Compound 82 are shown below.

Melting Point: 181 degrees C.,

MS m/z: 296, 428 (M⁺),

NMR (CDCl₃) δ: 3.18-3.22 (4H, m), 3.54-3.58 (8H, m), 3.76-3.82 (12H, m), 6.85-7.31 (5H, m).

Example 12

Using a similar method to that for Example 11, the following compounds (Compounds 83-129, Compounds 149-164, Compounds 166-169, Compound 171, Compounds 177-194, Compound 204, and Compound 216) were produced from corresponding starting materials.

5-fluoro-2,4-dimorpholino-6-(4-phenylpiperazin-1-yl)pyrimidine (Compound 83)

(See Formula (94) below)
The NMR data for the obtained Compound 83 are shown below.

[Chemical 108]

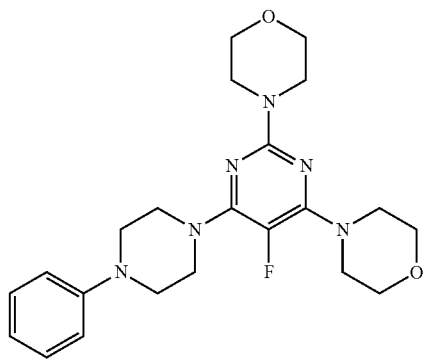

(94)

NMR (CDCl₃) δ: 3.24 (4H, m), 3.54-3.78 (20H, m), 6.85-6.96 (3H, m), 7.24-7.31 (2H, m).

6-dimethylamino-5-fluoro-4-morpholino-2-(4-phenylpiperazin-1-yl)pyrimidine (Compound 84)

(See Formula (95) below)
The NMR data for the obtained Compound 84 are shown below.

[Chemical 109]

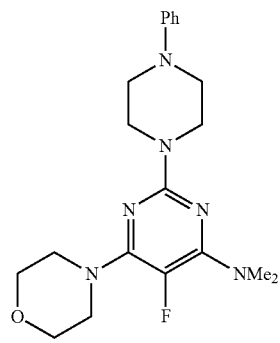

(95)

NMR (CDCl₃) δ: 3.07 (6H, s), 3.20 (4H, m), 3.53 (4H, m), 3.80 (8H, m), 6.84-6.98 (3H, m), 7.30 (2H, m).

2-dimethylamino-5-fluoro-6-morpholino-4-(4-phenylpiperazin-1-yl)pyrimidine (Compound 85)

(See Formula (96) below)
The NMR data for the obtained Compound 85 are shown below.

[Chemical 110]

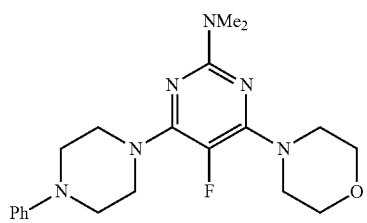

(96)

NMR (CDCl₃) δ: 3.05 (6H, s), 3.25 (4H, m), 3.54 (4H, m), 3.70-3.79 (8H, m), 6.85-6.97 (3H, m), 7.25-7.31 (2H, m).

4-(4-benzylpiperidin-1-yl)-2-dimethylamino-5-fluoro-6-morpholinopyrimidine (Compound 86)

(See Formula (97) below)
The NMR data for the obtained Compound 86 are shown below.

[Chemical 111]

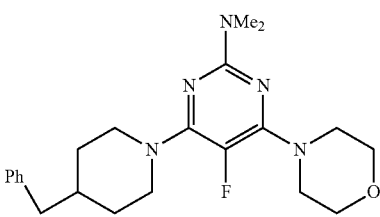

(97)

NMR (CDCl₃) δ: 1.32 (2H, m), 1.68-1.75 (3H, m), 2.54 (2H, m), 2.78 (2H, m), 3.03 (6H, s), 3.52 (4H, m), 3.76 (4H, m), 4.20 (2H, m), 7.13-7.31 (5H, m).

5-fluoro-4-(3,4-dihydro-1H-isoquinolin-2-yl)-2,6-dimorpholinopyrimidine (Compound 87)

(See Formula (98) below)
The NMR data for the obtained Compound 87 are shown below.

[Chemical 112]

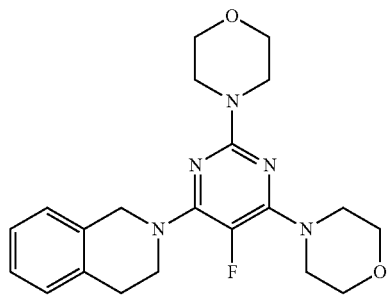
(98)

NMR (CDCl$_3$) δ: 2.94 (2H, m), 3.52-3.84 (18H, m), 4.72 (2H, s), 7.15 (4H, m).

4-(N-ethyl-N-phenylamino)-5-fluoro-2,6-dimorpholinopyrimidine (Compound 88)

(See Formula (99) below)
The NMR data for the obtained Compound 88 are shown below.

[Chemical 113]

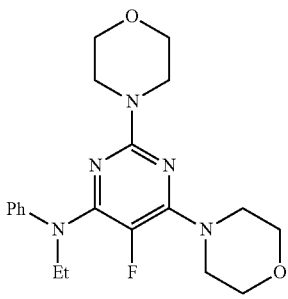
(99)

NMR (CDCl$_3$) δ: 1.19 (3H, t, J=6.9 Hz), 3.46 (4H, m), 3.63-3.86 (12H, m), 3.93 (2H, q, J=6.9 Hz), 7.13 (2H, m), 7.26-7.33 (3H, m).

5-fluoro-2-(isoindolin-2-yl)-4,6-dimorpholinopyrimidine (Compound 89)

(See Formula (100) below)
The melting point measurement result, the MS measurement result, and the NMR data for the obtained Compound 89 are shown below.

[Chemical 114]

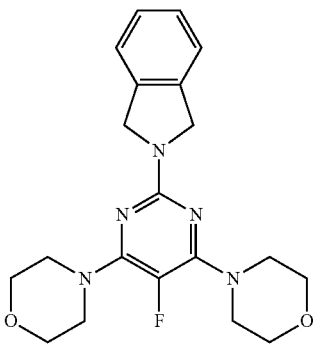
(100)

Melting Point: 172.0-175.0 degrees C.,
MS m/z: 385 (M+),
NMR (CDCl$_3$) δ: 3.62 (8H, t, J=4.8 Hz), 3.79 (8H, t, J=4.8 Hz), 4.79 (4H, s), 7.25-7.30 (4H, m).

4-(4-benzyl piperazin-1-yl)-5-fluoro-2,6-dimorpholinopyrimidine (Compound 90)

(See Formula (101) below)
The melting point measurement result, the MS measurement result, and the NMR data for the obtained Compound 90 are shown below.

[Chemical 115]

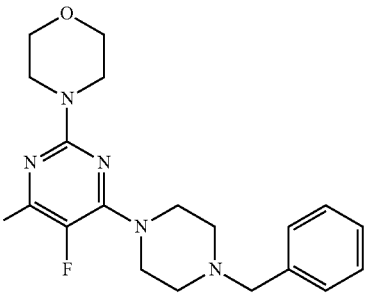
(101)

Melting Point: 108.0-111.0 degrees C.,
MS m/z: 442 (M+),
NMR (CDCl$_3$) δ: 2.50 (4H, t, J=5.0 Hz), 3.50-3.60 (14H, m), 3.70-3.80 (8H, m), 7.25-7.35 (5H, m).

2-dimethylamino-5-fluoro-6-morpholino-4-[4-(pyridin-2-yl)piperazin-1-yl]pyrimidine (Compound 91)

(See Formula (102) below)
The NMR data for the obtained Compound 91 are shown below.

[Chemical 116]

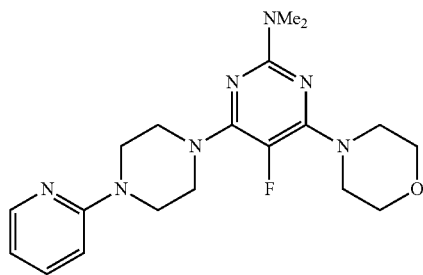
(102)

NMR (CDCl$_3$) δ: 3.05 (6H, s), 3.54-3.79 (16H, m), 6.64 (2H, m), 7.51 (1H, m), 8.21 (1H, m).

5-fluoro-4,6-dimorpholino-2-[4-(pyrimidin-2-yl)piperazin-1-yl]pyrimidine (Compound 92)

(See Formula (103) below)
The NMR data for the obtained Compound 92 are shown below.

[Chemical 117]

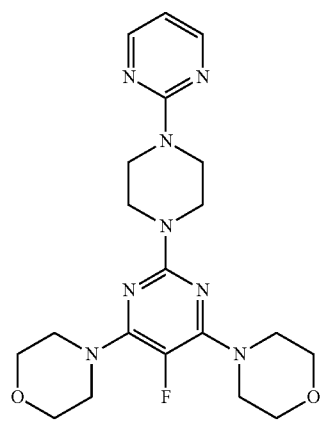
(103)

Melting Point: 163.0-165.0 degrees C.,
MS m/z: 430 (M+),
NMR (CDCl$_3$) δ: 3.54 (8H, t, J=4.9 Hz), 3.70-3.90 (16H, m), 6.50 (1H, t, J=4.7 Hz), 8.32 (2H, d, J=4.7 Hz).

5-fluoro-4,6-dimorpholino-2-(3-phenylpiperazin-1-yl)pyrimidine (Compound 93)

(See Formula (104) below)
The melting point measurement result, the MS measurement result, and the NMR data for the obtained Compound 93 are shown below.

[Chemical 118]

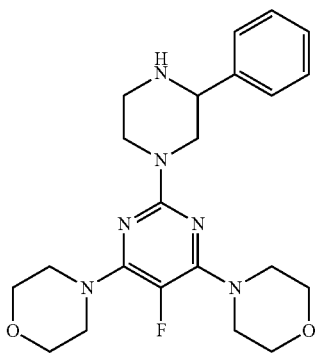
(104)

Melting Point: 170.0-175.0 degrees C.,
MS m/z: 428 (M$^+$),
NMR (CDCl$_3$) δ: 2.81 (1H, dd, J=13.1, 10.6 Hz), 2.96 (2H, dd, J=10.6, 5.3 Hz), 3.12 (1H, d, J=9.2 Hz), 3.50 (8H, t, J=4.7 Hz), 3.75 (10H, t, J=4.7 Hz), 4.50 (2H, d, J=12.2 Hz), 7.25-7.45 (5H, m).

5-fluoro-2,4-dimorpholino-6-(3-phenylpiperazin-1-yl)pyrimidine (Compound 94)

(See Formula (105) below)
The melting point measurement result, the MS measurement result, and the NMR data for the obtained Compound 94 are shown below.

[Chemical 119]

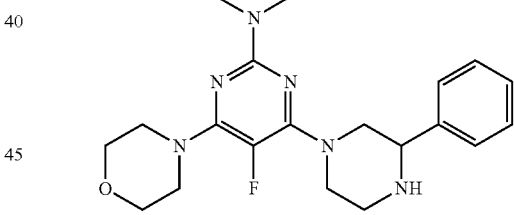
(105)

Melting Point: 121.0-124.0 degrees C.,
MS m/z: 428 (M$^+$),
NMR (CDCl$_3$) δ: 2.79 (1H, dd, J=13.1, 10.6 Hz), 2.90-3.00 (2H, m), 3.42 (4H, t, J=4.7 Hz), 3.52 (4H, t, J=4.7 Hz), 3.62 (8H, t, J=4.7 Hz), 3.78 (1H, dd, J=10.4, 2.6 Hz), 4.07 (2H, d, J=8.1 Hz), 7.25-7.45 (5H, m).

5-fluoro-2,4-dimorpholino-6-[4-(4-nitrophenyl)piperazin-1-yl]pyrimidine (Compound 95)

(See Formula (106) below)
The NMR data for the obtained Compound 95 are shown below.

[Chemical 120]

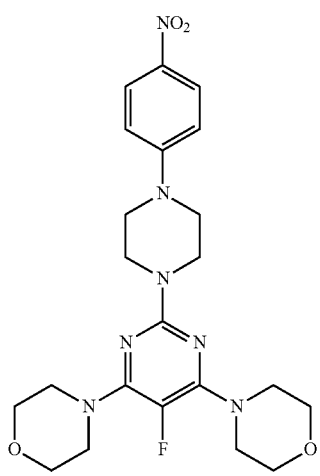
(106)

NMR (CDCl$_3$) δ: 3.47 (4H, m), 3.56 (8H, m), 3.75-3.84 (12H, m), 6.84 (2H, d, J=9.4 Hz), 8.15 (2H, d, J=9.4 Hz).

5-fluoro-2-[4-(4-fluorophenyl)piperazin-1-yl]-4,6-dimorpholinopyrimidine (Compound 96)

(See Formula (107) below)
The melting point measurement result, the MS measurement result, and the NMR data for the obtained Compound 96 are shown below.

[Chemical 121]

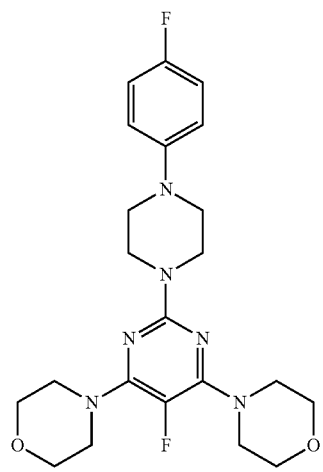
(107)

Melting Point: 195.0-198.0 degrees C.,
MS m/z: 446 (M$^+$),
NMR (CDCl$_3$) δ: 3.11 (4H, t, J=5.0 Hz), 3.56 (4H, t, J=4.9 Hz), 3.78 (8H, t, J=4.9 Hz), 3.88 (12H, m), 6.85-7.05 (4H, m).

5-fluoro-4-[4-(4-fluorophenyl)piperazin-1-yl]-2,6-dimorpholinopyrimidine (Compound 97)

(See Formula (108) below)
The melting point measurement result, the MS measurement result, and the NMR data for the obtained Compound 97 are shown below.

[Chemical 122]

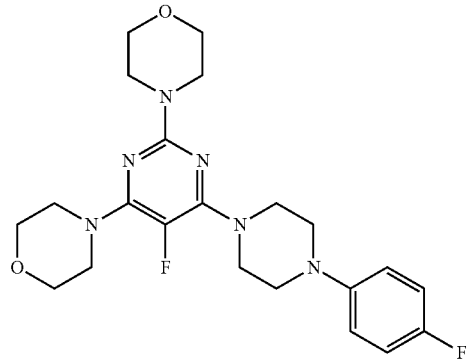
(108)

Melting Point: 171.0-174.0 degrees C.,
MS m/z: 446 (M$^+$),
NMR (CDCl$_3$) δ: 3.16 (4H, t, J=5.0 Hz), 3.56 (4H, t, J=5.0 Hz), 3.62 (4H, t, J=5.0 Hz), 3.70-3.80 (12H, m), 6.85-7.05 (4H, m).

5-fluoro-2-[4-(4-methylphenyl)piperazin-1-yl]-4,6-dimorpholinopyrimidine (Compound 98)

(See Formula (109) below)
The melting point measurement result, the MS measurement result, and the NMR data for the obtained Compound 98 are shown below.

[Chemical 123]

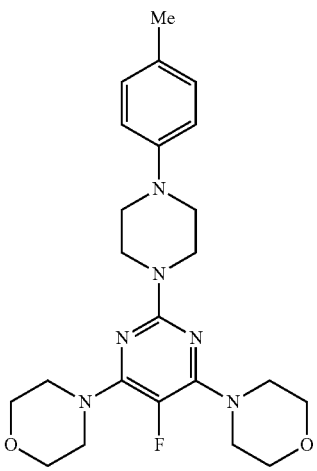
(109)

Melting Point: 201.0-203.0 degrees C.,
MS m/z: 442 (M$^+$),
NMR (CDCl$_3$) δ: 2.28 (3H, s), 3.14 (4H, t, J=5.0 Hz), 3.56 (8H, t, J=4.9 Hz), 3.78 (12H, m), 6.88 (2H, d, J=8.6 Hz), 7.09 (2H, d, J=8.6 Hz).

5-fluoro-4-[4-(4-methylphenyl)piperazin-1-yl]-2,6-dimorpholinopyrimidine (Compound 99)

(See Formula (110) below)
The melting point measurement result, the MS measurement result, and the NMR data for the obtained Compound 99 are shown below.

[Chemical 124]

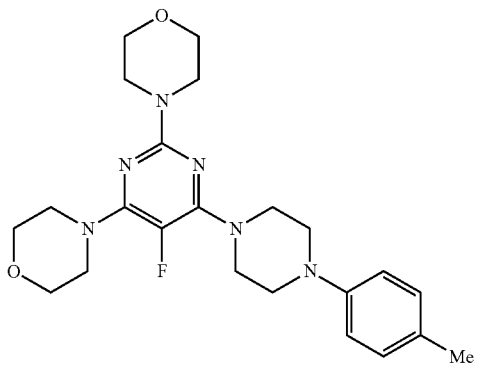
(110)

Melting Point: 177.0-180.0 degrees C.,
MS m/z: 442 (M+),
NMR (CDCl$_3$) δ: 2.28 (3H, s), 3.18 (4H, t, J=5.0 Hz), 3.55 (4H, t, J=5.0 Hz), 3.62 (4H, t, J=5.0 Hz), 3.65-3.80 (12H, m), 6.86 (2H, d, J=8.6 Hz), 7.09 (2H, d, J=8.6 Hz).

2-[4-(4-acetylphenyl)piperazin-1-yl]-5-fluoro-4,6-dimorpholinopyrimidine (Compound 100)

(See Formula (111) below)
The melting point measurement result, the MS measurement result, and the NMR data for the obtained Compound 100 are shown below.

[Chemical 125]

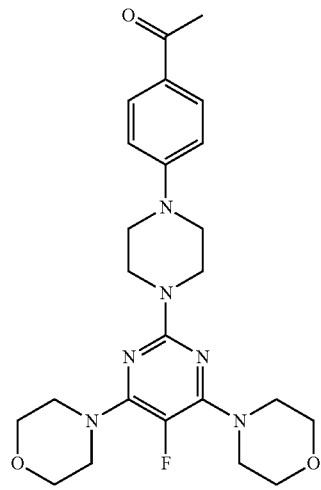
(111)

Melting Point: 195.0-198.0 degrees C.,
MS m/z: 470 (M+),
NMR (CDCl$_3$) δ: 2.53 (3H, s), 3.40 (4H, t, J=5.0 Hz), 3.56 (8H, t, J=4.9 Hz), 3.78 (12H, m), 6.89 (2H, d, J=9.1 Hz), 7.09 (2H, d, J=9.1 Hz).

4-[4-(4-acetylphenyl)piperazin-1-yl]-5-fluoro-2,6-dimorpholinopyrimidine (Compound 101)

(See Formula (112) below)
The melting point measurement result, the MS measurement result, and the NMR data for the obtained Compound 101 are shown below.

[Chemical 126]

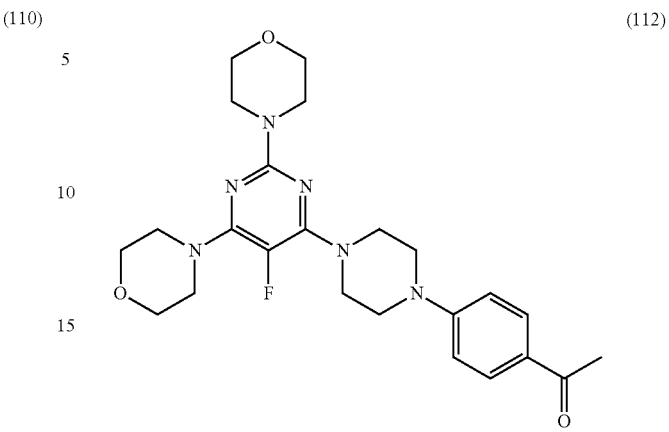
(112)

Melting Point: 186.0-190.0 degrees C.,
MS m/z: 442 (M+),
NMR (CDCl$_3$) δ: 2.54 (3H, s), 3.43 (4H, t, J=5.0 Hz), 3.65 (4H, t, J=5.0 Hz), 3.62 (4H, t, J=5.0 Hz), 3.70-3.80 (12H, m), 6.88 (2H, d, J=8.6 Hz), 7.90 (2H, d, J=8.6 Hz).

2-[4-(2-chlorophenyl)piperazin-1-yl]-5-fluoro-4,6-dimorpholinopyrimidine (Compound 102)

(See Formula (113) below)
The melting point measurement result, the MS measurement result, and the NMR data for the obtained Compound 102 are shown below.

[Chemical 127]

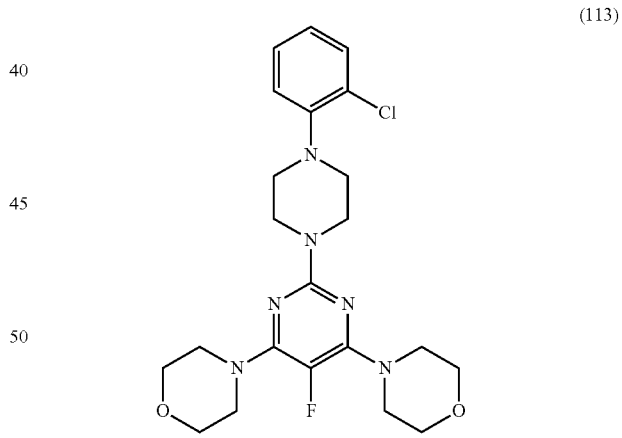
(113)

Melting Point: 118 degrees C.,
MS m/z: 462 (M+),
NMR (CDCl$_3$) δ: 3.46 (4H, t, J=4.9 Hz), 3.56 (8H, t, J=4.8 Hz), 3.77-3.82 (12H, m), 6.97-7.04 (4H, m).

2-[4-(2-ethoxyphenyl)piperazin-1-yl]-5-fluoro-4,6-dimorpholinopyrimidine (Compound 103)

(See Formula (114) below)
The melting point measurement result, the MS measurement result, and the NMR data for the obtained Compound 103 are shown below.

[Chemical 128]

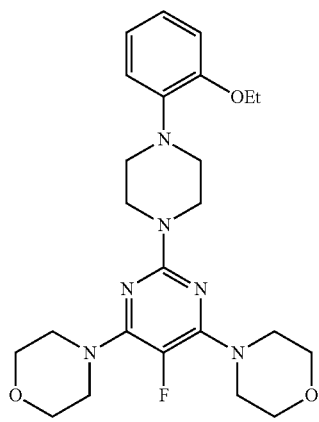

(114)

Melting Point: 145 degrees C.,
MS m/z: 472 (M+),
NMR (CDCl$_3$) δ: 1.48 (3H, t, J=7.0 Hz), 3.10 (4H, t, J=5.0 Hz), 3.56 (8H, t, J=4.7 Hz), 3.75-3.81 (12H, m), 4.09 (2H, q, J=7.0 Hz), 6.86-7.02 (4H, m).

5-fluoro-2-[4-(2-methylphenyl)piperazin-1-yl]-4,6-dimorpholinopyrimidine (Compound 104)

(See Formula (115) below)
The melting point measurement result, the MS measurement result, and the NMR data for the obtained Compound 104 are shown below.

[Chemical 129]

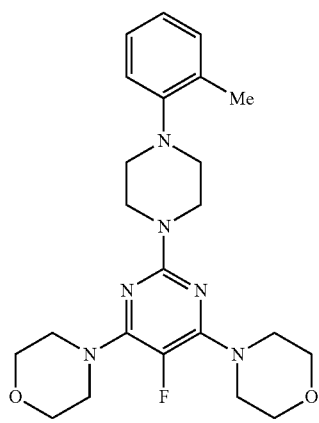

(115)

Melting Point: 72 degrees C.,
MS m/z: 442 (M+),
NMR (CDCl$_3$) δ: 2.35 (3H, s), 2.92 (4H, t, J=4.7 Hz), 3.56 (8H, t, J=4.7 Hz), 3.77 (12H, t, J=4.7 Hz), 6.98-7.16 (4H, m).

5-fluoro-4,6-dimorpholino-2-[4-(2,3-xylyl)piperazin-1-yl]pyrimidine (Compound 105)

(See Formula (116) below)
The melting point measurement result, the MS measurement result, and the NMR data for the obtained Compound 105 are shown below.

[Chemical 130]

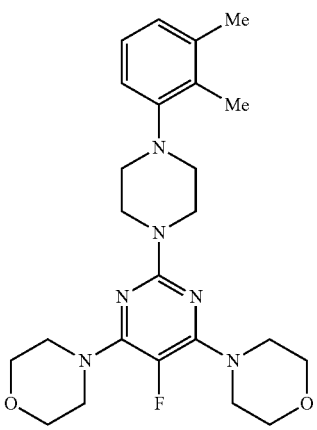

(116)

Melting Point: 132 degrees C.,
MS m/z: 456 (M+),
NMR (CDCl$_3$) δ: 2.26 (3H, s), 2.28 (3H, s), 2.89 (4H, t, J=4.7 Hz), 3.56 (8H, t, J=4.7 Hz), 3.77 (12H, t, J=4.7 Hz), 6.91-7.09 (3H, m).

5-fluoro-2-[4-(2-fluorophenyl)piperazin-1-yl]-4,6-dimorpholinopyrimidine (Compound 106)

(See Formula (117) below)
The melting point measurement result, the MS measurement result, and the NMR data for the obtained Compound 106 are shown below.

[Chemical 131]

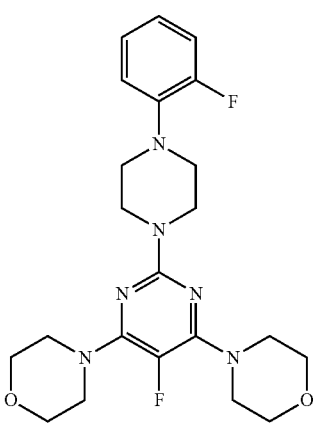

(117)

Melting Point: 144 degrees C.,
MS m/z: 446 (M+),
NMR (CDCl$_3$) δ: 3.10 (4H, t, J=4.9 Hz), 3.56 (8H, t, J=4.7 Hz), 3.76-3.83 (12H, m), 6.96-7.04 (4H, m).

5-fluoro-2-[4-(4-hydroxyphenyl)piperazin-1-yl]-4,6-dimorpholinopyrimidine (Compound 107)

(See Formula (118) below)
The melting point measurement result, the MS measurement result, and the NMR data for the obtained Compound 107 are shown below.

[Chemical 132]

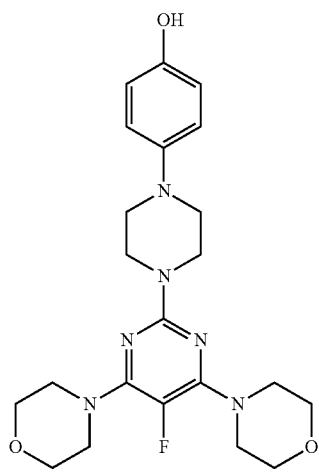

(118)

Melting Point: 141 degrees C.,
MS m/z: 444 (M$^+$)
NMR (CDCl$_3$) δ: 2.05 (1H, bs), 3.07 (4H, t, J=4.7 Hz), 3.56 (8H, t, J=4.7 Hz), 3.77 (12H, t, J=4.7 Hz), 6.80-6.92 (4H, m).

5-fluoro-2-[4-(2-methoxyphenyl)piperazin-1-yl]-4,6-dimorpholinopyrimidine (Compound 108)

(See Formula (119) below)
The melting point measurement result, the MS measurement result, and the NMR data for the obtained Compound 108 are shown below.

[Chemical 133]

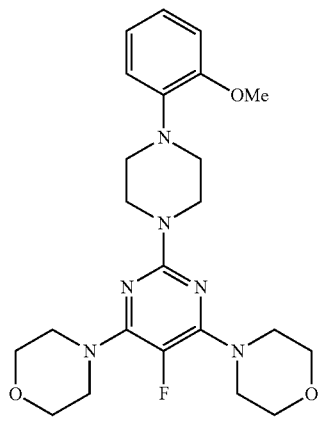

(119)

Melting Point: 171 degrees C.,
MS m/z: 458 (M$^+$),
NMR (CDCl$_3$) δ: 3.08 (4H, t, J=5.0 Hz), 3.56 (8H, t, J=4.8 Hz), 3.77 (8H, t, J=4.8 Hz), 3.83 (4H, t, J=5.0 Hz), 3.89 (3H, s), 6.87-7.02 (4H, m).

2-[4-(4-chlorophenyl)piperazin-1-yl]-5-fluoro-4,6-dimorpholinopyrimidine (Compound 109)

(See Formula (120) below)
The melting point measurement result, the MS measurement result, and the NMR data for the obtained Compound 109 are shown below.

[Chemical 134]

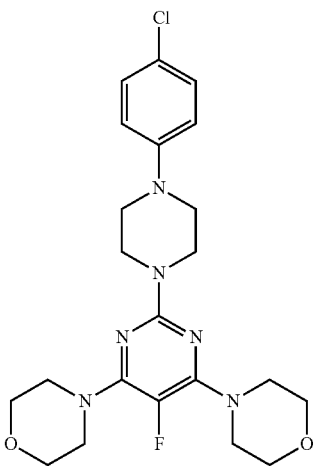

(120)

Melting Point: 215 degrees C.,
MS m/z: 462 (M$^+$),
NMR (CDCl$_3$) δ: 3.16 (4H, t, J=4.6 Hz), 3.56 (8H, t, J=4.6 Hz), 3.77 (12H, t, J=4.6 Hz), 6.87 (2H, d, J=8.9 Hz), 7.22 (2H, d, J=8.9 Hz).

4-[4-(2-chlorophenyl)piperazin-1-yl]-2-dimethylamino-5-fluoro-6-morpholinopyrimidine (Compound 110)

(See Formula (121) below)
The melting point measurement result, the MS measurement result, and the NMR data for the obtained Compound 110 are shown below.

[Chemical 135]

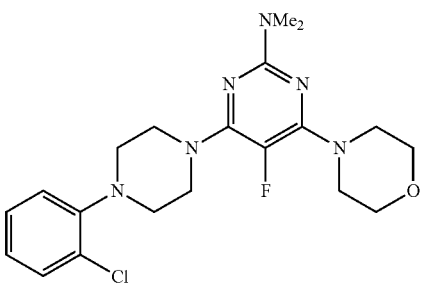

(121)

Melting Point: 98 degrees C.,
MS m/z: 420 (M$^+$),
NMR (CDCl$_3$) δ: 3.06 (6H s), 3.12 (4H, t, J=4.8 Hz), 3.56 (4H, t, J=4.7 Hz), 3.73-3.79 (8H, m), 6.95-7.06 (2H, m), 7.21 (1H, dd, J=1.2, 7.7 Hz), 7.37 (1H, dd, J=1.5, 7.9 Hz).

2-dimethylamino-5-fluoro-4-[4-(2-methoxyphenyl)piperazin-1-yl]-6-morpholinopyrimidine (Compound 111)

(See Formula (122) below)

The melting point measurement result, the MS measurement result, and the NMR data for the obtained Compound 111 are shown below.

[Chemical 136]

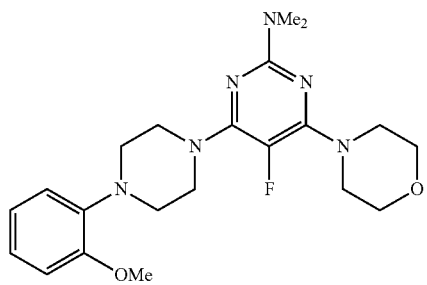

(122)

Melting Point: 108 degrees C.,
MS m/z: 416 (M$^+$),
NMR (CDCl$_3$) δ: 3.06 (6H, s), 3.13 (4H, t, J=4.8 Hz), 3.55 (4H, t, J=4.8 Hz), 3.77 (8H, m), 3.89 (3H, s), 6.87-7.05 (4H, m).

2-dimethylamino-5-fluoro-4-[4-(2-fluorophenyl)piperazin-1-yl]-6-morpholinopyrimidine (Compound 112)

(See Formula (123) below)
The melting point measurement result, the MS measurement result, and the NMR data for the obtained Compound 112 are shown below.

[Chemical 137]

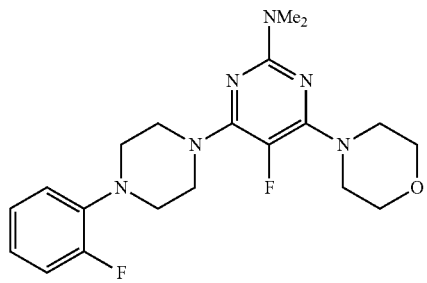

(123)

Melting Point: 95 degrees C.,
Ms m/z: 404 (M$^+$),
NMR (CDCl$_3$) δ: 3.06 (6H, s), 3.15 (4H, t, J=4.9 Hz), 3.56 (4H, t, J=4.8 Hz), 3.72-3.79 (8H, m), 6.93-7.07 (4H, m).

4-[4-(4-chlorophenyl)piperazin-1-yl]-2-dimethylamino-5-fluoro-6-morpholinopyrimidine (Compound 113)

(See Formula (124) below)
The melting point measurement result, the MS measurement result, and the NMR data for the obtained Compound 113 are shown below.

[Chemical 138]

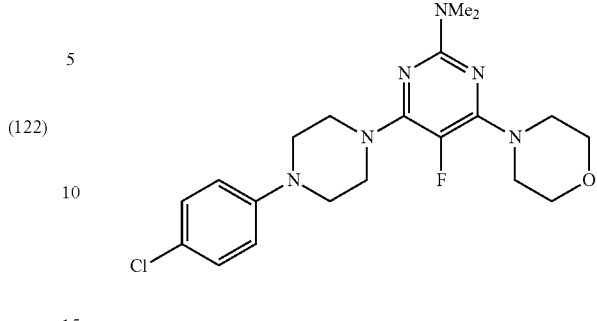

(124)

Melting Point: 152 degrees C.,
MS m/z: 420 (M$^+$),
NMR (CDCl$_3$) δ: 3.06 (6H, s), 3.21 (4H, t, J=5.0 Hz), 3.56 (4H, t, J=4.8 Hz), 3.71 (4H, t, J=5.0 Hz), 3.77 (4H, t, J=4.8 Hz), 6.86 (2H, d, J=8.9 Hz), 7.22 (2H, d, J=8.9 Hz).

2-(4-cyano-4-phenylpiperidin-1-yl)-5-fluoro-4,6-dimorpholinopyrimidine (Compound 114)

(See Formula (125) below)
The NMR data for the obtained Compound 114 are shown below.

[Chemical 139]

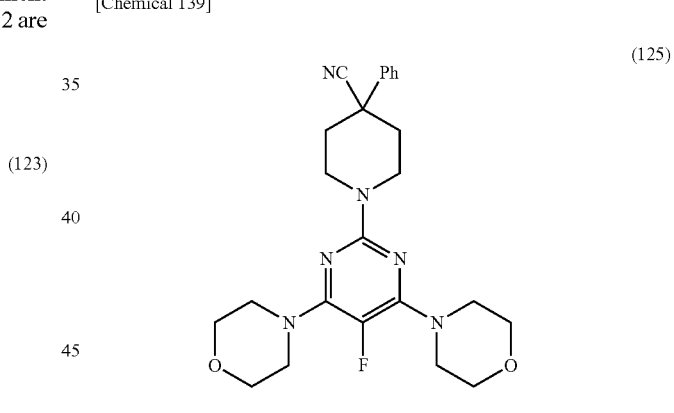

(125)

NMR (CDCl$_3$) δ: 1.95-2.15 (4H, m), 3.22 (2H, m), 3.55 (8H, m), 3.77 (8H, m), 4.75 (2H, m), 7.30-7.50 (5H, m).

4-(4-cyano-4-phenylpiperidin-1-yl)-5-fluoro-2,6-dimorpholinopyrimidine (Compound 115)

(See Formula (126) below)
The NMR data for the obtained Compound 115 are shown below.

[Chemical 140]

-continued (126)

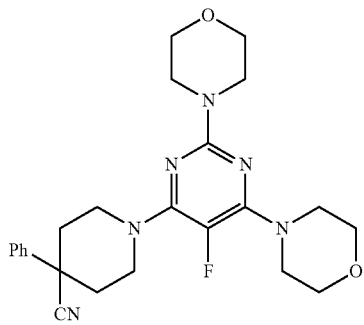

NMR (CDCl₃) δ: 2.13 (4H, m), 3.37 (2H, m), 3.55-3.78 (16H, m), 4.36 (2H, m), 7.31-7.51 (5H, m).

5-fluoro-2-(4-hydroxy-4-phenylpiperidin-1-yl)-4,6-dimorpholinopyrimidine (Compound 116)

(See Formula (127) below)
The melting point measurement result, the MS measurement result, and the NMR data for the obtained Compound 116 are shown below.

[Chemical 141]

(127)

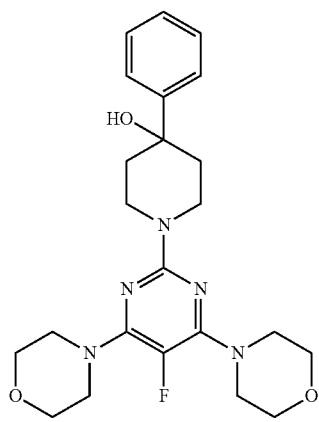

Melting Point: 177.0-180.0 degrees C.,
MS m/z: 443 (M⁺),
NMR (CDCl₃) δ: 1.74 (2H, d, J=12.0 Hz), 2.04 (2H, dd, J=18.8, 6.6 Hz), 3.26 (2H, dd, J=12.9, 2.6 Hz), 3.53 (8H, t, J=4.8 Hz), 3.75 (8H, t, J=4.8 Hz), 4.47 (2H, d, J=13.0 Hz), 7.25 (1H, m), 7.34 (2H, t, J=7.4 Hz), 7.48 (2H, d, J=7.4 Hz).

5-fluoro-4-(4-hydroxy-4-phenylpiperidin-1-yl)-2,6-dimorpholinopyrimidine (Compound 117)

(See Formula (128) below)
The melting point measurement result, the MS measurement result, and the NMR data for the obtained Compound 117 are shown below.

[Chemical 142]

(128)

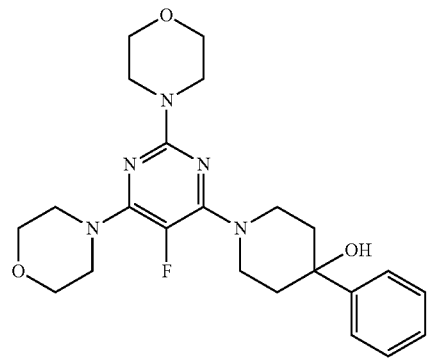

Melting Point: 128.0-131.0 degrees C.,
MS m/z: 443 (M⁺),
NMR (CDCl₃) δ: 1.75 (2H, d, J=12.0 Hz), 2.15 (2H, dd, J=13.2, 4.5 Hz), 3.39 (2H, dd, J=12.9, 2.6 Hz), 3.53 (4H, t, J=4.7 Hz), 3.60 (4H, t, J=4.7 Hz), 3.60-3.80 (8H, m), 4.15 (2H, d, J=14.5 Hz), 7.26 (1H, t, J=7.2 Hz), 7.34 (2H, t, J=7.4 Hz), 7.47 (2H, d, J=7.4 Hz).

2-(4-acetyl-4-phenylpiperidin-1-yl)-5-fluoro-4,6-dimorpholinopyrimidine (Compound 118)

(See Formula (129) below)
The melting point measurement result, the MS measurement result, and the NMR data for the obtained Compound 118 are shown below.

[Chemical 143]

(129)

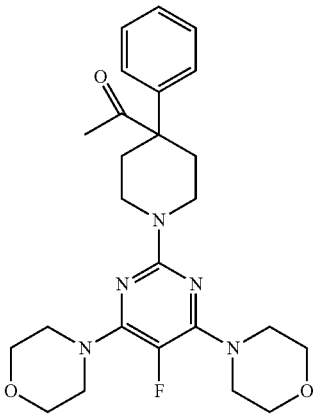

Melting Point: 201.0-205.0 degrees C.,
MS m/z: 469 (M⁺),
NMR (CDCl₃) δ: 1.95 (3H, s), 2.00-2.10 (2H, m), 2.42 (2H, d, J=14.0 Hz), 3.20-3.30 (2H, m), 3.49 (8H, t, J=4.9 Hz), 3.76 (8H, t, J=4.9 Hz), 4.15-4.25 (2H, m), 7.25-7.40 (5H, m).

4-(4-acetyl-4-phenylpiperidin-1-yl)-5-fluoro-2,6-dimorpholinopyrimidine (Compound 119)

(See Formula (130) below)
The MS measurement result, and the NMR data for the obtained Compound 119 are shown below.

[Chemical 144]

(130)

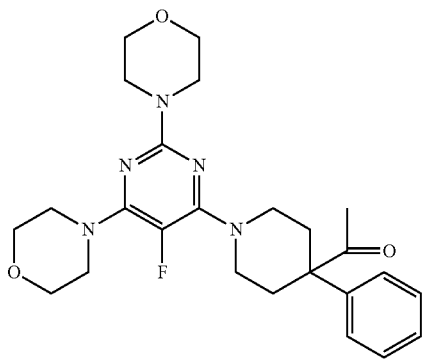

MS m/z: 469 (M⁺),

NMR (CDCl₃) δ: 1.94 (3H, s), 2.05-2.15 (2H, m), 2.45 (2H, d, J=14.0 Hz), 3.25-3.35 (2H, m), 3.52 (4H, t, J=4.9 Hz), 3.60 (4H, t, J=4.9 Hz), 3.70-3.80 (8H, m), 3.85-3.95 (2H, m), 7.25-7.40 (5H, m).

5-fluoro-4,6-dimorpholino-2-[4-phenyl-1,2,5,6-tetrahydropyridin-1-yl]pyrimidine (Compound 120)

(See Formula (131) below)
The melting point measurement result, the MS measurement result, and the NMR data for the obtained Compound 120 are shown below.

[Chemical 145]

(131)

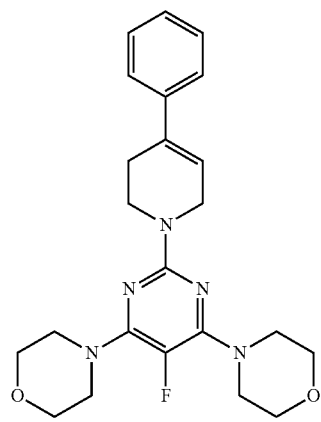

Melting Point: 132.0-135.0 degrees C.,
MS m/z: 425 (M⁺),

NMR (CDCl₃) δ: 2.56 (2H, brs), 3.55 (8H, t, J=4.8 Hz), 3.76 (8H, t, J=4.8 Hz), 3.89 (2H, t, J=3.0 Hz), 4.24 (2H, brs), 6.12 (1H, brs), 7.25-7.40 (5H, m).

5-fluoro-2,4-dimorpholino-6-(4-phenyl-1,2,5,6-tetrahydropyridin-1-yl)pyrimidine (Compound 121)

(See Formula (132) below)
The melting point measurement result, the MS measurement result, and the NMR data for the obtained Compound 121 are shown below.

[Chemical 146]

(132)

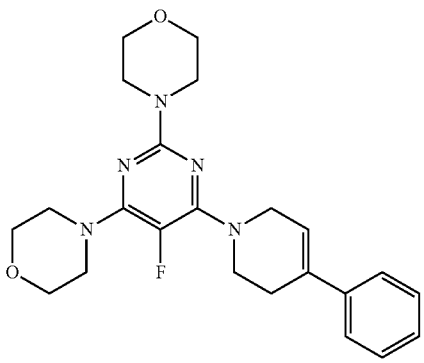

Melting Point: 139.0-142.0 degrees C.,
MS m/z: 425 (M⁺),

NMR (CDCl₃) δ: 2.62 (2H, brs), 3.53 (4H, t, J=4.8 Hz), 3.62 (4H, t, J=4.8 Hz), 3.70-3.80 (10H, m), 4.22 (2H, brs), 6.10 (1H, brs), 7.25-7.40 (5H, m).

5-fluoro-4,6-dimorpholino-2-(1,2,3,4-tetrahydro-2H-isoquinolin-2-yl)pyrimidine (Compound 122)

(See Formula (133) below)
The NMR data for the obtained Compound 122 are shown below.

[Chemical 147]

(133)

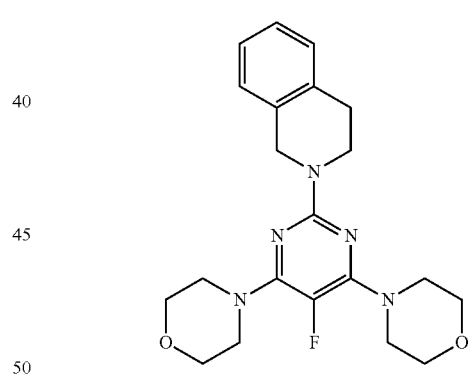

NMR (CDCl₃) δ: 2.87 (2H, m), 3.57 (8H, m), 3.78 (8H, m), 3.91 (2H, m), 4.78 (2H, s), 7.15 (4H, m).

2-(4-cyclohexylpiperazin-1-yl)-5-fluoro-4,6-dimorpholinopyrimidine (Compound 123)

(See Formula (134) below)
The melting point measurement result, the MS measurement result, and the NMR data for the obtained Compound 123 are shown below.

[Chemical 148]

(134)

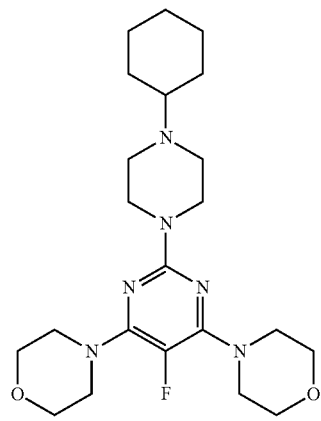

Melting Point: 132.0-135.0 degrees C.,
MS m/z: 416 (M+),
NMR (CDCl$_3$) δ: 1.15-1.25 (4H, m), 1.60-1.70 (2H, m), 1.75-1.95 (4H, m), 2.27 (1H, brs), 2.58 (4H, t, J=5.0 Hz), 3.49 (8H, t, J=4.9 Hz), 3.74 (12H, t, J=5.7 Hz).

4-(4-cyclohexylpiperazin-1-yl)-5-fluoro-2,6-dimorpholinopyrimidine (Compound 124)

(See Formula (135) below)
The melting point measurement result, the MS measurement result, and the NMR data for the obtained Compound 124 are shown below.

[Chemical 149]

(135)

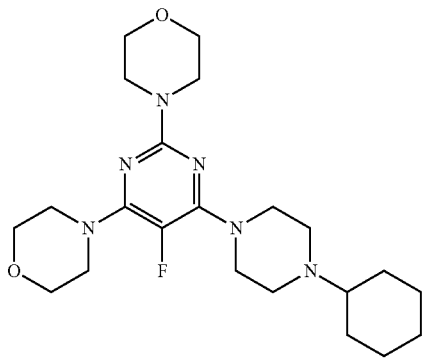

Melting Point: 125.0-128.0 degrees C.,
MS m/z: 416 (M+),
NMR (CDCl$_3$) δ: 1.15-1.25 (4H, m), 1.60-1.70 (2H, m), 1.75-1.95 (4H, m), 2.28 (1H, brs), 2.65 (4H, t, J=4.7 Hz), 3.53 (4H, t, J=4.9 Hz), 3.60 (8H, t, J=5.7 Hz), 3.81 (8H, t, J=5.7 Hz).

5-fluoro-4-[4-(2-fluorophenyl)piperazin-1-yl]-6-morpholino-2-(4-phenylpiperazin-1-yl)pyrimidine (Compound 125)

(See Formula (136) below)
The melting point measurement result, the MS measurement result, and the NMR data for the obtained Compound 125 are shown below.

[Chemical 150]

(136)

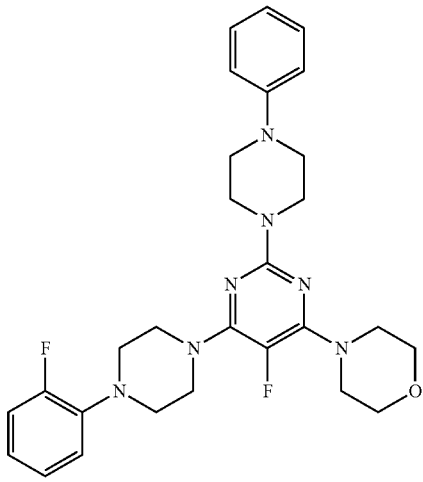

Melting Point: 140-141 degrees C.,
Ms m/z: 521 (M+),
NMR (CDCl$_3$) δ: 3.19 (8H, m), 3.57 (4H, t, J=4.5 Hz), 3.74-3.84 (12H, m), 6.90-7.04 (7H, m), 7.27-7.31 (2H, m).

2,4-bis[4-(2-fluorophenyl)piperazin-1-yl]-5-fluoro-6-morpholinopyrimidine (Compound 126)

(See Formula (137) below)
The melting point measurement result, the MS measurement result, and the NMR data for the obtained Compound 126 are shown below.

[Chemical 151]

(137)

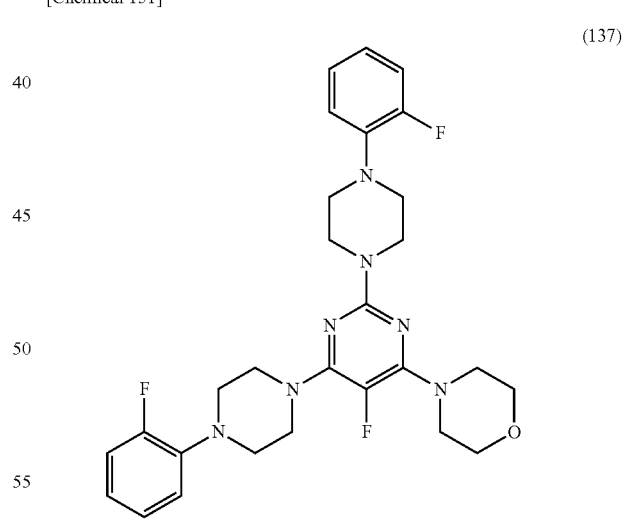

Melting Point: 131-132 degrees C.,
MS m/z: 539 (M+),
NMR (CDCl$_3$) δ: 3.13 (8H, m), 3.57 (4H, t, J=4.7 Hz), 3.77-3.83 (12H, m), 6.94-7.10 (8H, m).

5-fluoro-2-[4-(2-fluorophenyl)piperazin-1-yl]-4-[4-(2-methylphenyl)piperazin-1-yl]-6-morpholinopyrimidine (Compound 127)

(See Formula (138) below)

The melting point measurement result, the MS measurement result, and the NMR data for the obtained Compound 127 are shown below.

[Chemical 152]

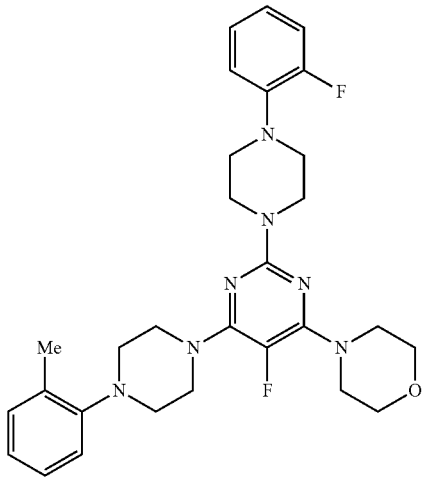

(138)

Melting Point: 71-72 degrees C.,
MS m/z: 535 (M+),
NMR (CDCl$_3$) δ: 2.35 (3H, s), 2.98 (4H, t, J=4.9 Hz), 3.11 (4H, t, J=4.9 Hz), 3.57 (4H, t, J=4.7 Hz), 3.72 (4H, t, J=4.8 Hz), 3.78 (4H, t, J=4.7 Hz), 3.84 (4H, t, J=4.8 Hz), 6.98-7.07 (6H, m), 7.17-7.20 (2H, m).

5-fluoro-2-[4-(2-methylphenyl)piperazin-1-yl]-6-morpholino-4-(4-phenylpiperazin-1-yl)pyrimidine (Compound 128)

(See Formula (139) below)
The melting point measurement result, the MS measurement result, and the NMR data for the obtained Compound 128 are shown below.

[Chemical 153]

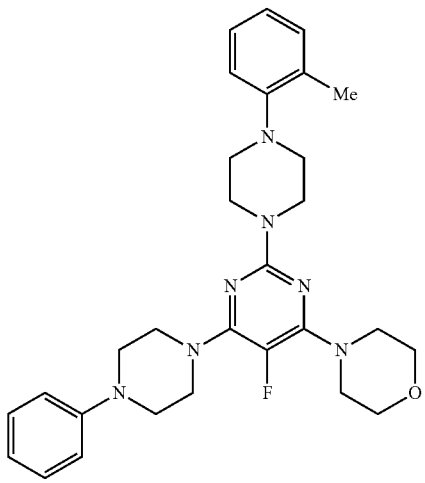

(139)

Melting Point: 77-78 degrees C.,
Ms m/z: 517 (M+),
NMR (CDCl$_3$) δ: 2.35 (3H, s), 2.94 (4H, t, J=4.9 Hz), 3.26 (4H, t, J=4.9 Hz), 3.58 (4H, t, J=4.6 Hz), 3.72-3.80 (12H, m), 6.91-7.00 (6H, m), 7.18-7.29 (3H, m).

2,4-bis[4-(2-methylphenyl)piperazin-1-yl]-5-fluoro-6-morpholinopyrimidine (Compound 129)

(See Formula (140) below)
The melting point measurement result, the MS measurement result, and the NMR data for the obtained Compound 129 are shown below.

[Chemical 154]

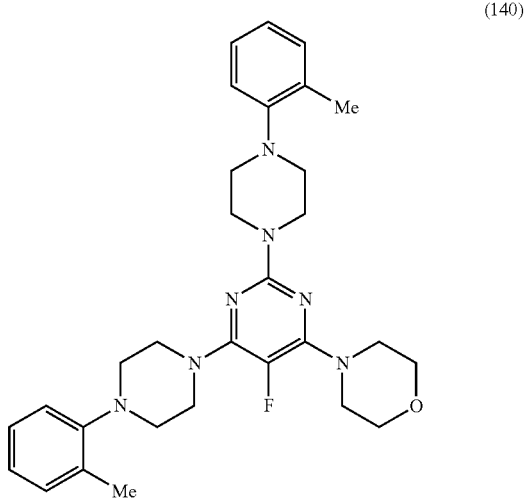

(140)

Melting Point: 106-107 degrees C.,
Ms m/z: 531 (M+),
NMR (CDCl$_3$) δ: 2.34 (6H, bs), 3.11 (8H, t, J=5.6 Hz), 3.92-3.94 (8H, m), 4.11-4.13 (4H, m), 4.24-4.26 (4H, m), 7.03-7.06 (4H, m), 7.16-7.23 (4H, m).

Example 13

Synthesis of 5-chloro-4,6-dimorpholino-2-(4-phenylpiperazin-1-yl)pyrimidine (Compound 130)

(See Reaction Formula (141) below)

[Chemical 155]

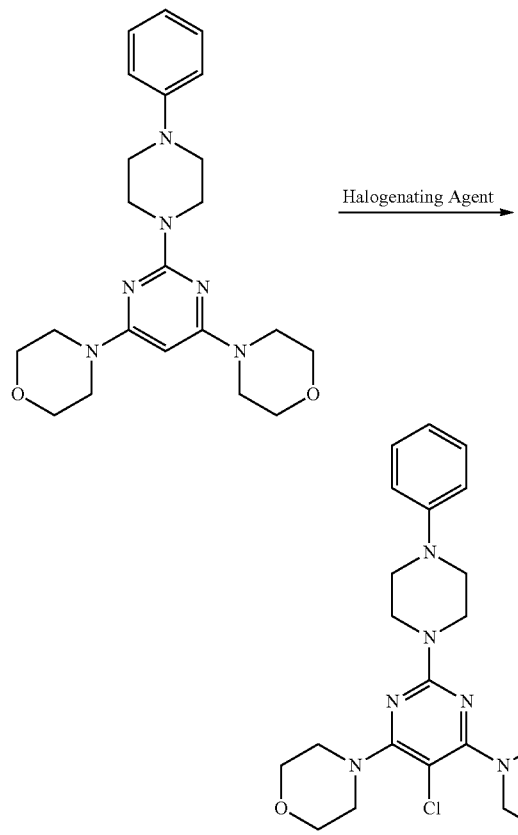

(141)

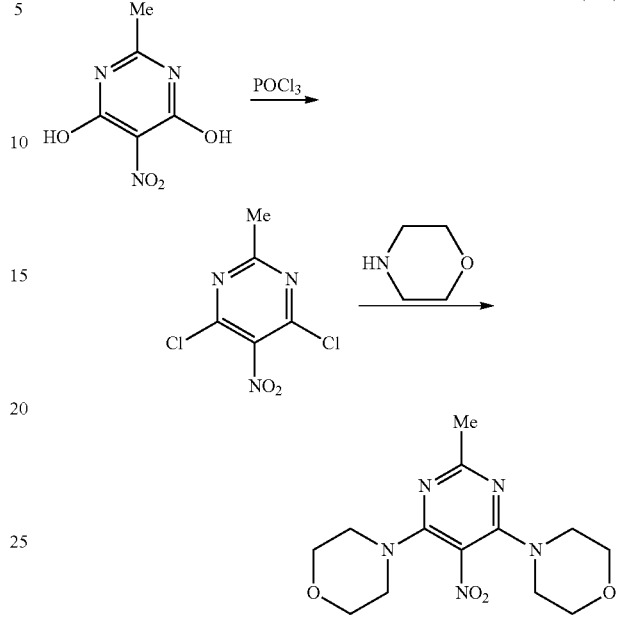

(142)

[Chemical 156]

The synthesis method shall be explained concretely, and in order, below. 4,6-dimorpholino-2-(4-phenylpiperazin-1-yl)pyrimidine (300 mg, 0.73 mmol) was dissolved in chloroform solution (5 ml), benzoyl peroxide (0.3 mg, 0.0014 mmol) and N-chlorosuccinimide (117 mg, 0.87 mmol) was added, and refluxed under heating for 1 hour. Water was added, and extraction was done with dichloromethane. After washing the organic layer with saturated saline, drying was done with $MgSO_4$, and the solvent was distilled away under reduced pressure. Purification was done by silica gel chromatography (hexane:ethyl acetate=4:1), and 142 mg of 5-chloro-4,6-dimorpholino-2-(4-phenylpiperazin-1-yl)pyrimidine was obtained (yield 46%). The melting point measurement result, the MS measurement result, and the NMR data for the obtained Compound 130 are shown below.

Melting Point: 131-133 degrees C.,

MS m/z: 312, 444 (M+),

NMR ($CDCl_3$) δ: 3.19-3.22 (4H, m), 3.48-3.51 (8H, m), 3.77-3.89 (12H, m), 6.86-7.32 (5H, m).

Example 14

Synthesis of 5-amino-2-[2-(4-methoxyphenyl)vinyl]-4,6-dimorpholinopyrimidine (Compound 131)

(13-1) Synthesis of 2-methyl-4,6-dimorpholino-5-nitropyrimidine (See Reaction Formula (142) below)

The synthesis method shall be explained concretely, and in order, below. To a solution of 4,6-dihydroxy-2-methyl-5-nitropyrimidine (4.37 g, 25.5 mmol) in toluene (22 ml), phosphorus oxychloride (9.54 ml, 102 mmol) and diisopropylethylamine (17.8 ml, 102 mmol) was added and agitated under heating for 1 hour at 100 degrees Celsius. The reaction liquid was poured into ice water, and after a period of agitation, extraction was carried out 2 times using ethyl acetate. Morpholine (22 ml) was added to the ethyl acetate layer and agitation was done overnight at room temperature. Water was added and extraction was carried out 2 times using ethyl acetate. After washing the organic layer with saturated saline, drying was done with $MgSO_4$, and the solvent was distilled away under reduced pressure. Purification was done by silica gel chromatography (hexane:ethyl acetate=1:1), and 5.13 g of 2-methyl-4,6-dimorpholino-5-nitropyrimidine (yield 65%) was obtained. The NMR data for the obtained 2-methyl-4,6-dimorpholino-5-nitropyrimidine is shown below.

NMR ($CDCl_3$) δ: 2.31 (3H, s), 3.73 (8H, m), 3.81 (8H, m).

(13-2) Synthesis of 2-[2-(4-methoxyphenyl)vinyl]-4,6-dimorpholino-5-nitropyrimidine (See Reaction Formula (143) below)

[Chemical 157]

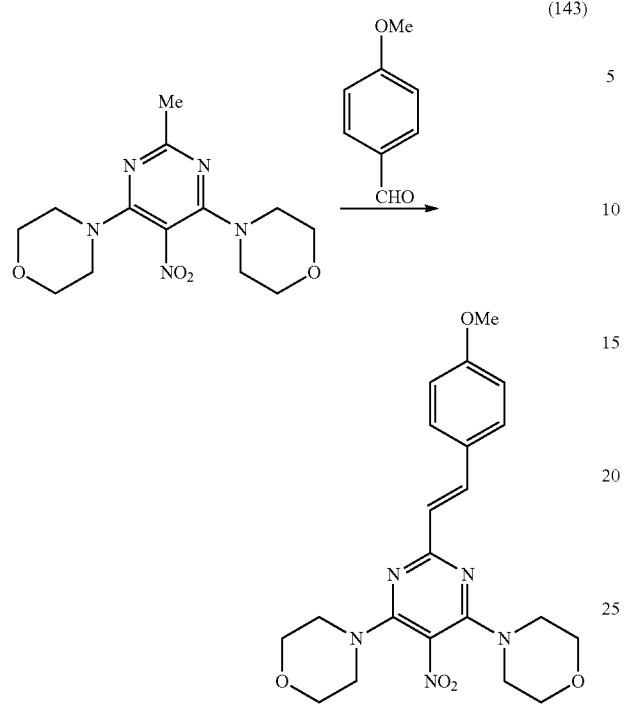

(143)

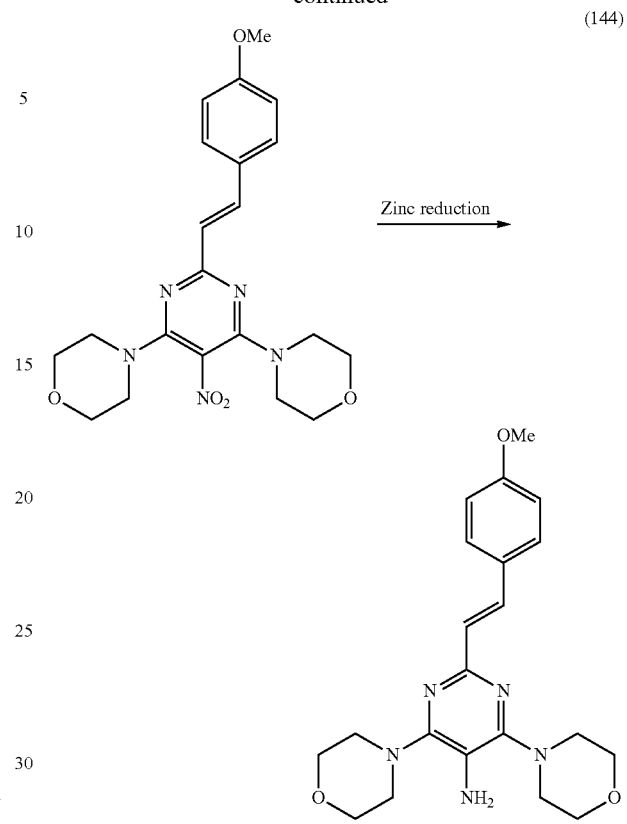

(144)

The synthesis method shall be explained concretely, and in order, below. A solution of 2-methyl-4,6-dimorpholino-5-nitropyrimidine (1.13 g, 3.65 mmol) and p-anisaldehyde (3.50 ml, 29.3 mmol) in piperidine (5 ml) was agitated under heating for 4 hours at 130 degrees Celsius. Water was added, and extraction was carried out 2 times using ethyl acetate. After washing the organic layer with saturated saline, drying was done with $MgSO_4$, and the solvent was distilled away under reduced pressure. Purification was done by silica gel chromatography (hexane:ethyl acetate=1:1), and 535 mg of 2-[2-(4-methoxyphenyl)vinyl]-4,6-dimorpholino-5-nitropyrimidine (yield 58%) was obtained. The NMR data for the obtained 2-[2-(4-methoxyphenyl)vinyl]-4,6-dimorpholino-5-nitropyrimidine is shown below.

NMR ($CDCl_3$) δ: 3.41-3.86 (16H, m), 3.84 (3H, s), 6.72 (1H, d, J=15.8 Hz), 6.90 (2H, d, J=8.9 Hz), 7.54 (2H, d, J=8.9 Hz), 7.80 (1H, d, J=15.8 Hz).

(7-3) Synthesis of 5-amino-2-[2-(4-methoxyphenyl) vinyl]-4,6-dimorpholinopyrimidine (Compound 131)

(See Reaction Formula (144) below)

[Chemical 158]

The synthesis method shall be explained concretely, and in order, below. A mixed solution of 2-[2-(4-methoxyphenyl) vinyl]-4,6-dimorpholino-5-nitropyrimidine (1.35 g, 3.16 mmol), zinc dust (6.19 g, 94.8 mmol), and calcium chloride (224 mg, 2.02 mmol) in acetonitrile (80 ml) and water (20 ml) was refluxed under heating for 1 hour. The undissolved matter was separated out by celite filtering, the filtrate was distilled away under reduced pressure, water was added to the residue, the precipitated crystals were taken out by filtering, and 5-amino-2-[2-(4-methoxyphenyl)vinyl]-4,6-dimorpholinopyrimidine (940 mg, yield 75%) was obtained. The melting point measurement result, the MS measurement result, and the NMR data for the obtained Compound 131 are shown below.

Melting Point: 173-182 degrees C.,
MS m/z: 397 ($M^+$),
NMR ($CDCl_3$) δ: 3.24-3.34 (8H, m), 3.44 (2H, bs), 3.75-3.88 (8H, m), 3.83 (3H, s), 6.88 (2H, d, J=8.6 Hz), 6.90 (1H, d, J=15.8 Hz), 7.52 (2H, d, J=8.6 Hz), 7.66 (1H, d, J=15.8 Hz).

Example 15

Using a similar method to that for Example 14, the following compounds (Compounds 132-140, Compound 170, Compounds 172-176, Compounds 195-203, Compounds 205-215) were produced from corresponding starting materials.

5-amino-4,6-dimorpholino-2-[2-(2-thienyl)vinyl] pyrimidine (Compound 132)

(See Formula (145) below)

The melting point measurement result, the MS measurement result, and the NMR data for the obtained Compound 132 are shown below.

[Chemical 159]

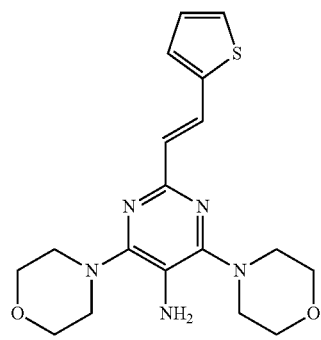

(145)

Melting Point: 221.0-223.0 degrees C.,

MS m/z: 373 (M$^+$),

NMR (CDCl$_3$) δ: 3.32 (8H, t, J=4.6 Hz), 3.82 (2H, s), 3.86 (8H, t, J=4.6 Hz), 6.85 (1H, d, J=15.7 Hz), 7.01 (1H, dd, J=5.1, 3.6 Hz), 7.16 (1H, d, J=3.6 Hz), 7.23 (1H, d, J=5.1 Hz), 7.80 (1H, d, J=15.7 Hz).

5-amino-2-[2-(4-methylthiopheno[1,2-b]pyrrol-5-yl)vinyl]-4,6-dimorpholinopyrimidine (Compound 133)

(See Formula (146) below)

The melting point measurement result, the MS measurement result, and the NMR data for the obtained Compound 133 are shown below.

[Chemical 160]

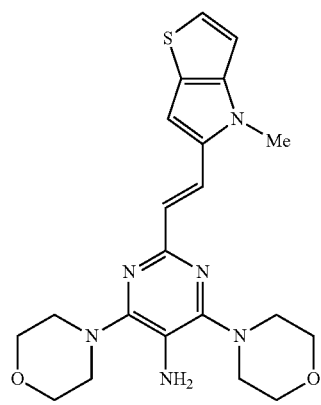

(146)

Melting Point: 175.0-178.0 degrees C.,

MS m/z: 426 (M$^+$),

NMR (CDCl$_3$) δ: 3.33 (8H, t, J=4.6 Hz), 3.49 (2H, s), 3.87 (3H, s), 3.89 (8H, t, J=4.6 Hz), 6.80 (1H, brs), 6.90 (1H, d, J=15.7 Hz), 6.91 (1H, d, J=5.3 Hz), 7.09 (1H, d, J=5.3 Hz), 7.70 (1H, d, J=15.7 Hz).

5-amino-4,6-dimorpholino-2-[2-(pyridin-4-yl)vinyl]pyrimidine (Compound 134) (See Formula (147) below)

The melting point measurement result, the MS measurement result, and the NMR data for the obtained Compound 134 are shown below.

[Chemical 161]

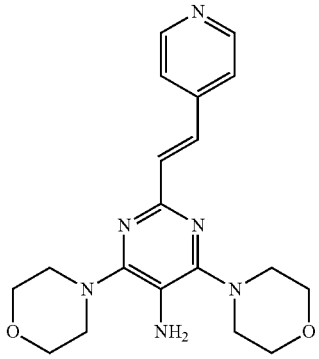

(147)

Melting Point: 216.0-220.0 degrees C.,

MS m/z: 368 (M$^+$),

NMR (CDCl$_3$) δ: 3.33 (8H, t, J=4.5 Hz), 3.58 (2H, s), 3.85 (8H, t, J=4.5 Hz), 7.20 (1H, d, J=15.7 Hz), 7.53 (2H, d, J=5.7 Hz), 7.59 (1H, d, J=15.7 Hz), 8.66 (2H, d, J=5.7 Hz).

5-amino-2-[2-(4-fluorophenyl)vinyl]-4,6-dimorpholinopyrimidine (Compound 135)

(See Formula (148) below)

The melting point measurement result, the MS measurement result, and the NMR data for the obtained Compound 135 are shown below.

[Chemical 162]

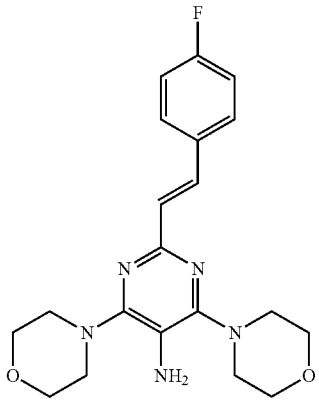

(148)

Melting Point: 193.0-195.0 degrees C.,

MS m/z: 385 (M$^+$),

NMR (CDCl$_3$) δ: 3.33 (8H, t, J=4.6 Hz), 3.55 (2H, s), 3.87 (8H, t, J=4.6 Hz), 6.95 (1H, d, J=15.7 Hz), 7.04 (2H, t, J=8.9 Hz), 7.55 (1H, dd, J=8.9, 5.4 Hz), 7.66 (1H, d, J=15.7 Hz).

5-amino-4,6-dimorpholino-2-[2-(4-piperidinophenyl)vinyl]pyrimidine (Compound 136)

(See Formula (149) below)
The melting point measurement result, the MS measurement result, and the NMR data for the obtained Compound 136 are shown below.

[Chemical 163]

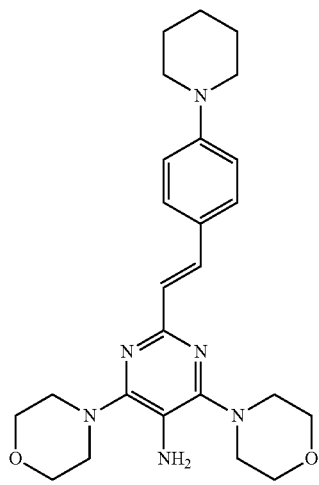

(149)

Melting Point: 185.0-188.0 degrees C.,
MS m/z: 450 (M+),
NMR (CDCl$_3$) δ: 1.5-1.7 (6H, m), 3.22 (4H, t, J=4.6 Hz), 3.32 (8H, t, J=4.6 Hz), 3.42 (2H, s), 3.86 (8H, t, J=4.6 Hz), 6.86 (1H, d, J=15.7 Hz), 6.89 (2H, t, J=8.7 Hz), 7.47 (2H, d, J=8.7 Hz), 7.65 (1H, d, J=15.7 Hz).

5-amino-2-[2-(2-methylphenyl)vinyl]-4,6-dimorpholinopyrimidine (Compound 137)

(See Formula (150) below)
The melting point measurement result, the MS measurement result, and the NMR data for the obtained Compound 137 are shown below.

[Chemical 164]

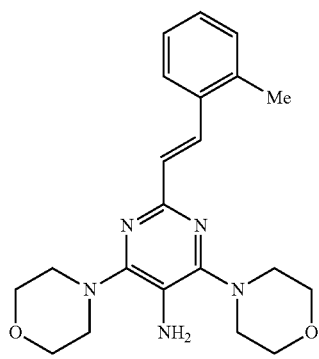

(150)

Melting Point: 151.0-154.0 degrees C.,
MS m/z: 381 (M+),

NMR (CDCl$_3$) δ: 2.46 (3H, s), 3.33 (8H, t, J=4.6 Hz), 3.46 (2H, s), 3.87 (8H, t, J=4.6 Hz), 6.95 (1H, d, J=15.7 Hz), 7.15-7.25 (3H, m), 7.67 (1H, m), 7.99 (1H, d, J=15.7 Hz).

5-amino-4-dimethylamino-2-[2-(4-methoxyphenyl)vinyl]-6-morpholinopyrimidine (Compound 138)

(See Formula (151) below)
The melting point measurement result, the MS measurement result, and the NMR data for the obtained Compound 138 are shown below.

[Chemical 165]

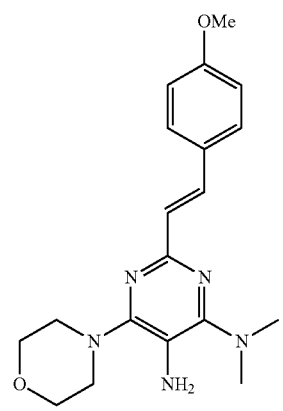

(151)

Melting Point: 130.0-133.0 degrees C.,
MS m/z: 355 (M+),
NMR (CDCl$_3$) δ: 2.93 (6H, s), 3.32 (4H, t, J=4.6 Hz), 3.44 (2H, s), 3.83 (3H, s), 3.87 (4H, t, J=4.6 Hz), 6.88 (2H, d, J=8.9 Hz), 6.92 (1H, d, J=15.5 Hz), 7.52 (2H, d, J=8.9 Hz), 7.68 (1H, d, J=15.5 Hz).

5-amino-2-[2-(4-methoxyphenyl)vinyl]-4-methylamino-6-morpholinopyrimidine (Compound 139)

(See Formula (152) below)
The NMR data for the obtained Compound 139 are shown below.

[Chemical 166]

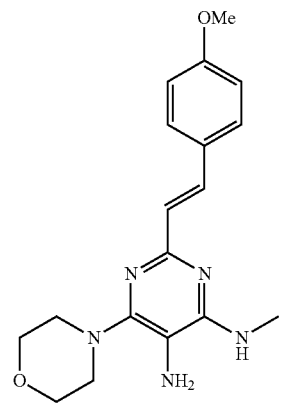

(152)

NMR (CDCl$_3$) δ: 3.11 (3H, d, J=4.3 Hz), 3.17 (4H, t, J=4.7 Hz), 3.82 (3H, s), 3.86 (4H, t, J=4.7 Hz), 4.34-4.36 (1H, br), 6.88 (2H, d, J=8.7 Hz), 6.92 (1H, d, J=16.0 Hz), 7.53 (2H, d, J=8.7 Hz), 7.70 (1H, d, J=16.0 Hz).

5-amino-4,6-bis(dimethylamino)-2-[2-(4-methoxyphenyl)vinyl]pyrimidine (Compound 140)

(See Formula (153) below)

The melting point measurement result, the MS measurement result, and the NMR data for the obtained Compound 140 are shown below.

[Chemical 167]

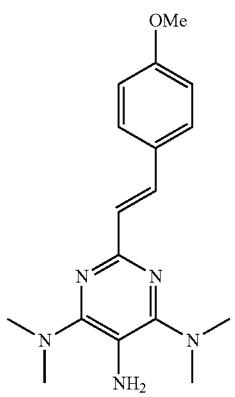

(153)

Melting Point: 135.0-138.0 degrees C.,

MS m/z: 313 (M+),

NMR (CDCl$_3$) δ: 2.92 (12H, s), 3.42 (2H, s), 3.85 (3H, s), 6.87 (2H, d, J=8.9 Hz), 6.94 (1H, d, J=15.5 Hz), 7.52 (2H, d, J=8.9 Hz), 7.66 (1H, d, J=15.5 Hz).

Example 16

Synthesis of 5-dimethylamino-4,6-dimorpholino-2-(4-phenylpiperazin-1-yl)pyrimidine (Compound 141)

(See Reaction Formula (154) below)

[Chemical 168]

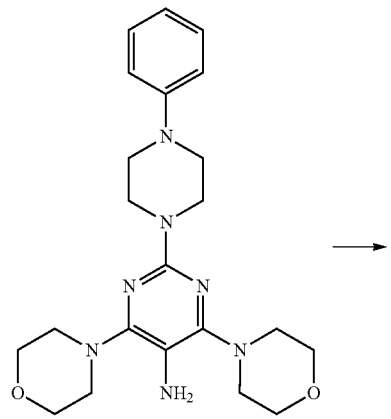

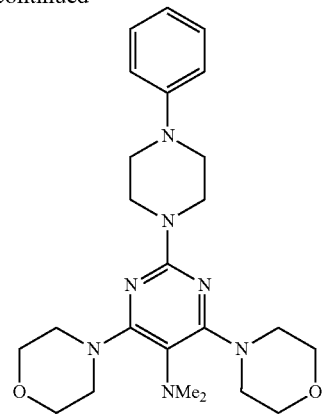

The synthesis method shall be explained concretely, and in order, below. To a solution of 5-amino-4,6-dimorpholino-2-(4-phenylpiperazin-1-yl)pyrimidine (425 mg, 1.0 mmol) in acetonitrile (10 ml), formalin (0.8 ml, 10 mmol), sodium cyanotrihydridoborate (188 mg, 3.0 mmol), and acetic acid (0.1 ml) was added and this was agitated for 1 hour. 2N NaOH solution was added, and extraction was carried out 2 times with dichloromethane. After washing the organic layer with saturated saline, drying was done with MgSO$_4$, and the solvent was distilled away under reduced pressure. Purification was done by silica gel chromatography (hexane:ethyl acetate=2:1), and 260 mg of 5-dimethylamino-4,6-dimorpholino-2-(4-phenylpiperazin-1-yl)pyrimidine (yield 57%) was obtained. The melting point measurement result, the MS measurement result, and the NMR data for the obtained Compound 141 are shown below.

Melting Point: 208-210 degrees C.,

MS m/z: 453 (M+),

NMR (CDCl$_3$) δ: 2.65 (6H, s), 3.19-3.33 (12H, m), 3.82-3.85 (12H, m), 6.85-7.31 (5H, m).

Example 17

Synthesis of 5-formyl-4,6-dimorpholino-2-(4-phenylpiperazin-1-yl)pyrimidine (Compound 142)

(See Reaction Formula (155) below)

[Chemical 169]

(155)

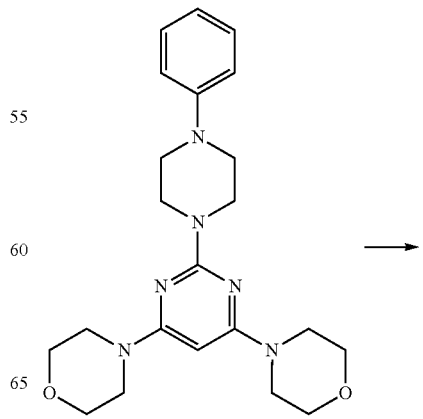

-continued

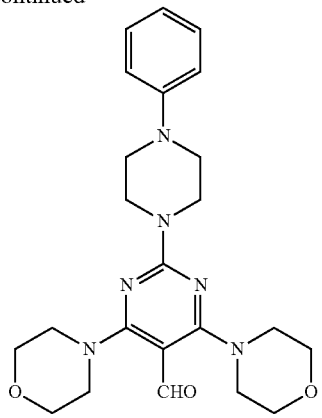

The synthesis method shall be explained concretely, and in order, below. Phosphorus oxychloride (0.12 ml, 1.3 mmol) was added to dimethylformamide (0.3 ml, 4.0 mmol) at 0 degrees Celsius, and this was agitated for 5 minutes at 0 degrees Celsius. To this solution, 4,6-dimorpholino-2-(4-phenylpiperazin-1-yl)pyrimidine was dissolved in dimethylformamide (6 ml) and added, and this was agitated under heating for 1 hour at 100 degrees Celsius. After 2N NaOH solution was added to make the reaction liquid basic, extraction was carried out 2 times with ethyl acetate. After washing the organic layer with saturated saline, drying was done with MgSO$_4$, and the solvent was distilled away under reduced pressure. Purification was done by silica gel chromatography (hexane:ethyl acetate=2:3), and 350 mg of 4,6-dimorpholino-5-formyl-2-(4-phenylpiperazin-1-yl)pyrimidine (yield 80%) was obtained. The melting point measurement result, the MS measurement result, and the NMR data for the obtained Compound 142 are shown below.

Melting Point: 162-163 degrees C.,
MS m/z: 438 (M$^+$),
NMR (CDCl$_3$) δ: 3.20 (4H, m), 3.67-3.99 (20H, m), 6.87-7.32 (5H, m), 9.23 (1H, s).

Example 18

Synthesis of 6-dimethylamino-2-methyl-4-morpholino-5-nitropyrimidine (Compound 143)

(See Reaction Formula (156) below)

[Chemical 170]

(156)

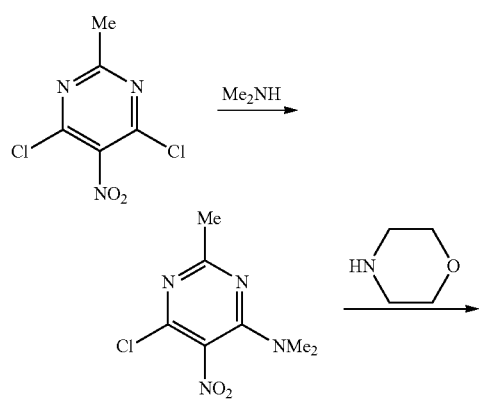

-continued

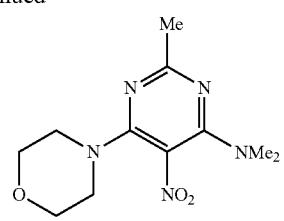

The synthesis method shall be explained concretely, and in order, below. To a solution of 4,6-dichloro-2-methyl-5-nitropyrimidine (2.65 g, 12.5 mmol) in ethyl acetate (200 ml), a 50% aqueous dimethylamine solution (1.10 ml) was dripped in at −15 degrees Celsius, this was further agitated for 1 hour, then agitated for 1 hour at 0 degrees Celsius, then at room temperature for 16 hours. The reaction liquid was poured into ice water and extraction was carried out 2 times with ethyl acetate. After washing together with the ethyl acetate layer with saturated saline, drying was done with MgSO$_4$, and the solvent was distilled away under reduced pressure. Purification was done by silica gel chromatography (hexane:ethyl acetate=1:1), and 827.4 mg of 6-chlor-4-dimethylamino 2-methyl-5-nitropyrimidine (yield 31%) was obtained. The MS measurement result, and the NMR data for the obtained 6-chlor-4-dimethylamino-2-methyl-5-nitropyrimidine are shown below.

MS m/z: 216 (M$^+$),
NMR (CDCl$_3$) δ: 3.15 (6H, s), 2.52 (3H, s).

Further, 432.0 mg (2.0 mmol) of 6-chlor-4-dimethylamino-2-methyl-5-nitropyrimidine was added to 2.0 ml of morpholine under ice cooling, and this was refluxed under heating for 8 hours. After allowing to cool, the reaction liquid was poured into ice water and extraction was carried out 2 times with ethyl acetate. After washing together with the ethyl acetate layer with saturated saline, drying was done with MgSO$_4$, and the solvent was distilled away under reduced pressure. Separation was done by silica gel chromatography (ethyl acetate), and 319.9 mg of 6-dimethylamino-2-methyl-4-morpholino-5-nitropyrimidine (Compound 143) (yield 60%) was obtained. The MS measurement result, and the NMR data for the obtained Compound 143 are shown below.

MS m/z: 267 (M$^+$),
NMR (CDCl$_3$) δ: 3.9-3.7 (8H, s), 3.20 (6H, s), 2.52 (3H, s).

Example 19

Using a similar method to that for Example 14, 5-amino-2-[4-(4-diethylaminophenyl) butan-1,3-dienyl]-4,6-dimorpholinopyrimidine (Compound 144) (See Formula (157) below) was produced from corresponding starting materials. The MS measurement result, and the NMR data for the obtained Compound 144 are shown below.

[Chemical 171]

(157)

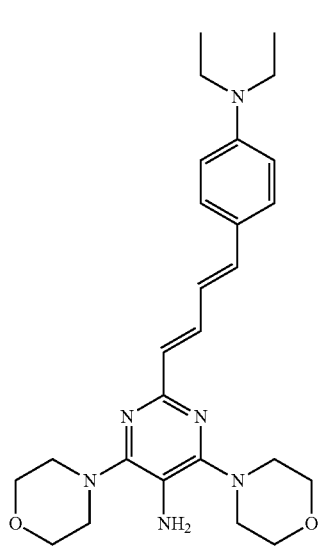

MS m/z: 464 (M⁺)

NMR (CDCl₃) δ: 1.17 (6H, t, J=7.1 Hz), 3.31 (8H, t, J=4.6 Hz), 3.37 (4H, q, J=7.1 Hz), 3.41 (2H, brs), 3.83 (8H, t, J=4.6 Hz), 6.49 (1H, d, J=15.0 Hz), 6.63 (2H, d, J=8.9 Hz), 6.69 (1H, d, J=15.5 Hz), 6.79 (1H, dd, J=10.2, 15.0 Hz), 7.32 (2H, d, J=8.9 Hz), 7.52 (1H, dd, J=10.2, 15.5 Hz).

Example 20

Synthesis of 5-amino-2-[4-(4-diethylaminophenyl)butyl]-4,6-dimorpholinopyrimidine (Compound 145)

(See Reaction Formula (158) below)

[Chemical 172]

(158)

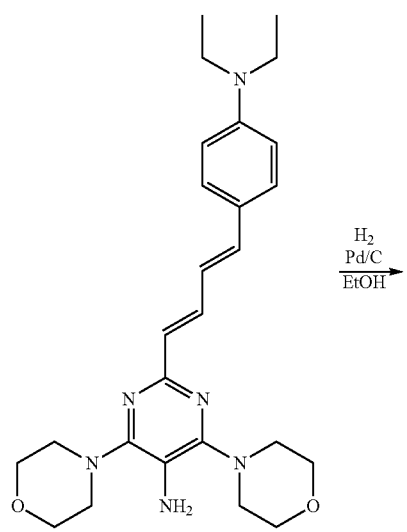

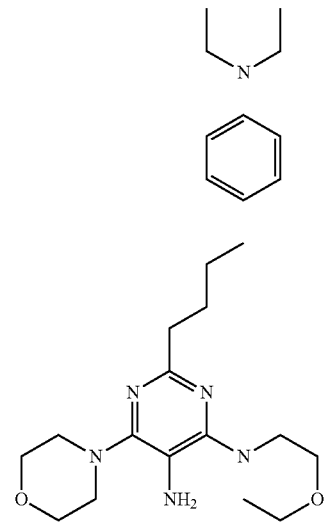

The synthesis method shall be explained concretely, and in order, below. 5-amino-2-[4-(4-diethylaminophenyl)butan-1,3-dienyl]-4,6-dimorpholinopyrimidine (500 mg, 1.08 mmol) (Compound 144) was dissolved in ethanol (30 ml), 300 mg of Pd/C was added, and catalytic reduction was carried out for 18 hours at room temperature. The Pd/C was filtered out of the reaction liquid using celite, the filtrate was taken and the solvent was distilled away under reduced pressure. The residue was separated and purified by silica gel chromatography (hexane:ethyl acetate=1:1), and 131.4 mg of 5-amino-2-[4-(4-diethylaminophenyl)butyl]-4,6-dimorpholino pyrimidine (Compound 145) was obtained (yield 26%). The MS measurement result, and the NMR data for the obtained Compound 145 are shown below.

MS m/z: 468 (M⁺)

NMR (CDCl₃) δ: 1.31 (6H, t, J=7.1 Hz), 1.61 (2H, quint, J=7.8 Hz), 1.79 (2H, quint, J=7.8 Hz), 2.53 (2H, quint, J=7.8 Hz), 2.72 (2H, quint, J=7.8 Hz), 3.25-3.35 (14H, m), 3.82 (8H, t, J=4.5 Hz), 6.61 (2H, d, J=8.8 Hz), 7.02 (2H, d, J=8.8 Hz).

Example 21

Using a similar method to that for Example 11, 4-[4-(4-aminophenyl)piperazin-1-yl]-5-fluoro-2,6-dimorpholinopyrimidine (Compound 146) (See Formula (159) below) was produced from corresponding starting materials. The MS measurement result, and the NMR data for the obtained Compound 146 are shown below.

[Chemical 173]

-continued (159)

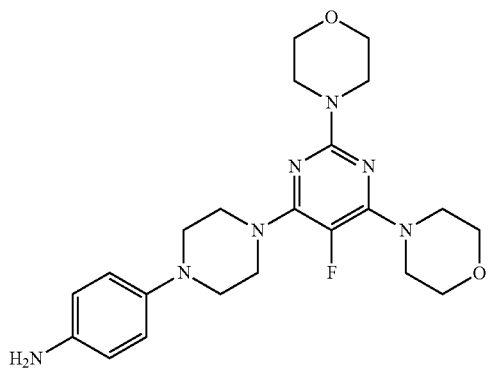

NMR (CDCl₃) δ: 3.06-3.10 (4H, m), 3.45 (2H, bs), 3.53-3.57 (4H, m), 3.59-3.63 (4H, m), 3.69-3.78 (12H, m), 6.65 (2H, m), 6.83 (2H, m).

Example 22

Synthesis of 4-dimethylamino-6-morpholino-2-(4-phenylpiperazin-1-yl)pyrimidine (Compound 2) with 4,6-dichloro-2-methylsulfinylpyrimidine as an intermediate i) Synthesis of 4-dimethylamino-2-methylsulfanyl-6-morpholinopyrimidine (Compound 147)

[Chemical 174]

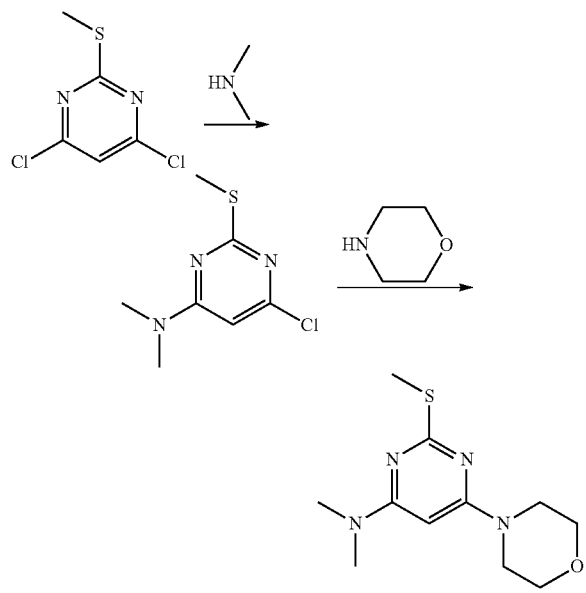

4,6-dichloro-2-methylmercaptopyrimidine (10.0 g, 51 mmol) and diisopropyl ethylamine (17.5 ml, 102 mmol) was dissolved in tetrahydrofuran (400 ml), and a 50% aqueous dimethylamine solution (7.6 ml, 84 mmol) was dripped over the course of 1 hour into this solution under ice cooling. After this mixture liquid was agitated overnight at room temperature, water was added and extraction was carried out 2 times with ethyl acetate. After washing the organic layer with saturated saline, drying was done with MgSO₄, the solvent was distilled away under reduced pressure, and 6-chloro-4-dimethylamino-2-methylmercaptopyrimidine was obtained. This was used for the next reaction without separation or refinement. Morpholine (100 ml) was added to this, and it was agitated overnight at 100 degrees Celsius. After allowing to cool, water was added and extraction was carried out 2 times with dichloromethane. After washing the organic layer with saturated saline, drying was done with MgSO₄, the solvent was distilled away under reduced pressure. The residue was washed with ether and 11.3 g of coarse crystals of 4-dimethylamino-2-methylsulfanyl-6-morpholinopyrimidine was obtained (2 step yield: 87%).

MS m/z: 254 (M⁺),
NMR (CDCl₃) δ: 2.48 (3H, s), 3.05 (6H, s), 3.53 (4H, t, J=5.1 Hz), 3.76 (4H, t, J=5.1 Hz), 5.17 (1H, s).

ii) Synthesis of 4-dimethylamino-2-methylsulfanyl-6-morpholinopyrimidine (Compound 148)

[Chemical 175]

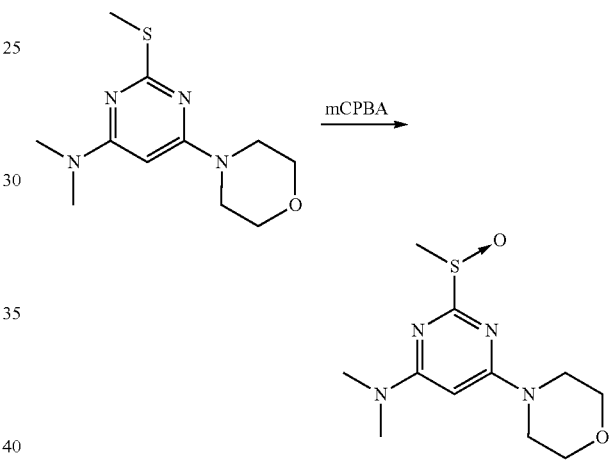

To a solution of 4-dimethylamino-2-methylsulfanyl-6-morpholinopyrimidine (3.8 g, 14.7 mmol) in dichloromethane (200 ml), a solution of 80% mCPBA (8.0 g, 36.9 mmol) in dichloromethane (100 ml) was dripped in over the course of 30 minutes under ice cooling. After agitation for 2 hours at the same temperature, a saturated sodium hydrogen carbonate aqueous solution (100 ml) was added, and agitation was done for 5 minutes. After washing the dichloromethane layer with saturated saline, drying was done with MgSO₄, the solvent was distilled away under reduced pressure. Purification was done with silica gel chromatography (dichloromethane: methanol=20:1), and 1.8 g of 4-dimethylamino-2-methylsulfanyl-6-morpholinopyrimidine was obtained (yield 45%).

MS m/z: 270 (M⁺),
NMR (CDCl₃) δ: 2.85 (3H, s), 3.10 (6H, s), 3.59 (4H, t, J=5.1 Hz), 3.78 (4H, t, J=5.1 Hz), 5.33 (1H, s).

iii) Synthesis of 6-dimethylamino-6-morpholino-2-(4-phenylpiperazin-1-yl)pyrimidine

[Chemical 176]

-continued

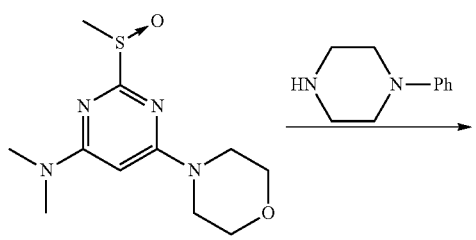

(152)

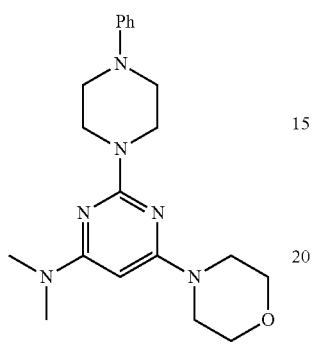

1-phenylpiperadine (5 ml) was added to 4-dimethylamino-2-methylsulfanyl-6-morpholinopyrimidine (800 mg, 2.96 mmol), and this was agitated under heating overnight at 100 degrees Celsius. After allowing to cool, water was added and extraction was carried out 2 times with dichloromethane. After washing the organic layer with saturated saline, drying was done with MgSO$_4$, the solvent was distilled away under reduced pressure. Purification was done with silica gel chromatography (hexane:ethyl acetate=2:1), and 511 mg of 6-dimethylamino-4-morpholino-2-(4-phenylpiperazin-1-yl) pyrimidine was obtained (yield 51%). The MS and NMR spectrum data for the obtained compound matched the structure of Compound 2.

5-fluoro-4-[4-(4-methylphenyl)piperazin-1-yl]-6-morpholino-2-(1-piperazinyl)pyrimidine (Compound 149)

(See Formula (153) below)
The NMR data for the obtained Compound 149 are shown below.

[Chemical 177]

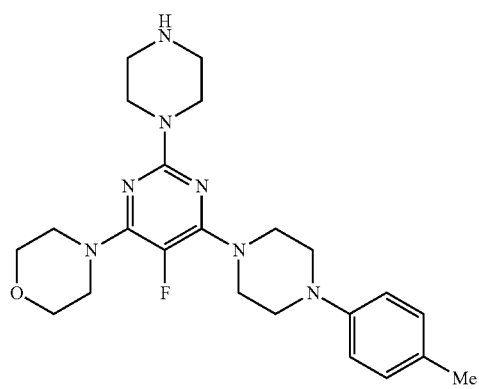

(153)

NMR (CDCl$_3$) δ: 2.28 (3H, s), 2.92 (4H, t, J=5.0 Hz), 3.19 (4H, t, J=4.9 Hz), 3.55 (4H, m), 3.72 (12H, m), 6.87 (2H, d, J=8.6 Hz), 7.09 (2H, d, J=8.6 Hz).

2-[4-(tert-butoxycarbonyl)piperazin-1-yl]-5-fluoro-4-[4-(4-methylphenyl)piperazin-1-yl]-6-morpholinopyrimidine (Compound 150)

(See Formula (154) below)
The NMR data for the obtained Compound 150 are shown below.

[Chemical 178]

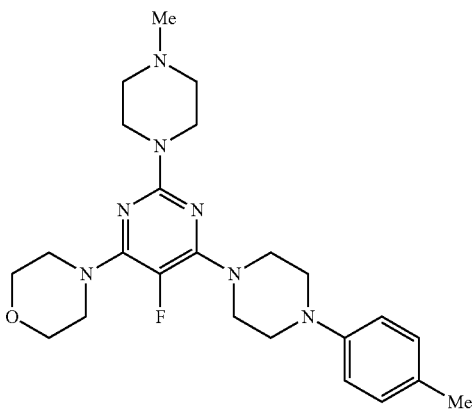

(154)

NMR (CDCl$_3$) δ: 1.48 (9H, s), 2.28 (3H, s), 3.18 (4H, t, J=4.9 Hz), 3.40-3.80 (20H, m), 6.87 (2H, d, J=8.6 Hz), 7.09 (2H, d, J=8.6 Hz).

5-fluoro-4-[4-(4-methylphenyl)piperazin-1-yl]-2-(4-methylpiperazin-1-yl)-6-morpholinopyrimidine (Compound 151)

(See Formula (155) below)
The NMR data for the obtained Compound 151 are shown below.

[Chemical 179]

(155)

NMR (CDCl$_3$) δ: 2.33 (3H, s), 2.51 (3H, s), 2.63 (4H, t, J=4.9 Hz), 3.18 (4H, t, J=4.9 Hz), 3.55 (4H, t, J=4.9 Hz), 3.74 (12H, m), 6.87 (2H, d, J=8.6 Hz), 7.09 (2H, d, J=8.6 Hz).

5-fluoro-2-[4-(4-methylphenyl)piperazin-1-yl]-4-morpholino-6-(1-piperazinyl)pyrimidine (Compound 152)

(See Formula (156) below)
The NMR data for the obtained Compound 152 are shown below.

[Chemical 180]

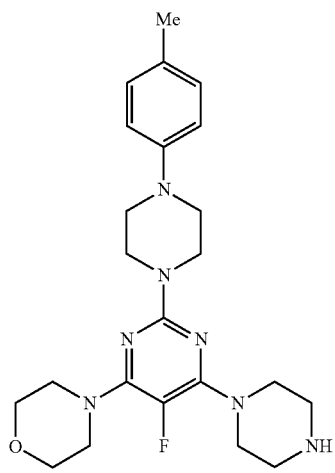

(156)

NMR (CDCl$_3$) δ: 2.28 (3H, s), 2.97 (4H, t, J=4.9 Hz), 3.14 (4H, t, J=4.9 Hz), 3.55 (8H, t, J=4.6 Hz), 3.78 (8H, t, J=4.6 Hz), 6.88 (2H, d, J=8.5 Hz), 7.09 (2H, d, J=8.5 Hz).

4-[4-(tert-butoxycarbonyl)piperazin-1-yl]-5-fluoro-2-[4-(4-methylphenyl)piperazin-1-yl]-6-morpholinopyrimidine (Compound 153)

(See Formula (157) below)
The NMR data for the obtained Compound 153 are shown below.

[Chemical 181]

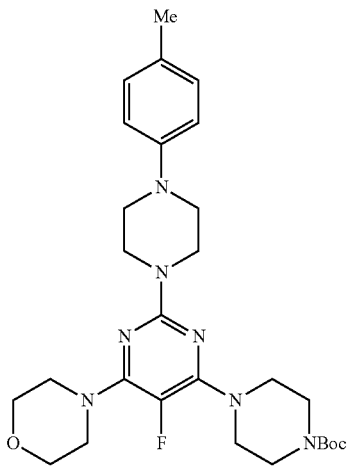

(157)

NMR (CDCl$_3$) δ: 1.48 (9H, s), 2.28 (3H, s), 3.14 (4H, t, J=4.9 Hz), 3.50-3.60 (12H, m), 3.78 (8H, m), 6.88 (2H, d, J=8.4 Hz), 7.10 (2H, d, J=8.4 Hz).

5-fluoro-2-[4-(4-methylphenyl)piperazin-1-yl]-4-(4-methylpiperazin-1-yl)-6-morpholinopyrimidine (Compound 154)

(See Formula (158) below)
The NMR data for the obtained Compound 154 are shown below.

[Chemical 182]

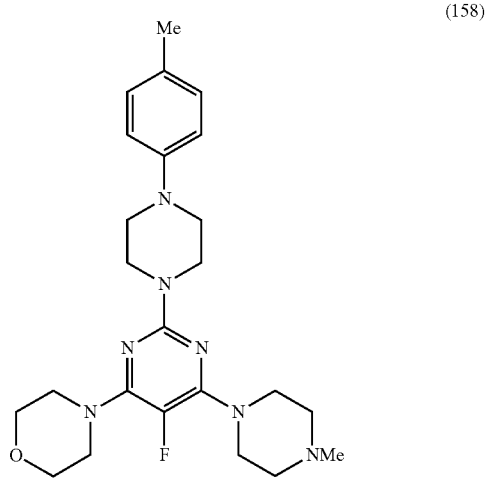

(158)

NMR (CDCl$_3$) δ: 2.28 (3H, s), 2.36 (3H, s), 2.53 (4H, t, J=4.9 Hz), 3.14 (4H, t, J=4.9 Hz), 3.62-3.55 (8H, m), 3.78 (8H, m), 6.88 (2H, d, J=8.6 Hz), 7.09 (2H, d, J=8.6 Hz).

5-fluoro-4-[4-(4-methylphenyl)piperazin-1-yl]-6-(4-methylpiperazin-1-yl)-2-morpholinopyrimidine (Compound 155)

(See Formula (159) below)
The NMR data for the obtained Compound 155 are shown below.

[Chemical 183]

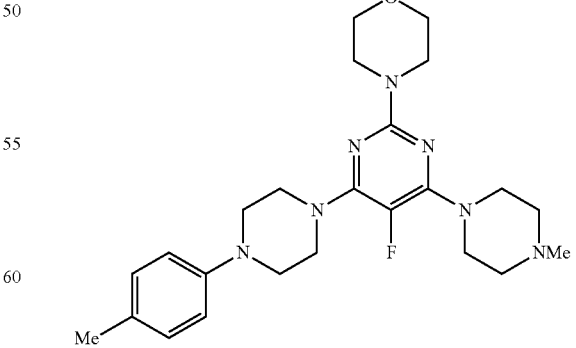

(159)

NMR (CDCl$_3$) δ: 2.28 (3H, s), 2.36 (3H, s), 2.50 (4H, t, J=4.9 Hz), 3.22 (4H, t, J=4.9 Hz), 3.50-3.77 (16H, m), 6.87 (2H, d, J=8.6 Hz), 7.09 (2H, d, J=8.6 Hz).

2-[4-(2-aminoethyl)piperazin-1-yl]-5-fluoro-4-[4-(4-methylphenyl)piperazin-1-yl]-6-morpholinopyrimidine (Compound 156)

(See Formula (160) below)
The NMR data for the obtained Compound 156 are shown below.

[Chemical 184]

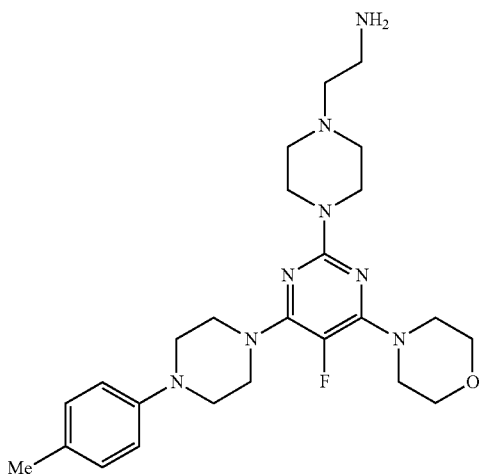

(160)

NMR (CDCl$_3$) δ: 2.29 (3H, s), 2.50 (8H, m), 2.94 (4H, t, J=4.8 Hz), 3.17 (4H, t, J=4.8 Hz), 3.46 (4H, m), 3.70 (8H, m), 6.87 (2H, d, J=8.6 Hz), 7.10 (2H, d, J=8.6 Hz).

5-fluoro-2-{4-[2-(tert-butoxycarbonylamino)ethyl]piperazin-1-yl}-4-[4-(4-methylphenyl)piperazin-1-yl]-6-morpholinopyrimidine (Compound 157)

(See Formula (161) below)
The NMR data for the obtained Compound 157 are shown below.

[Chemical 185]

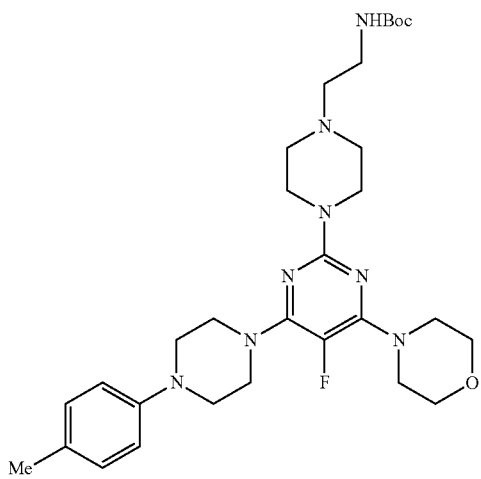

(161)

NMR (CDCl$_3$) δ: 1.49 (9H, s), 2.29 (3H, s), 2.50 (8H, m), 2.94 (4H, t, J=4.8 Hz), 3.17 (4H, t, J=4.8 Hz), 3.46 (4H, m), 3.70 (8H, m), 6.87 (2H, d, J=8.6 Hz), 7.10 (2H, d, J=8.6 Hz).

5-fluoro-4-[4-(4-methylphenyl)piperazin-1-yl]-6-morpholino-2-[2-(piperazin-1-yl)-ethylamino]pyrimidine (Compound 158)

(See Formula (162) below)
The NMR data for the obtained Compound 158 are shown below.

[Chemical 186]

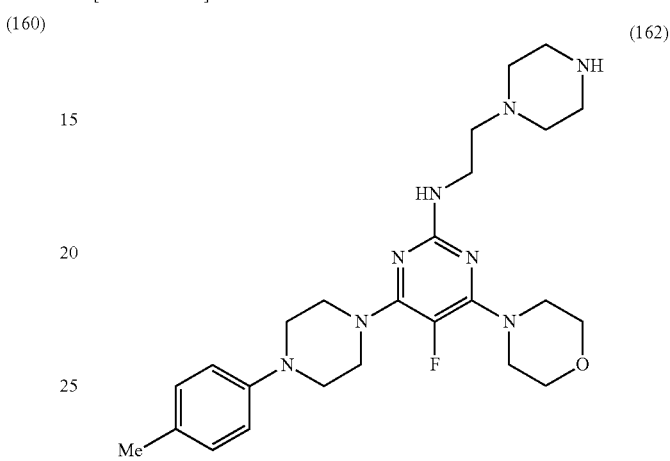

(162)

NMR (CDCl$_3$) δ: 2.28 (3H, s), 2.46 (6H, t, J=5.0 Hz), 2.86 (2H, t, J=5.0 Hz), 3.14 (4H, t, J=5.0 Hz), 3.50-3.75 (16H, m), 6.87 (2H, d, J=8.6 Hz), 7.09 (2H, d, J=8.6 Hz).

2-[2-(4-tert-butoxycarbonylpiperazin-1-yl)ethylamino]-5-fluoro-4-[4-(4-methylphenyl)piperazin-1-yl]-6-morpholinopyrimidine (Compound 159)

(See Formula (163) below)
The NMR data for the obtained Compound 159 are shown below.

[Chemical 187]

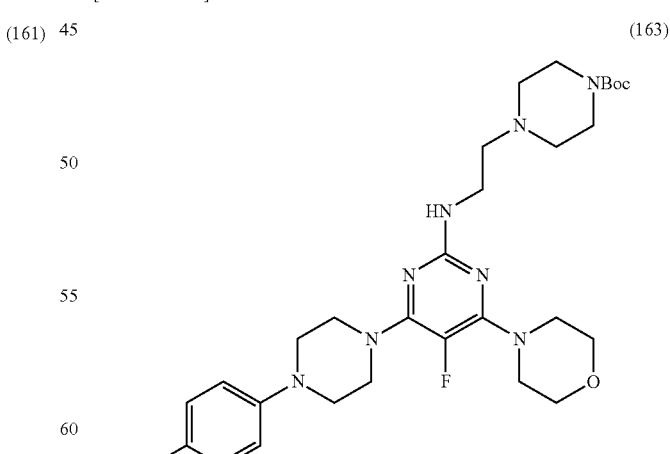

(163)

NMR (CDCl$_3$) δ: 1.48 (9H, s), 2.28 (3H, s), 2.46 (6H, t, J=5.0 Hz), 2.86 (2H, t, J=5.0 Hz), 3.14 (4H, t, J=5.0 Hz), 3.50-3.75 (16H, m), 6.87 (2H, d, J=8.6 Hz), 7.10 (2H, d, J=8.6 Hz).

5-fluoro-4-[4-(4-methylphenyl)piperazin-1-yl]-2-morpholino-6-(2-morpholinoethyl amino)pyrimidine (Compound 160)

(See Formula (164) below)
The NMR data for the obtained Compound 160 are shown below.

[Chemical 188]

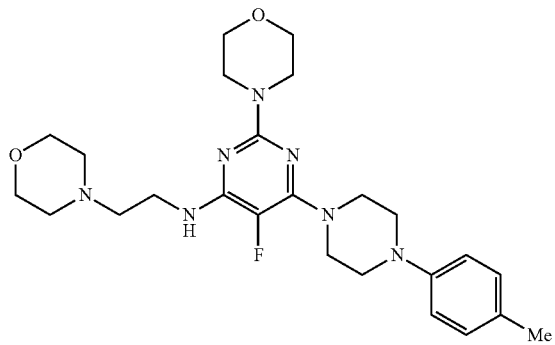

(164)

NMR (CDCl$_3$) δ: 2.28 (3H, s), 2.48 (6H, t, J=5.0 Hz), 2.86 (2H, t, J=6.0 Hz), 3.18 (4H, t, J=5.0 Hz), 3.50-3.80 (16H, m), 6.87 (2H, d, J=8.4 Hz), 7.09 (2H, d, J=8.4 Hz).

4-[4-(tert-butoxycarbonyl)piperazin-1-yl]-5-fluoro-6-morpholino-2-[4-(2-pyridyl)piperazin-1-yl]pyrimidine (Compound 161)

(See Formula (165) below)
The NMR data for the obtained Compound 161 are shown below.

[Chemical 189]

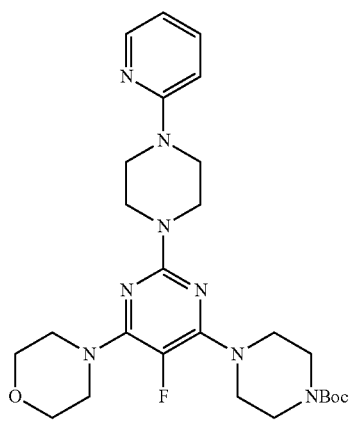

(165)

NMR (CDCl$_3$) δ: 1.48 (9H, s), 3.51-3.59 (16H, m), 3.75 (8H, m), 6.65 (2H, m), 7.49 (1H, m), 8.21 (1H, m).

5-fluoro-4-morpholino-6-(1-piperazinyl)-2-[4-(2-pyridyl)piperazin-1-yl]pyrimidine (Compound 162)

(See Formula (166) below)
The NMR data for the obtained Compound 162 are shown below.

[Chemical 190]

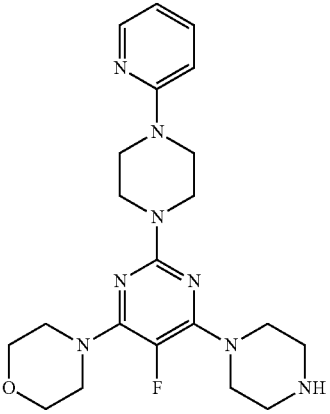

(166)

NMR (CDCl$_3$) δ: 2.95 (4H, m), 3.45-3.86 (20H, m), 6.65 (2H, m), 7.50 (1H, m), 8.20 (1H, m).

5-fluoro-4,6-dimorpholino-2-[4-(2-pyridyl)piperazin-1-yl]pyrimidine (Compound 163)

(See Formula 167 below)
The NMR data for the obtained Compound 163 are shown below.

[Chemical 191]

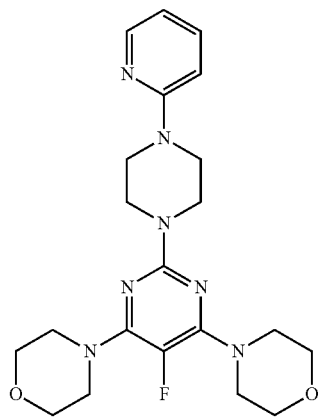

(167)

NMR (CDCl$_3$) δ: 3.56 (12H, m), 3.77 (12H, m), 6.64 (2H, m), 7.50 (1H, m), 8.21 (1H, m).

5-fluoro-2,4-dimorpholino-6-[4-(2-pyridyl)piperazin-1-yl]pyrimidine (Compound 164)

(See Formula 168 Below)
The NMR data for the obtained Compound 164 are shown below.

[Chemical 192]

(168)

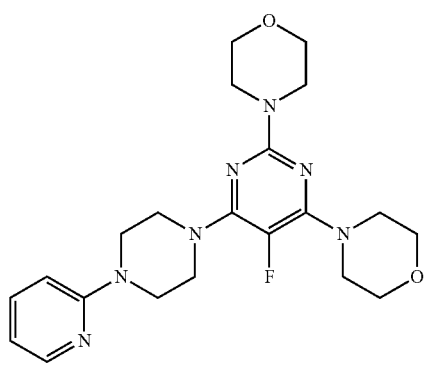

NMR (CDCl₃) δ: 3.59-3.79 (24H, m), 6.65 (2H, m), 7.50 (1H, m), 8.20 (1H, m).

4-(4-methylpiperazin-1-yl)-2-morpholino-6-(1,2,3,4-tetrahydro-2H-isoquinolin-2-yl)pyrimidine (Compound 165)

(See Formula (169) below)
The NMR data for the obtained Compound 165 are shown below.

[Chemical 193]

(169)

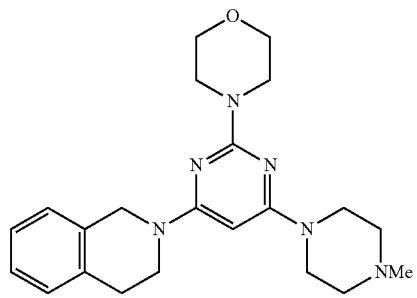

NMR (CDCl₃) δ: 2.33 (3H, s), 2.47 (4H, m), 2.90 (2H, m), 3.57 (4H, m), 3.75 (8H, s), 3.82 (2H, m), 4.65 (2H, s), 5.17 (1H, s), 7.17 (4H, m).

5-fluoro-4-(4-methylpiperazin-1-yl)-6-morpholino-2-[4-(2-pyridyl)piperazin-1-yl]pyrimidine (Compound 166)

(See Formula (170) below)
The NMR data for the obtained Compound 166 are shown below.

[Chemical 194]

(170)

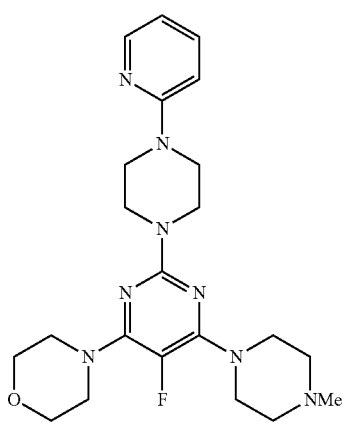

NMR (CDCl₃) δ: 2.35 (3H, s), 2.52 (4H, m), 3.58 (12H, m), 3.76 (8H, m), 6.64 (2H, m), 7.49 (1H, m), 8.21 (1H, m).

5-fluoro-4-(4-methylpiperazin-1-yl)-6-morpholino-2-(1,2,3,4-tetrahydro-1H-quinolin-1-yl)pyrimidine (Compound 167)

(See Formula (171) below)
The NMR data for the obtained Compound 167 are shown below.

[Chemical 195]

(171)

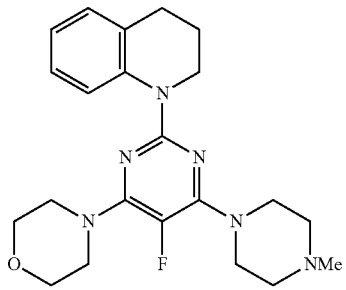

NMR (CDCl₃) δ: 1.94 (2H, m), 2.34 (3H, s), 2.51 (4H, m), 2.76 (2H, m), 3.53 (4H, m), 3.61 (4H, m), 3.76 (4H, m), 3.92 (2H, m), 6.90 (1H, m), 7.07 (2H, m), 7.76 (1H, m).

4-[4-(tert-butoxycarbonyl)piperazin-1-yl]-5-fluoro-6-morpholino-2-(1,2,3,4-tetrahydro-1H-quinolin-1-yl)pyrimidine (Compound 168)

(See Formula (172) below)
The NMR data for the obtained Compound 168 are shown below.

[Chemical 196]

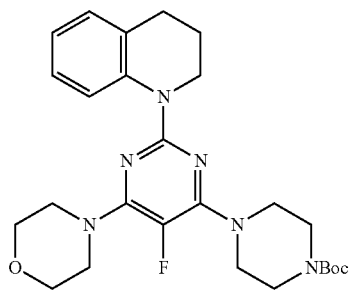
(172)

NMR (CDCl₃) δ: 1.48 (9H, m), 1.95 (2H, m), 2.75 (2H, m), 3.53 (12H, m), 3.76 (4H, m), 3.93 (2H, m), 6.92 (1H, m), 7.08 (2H, m), 7.75 (1H, m).

5-fluoro-2-(1-piperazinyl)-4-morpholino-6-(1,2,3,4-tetrahydro-1H-quinolin-1-yl)pyrimidine (Compound 169)

(See Formula (173) below)
The NMR data for the obtained Compound 169 are shown below.

[Chemical 197]

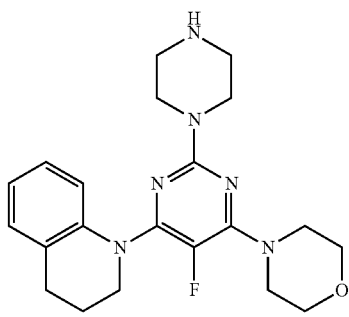
(173)

NMR (CDCl₃) δ: 2.00 (2H, m), 2.82 (2H, t, J=6.4 Hz), 2.93 (4H, m), 3.56-3.82 (14H, m), 6.85 (2H, m), 7.05 (2H, m).

5-amino-2-[2-(4-methoxyphenyl)vinyl]-4-morpholino-6-(1-piperazinyl)pyrimidine (Compound 170)

(See Formula (174) below)
The NMR data for the obtained Compound 170 are shown below.

[Chemical 198]

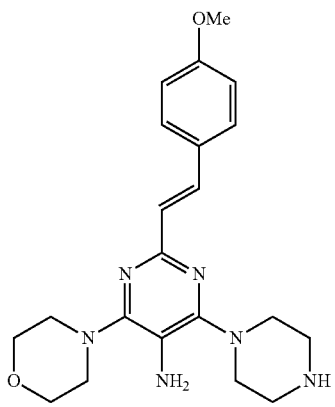
(174)

NMR (CDCl₃) δ: 3.03 (4H, m), 3.27 (4H, m), 3.32 (4H, m), 3.34 (2H, s), 3.83 (3H, s), 3.85 (4H, m), 6.88 (2H, d, J=8.7 Hz), 6.92 (1H, d, J=16.0 Hz), 7.52 (2H, d, J=8.7 Hz), 7.65 (1H, d, J=16.0 Hz).

5-fluoro-4-(4-methylpiperazin-1-yl)-2-morpholino-6-(4-phenylpiperazin-1-yl)pyrimidine (Compound 171)

(See Formula 175 Below)
The NMR data for the obtained Compound 171 are shown below.

[Chemical 199]

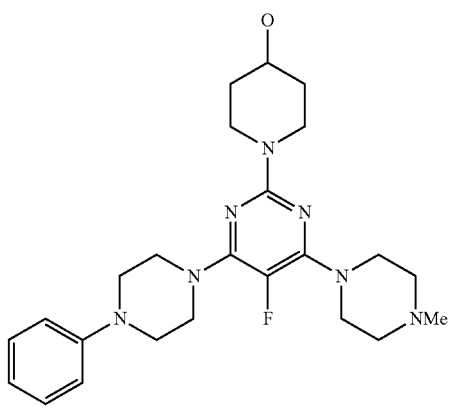
(175)

NMR (CDCl₃) δ: 2.31 (3H, s), 2.47 (4H, m), 3.24 (4H, m), 3.56 (8H, m), 3.73 (8H, m), 6.85-6.96 (3H, m), 7.28 (2H, m).

5-amino-2-[2-(4-methoxyphenyl)vinyl]-4-(4-methylpiperazin-1-yl)-6-morpholino pyrimidine (Compound 172)

(See Formula 176 Below)
The NMR data for the obtained Compound 172 are shown below.

[Chemical 200]

(176)

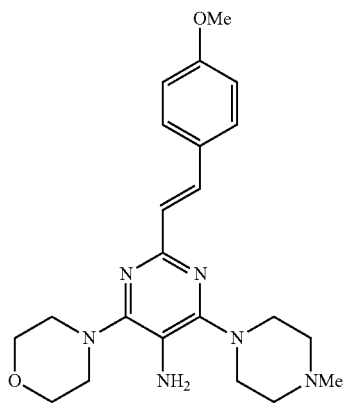

NMR (CDCl₃) δ: 2.36 (3H, s), 2.58 (4H, s), 3.30-3.40 (10H, m), 3.83 (3H, s), 3.86 (4H, m), 6.87 (2H, d, J=8.6 Hz), 6.90 (1H, d, J=16.0 Hz), 7.51 (2H, d, J=8.6 Hz), 7.65 (1H, d, J=16.0 Hz).

5-amino-2-[2-(4-methoxyphenyl)vinyl]-4-morpholino-6-[2-(1-piperazinyl)ethyl amino]pyrimidine (Compound 173)

(See Formula 177 below)
The NMR data for the obtained Compound 173 are shown below.

[Chemical 201]

(177)

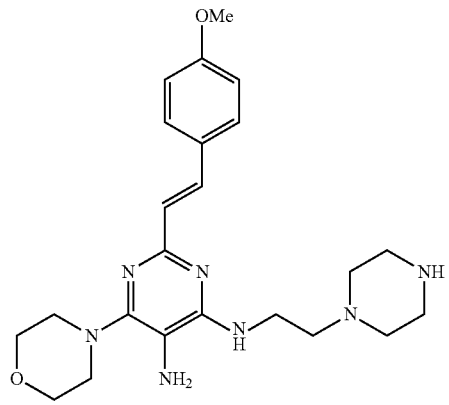

NMR (CDCl₃) δ: 2.83 (2H, t, J=5.7 Hz), 3.33 (2H, t, J=5.7 Hz), 3.32-3.43 (4H, m), 3.55-3.65 (4H, m), 3.66-3.76 (4H, m), 3.81 (3H, m), 3.83-3.87 (4H, m), 6.87 (2H, d, J=8.7 Hz), 6.91 (1H, d, J=16.0 Hz), 7.51 (2H, d, J=8.7 Hz), 7.65 (1H, d, J=16.0 Hz).

5-amino-4-(2-aminoethylamino)-2-[2-(4-methoxyphenyl)vinyl]-6-morpholinopyrimidine (Compound 174)

(See Formula 178 below)
The NMR data for the obtained Compound 174 are shown below.

[Chemical 202]

(178)

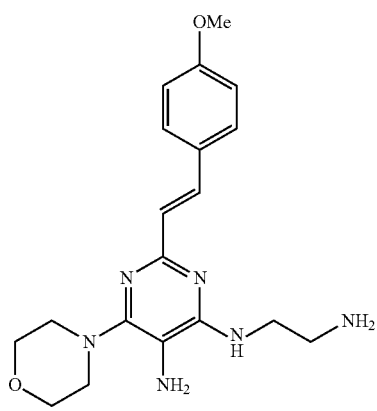

NMR (CDCl₃) δ: 3.10-3.17 (4H, m), 3.79-3.84 (8H, m), 3.82 (3H, s), 6.61-6.89 (3H, m), 7.51 (2H, d, J=8.7 Hz), 7.65 (1H, d, J=16.0 Hz).

5-amino-2-[2-(4-methoxyphenyl)vinyl]-4-[4-(2-dimethylaminoethyl-piperazin-1-yl)]-6-morpholinopyrimidine (Compound 175)

(See Formula 179 below)
The NMR data for the obtained Compound 175 are shown below.

[Chemical 203]

(179)

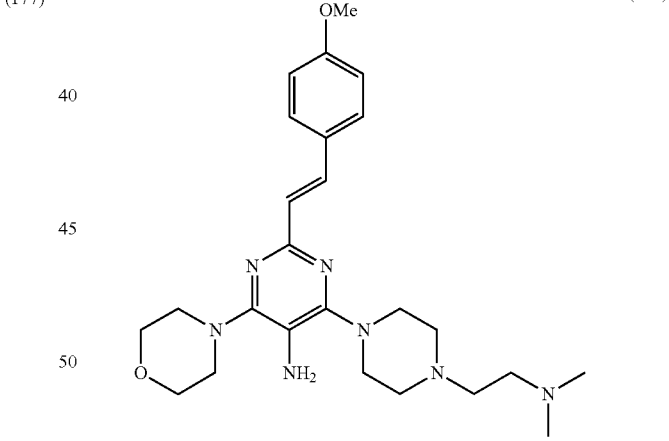

NMR (CDCl₃) δ: 2.28 (6H, s), 2.48-2.51 (1H, m), 2.54-2.58 (1H, m), 2.61-2.65 (2H, m), 3.30-3.45 (8H, m), 3.82 (3H, s), 3.84-3.87 (8H, s), 6.88 (2H, d, J=8.7 Hz), 6.90 (1H, d, J=16.0 Hz), 7.51 (2H, d, J=8.7 Hz), 7.64 (1H, d, J=16.0 Hz).

5-amino-4-(4-aminomethylcarbonylpiperazin-1-yl)-2-[2-(4-methoxyphenyl)vinyl]-6-morpholinopyrimidine (Compound 176)

(See Formula 180 below)
The NMR data for the obtained Compound 176 are shown below.

[Chemical 204]

(180)

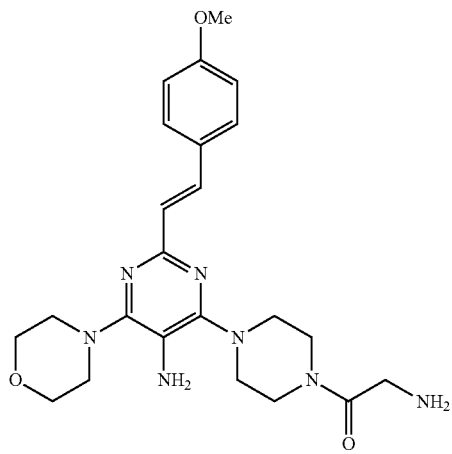

NMR (CDCl$_3$) δ: 3.17-3.45 (8H, m), 3.46-3.49 (2H, m), 3.67-3.88 (8H, m), 3.83 (3H, s), 6.83-6.92 (3H, m), 7.51 (2H, d, J=8.7 Hz), 7.64 (1H, d, J=16.0 Hz).

2-(4-tert-butoxycarbonylpiperazin-1-yl)-5-fluoro-4-morpholino-6-[4-(2,3-xylyl)piperazin-1-yl]pyrimidine (Compound 177)

(See Formula 181 below)
The NMR data for the obtained Compound 177 are shown below.

[Chemical 205]

(181)

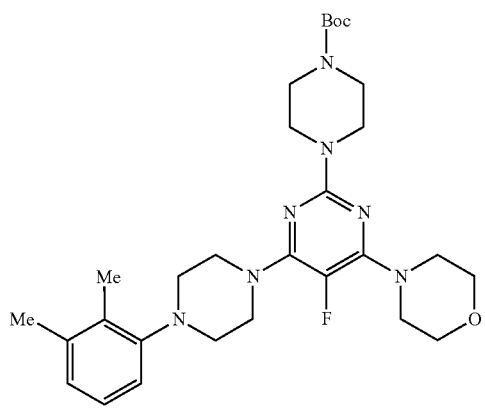

Melting Point: 81-82 degrees C.,
MS m/z: 555 (M$^+$)
NMR (CDCl$_3$) δ: 1.48 (9H, s), 2.26 (3H, s), 2.28 (3H, s), 2.94 (4H, t, J=4.6 Hz), 3.43-3.50 (4H, m), 3.55 (4H, t, J=4.6 Hz), 3.64-3.74 (12H, m), 6.89-6.92 (2H, m), 7.07 (1H, t, J=7.9 Hz).

5-fluoro-4-morpholino-2-(1-piperazinyl)-6-[4-(2,3-xylyl)piperazin-1-yl]pyrimidine (Compound 178)

(See Formula 182 Below)
The NMR data for the obtained Compound 178 are shown below.

[Chemical 206]

(182)

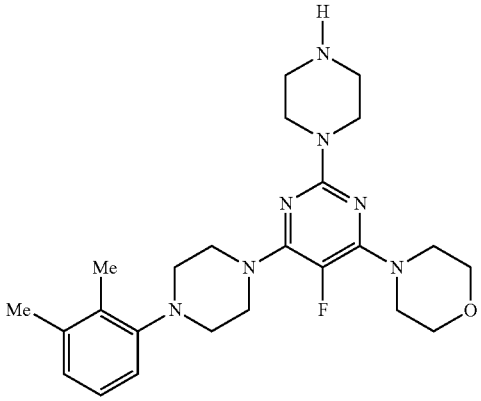

Melting Point: 76-77 degrees C.,
MS m/z: 455 (M$^+$)
NMR (CDCl$_3$) δ: 2.26 (3H, s), 2.28 (3H, s), 2.92-2.94 (8H, m), 3.55 (4H, t, J=4.5 Hz), 3.64-3.79 (12H, m), 6.90-6.93 (2H, m), 7.09 (1H, t, J=7.7 Hz).

4-(4-tert-butoxycarbonylpiperazin-1-yl)-5-fluoro-6-morpholino-2-[4-(2,3-xylyl)piperazin-1-yl]pyrimidine (Compound 179)

(See Formula 183 below)
The NMR data for the obtained Compound 179 are shown below.

[Chemical 207]

(183)

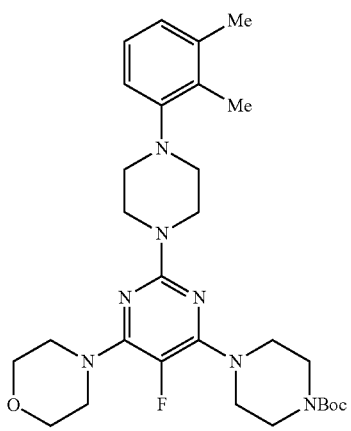

Melting Point: 62-63 degrees C.,
MS m/z: 555 (M$^+$)
NMR (CDCl$_3$) δ: 1.47 (9H, s), 2.26 (3H, s), 2.28 (3H, s), 2.87-2.91 (4H, m), 3.52-3.57 (12H, m), 3.77 (8H, t, J=4.6 Hz), 6.89-6.93 (2H, m), 7.09 (1H, t, J=7.8 Hz).

5-fluoro-4-morpholino-6-(1-piperazinyl)-2-[4-(2,3-xylyl)piperazin-1-yl]pyrimidine (Compound 180)

(See Formula 184 Below)
The NMR data for the obtained Compound 180 are shown below.

[Chemical 208]

(184)

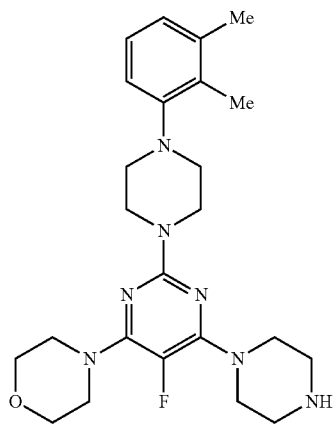

MS m/z: 455 (M⁺)
NMR (CDCl₃) δ: 2.26 (3H, s), 2.28 (3H, s), 2.82-3.07 (8H, m), 3.55-3.61 (8H, m), 3.72-3.86 (8H, m), 6.86-6.96 (2H, m), 7.09 (1H, t, J=7.9 Hz).

4-(4-tert-butoxycarbonylpiperazin-1-yl)-5-fluoro-2-[4-(2-fluorophenyl)piperazin-1-yl]-6-morpholinopyrimidine (Compound 181)

(See Formula 185 below)
The NMR data for the obtained Compound 181 are shown below.

[Chemical 209]

(185)

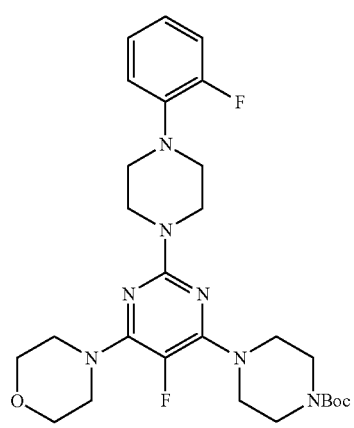

Melting Point: 137-138 degrees C.,
MS m/z: 545 (M⁺)
NMR (CDCl₃) δ: 1.48 (9H, s), 3.10 (4H, t, J=4.9 Hz), 3.52-3.57 (12H, m), 3.76-3.83 (8H, m), 6.90-7.10 (4H, m).

5-fluoro-2-[4-(2-fluorophenyl)piperazin-1-yl]-4-morpholino-6-(1-piperazinyl)pyrimidine (Compound 182)

(See Formula 186 Below)
The NMR data for the obtained Compound 182 are shown below.

[Chemical 210]

(186)

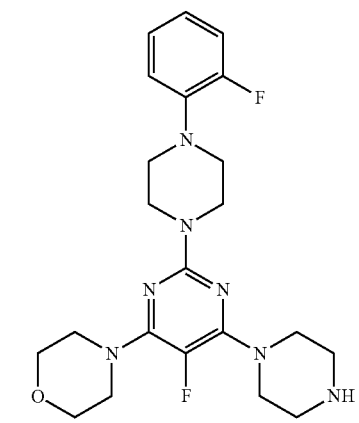

Melting Point: 51-52 degrees C.,
MS m/z: 445 (M⁺)
NMR (CDCl₃) δ: 2.94 (4H, t, J=4.6 Hz), 3.09 (4H, t, J=4.5 Hz), 3.54 (8H, m), 3.732-3.81 (8H, m), 6.96-7.04 (4H, m).

5-fluoro-2-(4-methylpiperazin-1-yl)-4-morpholino-6-[4-(2,3-xylyl)piperazin-1-yl]pyrimidine (Compound 183)

(See Formula 187 Below)
The NMR data for the obtained Compound 183 are shown below.

[Chemical 211]

(187)

Melting Point: 56-57 degrees C.,
MS m/z: 469 (M⁺)
NMR (CDCl₃) δ: 2.26 (3H, s), 2.28 (3H, s), 2.33 (3H, s), 2.43 (4H, t, J=4.6 Hz), 2.94 (4H, t, J=4.6 Hz), 3.55 (4H, t, J=4.6 Hz), 3.69-3.78 (12H, m), 6.90-6.93 (2H, m), 7.08 (1H, t, J=8.0 Hz).

5-fluoro-4-(4-methylpiperazin-1-yl)-6-morpholino-2-[4-(2,3-xylyl)piperazin-1-yl]pyrimidine (Compound 184)

(See Formula 188 Below)
The NMR data for the obtained Compound 184 are shown below.

[Chemical 212]

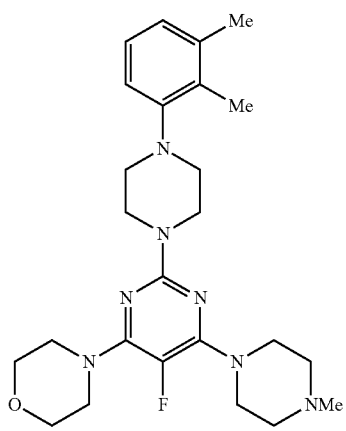

(188)

Melting Point: 67-68 degrees C.,
MS m/z: 469 (M$^+$)
NMR (CDCl$_3$) δ: 2.26 (3H, s), 2.28 (3H, s), 2.33 (3H, s), 2.47-2.50 (4H, m), 2.90 (4H, t, J=4.5 Hz), 3.53-3.61 (8H, m), 3.77 (8H, t, J=4.7 Hz), 6.90-6.93 (2H, m), 7.09 (1H, t, J=7.8 Hz).

5-fluoro-2-[4-(2-fluorophenyl)piperazin-1-yl]-4-(4-methylpiperazin-1-yl)-6-morpholinopyrimidine (Compound 185)

(See Formula 189 below)
The NMR data for the obtained Compound 185 are shown below.

[Chemical 213]

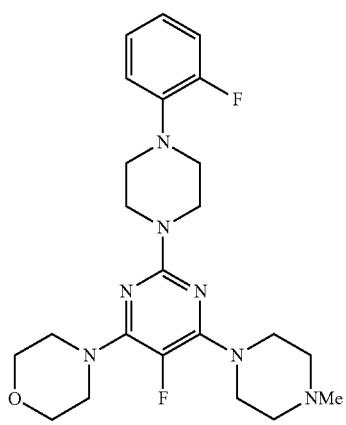

(189)

Melting Point: 128-129 degrees C.,
MS m/z: 459 (M$^+$)
NMR (CDCl$_3$) δ: 2.33 (3H, s), 2.42-2.48 (4H, m), 3.10-3.20 (4H, m), 3.56-3.59 (8H, m), 3.75-3.93 (8H, m), 6.93-7.07 (4H, m).

5-fluoro-4-(4-methylpiperazin-1-yl)-2-morpholino-6-[4-(2,3-xylyl)piperazin-1-yl]-pyrimidine (Compound 186)

(See Formula 190 Below)
The NMR data for the obtained Compound 186 are shown below.

[Chemical 214]

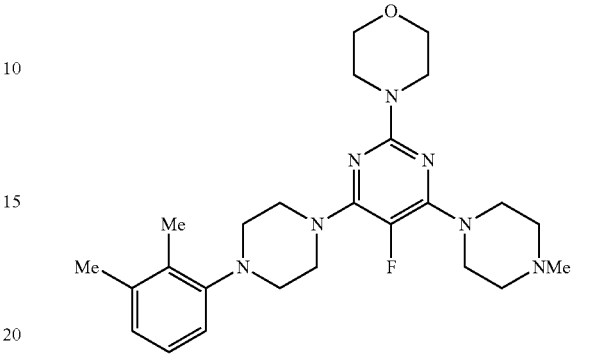

(190)

Melting Point: 67-68 degrees C.,
MS m/z: 469 (M$^+$)
NMR (CDCl$_3$) δ: 2.26 (3H, s), 2.28 (3H, s), 2.32 (3H, s), 2.48 (4H, t, J=4.7 Hz), 2.94 (4H, t, J=4.7 Hz), 3.60-3.62 (8H, m), 3.72-3.74 (8H, m), 6.89-6.92 (2H, m), 7.09 (1H, t, J=7.7 Hz).

2-[4-(2-chlorophenyl)piperazin-1-yl]-5-fluoro-6-(4-methylpiperazin-1-yl)-4-morpholino pyrimidine (Compound 187)

(See Formula 191 Below)
The NMR data for the obtained Compound 187 are shown below.

[Chemical 215]

(191)

MS m/z: 475 (M$^+$)
NMR (CDCl$_3$) δ: 2.32 (3H, s), 2.48 (4H, t, J=4.8 Hz), 3.07 (4H, t, J=4.8 Hz), 3.55-3.62 (8H, m), 3.76-3.87 (8H, m), 6.98-7.03 (2H, m), 7.20-7.40 (2H, m).

4-(4-tert-butoxycarbonylpiperazin-1-yl)-2-[4-(2-chlorophenyl)piperazin-1-yl]-5-fluoro-6-morpholinopyrimidine (Compound 188)

(See Formula 192 below)

The NMR data for the obtained Compound 188 are shown below.

[Chemical 216]

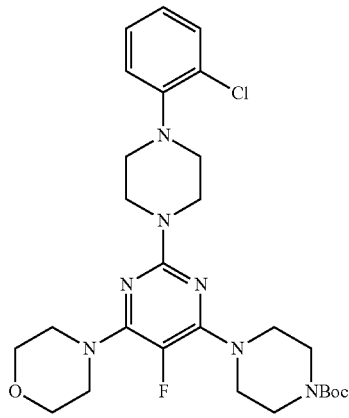

(192)

Melting Point: 75-76 degrees C.,
MS m/z: 561 (M⁺)
NMR (CDCl$_3$) δ: 1.48 (9H, s), 3.06 (4H, t, J=4.9 Hz), 3.51-3.58 (12H, m), 3.76-3.84 (8H, m), 6.96-7.05 (2H, m), 7.21-7.22 (1H, m), 7.38 (1H, dd, J=7.9, 1.5 Hz).

2-[4-(2-chlorophenyl)piperazin-1-yl]-5-fluoro-4-morpholino-6-(1-piperazinyl)pyrimidine (Compound 189)

(See Formula 193 Below)
The NMR data for the obtained Compound 189 are shown below.

[Chemical 217]

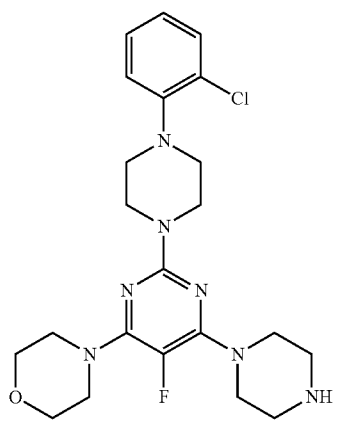

(193)

Melting Point: 70-71 degrees C.,
MS m/z: 461 (M⁺)
NMR (CDCl$_3$) δ: 3.06 (4H, t, J=4.8 Hz), 3.51-3.57 (12H, m), 3.77-3.82 (8H, m), 6.96-7.05 (2H, m), 7.21-7.22 (1H, m), 7.38 (1H, dd, J=7.9, 1.3 Hz).

2-[4-(2-ethoxyphenyl)piperazin-1-yl]-5-fluoro-4-(4-methylpiperazin-1-yl)-6-morpholinopyrimidine (Compound 190)

(See Formula 194 below)

The NMR data for the obtained Compound 190 are shown below.

[Chemical 218]

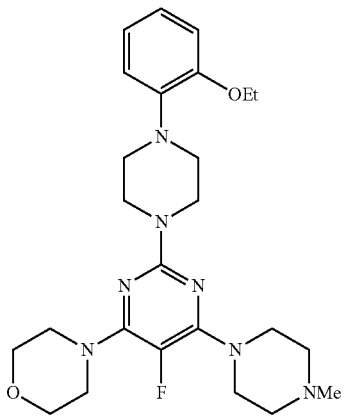

(194)

Melting Point: 41-42 degrees C.,
MS m/z: 485 (M⁺)
NMR (CDCl$_3$) δ: 1.48 (3H, t, J=6.9 Hz), 2.33 (3H, s), 2.49 (4H, t, J=4.9 Hz), 3.10 (4H, t, J=4.9 Hz), 3.55-3.61 (8H, m), 3.76-3.85 (8H, m), 4.09 (2H, q, J=7.0 Hz), 6.85-7.00 (4H, m).

5-fluoro-4-morpholino-2-[4-(4-pyridinylmethyl)piperazin-1-yl]-6-[4-(2,3-xylyl)piperazin-1-yl]-pyrimidine (Compound 191)

(See Formula 195 below)
The NMR data for the obtained Compound 191 are shown below.

[Chemical 219]

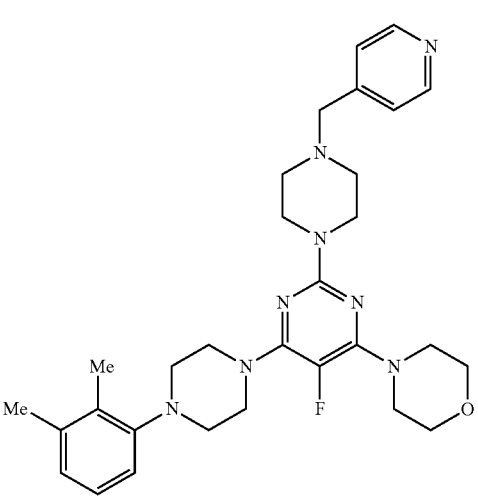

(195)

Melting Point: 127-128 degrees C.,
MS m/z: 546 (M⁺)
NMR (CDCl$_3$) δ: 2.25 (3H, s), 2.28 (3H, s), 2.47 (4H, t, J=4.8 Hz), 2.93 (4H, t, J=4.8 Hz), 3.53-3.55 (6H, m), 3.68-3.78 (12H, m), 6.90-6.92 (2H, m), 7.08 (1H, t, J=7.7 Hz), 7.30 (2H, d, J=5.9 Hz), 8.55 (2H, d, J=5.9 Hz).

5-fluoro-2-[4-(4-dimethylaminobenzyl)piperazin-1-yl]-4-morpholino-6-[4-(2,3-xylyl)piperazin-1-yl]pyrimidine (Compound 192)

(See Formula 196 below)
The NMR data for the obtained Compound 192 are shown below.

[Chemical 220]

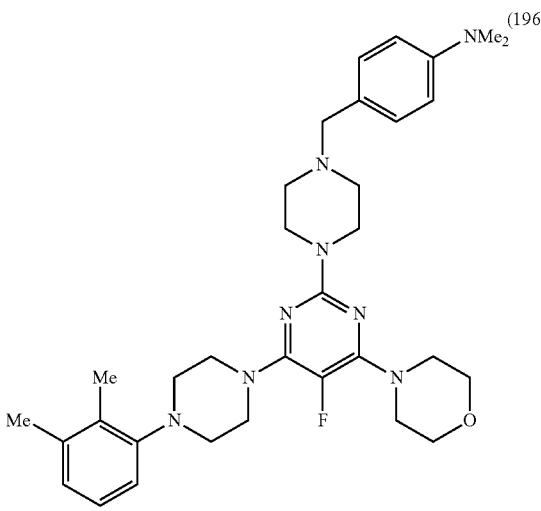

Melting Point: 79-80 degrees C.,
MS m/z: 588 (M⁺)

NMR (CDCl$_3$) δ: 2.25 (3H, s), 2.28 (3H, s), 2.44 (4H, bs), 2.92-2.95 (10H, m), 3.45 (2H, s), 3.53 (4H, t, J=4.6 Hz), 3.66-3.68 (8H, m), 3.76 (4H, t, J=4.6 Hz), 6.70 (2H, d, J=8.7 Hz) 6.91 (2H, d, J=7.8 Hz), 7.08 (1H, t, J=7.8 Hz), 7.18 (2H, d, J=8.7 Hz).

2-[4-(4-tert-butoxycarbonylaminobenzyl)piperazin-1-yl]-5-fluoro-4-morpholino-6-[4-(2,3-xylyl)piperazin-1-yl]pyrimidine (Compound 193)

(See Formula 197 below)
The NMR data for the obtained Compound 193 are shown below.

[Chemical 221]

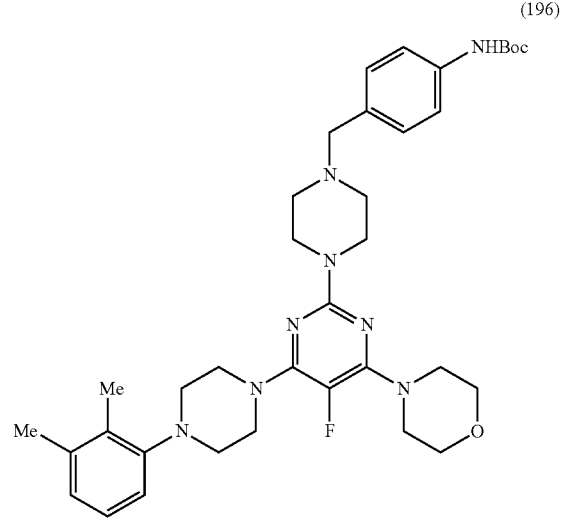

Melting Point: 104-105 degrees C.,
MS m/z: 660 (M⁺)

NMR (CDCl$_3$) δ: 1.52 (9H, s), 2.25 (3H, s), 2.28 (3H, s), 2.43-2.48 (4H, m), 2.93 (4H, t, J=4.6 Hz), 3.48 (2H, s), 3.53 (4H, t, J=4.6 Hz), 3.65-3.67 (8H, m), 3.76 (4H, t, J=4.6 Hz), 6.43 (1H, bs) 6.91 (2H, d, J=7.6 Hz), 7.08 (1H, t, J=7.6 Hz), 7.28-7.31 (4H, m).

2-[4-(4-aminobenzyl)piperazin-1-yl]-5-fluoro-4-morpholino-6-[4-(2,3-xylyl)piperazin-1-yl]pyrimidine (Compound 194)

(See Formula 198 below)
The NMR data for the obtained Compound 194 are shown below.

[Chemical 222]

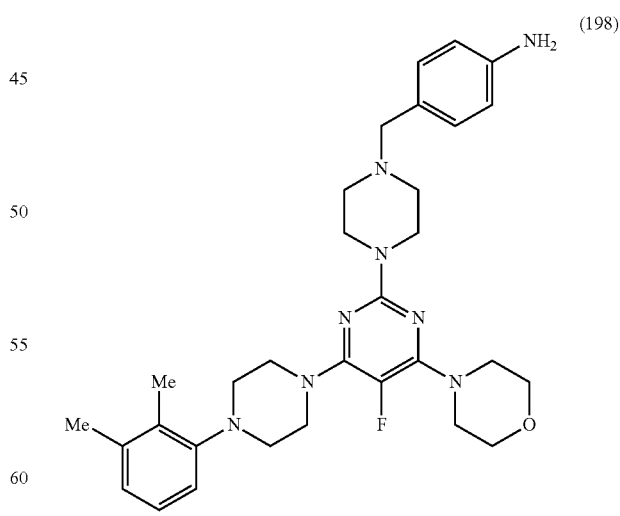

Melting Point: 77-78 degrees C.,
MS m/z: 560 (M⁺)

NMR (CDCl$_3$) δ: 2.25 (9H, s), 2.28 (3H, s), 2.28 (3H, s), 2.44 (4H, t, J=4.8 Hz), 2.94 (4H, t, J=4.8 Hz), 3.43 (2H, s), 3.53 (4H, t, J=4.5 Hz), 3.64-3.68 (8H, m), 3.75 (4H, t, J=4.5 Hz), 6.65 (2H, d, J=8.2 Hz), 6.91 (2H, d, J=8.2 Hz), 7.07-7.11 (3H, m).

5-amino-4-(4-tert-butoxycarbonylaminopiperidin-1-yl)-2-[2-(4-methoxyphenyl)vinyl]-6-morpholinopyrimidine (Compound 195)

(See Formula 199 below)
The NMR data for the obtained Compound 195 are shown below.

[Chemical 223]

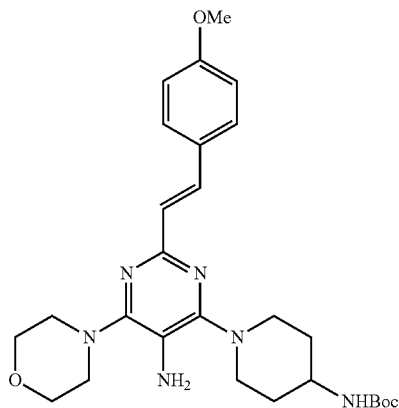

(199)

NMR (CDCl$_3$) δ: 1.46 (9H, s), 1.52 (2H, m), 1.97 (2H, m), 2.90 (3H, m), 3.33 (2H, m), 3.44 (2H, brs), 3.62-3.80 (4H, m), 3.80 (7H, m), 6.88 (2H, d, J=8.7 Hz), 6.90 (1H, d, J=16.0 Hz) 7.51 (2H, d, J=8.7 Hz), 7.65 (1H, d, J=16.0 Hz).

5-amino-4-(4-aminopiperidin-1-yl)-2-[2-(4-methoxyphenyl)vinyl]-6-morpholinopyrimidine (Compound 196)

(See Formula (200) below)
The NMR data for the obtained Compound 196 are shown below.

[Chemical 224]

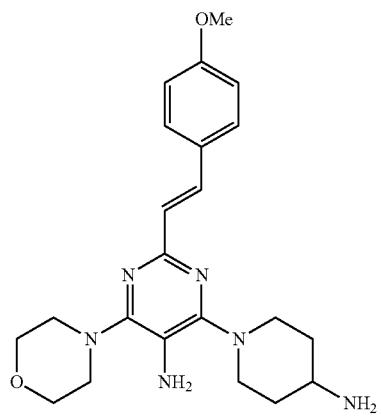

(200)

NMR (CDCl$_3$) δ: 1.52 (2H, m), 1.95 (2H, m), 2.91 (3H, m), 3.32 (2H, m), 3.45 (2H, brs), 3.60-3.80 (4H, m), 3.81 (7H, m), 6.90 (3H, m), 7.51 (2H, d, J=8.7 Hz), 7.65 (1H, d, J=16.0 Hz).

5-amino-4-(4-tert-butoxycarbonylmethylamino)-2-[2-(4-methoxyphenyl)vinyl]-6-morpholinopyrimidine (Compound 197)

(See Formula (201) below)
The NMR data for the obtained Compound 197 are shown below.

[Chemical 225]

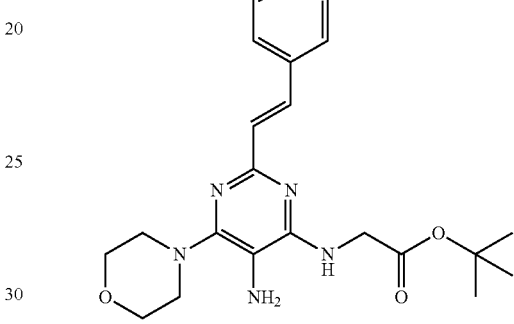

(201)

NMR (CDCl$_3$) δ: 1.50 (9H, s), 3.19 (4H, t, J=4.7 Hz), 3.84 (3H, s), 3.86 (4H, t, J=4.7 Hz), 4.21 (2H, t, J=5.1 Hz), 4.89 (1H, t, J=5.1 Hz), 6.87 (3H, m), 7.52 (2H, d, J=8.6 Hz), 7.67 (1H, d, J=16.0 Hz).

5-amino-2-[2-(4-methoxyphenyl)vinyl]-4-[N-methyl-N-(1-methylpiperidin-4-yl)amino]-6-morpholinopyrimidine (Compound 198)

(See Formula (202) below)
The NMR data for the obtained Compound 198 are shown below.

[Chemical 226]

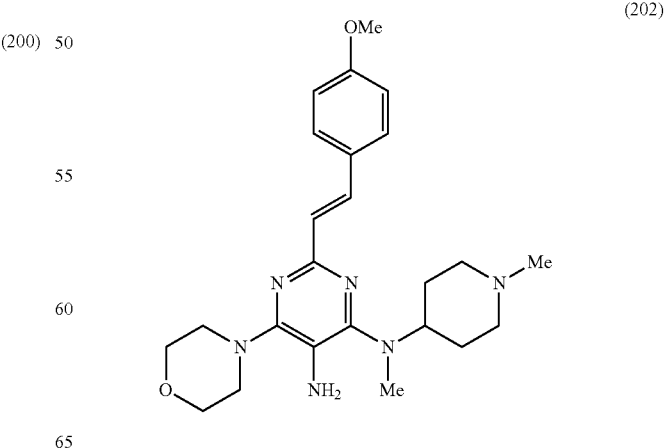

(202)

NMR (CDCl$_3$) δ: 1.81 (2H, m), 2.02 (2H, m), 2.37 (3H, s), 2.83 (3H, s), 3.00 (2H, m), 3.33 (4H, t, J=4.9 Hz), 3.45 (2H, brs), 3.60 (1H, m), 3.85 (3H, s), 3.88 (4H, t, J=4.9 Hz), 6.90 (3H, m), 7.51 (2H, d, J=8.7 Hz), 7.62 (1H, d, J=16.0 Hz).

5-amino-2-[2-(4-methoxyphenyl)ethyl]-4-(1-piperazinyl)-6-morpholinopyrimidine (Compound 199)

(See Formula (203) below)
The NMR data for the obtained Compound 199 are shown below.

[Chemical 227]

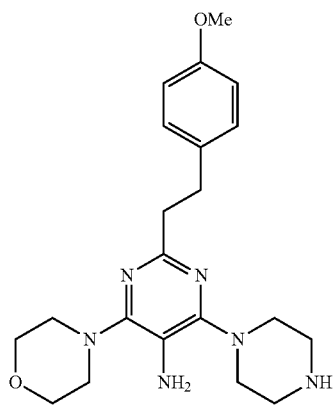

(203)

NMR (CDCl$_3$) δ: 2.99 (8H, m), 3.21-3.28 (10H, m), 3.78 (3H, s), 3.82 (4H, m), 6.80 (2H, d, J=8.6 Hz), 7.15 (2H, d, J=8.6 Hz).

5-amino-4-[4-(carboxymethyl)piperazin-1-yl]-2-[2-(4-methoxyphenyl)vinyl]-6-morpholinopyrimidine (Compound 200)

(See Formula (204) below)
The NMR data for the obtained Compound 200 are shown below.

[Chemical 228]

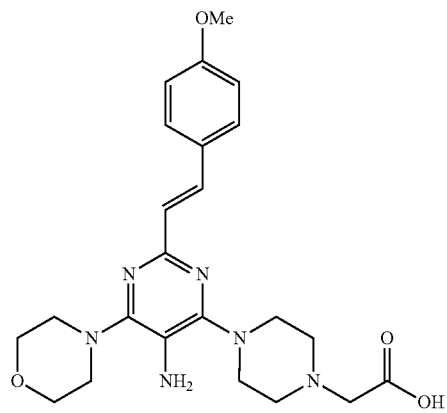

(204)

NMR (DMSO-d6) δ: 2.49-2.52 (4H, m), 3.18 (2H, s), 3.43-3.53 (8H, m), 3.60-3.67 (4H, m), 3.78 (3H, s), 6.82 (1H, d, J=15.9 Hz), 6.95 (2H, d, J=8.7 Hz), 7.63 (2H, d, J=8.7 Hz), 7.71 (1H, d, J=15.9 Hz).

4-amino-2-[2-(4-methoxyphenyl)vinyl]-6-morpholyl-5-nitropyrimidine (Compound 201)

(See Formula (205) below)
The NMR data for the obtained Compound 201 are shown below.

[Chemical 229]

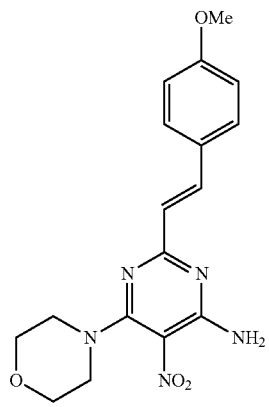

(205)

NMR (CDCl$_3$) δ: 3.63 (4H, t, J=4.5 Hz), 3.81 (4H, t, J=4.5 Hz), 3.84 (3H, s), 6.73 (1H, d, J=15.8 Hz), 6.92 (2H, d, J=8.7 Hz), 7.53 (2H, d, J=8.7 Hz), 7.83 (1H, d, J=15.8 Hz).

4,5-diamino-2-[2-(4-methoxyphenyl)vinyl]-6-morpholinopyrimidine (Compound 202)

(See Formula (206) below)
The NMR data for the obtained Compound 202 are shown below.

[Chemical 230]

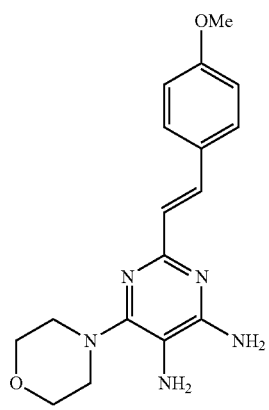

(206)

NMR (CDCl$_3$) δ: 3.25 (4H, t, J=4.6 Hz), 3.83 (3H, s), 3.87 (4H, t, J=4.6 Hz), 6.85 (1H, d, J=15.8 Hz), 6.89 (2H, d, J=8.7 Hz), 7.51 (2H, d, J=8.7 Hz), 7.64 (1H, d, J=15.8 Hz).

5-amino-4-[4 (3-aminopropionyl)piperazin-1-yl]-6-morpholino-2-[2-(4-methoxy phenyl)vinyl]pyrimidine (Compound 203)

(See Formula (207) below)

The NMR data for the obtained Compound 203 are shown below.

[Chemical 231]

(207)

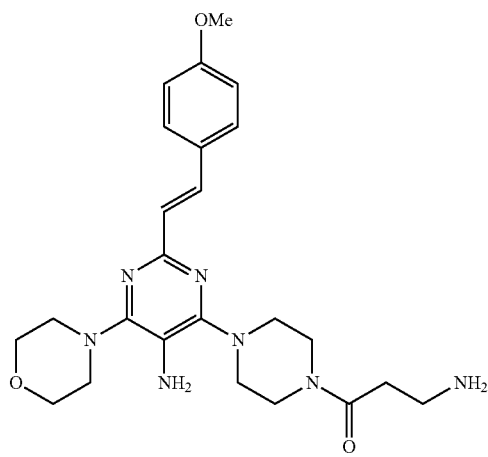

NMR (CDCl₃) δ: 3.33-3.47 (8H, m), 3.49-3.54 (8H, m), 3.83 (3H, s), 3.85-4.01 (4H, m), 6.86-6.91 (3H, m), 7.52 (2H, d, J=8.6 Hz), 7.64 (1H, d, J=16.1 Hz).

5-fluoro-4-(4-methylpiperazin-1-yl)-6-morpholino-2-[4-(4-pyridinylmethyl)piperazin-1-yl]pyrimidine (Compound 204)

(See Formula (208) below)
The NMR data for the obtained Compound 204 are shown below.

[Chemical 232]

(208)

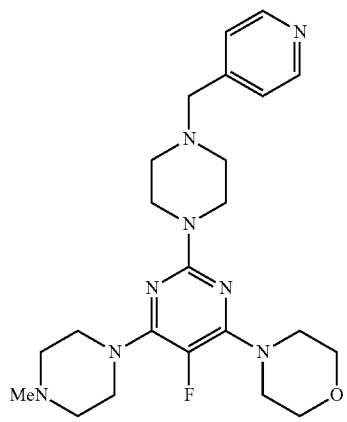

MS 456 m/z: (M⁺)
NMR (CDCl₃) δ: 2.40 (3H, s), 2.46 (4H, t, J=4.8 Hz), 2.58-2.61 (4H, m) 3.51-3.53 (6H, m), 3.65-3.70 (8H, m), 3.75 (4H, t, J=4.8 Hz), 7.29 (2H, d, J=5.9 Hz), 8.55 (2H, d, J=5.9 Hz).

5-amino-2-[2-(4-methoxyphenyl)vinyl]-4-(4-dimethylthiocarbamoylpiperazin-1-yl)-6-morpholinopyrimidine (Compound 205)

(See Formula (209) below)

The NMR data for the obtained Compound 205 are shown below.

[Chemical 233]

(209)

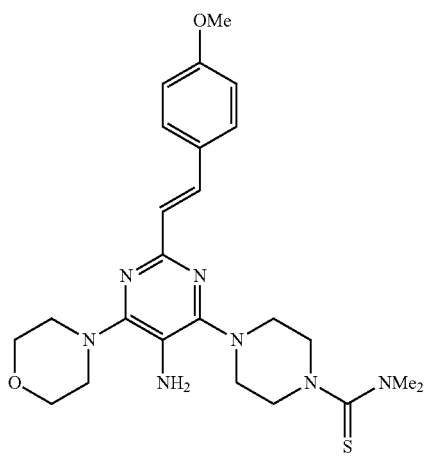

NMR (CDCl₃) δ: 3.21 (6H, s), 3.33 (4H, t, J=4.5 Hz), 3.39 (4H, t, J=4.5 Hz), 3.58 (4H, t, J=4.5 Hz), 3.83 (3H, s), 3.87 (4H, t, J=4.5 Hz), 6.89 (2H, d, J=8.7 Hz), 6.90 (1H, d, J=16.0 Hz), 7.51 (2H, d, J=8.7 Hz), 7.64 (1H, d, J=16.0 Hz).

5-amino-4-carbamoylmethylamino-2-[2-(4-methoxyphenyl)vinyl]-6-morpholinopyrimidine (Compound 206)

(See Formula (210) below)
The NMR data for the obtained Compound 206 are shown below.

[Chemical 234]

(210)

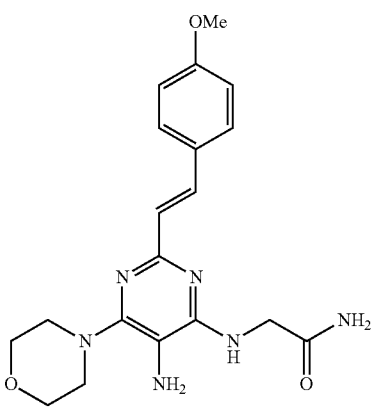

NMR (CDCl₃) δ: 3.19 (4H, t, J=4.7 Hz), 3.84 (3H, s), 3.86 (4H, t, J=4.7 Hz), 4.22 (2H, t, J=5.1 Hz), 6.82-6.93 (3H, m), 7.51 (2H, d, J=8.6 Hz), 7.60 (1H, d, J=16.0 Hz).

5-amino-2-[2-(4-methoxyphenyl)vinyl]-4-morpholino-6-(2-morpholinoethylamino)pyrimidine (Compound 207)

(See Formula (211) below)

The NMR data for the obtained Compound 207 are shown below.

[Chemical 235]

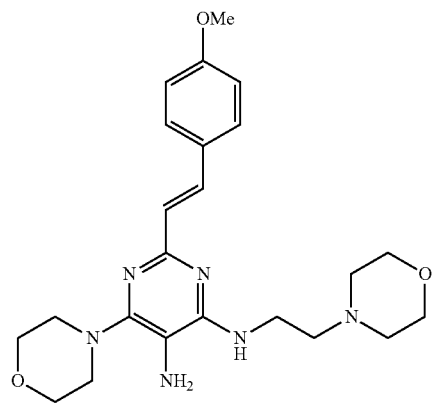

(211)

NMR (CDCl₃) δ: 2.60 (6H, m), 2.86 (2H, m), 3.20 (4H, m), 3.45 (2H, brs), 3.85 (3H, s), 3.88 (8H, m), 6.90 (3H, m), 7.52 (2H, d, J=8.7 Hz), 7.66 (1H, d, J=16.0 Hz).

5-amino-2-[2-(4-methoxyphenyl)vinyl]-4-(1-piperazinyl)-6-[2-(1-piperazinyl)ethyl amino)pyrimidine (Compound 208)

(See Formula (212) below)
The NMR data for the obtained Compound 208 are shown below.

[Chemical 236]

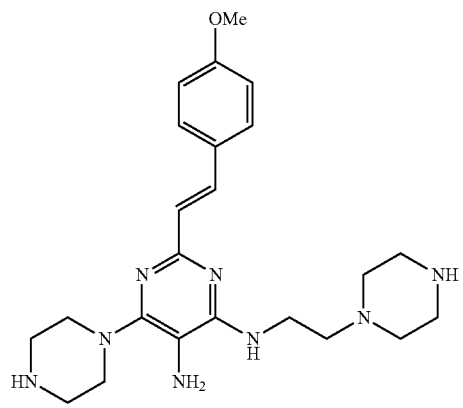

(212)

NMR (CD₃OD) δ: 2.62 (6H, brs), 3.05-3.10 (2H, m), 3.41-3.47 (8H, m), 3.50 (4H, brs), 3.67 (3H, s), 6.73 (1H, d, J=16.0 Hz), 6.78 (2H, d, J=8.7 Hz), 7.34 (2H, d, J=8.7 Hz), 7.46 (1H, d, J=16.0 Hz).

5-amino-4-(3-ethoxycarbonylthiomorpholin-4-yl)-2-[2-(4-methoxyphenyl)vinyl]-6-morpholinopyrimidine (Compound 209)

(See Formula (213) below)
The NMR data for the obtained Compound 209 are shown below.

[Chemical 237]

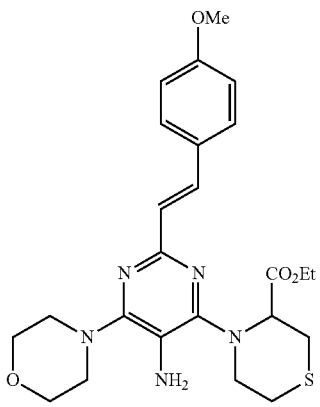

(213)

NMR (CDCl₃) δ: 1.28 (3H, t, J=7.1 Hz), 2.91-2.98 (2H, m), 3.13-3.22 (4H, m), 3.32 (1H, m), 3.84 (11H, m), 4.25 (2H, q, J=7.1 Hz), 6.89 (3H, m), 7.53 (2H, d, J=8.5 Hz), 7.71 (1H, d, J=15.8 Hz).

5-amino-4-dimethylamino-2-[2-(4-methoxyphenyl)vinyl]-6-(1-piperazinyl)pyrimidine (Compound 210)

(See Formula (214) below)
The NMR data for the obtained Compound 210 are shown below.

[Chemical 238]

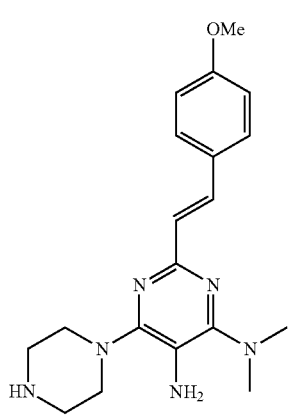

(214)

NMR (CD₃OD) δ: 2.96 (6H, s), 3.21-3.31 (3H, m), 3.40-3.44 (4H, m), 3.55-3.60 (4H, m), 3.80 (3H, s), 6.87 (1H, d, J=15.8 Hz), 6.90 (2H, d, J=8.7 Hz), 7.49 (2H, d, J=8.7 Hz), 7.63 (1H, d, J=15.8 Hz).

5-amino-2-[2-(4-methoxyphenyl)vinyl]-4-(4-methylpiperazin-1-yl)-6-(1-piperazinyl)pyrimidine (Compound 211)

(See Formula (215) below)
The NMR data for the obtained Compound 211 are shown below.

[Chemical 239]

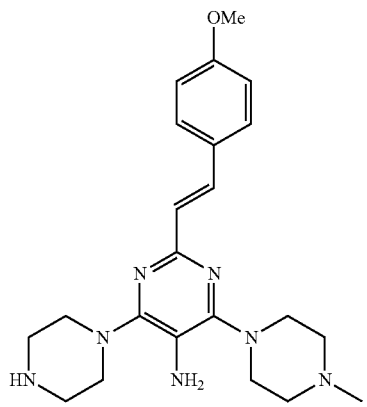

(215)

NMR (CD$_3$OD) δ: 2.35 (3H, m), 2.64 (4H, brs), 3.17-3.21 (4H, m), 3.30 (3H, brs), 3.31-3.39 (4H, m), 3.55-3.70 (4H, m), 3.78 (3H, s), 6.84 (1H, d, J=15.8 Hz), 6.89 (2H, d, J=8.7 Hz), 7.44 (2H, d, J=8.7 Hz), 7.56 (1H, d, J=15.8 Hz).

5-amino-4-(4-tert-butoxycarbonylmethylpiperazin-1-yl)-2-[2-(4-methoxyphenyl)vinyl]-6-morpholinopyrimidine (Compound 212)

(See Formula (216) below)
The NMR data for the obtained Compound 212 are shown below.

[Chemical 240]

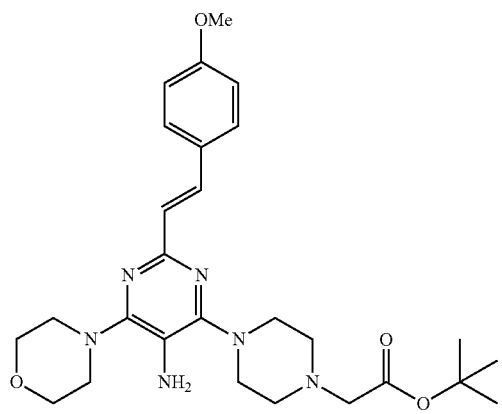

(216)

NMR (CDCl$_3$) δ: 1.48 (9H, s), 2.77 (4H, brs), 3.20 (2H, s), 3.29-3.32 (4H, m), 3.39-3.42 (6H, m) 3.81 (3H, s), 3.83-3.86 (4H, m), 6.87 (2H, d, J=8.7 Hz), 6.90 (1H, d, J=15.8 Hz), 7.50 (2H, d, J=8.7 Hz), 7.64 (1H, d, J=15.8 Hz).

4-(4-acetylpiperazin-1-yl)-5-amino-2-[2-(4-methoxyphenyl)vinyl]-6-(piperazin-1-yl)pyrimidine (Compound 213)

(See Formula (217) below)
The NMR data for the obtained Compound 213 are shown below.

[Chemical 241]

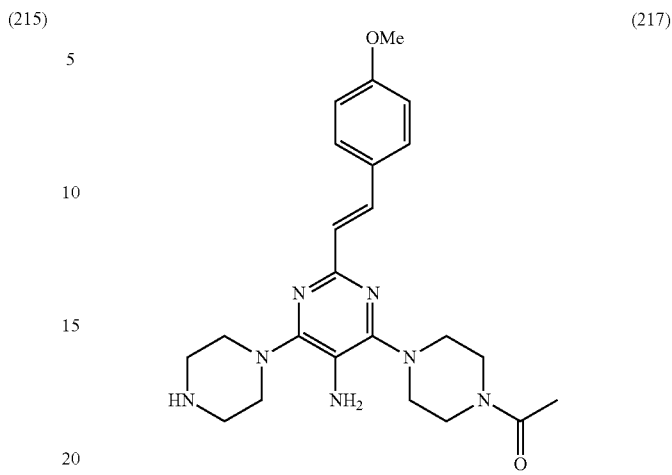

(217)

NMR (CD$_3$OD) δ: 2.02 (3H, s), 3.12-3.18 (6H, m), 3.20-3.27 (2H, m), 3.29-3.41 (4H, m), 3.45-3.50 (4H, m), 3.56-3.63 (3H, m), 3.67 (3H, s), 6.73 (1H, d, J=15.8 Hz), 6.77 (2H, d, J=8.7 Hz), 7.33 (2H, d, J=8.7 Hz), 7.45 (1H, d, J=15.8 Hz).

5-amino-4-(4-dimethylsulfamoylpiperazin-1-yl)-2-[2-(4-methoxyphenyl)ethyl]-6-morpholinopyrimidine (Compound 214)

(See Formula 218 below)
The NMR data for the obtained Compound 214 are shown below.

[Chemical 242]

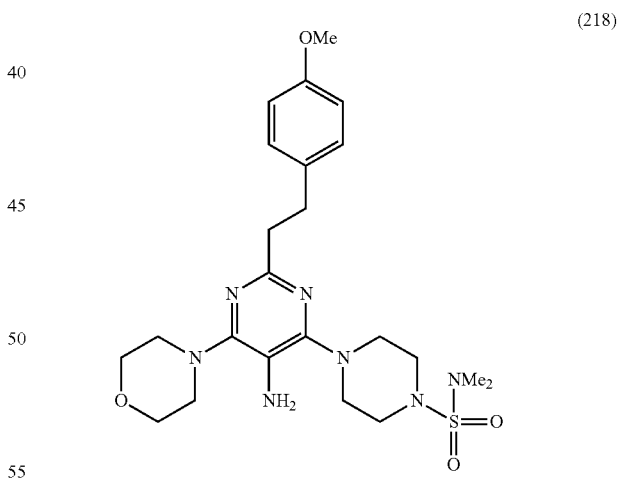

(218)

NMR (CDCl$_3$) δ: 2.86 (6H, s), 2.98-3.01 (4H, m), 3.28-3.32 (12H, m), 3.78 (3H, s), 3.82 (4H, t, J=4.6 Hz), 6.80 (2H, d, J=8.6 Hz), 7.14 (2H, d, J=8.6 Hz).

5-amino-4-(4-dimethylsulfamoylpiperazin-1-yl)-2-[2-(4-methoxyphenyl)vinyl]-6-morpholinopyrimidine (Compound 215)

(See Formula 219 below)
The NMR data for the obtained Compound 215 are shown below.

159

[Chemical 243]

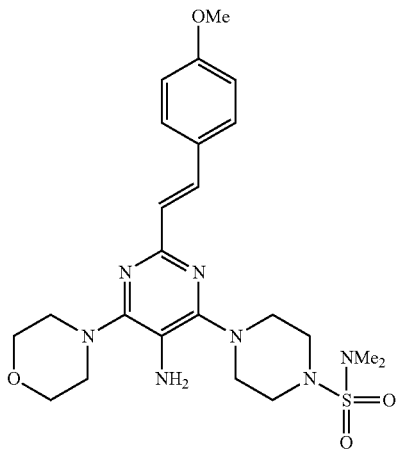

(219)

NMR (CDCl$_3$) δ: 2.87 (6H, s), 3.35-3.42 (12H, m), 3.83 (3H, s), 3.86 (4H, t, J=4.5 Hz), 6.89 (2H, d, J=8.7 Hz), 6.90 (1H, d, J=16.0 Hz), 7.52 (2H, d, J=8.7 Hz), 7.64 (1H, d, J=16.0 Hz).

5-fluoro-2-[2-(4-methoxyphenyl)vinyl]-4,6-dimorpholinopyrimidine (Compound 216)

(See Formula 220 below)

The NMR data for the obtained Compound 216 are shown below.

[Chemical 244]

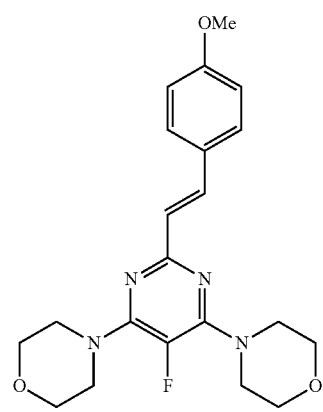

(220)

NMR (CDCl$_3$) δ: 3.64 (8H, m), 3.81 (8H, m), 3.83 (3H, s), 6.78 (1H, d, J=16.00 Hz), 6.89 (2H, d, J=8.7 Hz), 7.50 (2H, d, J=8.7 Hz), 7.62 (1H, d, J=16.00 Hz).

Next, the results of tests for verifying the actions and effects of the compounds (Compounds 1-216) explained in said Examples 1-22 shall be explained. The Test Compound Numbers in the trials correspond to the Compound Numbers (Compound 1-216) in said Examples 1-22.

160

Example 23

Pharmacological Test 1

Antioxidant Activity Test (Rat Brain Homogenate Autoxidation Test)

(Test Method)

The cerebrum was removed from 7 to 11 week old male Wistar rats (Nihon Ikagaku) or male Sprague-Dawley (IGS) rats (Charles River), physiological saline was added, and a 20% brain homogenate was made. 4 µl of test compound dissolved in DMSO was mixed with 200 µl of brain homogenate and 200 µl of PBS (–) (diluted 100 times), incubated for 2 hours at 37 degrees Celsius and shaken at a rate of 160 times per minute, thereby producing a lipid peroxide. After cooling for 5 minutes, the produced lipid peroxide was measured as a thiobarbituric acid reactive substance by using the thiobarbituric acid method. Briefly, 100 µl of 8.1% dodecyl sulfate, 750 µl of 20% acetic acid adjusted to a pH of 3.5, and 750 µl of 0.8% thiobarbituric acid were added, and boiled for 60 minutes, and then cooled. Next, 500 µl of distilled water and 2.5 ml of N-butanol/pyridine (15:1) were added and after 5 minutes of shaking, the supernatant was taken after centrifuging for 10 minutes at 3000 rpm, and the absorbance at 532 nm was measured. The number of examples was 2 examples. Calculation was done of the (absorbance at each concentration/ absorbance of a solvent control)×100, and after logit transformation, the lipid peroxide production suppression effect (IC 50 value) was calculated as an indicator of antioxidant activity.

(Test Results)

Said compounds (Compounds 1-216) showed a strong antioxidant activity. A portion of the results are shown in the table below.

Antioxidant Activity of Compounds

TABLE 1

| Compound | Antioxidant activity (IC$_{50}$ value) | Compound | Antioxidant activity (IC$_{50}$ value) |
|---|---|---|---|
| Compound 30 | 6.84 µM | Compound 123 | 13.29 µM |
| Compound 57 | 30.48 µM | Compound 131 | 7.04 µM |
| Compound 63 | 0.81 µM | Compound 133 | 1.04 µM |
| Compound 66 | 0.82 µM | Compound 136 | 1.69 µM |
| Compound 69 | 1.26 µM | Compound 139 | 0.11 µM |
| Compound 73 | 0.69 µM | Compound 140 | 0.55 µM |
| Compound 75 | 0.67 µM | Compound 146 | 1.91 µM |
| Compound 81 | 2.22 µM | Compound 149 | 9.75 µM |
| Compound 82 | 9.2 µM | Compound 151 | 8.41 µM |
| Compound 87 | 5.78 µM | Compound 170 | 3.10 µM |
| Compound 89 | 3.48 µM | Compound 173 | 2.08 µM |
| Compound 91 | 5.88 µM | Compound 175 | 2.08 µM |
| Compound 94 | 15.97 µM | Compound 176 | 2.16 µM |
| Compound 99 | 7.51 µM | Compound 196 | 2.73 µM |
| Compound 105 | 2.77 µM | Compound 197 | 0.99 µM |
| Compound 110 | 3.02 µM | Compound 198 | 1.04 µM |
| Compound 121 | 5.05 µM | Compound 199 | 8.12 µM |
| Compound 122 | 5.48 µM | Compound 216 | 0.86 µM |

Example 24

Pharmacological Test 2

Inhibitory Effect Against Brain Cell Damage Induced by Hydrogen Peroxide (1) Culture of Astrocytes The brain was removed from 1 to 2 day old Wistar rats (Charles River) or Sprague-Dawley (IGS) rats (Charles River), and the cerebral cortex including the hippocampus was excised under ice cooling. After this cerebral cortex was minced, it was digested with papain solution (9 U/ml) containing DNase I (30 U/ml) at 37 degrees Celsius for 15 minutes, dispersing the cells. After further carrying out mechanical dispersing by pipetting, it was passed through a cell strainer with a pore size of 70 μm, and a cell suspension was obtained. Cells derived from 1.4 cerebra were seeded on 150 mm tissue culture dish (Iwaki Glass), and primary culture was carried out at 37 degrees Celsius and 5% $CO_2$ using a D-MEM medium (Invitrogen) containing 10% heat-inactivated fetal calf serum (JRH). One day after the start of the culture, the nonadherent cells were removed, and the primary cultured astrocytes were obtained by continuing the culture for 4 to 5 further days. The primary cultured astrocytes were dispersed by trypsin treating, suspended in cryopreservation solution, and cryopreserved.

(2) Astrocyte/Neuron Co-Culture

After thawing the cryopreserved primary cultured astrocytes, they were seeded on tissue culture plates (Iwaki Glass), and a confluent astrocyte layer was produced by a further 7 days of secondary culture using a D-MEM medium containing 10% heat-inactivated fetal calf serum. Neurons to be used in the co-culture with the astrocyte layer were obtained from fetal rat cerebrum. Briefly, brains were removed from Wistar rats (Charles River) or Sprague-Dawley (IGS) rats (Charles River) of embryonic age 18.5 days, and the cerebral cortex including the hippocampus was excised under ice cooling. After this cerebral cortex was minced, it was digested in papain solution (9 U/ml) containing DNase I (30 U/ml) at 37 degrees Celsius for 15 minutes, dispersing the cells. After further carrying out mechanical dispersing by pipetting, it was passed through a cell strainer with a pore size of 70 μm, and a cell suspension was obtained. This cell suspension was plated at a density of $1.3 \times 10^5$ cells/cm$^2$ on the astrocyte layer, and a co-culture was carried out using D-MEM/F-12 medium (Invitrogen) containing 10% heat-inactivated fetal calf serum and 5% horse serum (Invitrogen). 2 days after the start of the co-culture, cells were treated for 24 hours with 10 μM cytosine arabinoside in order to suppress the excessive cell proliferation of microglia and the like. 8 to 9 days after the start of the co-culture, cells were used for the test. Additionally, using one portion of the cells, immunofluorescent staining and nuclear staining was carried out with astrocyte recognizing antibodies (anti-GFAP) and neuron recognizing antibodies (anti-MAP2), in order to confirm that the present culture system is a co-culture system of astrocytes and neurons.

(3) Induction of Cell Damage by Hydrogen Peroxide Treatment and Inhibitory Effect of Compound An astrocyte/neuron co-culture cultured on a 96 well plate was used in the test. A predetermined concentration of the test substance and hydrogen peroxide (250 μM) was simultaneously added to the cell culture in each well with continuing cultivation, and analysis was done 24 hours after this treatment. Using an LDH Cytotoxicity Detection Kit (Takara Bio), analysis was carried out in accordance with the included instruction manual, and the damage to the entire co-culture system by the hydrogen peroxide treatment and the protective effect (EC 50 value) of the test substance was evaluated. Further, the cell bodies and the neuronal processes of the neurons were observed by microscope, and the neuroprotective effect was evaluated.

(Test Results)

Cell death was induced in neurons by hydrogen peroxide treatment, and further, damage and cell death was produced in astrocytes. At low concentration levels, said compounds (Compounds 1-216) inhibited damage to astrocytes in particular among the entire system, while at higher concentration levels, they inhibited damage not just to astrocytes but also to neurons. One portion of the results is shown in Table 2 and Table 3.

Protective Effect of Compounds Against Brain Cell Damage Induced by Hydrogen Peroxide Treatment (LDH Assay)

TABLE 2

| Compound | 50% inhibition concentration against cell damage in entire co-culture system ($EC_{50}$ value) | Compound | 50% inhibition concentration against cell damage in entire co-culture system ($EC_{50}$ value) |
|---|---|---|---|
| Compound 2 | 18.40 μM | Compound 139 | 1.15 μM |
| Compound 6 | 8.24 μM | Compound 140 | 5.15 μM |
| Compound 30 | 3.01 μM | Compound 145 | 0.67 μM |
| Compound 52 | 3.16 μM | Compound 146 | 0.96 μM |
| Compound 56 | 2.95 μM | Compound 149 | 0.42 μM |
| Compound 57 | 5.12 μM | Compound 151 | 0.98 μM |
| Compound 61 | 6.45 μM | Compound 153 | 0.45 μM |
| Compound 63 | 8.30 μM | Compound 155 | 0.32 μM |
| Compound 66 | 2.86 μM | Compound 158 | 0.16 μM |
| Compound 67 | 1.78 μM | Compound 160 | 1.08 μM |
| Compound 68 | 0.86 μM | Compound 167 | 0.28 μM |
| Compound 69 | 0.29 μM | Compound 168 | 0.31 μM |
| Compound 71 | 1.96 μM | Compound 170 | 0.99 μM |
| Compound 73 | 10.62 μM | Compound 171 | 0.49 μM |
| Compound 75 | 9.46 μM | Compound 173 | 4.72 μM |
| Compound 78 | 9.75 μM | Compound 174 | 3.11 μM |
| Compound 81 | 0.82 μM | Compound 175 | 3.24 μM |
| Compound 82 | 0.60 μM | Compound 176 | 2.74 μM |
| Compound 87 | 0.68 μM | Compound 178 | 0.48 μM |
| Compound 89 | 0.53 μM | Compound 179 | 0.34 μM |
| Compound 91 | 0.88 μM | Compound 187 | 0.33 μM |
| Compound 94 | 0.68 μM | Compound 190 | 0.34 μM |
| Compound 99 | 0.40 μM | Compound 191 | 0.73 μM |
| Compound 105 | 0.29 μM | Compound 192 | 0.30 μM |
| Compound 110 | 0.33 μM | Compound 196 | 3.78 μM |
| Compound 115 | 0.63 μM | Compound 197 | 0.55 μM |
| Compound 121 | 0.32 μM | Compound 198 | 3.74 μM |
| Compound 122 | 0.29 μM | Compound 199 | 3.05 μM |
| Compound 123 | 2.98 μM | Compound 206 | 4.85 μM |
| Compound 125 | 0.56 μM | Compound 207 | 5.80 μM |
| Compound 126 | 0.80 μM | Compound 209 | 1.48 μM |
| Compound 128 | 0.30 μM | Compound 210 | 4.07 μM |
| Compound 131 | 8.99 μM | Compound 214 | 2.26 μM |
| Compound 133 | 2.03 μM | Compound 215 | 1.61 μM |
| Compound 136 | 0.73 μM | Compound 216 | 0.73 μM |

Protective Effect of Compounds Against Brain Cell Damage Induced by Hydrogen Peroxide Treatment (Neuroprotective Effect)

TABLE 3

| Compound | Concentration for complete inhibition of neuronal death | Compound | Concentration for complete inhibition of neuronal death |
|---|---|---|---|
| Compound 30 | 10 μM | Compound 149 | 10 μM |
| Compound 52 | 30 μM | Compound 153 | 3 μM |
| Compound 56 | 10 μM | Compound 155 | 3 μM |
| Compound 57 | 30 μM | Compound 158 | 1 μM |
| Compound 61 | 10 μM | Compound 160 | 3 μM |
| Compound 63 | 30 μM | Compound 168 | 3 μM |
| Compound 66 | 30 μM | Compound 170 | 3 μM |
| Compound 69 | 3 μM | Compound 173 | 30 μM |
| Compound 78 | 30 μM | Compound 174 | 10 μM |
| Compound 81 | 3 μM | Compound 175 | 10 μM |
| Compound 82 | 3 μM | Compound 176 | 10 μM |

TABLE 3-continued

| Compound | Concentration for complete inhibition of neuronal death | Compound | Concentration for complete inhibition of neuronal death |
|---|---|---|---|
| Compound 87 | 3 μM | Compound 178 | 3 μM |
| Compound 89 | 3 μM | Compound 179 | 3 μM |
| Compound 91 | 10 μM | Compound 187 | 1 μM |
| Compound 94 | 3 μM | Compound 190 | 3 μM |
| Compound 99 | 1 μM | Compound 192 | 1 μM |
| Compound 105 | 1 μM | Compound 196 | 10 μM |
| Compound 110 | 1 μM | Compound 197 | 3 μM |
| Compound 121 | 1 μM | Compound 198 | 10 μM |
| Compound 122 | 1 μM | Compound 199 | 10 μM |
| Compound 123 | 10 μM | Compound 206 | 10 μM |
| Compound 128 | 3 μM | Compound 207 | 10 μM |
| Compound 131 | 10 μM | Compound 209 | 10 μM |
| Compound 133 | 30 μM | Compound 210 | 10 μM |
| Compound 136 | 3 μM | Compound 214 | 10 μM |
| Compound 139 | 3 μM | Compound 215 | 10 μM |
| Compound 140 | 10 μM | Compound 216 | 3 μM |
| Compound 146 | 3 μM | | |

Example 25

Pharmacological Test 3

Damage to Neurons Induced by Glutamic Acid Treatment and Inhibitory Effect of Compounds (Test Method)
Inducement of Cell Death by Glutamic Acid Treatment and Inhibitory Effect of Compounds Cell cultures were produced in a similar manner to (1) and (2) of Example 24, and astrocyte—neuron cultures that were cultured on 24 well plates were used in the test. A predetermined concentration of the test substance was added to each cell medium, and after 1 hour of pre-treatment was carried out, glutamic acid (0.5 mM) was added under the presence of the test substance and the culture was continued, and 48 hours after the glutamic acid treatment, analysis was carried out. After microscopic observation was carried out, an LDH Cytotoxicity Detection Kit was used to carry out the analysis in accordance with the included instruction manual, and the damage to the entire cell-culture system induced by glutamic acid, and the protective effect of the test substance, was evaluated.
(Test Results)

Figure 2:
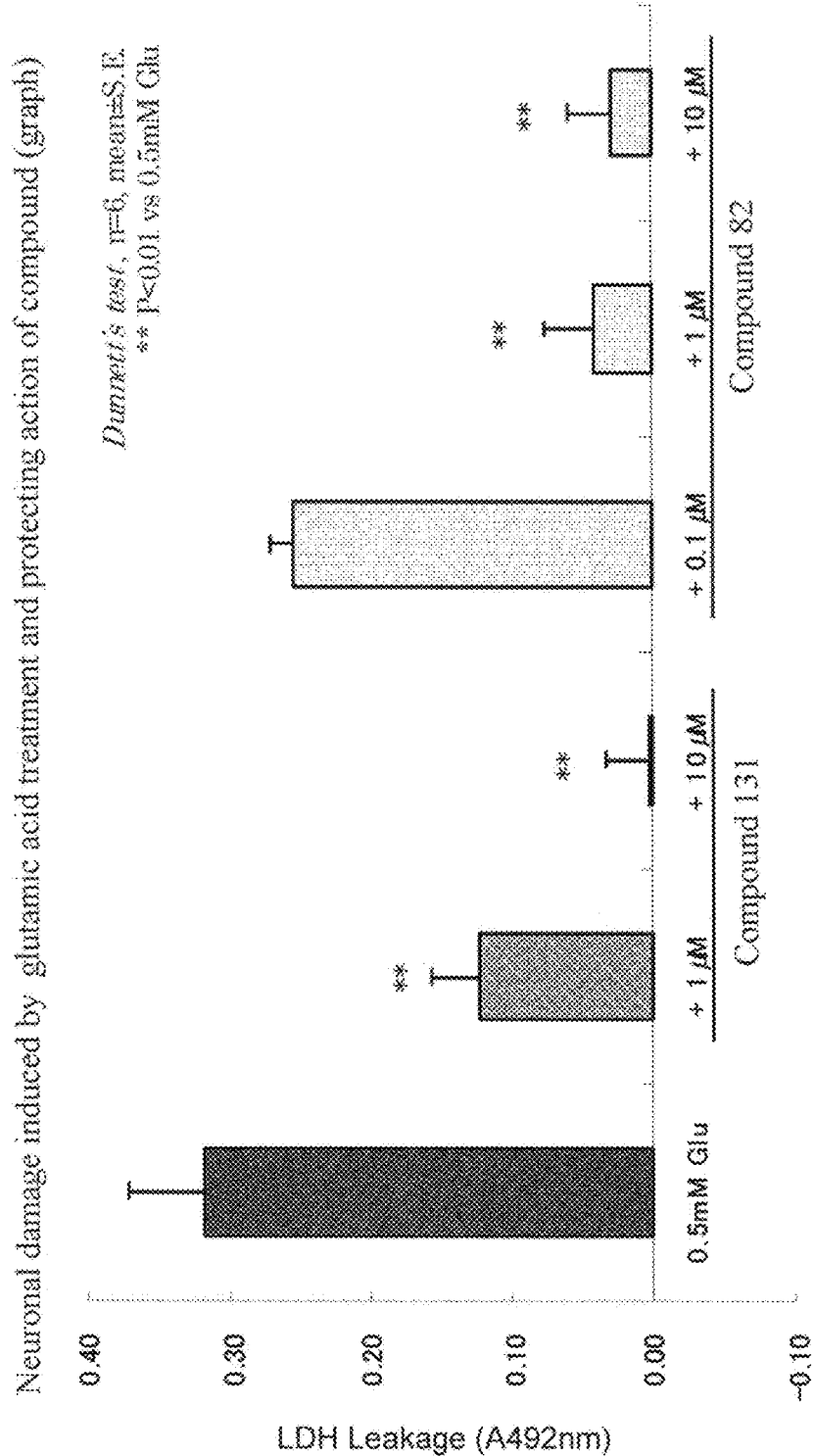
FIG. 2 Graph for explaining the neuronal damage induced by glutamic acid treatment and the protecting action of the compound.

The results of the microscope observation were that at the glutamic acid concentrations used in the present test (0.5 mM), around half of the neurons underwent cell death, while the astrocytes did not receive any damage. Whereby, we can define the test results obtained using the LDH Cytotoxicity Detection Kit as showing damage that was produced only in neurons. As shown in FIG. 1 and FIG. 2, said compounds (Compounds 1-216) completely suppressed neuronal death.

Example 26

Pharmacological Test 4

Inhibitory Effect Against Infarct Formation Induced by Transient Cerebral Ischemia (Test Method)
(1) Rat Transient Focal Cerebral Ischemia Model (Middle Cerebral Artery 90 Minute Occlusion—Reperfusion Model)
230-340 g Sprague-Dawley (IGS) male rats (Charles River) were anesthetized with pentobarbital, a 3.5 Fr Safeed feeding tube (Terumo) was inserted into the left jugular vein and an intravenous cannula was installed. The next day, after a median incision to the neck was made under anesthesia by halothane inhalation, the right internal carotid artery and the common carotid artery were clamped with microvascular clamps (F.T.F.). After a 3-0 size nylon monofilament (Akiyama Medical Mfg.) with the tip rounded by flame and coated with 0.1% poly-L-lysine was inserted from the right external carotid artery incision site, the clamp on the right internal carotid artery was removed, and the monofilament was further inserted until a light resistance could be felt, occluding the origin of the right middle cerebral artery. After the occlusion, the clamp was removed from the common carotid artery, the surgical site was sutured up, and the animal was awakened. 90 minutes after occlusion of the right middle cerebral artery, the nylon monofilament was pulled out under halothane anesthesia, thereby allowing reperfusion, the surgical site was sutured up, and the animal was awakened. 24 hours after reperfusion, the cerebrum was removed, and using a brain slicer (Muromachi Kikai), a 2 mm thick slice sample was taken from a position 6 mm from the frontal pole, and this was stained (38 degrees Celsius, 10 minutes) in 1.5% 2,3,5-trichlorotetrazolium chloride (TCC), and fixed in 10% formalin solution. The stained and fixed sample was photographed with a digital camera, and the cerebral infarct ratio (number of pixels of cerebral infarct/number of pixels of right cerebral hemisphere×100) of the image was calculated using Adobe Photoshop (Adobe Systems), and this was defined as the cerebral infarct ratio of the right brain.

(2) Rat Transient Focal Cerebral Ischemia Model (Middle Cerebral Artery 180 Minute Occlusion—Reperfusion Model)

In the middle cerebral artery 180 minute occlusion—reperfusion model, after occluding the right middle cerebral artery for 180 minutes, the nylon monofilament was pulled out under halothane anesthesia, thereby allowing reperfusion, the surgical site was sutured, and the animal was awakened. 24 hours after middle cerebral artery occlusion, scoring of the neurological symptoms was done based upon a modification of Bederson's method (S. G. Sydserff et al., British J. Pharmacol. 135, (2002)). The scoring was done by assigning a score of 0, 1, or 2 to the four items left forelimb paralysis, leftward rotation motion, leftward leaning posture, and left hind limb pain—flexor reflex reduction, and the scores for each item were added together. After scoring, the cerebrum was removed, and using a brain slicer (Muromachi Kikai), 2 mm thick slice samples were taken from a position from 2 mm to 10 mm from the frontal pole, and these were stained (38 degrees Celsius, 10 minutes) in 1.5% 2,3,5-trichlorotetrazolium chloride (TCC), and fixed in 10% formalin solution. The stained and fixed sample was photographed with a digital camera, and the cerebral infarct ratio (number of pixels of cerebral infarct/number of pixels of right cerebral hemisphere×100) of the image was calculated using Adobe Photoshop (Adobe Systems), and this was defined as the cerebral infarct ratio of the right brain.

(3) Adjustment and Administration of Test Compounds

In the middle cerebral artery 90 minute occlusion—reperfusion model, the test compound was dissolved in 0.06 N HCl/normal saline solution (0.2 N HCl/normal saline solution for Compound 131) as the final concentration, and 3 mg/kg (1 mg/kg for Compound 131) was intravenously administered 1 minute before middle cerebral artery occlusion, immediately after reperfusion, and 90 minutes after reperfusion. In the middle cerebral artery 180 minute occlusion—reperfusion model, the test compound was dissolved in 0.2 N HCl/normal saline solution as the final concentration, and 1 mg/kg was intravenously administered 1 minute before middle cerebral artery occlusion, 90 minutes after reperfusion, and 180 minutes after reperfusion.

(Test Results)

As shown in FIG. 3, said compounds (Compounds 1-216) significantly suppressed the formation of infarcts induced by transient focal cerebral ischemia. Further, as shown in FIG. 4 and FIG. 5, in the more severe middle cerebral artery 180 minute occlusion—reperfusion model as well, they significantly suppressed the formation of infarcts (FIG. 4), and also improved neurological symptoms (FIG. 5). From these results, it is clear that said compounds (Compounds 1-216) suppress the formation of infarcts induced by transient cerebral ischemia and improves neurological symptoms. Additionally, there are cases where the recirculation results in worsening brain damage, but by treatment with said compounds (Compounds 1-216), the risk associated with the recirculation can be reduced.

Example 27

Pharmacological Test 5

Inhibitory Effect Against Infarct Formation Induced by Permanent Cerebral Artery Occlusion (Test Method)

(1) Production of Permanent Cerebral Artery Occlusion Cerebral Infarction Model by Microsphere Embolism 200 to 300 g Wistar male rats (Nihon Ikagaku) were anesthetized with pentobarbital, a 3.5 Fr Safeed feeding tube (Terumo) was inserted into the left jugular vein and an intravenous cannula was installed. The next day, these rats were anesthetized with halothane, and were dorsally fixed to a warm plate. After a median incision to the neck was made, the right external carotid artery and the right pterygopalatine artery were detached, and they were temporarily ligated, and a polyethylene tube with a 25 G needle attached was inserted into the right common carotid artery. After 3000 particles/ 0.15 ml/animal of 50 μm diameter microspheres (Perkin Elmer) suspended in 20% dextran 40 (Tokyo Kasei) solution with heparin mixed in was injected into the right internal carotid artery, the needle withdrawal site of the right carotid artery was repaired with Aron Alpha instant adhesive, and the temporarily ligated vessels were reopened, and the surgical site was sutured up. After observing the neurological symptoms 24 hours after the injection of microspheres, the brain was removed, and the cerebral infarct ratio of the right brain was determined by TTC staining.

(2) Administration of Drug

The test compound was dissolved in 0.06 N HCl/normal saline solution as the final concentration, and 10 minutes, 90 minutes, and 180 minutes after the injection of microspheres, 1 mg/kg of Compound 131, and 3 mg/kg of all other compounds, was intravenously administered through the venous cannula.

(3) Neurological Evaluation

Neural symptoms were scored in accordance with a method used in microsphere induced cerebral infarction models (Takeo S, et al., *Stroke* 23, 62-68, (1992)), by selecting the three items of paucity of movement, truncal curvature, and force circling during locomotion, and assigning a score of 0, 1, or 2 for each item depending upon the degree of severity of the symptom. That is, the symptoms for each animal were represented by the total score for the three items, where for paucity of movement, 0 was assigned for no paucity of movement, 1 for movement upon touching, and 2 for no movement upon touching, for leaning posture, 0 was assigned for no lean in the posture, 1 for a lean from the head to the forelimbs, and 2 for a lean throughout the entire body, and for unidirectional turning during walking, 0 was assigned for no unidirectional turning, 1 for both turning and straight movement, and 2 for only turning movement.

(4) Measurement of Cerebral Infarct Ratio

For the cerebral infarct ratio, the removed brain was sliced at portions 6, 8, and 10 mm from the frontal pole using a brain slicer (Muromachi Kikai), and each portion was reacted at 37 degrees Celsius for 10 minutes in 1.5% TTC, and the healthy red-colored portion and the necrotic white-colored portion were separated by staining. These slices were fixed in 10% formalin solution, photographed with a digital camera, and the cerebral infarct ratio (number of pixels of cerebral infarct/ number of pixels of right cerebral hemisphere×100) of the image was determined using Adobe Photoshop (Adobe Systems), and the average value of the infarct ratio for the three slices was defined as the cerebral infarct ratio of the right brain.

(Test Results)

As shown in FIG. 6, said compounds (Compounds 1-216) significantly suppressed the formation of cerebral infarct induced by permanent cerebral artery occlusion. From these results, it can be said that said compounds (Compounds 1-216) can suppress the spreading of brain damage even in cases of cerebral infarction in which the blood flow does not recirculate spontaneously after a cerebral infarction and a thrombolytic agent is not applied. Further, as shown in FIG. 7, said compounds (Compounds 1-216) improved neurological symptoms. From these results, it is clear that said compounds (Compounds 1-216) have a suppressing action on the occurrence of sequelae after cerebral infarction.

[Overall]

From said experimental examples as well, it was confirmed that said compounds (e.g., Compounds 1-216) have strong antioxidant activity, and are effective as cell protecting agents for various diseases, whether involving peripheral tissues or central tissues. Further, it was confirmed that said compounds (e.g., Compounds 1-216) can inhibit brain cell damage due to hydrogen peroxide, and can inhibit nerve cell disorders due to glutamic acid. From these results, it is clear that said compounds (e.g., Compounds 1-216) are effective as excellent prophylactic and/or therapeutic agents against nerve diseases such as ischemic brain disease, neurodegenerative disease, and neuropsychiatric disease, and/or excellent inhibitors of brain cell death associated with nerve diseases such as ischemic brain disease or neurodegenerative disease, and in particular as excellent prophylactic and therapeutic agents against ischemic brain diseases due to transient cerebral ischemia or permanent cerebral artery occlusion.

The examples above were explanations of the present invention by example based upon the examples, and it will be understood by those skilled in the art that various modified examples are possible, and additionally, that such modified examples would fall within the scope of the present invention. For example, said examples are nothing more than concrete explanations using one portion of the compounds for which experimental results have been confirmed, and the fact that compounds other than the compounds used in said examples will also give rise to similar effects, and the use of such compounds, are also included within the technical scope of the present invention. Additionally, uses for diseases other than the diseases (models) used in the examples are also possible, and are included within the technical scope of the present invention.

Further, the various modes explained through the recitation of the Modes of Embodiment of the Invention have been disclosed not with the aim of restricting, but with the aim of exemplifying the present invention. The technical scope is determined by the recitation of the Claims, and it is possible for those skilled in the art to make various design modifications within the technical scope of the invention recited in the Claims.

The disclosed contents of all patents, patent applications, and publications cited in the present specification are incorporated in the present specification by reference.

The invention claimed is:

1. A compound represented by Formula (1a), or a pharmaceutically acceptable salt thereof:

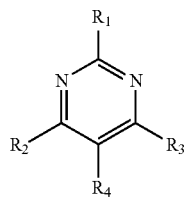

(1a)

wherein $R_1$, $R_2$, and $R_3$ are each selected independently from Formula (2a):

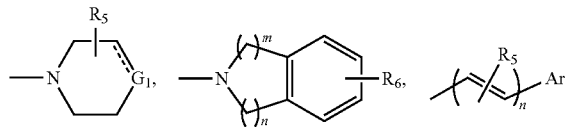

(2a)

wherein n is 1, 2, or 3;

$R_5$ represents —H, carboxyl, (C1-C6) alkyl, (C1-C6) alkoxycarbonyl, (C1-C6) alkoxycarbonylmethyl, amino (C1-C6) alkyl (said amino group may be substituted with 1 or 2 (C1-C6) alkyl groups; or 1 (C1-C6) alkoxycarbonyl group; additionally, a carbonyl group may be contained in the carbon chain), piperazinyl (C1-C6) alkyl, (C1-C6) alkoxycarbonylpiperazinyl (C1-C6) alkyl, morpholino (C1-C6) alkyl, (C1-C6) alkylpiperizine, (C2-C6) alkenyl, (C2-C6) alkynyl, or phenyl group, wherein said phenyl group may further be substituted with 1 or 2 of $R_6$;

$R_6$ represents —H, —F, —Cl, —Br, —I, (C1-C6) alkyl, (C1-C6) alkylamino, di (C1-C6) alkylamino, (C1-C6) alkoxy, (C1-C6) alkylthio, (C1-C6) acyl, pyrrolidinyl, piperidino, piperazinyl, (C1-C6) alkoxycarbonyl, (C1-C6) alkoxycarbonylamino, phenyl, benzyl, phenyl (C1-C6) alkyloxy, nitro, amino or hydroxyl group;

Ar represents a phenyl, benzyl, pyridyl, pyrimidyl, thienyl, pyrrole, quinolinyl, thiazolyl, benzothiazolyl, thiadiazolyl, imidazolyl, tetrazolyl or pyridazinyl group which may be substituted with 1 or 2 of $R_6$; or a condensed ring group wherein 2 or more phenyl, benzyl, pyridyl, pyrimidyl, thienyl, pyrrole, quinolinyl, thiazolyl, benzothiazolyl, thiadiazolyl, imidazolyl, tetrazolyl or pyridazinyl groups, which may be substituted with 1 or 2 of $R_6$, are condensed;

$G_1$ is an oxygen atom, a sulfur atom, or a carbon atom or nitrogen atom substituted with $R_7$; further, in cases where it is a carbon atom substituted with $R_7$, said carbon atom may form an unsaturated bond with an adjacent carbon atom;

$R_7$ represents —H, (C1-C6) alkyl, amino (C1-C6) alkyl (which may contain a carbonyl group in the carbon chain), (C1-C6) alkylaminocarbonyl, (C1-C6) alkylaminothiocarbonyl, di (C1-C6) alkylaminosulfamoyl, (C1-C6) alkoxycarbonyl, (C1-C6) alkoxycarbonyl (C1-C6) alkyl, carboxy (C1-C6) alkyl, (C1-C6) alkoxycarbonylamino, (C1-C6) alkoxycarbonylamino (C1-C6) alkyl, (C2-C6) alkenyl, (C2-C6) alkynyl, (C3-C6) cycloalkyl, (C1-C6) acyl, nitro, cyano, hydroxyl or amino group; or a phenyl, benzyl, pyridyl, picolyl, pyrimidyl, quinolinyl, thiazolyl, benzothiazolyl, thiadiazolyl, imidazolyl, tetrazolyl or pyridazinyl group, which may be substituted with $R_6$;

or, one of them is an amino group substituted with 1 or 2 of $R_5$, or is a phenyl (C1-C6) alkyl group, and the remaining two are independently selected from said Formula (2a), and $R_4$ represents —F, —Cl, —Br, —I, formyl, phenyl, or (C1-C6) alkoxy group, wherein said phenyl group may be substituted with 1 or 2 of $R_6$, provided that if any one of $R_1$, $R_2$, or $R_3$ is a phenyl (C1-C6) alkyl group, or Formula (4):

(4)

then $R_4$ is —F, —Cl, —Br, —I, formyl, (C1-C6) alkyl, (C1-C6) alkoxy, amino, acetylamino, (C1-C6) alkylamino, di (C1-C6) alkylamino or cyano group, wherein said phenyl group may be substituted with 1 or 2 of $R_6$.

2. The compound according to claim 1, or a pharmaceutically acceptable salt thereof, wherein any one of $R_1$, $R_2$, and $R_3$ is Formula (5):

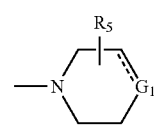

(5)

wherein $G_1$ is an oxygen atom, a sulfur atom, or it may be a carbon atom or nitrogen atom substituted by $R_7$; further, in cases where it is a carbon atom substituted by $R_7$, said carbon atom may form an unsaturated bond with an adjacent carbon atom, $R_7$ represents a —H, (C1-C6) alkyl, amino (C1-C6) alkyl (which may contain a carbonyl group in the carbon chain), (C1-C6) alkylaminocarbonyl, (C1-C6) alkylaminothiocarbonyl, di (C1-C6) alkylaminosulfamoyl, (C1-C6) alkoxycarbonyl, (C1-C6) alkoxycarbonyl (C1-C6) alkyl, carboxy (C1-C6) alkyl, (C1-C6) alkoxycarbonylamino, (C1-C6) alkoxycarbonylamino (C1-C6) alkyl, (C2-C6) alkenyl, (C2-C6) alkynyl, (C3-C6)cycloalkyl, (C1-C6) acyl, nitro, cyano, hydroxyl or amino group; or a phenyl, benzyl, pyridyl, picolyl, pyrimidyl, quinolinyl, thiazolyl, benzothiazolyl, thiadiazolyl, imidazolyl, tetrazolyl or pyridazinyl group, which may be substituted with $R_6$.

3. The compound according to claim 1 or 2, or a pharmaceutically acceptable salt thereof, wherein $R_2$, and $R_3$ is Formula (5):

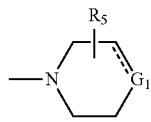

(5)

wherein $G_1$ is an oxygen atom, a sulfur atom, or it may be a carbon atom or nitrogen atom substituted by $R_7$; further, in cases where it is a carbon atom substituted by $R_7$, said carbon atom may form an unsaturated bond with an adjacent carbon atom, and $R_7$ represents a —H, (C1-C6) alkyl, amino (C1-C6) alkyl (which may contain a carbonyl group in the carbon chain), (C1-C6) alkylaminocarbonyl, (C1-C6) alkylaminothiocarbonyl, di (C1-C6) alkylaminosulfamoyl, (C1-C6) alkoxycarbonyl, (C1-C6) alkoxycarbonyl (C1-C6) alkyl, carboxy (C1-C6) alkyl, (C1-C6) alkoxycarbonylamino, (C1-C6) alkoxycarbonylamino (C1-C6) alkyl, (C2-C6) alkenyl, (C2-C6) alkynyl, (C3-C6)cycloalkyl, (C1-C6) acyl, nitro, cyano, hydroxyl or amino group; or a phenyl, benzyl, pyridyl, picolyl, pyrimidyl, quinolinyl, thiazolyl, benzothiazolyl, thiadiazolyl, imidazolyl, tetrazolyl or pyridazinyl group, which may be substituted with $R_6$.

4. The compound according to claim 1 or a pharmaceutically acceptable salt thereof, wherein $R_1$ is Formula (4):

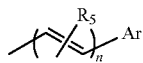

(4)

wherein n is 1, 2, or 3, $R_5$ represents —H, carboxyl, (C1-C6) alkyl, (C1-C6) alkoxycarbonyl, (C1-C6) alkoxycarbonylmethyl, amino (C1-C6) alkyl (said amino group may be substituted by 1 or 2 (C1-C6) alkyl groups, or 1 (C1-C6) alkoxycarbonyl group; additionally, a carbonyl group may be contained in the carbon chain), piperazinyl (C1-C6) alkyl, (C1-C6) alkoxycarbonylpiperazinyl (C1-C6) alkyl, morpholino (C1-C6) alkyl, (C1-C6) alkylpiperizine, (C2-C6) alkenyl, (C2-C6) alkynyl or phenyl group, wherein said phenyl group may be further substituted with 1 or 2 of $R_6$, $R_6$ represents a —H, —F, —Cl, —Br, —I, (C1-C6) alkyl, (C1-C6) alkylamino, di (C1-C6) alkylamino, (C1-C6) alkoxy, (C1-C6) alkylthio, (C1-C6) acyl, pyrrolidinyl, piperidino, piperazinyl, (C1-C6) alkoxycarbonyl, (C1-C6) alkoxycarbonylamino, phenyl, benzyl, phenyl (C1-C6) alkyloxy, nitro, amino or hydroxyl group; and Ar represents a phenyl, benzyl, pyridyl, pyrimidyl, thienyl, pyrrole, quinolinyl, thiazolyl, benzothiazolyl, thiadiazolyl, imidazolyl, tetrazolyl or pyridazinyl group which may be substituted with 1 or 2 of $R_6$; or a condensed ring group wherein 2 or more phenyl, benzyl, pyridyl, pyrimidyl, thienyl, pyrrole, quinolinyl, thiazolyl, benzothiazolyl, thiadiazolyl, imidazolyl, tetrazolyl or pyridazinyl groups, which may be substituted with 1 or 2 of $R_6$, are condensed.

5. The compound according to claim 1, or a pharmaceutically acceptable salt thereof, wherein said compound is:
5-methoxy-2,4-dimorpholino-6-(4-phenylpiperazin-1-yl)pyrimidine;
5-acetylamino-2-[2-(4-methoxyphenyl)vinyl]-4,6-dimorpholinopyrimidine;
5-fluoro-4,6-dimorpholino-2-(4-phenylpiperazin-1-yl)pyrimidine;
5-fluoro-2,4-dimorpholino-6-(4-phenylpiperazin-1-yl)pyrimidine;
6-dimethylamino-5-fluoro-4-morpholino-2-(4-phenylpiperazin-1-yl)pyrimidine;
2-dimethylamino-5-fluoro-6-morpholino-4-(4-phenylpiperazin-1-yl)pyrimidine;
4-(4-benzylpiperidin-1-yl)-2-dimethylamino-5-fluoro-6-morpholinopyrimidine;
5-fluoro-4-(3,4-dihydro-1H-isoquinolin-2-yl)-2,6-dimorpholinopyrimidine;
4-(N-ethyl-N-phenylamino)-5-fluoro-2,6-dimorpholinopyrimidine;
5-fluoro-2-(isoindolin-2-yl)-4,6-dimorpholinopyrimidine;
2-(4-benzylpiperazin-1-yl)-5-fluoro-4,6-dimorpholinopyrimidine;
2-dimethylamino-5-fluoro-6-morpholino-4-[4-(pyridin-2-yl)piperazin-1-yl]pyrimidine;
5-fluoro-4,6-dimorpholino-2-[4-(pyrimidin-2-yl)piperazin-1-yl]pyrimidine;
5-fluoro-4,6-dimorpholino-2-(3-phenylpiperazin-1-yl)pyrimidine;
5-fluoro-2,4-dimorpholino-6-(3-phenylpiperazin-1-yl)pyrimidine;
5-fluoro-2,4-dimorpholino-6-[4-(4-nitrophenyl)piperazin-1-yl]pyrimidine;
5-fluoro-2-[4-(4-fluorophenyl)piperazin-1-yl]-4,6-dimorpholino-pyrimidine;
5-fluoro-4-[4-(4-fluorophenyl)piperazin-1-yl]-2,6-dimorpholinopyrimidine;
5-fluoro-2-[4-(4-methylphenyl)piperazin-1-yl]-4,6-dimorpholinopyrimidine;
5-fluoro-4-[4-(4-methylphenyl)piperazin-1-yl]-2,6-dimorpholinopyrimidine;
2-[4-(4-acetylphenyl)piperazin-1-yl]-5-fluoro-4,6-dimorpholinopyrimidine;
4-[4-(4-acetylphenyl)piperazin-1-yl]-5-fluoro-2,6-dimorpholinopyrimidine;
2-[4-(2-chlorophenyl)piperazin-1-yl]-5-fluoro-4,6-dimorpholinopyrimidine;
2-[4-(2-ethoxyphenyl)piperazin-1-yl]-5-fluoro-4,6-dimorpholinopyrimidine;
5-fluoro-2-[4-(2-methylphenyl)piperazin-1-yl]-4,6-dimorpholinopyrimidine;
5-fluoro-4,6-dimorpholino-2-[4-(2,3-xylyl)piperazin-1-yl];
5-fluoro-2-[4-(2-fluorophenyl)piperazin-1-yl]-4,6-dimorpholinopyrimidine;
5-fluoro-2-[4-(4-hydroxyphenyl)piperazin-1-yl]-4,6-dimorpholinopyrimidine;
5-fluoro-2-[4-(2-methoxyphenyl)piperazin-1-yl]-4,6-dimorpholinopyrimidine;
2-[4-(4-chlorophenyl)piperazin-1-yl]-5-fluoro-4,6-dimorpholinopyrimidine;
6-[4-(2-chlorophenyl)piperazin-1-yl]-2-dimethylamino-5-fluoro-4-morpholinopyrimidine;
2-dimethylamino-5-fluoro-4-[4-(2-methoxyphenyl)piperazin-1-yl]-6-morpholinopyrimidine;

2-dimethylamino-5-fluoro-4-[4-(2-fluorophenyl)piper-azin-1-yl]-6-morpholinopyrimidine;
4-[4-(2-chlorophenyl)piperazin-1-yl]-2-dimethylamino-5-fluoro-6-morpholinopyrimidine;
2-(4-cyano-4-phenylpiperidin-1-yl)-5-fluoro-4,6-dimorpholinopyrimidine;
4-(4-cyano-4-phenylpiperidin-1-yl)-5-fluoro-2,6-dimorpholinopyrimidine;
5-fluoro-2-(4-hydroxy-4-phenylpiperidin-1-yl)-4,6-dimorpholinopyrimidine;
5-fluoro-4-(4-hydroxy-4-phenylpiperidin-1-yl)-2,6-dimorpholinopyrimidine;
2-(4-acetyl-4-phenylpiperidin-1-yl)-5-fluoro-4,6-dimorpholinopyrimidine;
4-(4-acetyl-4-phenylpiperidin-1-yl)-5-fluoro-2,6-dimorpholinopyrimidine;
5-fluoro-4,6-dimorpholino-2-[4-phenyl(1,2,5,6-tetrahydropyridyl)]pyrimidine;
5-fluoro-2,4-dimorpholino-6-[4-phenyl(1,2,5,6-tetrahydropyridyl)]pyrimidine;
5-fluoro-4,6-dimorpholino-2-(1,2,3,4-tetrahydro-2H-isoquinolin-2-yl)pyrimidine;
2-(4-cyclohexylpiperazin-1-yl)-5-fluoro-4,6-dimorpholinopyrimidine;
4-(4-cyclohexylpiperazin-1-yl)-5-fluoro-2,6-dimorpholinopyrimidine;
5-fluoro-4-[4-(2-fluorophenyl)piperazin-1-yl]-6-morpholino-2-(4-phenylpiperazin-1-yl)pyrimidine;
2,4-bis[4-(2-fluorophenyl)piperazin-1-yl]-5-fluoro-6-morpholinopyrimidine;
5-fluoro-2-[4-(2-fluorophenyl)piperazin-1-yl]-4-[4-(2-methylphenyl)piperazin-1-yl]-6-morpholinopyrimidine;
5-fluoro-6-morpholino-4-(4-phenylpiperazin-1-yl)-2-[4-(2-methylphenylpiperazin-1-yl]pyrimidine;
2,4-bis[4-(2-methylphenyl)piperazin-1-yl]-5-fluoro-6-morpholinopyrimidine;
5-chloro-4,6-dimorpholino-2-(4-phenylpiperazin-1-yl)pyrimidine;
5-amino-2-[2-(4-methoxyphenyl)vinyl]-4,6-dimorpholinopyrimidine;
5-amino-4,6-dimorpholino-2-[2-(2-thienyl)vinyl]pyrimidine;
5-amino-2-[2-(4-methylthiopheno[1,2-b]pyrrol-5-yl)vinyl]-4,6-dimorpholinopyrimidine;
5-amino-4,6-dimorpholino-2-[2-(pyridin-4-yl)vinyl]pyrimidine;
5-amino-2-[2-(4-fluorophenyl)vinyl]-4,6-dimorpholinopyrimidine;
5-amino-4,6-dimorpholino-2-[2-(4-piperidin-1-ylphenyl)vinyl]pyrimidine;
5-amino-2-[2-(2-methylphenyl)vinyl]-4,6-dimorpholinopyrimidine;
5-amino-4-dimethylamino-2-[2-(4-methoxyphenyl)vinyl]-6-morpholinopyrimidine;
5-amino-2-[2-(4-methoxyphenyl)vinyl]-4-methylamino-6-morpholinopyrimidine;
5-formyl-4,6-dimorpholino-2-(4-phenylpiperazin-1-yl)pyrimidine;
5-amino-2-[4-(4-diethylaminophenyl)butan-1,3-dienyl]-4,6-dimorpholinopyrimidine;
5-amino-2-[4-(4-diethylaminophenyl)butyl]-4,6-dimorpholinopyrimidine;
4-[4-(4-aminophenyl)piperazin-1-yl]-5-fluoro-2,6-dimorpholinopyrimidine;
5-fluoro-4-[4-(4-methylphenyl)piperazin-1-yl]-6-morpholino-2-(1-piperazinyl)pyrimidine;
2-[4-(tert-butoxycarbonyl)piperazin-1-yl]-5-fluoro-4-[4-(4-methylphenyl)piperazin-1-yl]-6-morpholinopyrimidine;
5-fluoro-4-[4-(4-methylphenyl)piperazin-1-yl]-2-(4-methylpiperazin-1-yl)-6-morpholinopyrimidine;
5-fluoro-2-[4-(4-methylphenyl)piperazin-1-yl]-4-morpholino-6-(1-piperazinyl)pyrimidine;
4-[4-(tert-butoxycarbonyl)piperazin-1-yl]-5-fluoro-2-[4-(4-methylphenyl)piperazin-1-yl]-6-morpholinopyrimidine;
5-fluoro-2-[4-(4-methylphenyl)piperazin-1-yl]-4-(4-methylpiperazin-1-yl)-6-morpholinopyrimidine;
5-fluoro-4-[4-(4-methylphenyl)piperazin-1-yl]-6-(4-methylpiperazin-1-yl)-2-morpholinopyrimidine;
2-[4-(2-aminoethyl)piperazin-1-yl]-5-fluoro-4-[4-(4-methylphenyl)piperazin-1-yl]-6-morpholinopyrimidine;
5-fluoro-2-{4-[2-(tert-butoxycarbonylamino)ethyl]piperazin-1-yl}-4-[4-(4-methylphenyl)piperazin-1-yl]-6-morpholinopyrimidine;
5-fluoro-4-[4-(4-methylphenyl)piperazin-1-yl]-6-morpholino-2-[2-(piperazin-1-yl)-ethylamino]pyrimidine;
2-[2-(4-tert-butoxycarbonylpiperazin-1-yl)ethylamino]-5-fluoro-4-[4-(4-methylphenyl)piperazin-1-yl]-6-morpholinopyrimidine;
5-fluoro-4-[4-(4-methylphenyl)piperazin-1-yl]-2-morpholino-6-(2-morpholinoethylamino)pyrimidine;
4-[4-(tert-butoxycarbonyl)piperazin-1-yl]-5-fluoro-6-morpholino-2-[4-(2-pyridyl)piperazin-1-yl]pyrimidine;
5-fluoro-4-morpholino-6-(1-piperazinyl)-2-[4-(2-pyridyl)piperazin-1-yl]pyrimidine;
5-fluoro-4,6-dimorpholino-2-[4-(2-pyridyl)piperazin-1-yl]pyrimidine;
5-fluoro-2,4-dimorpholino-6-[4-(2-pyridyl)piperazin-1-yl]pyrimidine;
5-fluoro-4-(4-methylpiperazin-1-yl)-6-morpholino-2-[4-(2-pyridyl)piperazin-1-yl]pyrimidine;
5-fluoro-4-(4-methylpiperazin-1-yl)-6-morpholino-2-(1,2,3,4-tetrahydro-1H-quinolin-1-yl)pyrimidine;
4-[4-(tert-butoxycarbonyl)piperazin-1-yl]-5-fluoro-6-morpholino-2-(1,2,3,4-tetrahydro-1H-quinolin-1-yl)pyrimidine;
5-fluoro-2-(1-piperazinyl)-4-morpholino-6-(1,2,3,4-tetrahydro-1H-quinolin-1-yl)pyrimidine;
5-amino-2-[2-(4-methoxyphenyl)vinyl]-4-morpholino-6-(1-piperazinyl)pyrimidine;
5-fluoro-4-(4-methylpiperazin-1-yl)-2-morpholino-6-(4-phenylpiperazin-1-yl)pyrimidine;
5-amino-2-[2-(4-methoxyphenyl)vinyl]-4-(4-methylpiperazin-1-yl)-6-morpholinopyrimidine;
5-amino-2-[2-(4-methoxyphenyl)vinyl]-4-morpholino-6-[2-(1-piperazinyl)ethylamino]pyrimidine;
5-amino-4-(2-aminoethylamino)-2-[2-(4-methoxyphenyl)vinyl]-6-morpholinopyrimidine;
5-amino-2-[2-(4-methoxyphenyl)vinyl]-4-[4-(2-dimethylaminoethyl-piperazin-1-yl)]-6-morpholinopyrimidine;
5-amino-4-(4-aminomethylcarbonylpiperazin-1-yl)-2-[2-(4-methoxyphenyl)vinyl]-6-morpholinopyrimidine;
2-(4-tert-butoxycarbonylpiperazin-1-yl)-5-fluoro-4-morpholino-6-[4-(2,3-xylyl)piperazin-1-yl]pyrimidine;
5-fluoro-4-morpholino-2-(1-piperazinyl)-6-[4-(2,3-xylyl)piperazin-1-yl]pyrimidine;
4-(4-tert-butoxycarbonylpiperazin-1-yl)-5-fluoro-6-morpholino-2-[4-(2,3-xylyl)piperazin-1-yl]pyrimidine;
5-fluoro-4-morpholino-6-(1-piperazinyl)-2-[4-(2,3-xylyl)piperazin-1-yl]pyrimidine;

4-(4-tert-butoxycarbonylpiperazin-1-yl)-5-fluoro-2-[4-(2-fluorophenyl)piperazin-1-yl]-6-morpholinopyrimidine;

5-fluoro-2-[4-(2-fluorophenyl)piperazin-1-yl]-4-morpholino-6-(1-piperazinyl)pyrimidine;

5-fluoro-2-(4-methylpiperazin-1-yl)-4-morpholino-6-[4-(2,3-xylyl)piperazin-1-yl]pyrimidine;

5-fluoro-4-(4-methylpiperazin-1-yl)-6-morpholino-2-[4-(2,3-xylyl)piperazin-1-yl]pyrimidine;

5-fluoro-2-[4-(2-fluorophenyl)piperazin-1-yl]-4-(4-methylpiperazin-1-yl)-6-morpholinopyrimidine;

5-fluoro-4-(4-methylpiperazin-1-yl)-2-morpholino-6-[4-(2,3-xylyl)piperazin-1-yl]-pyrimidine;

2-[4-(2-chlorophenyl)piperazin-1-yl]-5-fluoro-6-(4-methylpiperazin-1-yl)-4-morpholinopyrimidine;

4-(4-tert-butoxycarbonylpiperazin-1-yl)-2-[4-(2-chlorophenyl)piperazin-1-yl]-5-fluoro-6-morpholinopyrimidine;

2-[4-(2-chlorophenyl)piperazin-1-yl]-5-fluoro-4-morpholino-6-(1-piperazinyl)pyrimidine;

2-[4-(2-ethoxyphenyl)piperazin-1-yl]-5-fluoro-4-(4-methylpiperazin-1-yl)-6-morpholinopyrimidine;

5-fluoro-4-morpholino-2-[4-(4-pyridinylmethyl)piperazin-1-yl]-6-[4-(2,3-xylyl)piperazin-1-yl]-pyrimidine;

5-fluoro-2-[4-(4-dimethylaminobenzyl)piperazin-1-yl]-4-morpholino-6-[4-(2,3-xylyl)piperazin-1-yl]pyrimidine;

2-[4-(4-tert-butoxycarbonylaminobenzyl)piperazin-1-yl]-5-fluoro-4-morpholino-6-[4-(2,3-xylyl)piperazin-1-yl]pyrimidine;

2-[4-(4-aminobenzyl)piperazin-1-yl]-5-fluoro-4-morpholino-6-[4-(2,3-xylyl)piperazin-1-yl]pyrimidine;

5-amino-4-(4-tert-butoxycarbonylaminopiperidin-1-yl)-2-[2-(4-methoxyphenyl)vinyl]-6-morpholinopyrimidine;

5-amino-4-(4-aminopiperidin-1-yl)-2-[2-(4-methoxyphenyl)vinyl]-6-morpholinopyrimidine;

5-amino-4-(4-tert-butoxycarbonylmethylamino)-2-[2-(4-methoxyphenyl)vinyl]-6-morpholinopyrimidine;

5-amino-2-[2-(4-methoxyphenyl)vinyl]-4-[N-methyl-N-(1-methylpiperidin-4-yl)amino]-6-morpholinopyrimidine;

5-amino-2-[2-(4-methoxyphenyl)ethyl]-4-(1-piperazinyl)-6-morpholinopyrimidine;

5-amino-4-[4-(carboxymethyl)piperazin-1-yl]-2-[2-(4-methoxyphenyl)vinyl]-6-morpholinopyrimidine;

4,5-diamino-2-[2-(4-methoxyphenyl)vinyl]-6-morpholinopyrimidine;

5-amino-4-[4(3-aminopropionyl)piperazin-1-yl]-6-morpholino-2-[2-(4-methoxyphenyl)vinyl]pyrimidine;

5-fluoro-4-(4-methylpiperazin-1-yl)-6-morpholino-2-[4-(4-pyridinylmethyl)piperazin-1-yl]pyrimidine;

5-amino-2-[2-(4-methoxyphenyl)vinyl]-4-(4-dimethylthiocarbamoylpiperazin-1-yl)-6-morpholinopyrimidine;

5-amino-4-carbamoylmethylamino-2-[2-(4-methoxyphenyl)vinyl]-6-morpholinopyrimidine;

5-amino-2-[2-(4-methoxyphenyl)vinyl]-4-morpholino-6-(2-morpholinoethylamino)pyrimidine;

5-amino-2-[2-(4-methoxyphenyl)vinyl]-4-(1-piperazinyl)-6-[2-(1-piperazinyl)ethylamino)pyrimidine;

5-amino-4-(3-ethoxycarbonylthiomorpholin-4-yl)-2-[2-(4-methoxyphenyl)vinyl]-6-morpholinopyrimidine;

5-amino-4-dimethylamino-2-[2-(4-methoxyphenyl)vinyl]-6-(1-piperazinyl)pyrimidine;

5-amino-2-[2-(4-methoxyphenyl)vinyl]-4-(4-methylpiperazin-1-yl)-6-(1-piperazinyl)pyrimidine;

5-amino-4-(4-tert-butoxycarbonylmethylpiperazin-1-yl)-2-[2-(4-methoxyphenyl)vinyl]-6-morpholinopyrimidine;

4-(4-acetylpiperazin-1-yl)-5-amino-2-[2-(4-methoxyphenyl)vinyl]-6-(piperazin-1-yl)pyrimidine;

5-amino-4-(4-dimethylsulfamoylpiperazin-1-yl)-2-[2-(4-methoxyphenyl)ethyl]-6-morpholinopyrimidine;

5-amino-4-(4-dimethylsulfamoylpiperazin-1-yl)-2-[2-(4-methoxyphenyl)vinyl]-6-morpholinopyrimidine; or 5-fluoro-2-[2-(4-methoxyphenyl)vinyl]-4,6-dimorpholinopyrimidine.

6. A method for protecting from ischemic brain disease in a subject in need thereof, the method comprising administering to the subject an effective amount of at least one compound according to claim 1.

* * * * *